(12) United States Patent
Rao et al.

(10) Patent No.: US 8,802,850 B2
(45) Date of Patent: Aug. 12, 2014

(54) CYCLOPROPYL MODULATORS OF P2Y12 RECEPTOR

(75) Inventors: Tadimeti Rao, San Diego, CA (US); Chengzhi Zhang, San Diego, CA (US)

(73) Assignee: Auspex Pharmaceuticals, Inc., Lajolla, CA (US)

(*) Notice: Subject to any disclaimer, the term of this patent is extended or adjusted under 35 U.S.C. 154(b) by 0 days.

(21) Appl. No.: 12/844,017

(22) Filed: Jul. 27, 2010

(65) Prior Publication Data

US 2012/0301458 A1    Nov. 29, 2012

Related U.S. Application Data

(60) Provisional application No. 61/228,913, filed on Jul. 27, 2009.

(51) Int. Cl.
| | | |
|---|---|---|
| *A61K 31/519* | (2006.01) | |
| *C07D 487/04* | (2006.01) | |
| *A61P 7/02* | (2006.01) | |
| *A61P 9/00* | (2006.01) | |
| *A61K 31/551* | (2006.01) | |
| *A61K 31/675* | (2006.01) | |
| *A61K 31/727* | (2006.01) | |
| *A61K 38/17* | (2006.01) | |
| *A61K 39/395* | (2006.01) | |
| *A61K 38/48* | (2006.01) | |
| *A61K 31/616* | (2006.01) | |
| *A61K 38/49* | (2006.01) | |

(52) U.S. Cl.
CPC ............ *C07D 487/04* (2013.01); *A61K 31/519* (2013.01)
USPC ........................................ 544/254; 424/133.1

(58) Field of Classification Search
None
See application file for complete search history.

(56) References Cited

U.S. PATENT DOCUMENTS

| | | | |
|---|---|---|---|
| 5,846,514 A | 12/1998 | Foster et al. | |
| 6,221,335 B1 | 4/2001 | Foster | |
| 6,251,910 B1 | 6/2001 | Guile et al. | |
| 6,440,710 B1 | 8/2002 | Keinan et al. | |
| 6,525,060 B1 | 2/2003 | Hardern et al. | |
| 6,603,008 B1 | 8/2003 | Ando et al. | |
| 7,250,419 B2 | 7/2007 | Hardern et al. | |
| 7,265,124 B2 | 9/2007 | Bohlin et al. | |
| 7,517,990 B2 | 4/2009 | Ito et al. | |
| 2002/0013372 A1 | 1/2002 | Ekins | |
| 2007/0197695 A1 | 8/2007 | Potyen et al. | |
| 2008/0033011 A1 | 2/2008 | Tung | |

FOREIGN PATENT DOCUMENTS

| | | |
|---|---|---|
| WO | 9526325 A2 | 10/1995 |
| WO | 9905142 A1 | 2/1999 |
| WO | 0034283 A1 | 6/2000 |
| WO | 0192262 A1 | 12/2001 |
| WO | 0192263 A1 | 12/2001 |
| WO | 2011017108 A2 | 2/2011 |
| WO | 2011017108 A3 | 2/2011 |

OTHER PUBLICATIONS

Husted et al. In the European Heart Journal 27, 1038-1047 (2006).*
Haskins, N.J. In Biomedical Mass Spectrometry, 9(7) 269-276 (1982).*
Jones et al. In Journal of Pharmaceutical and Biomedical Analysis 29, 221-228 (2002).*
Wiltshire et al. In Journal of Chromatography B, 745, 373-388 (2000).*
Springthorpe et al. In Bioorganic & Medicinal Chemistry Letters 17, 6013-6018 (2007).*
Leis et al. In Current Organic Chemistry 2, 131-144 (1998).*
Mishra et al. In the American Journal of Sports Medicine, 34 (11), 1774-1778 (2006).*
"Deuterium" in www.britannica.com/EBchecked/ topic/ 159684/ deuterium.*
Auspex in www.businesswire.com/news/home/20081023005201/en/Auspex-Pharmaceuticals-Announces-Positive-Results-Clinical-Study (published: Oct. 23, 2008) (retrieved from the internet Oct. 22, 2013).*
Concert in www.concertpharma.com/news/ConcertPresentsPreclinical ResultsNAMS.htm (published: Sep. 25, 2008) (retrieved from the internet Oct. 22, 2013).*
Concert2 in Expert Rev. Anti Infect. Ther. 6(6), 782 (2008) (retrieved from the internet Oct. 22, 2013).*
Drug Topics in drugtopics.modern medicine.com/drug-topics/news/modernmedicine/modern-medicine-news/ overview-pharmaceutical-excipients-used-tablets (published: Oct. 24, 2008). (retrieved from the internet Oct. 22, 2013).*

(Continued)

*Primary Examiner* — Dennis Heyer
(74) *Attorney, Agent, or Firm* — Dennis A. Bennett; Jonathan Duffield

(57) ABSTRACT

The present invention relates to new cyclopropyl modulators of P2Y12 receptor activity, pharmaceutical compositions thereof, and methods of use thereof.

5 Claims, No Drawings

(56) References Cited

OTHER PUBLICATIONS

Kushner, D.J. et al.; Pharmacological uses and perspectives of heavy water and deuterated compounds; Canadian Journal of Physiology and Pharmacology (1999), 77(2), 79-88.
Bauer, LA et. al.; Influence of long-term infusions on lidocaine kinetics; Clin. Pharmacol. Ther. 1982, 433-7.
Borgstrom, L et al.; Comparative Pharmacokinetics of Unlabeled and Deuterium-Labeled Terbutaline: Demonstration of a Small Isotope Effect; Pharm Sci, 1988, 77(11), 952-4.
Browne, T.R.; Isotope effect: implications for pharmaceutical investigations; Pharmacochemistry Library (1997), 26 (Stable Isotopes in Pharmaceutical Research), 13-18.
Browne, TR et. al.; Pharmacokinetic Equivalence of Stable-Isotope-Labeled and Unlabeled Drugs. Phenobarbital in Man; J Clin Pharmacol, 1982, 22, 309-315.
Burm, AGL et. al.; Pharmacokinetics of Lidocaine and bupivacaine and stable isotope-labeled analogs: a study in healthy volunteers; Biopharmaceutics and Drug Disposition, 1988, 9, 85-95.
Elison, C.; Effect of deuteration of N-CH3 group on potency and enzymatic N-demethylation of morphine; Science, 1961, 134(3485), 1078-9.
Farmer, PB et. al.; Synthesis, Metabolism, and Antitumor Activity of Deuterated Analogues of 1-(2-Choloroethyl)-3-cyclohexyl-1-nitrosourea; Journal of Medicinal Chemistry, 1978, vol. 21, No. 6, 514-20.
Fisher, MB et. al.; The complexities inherent in attempts to decrease drug clearance by blocking sites of CYP-mediated metabolism; Curr Opin Drug Discov Develop; 2006, 9(1), 101-9.
Foster, A.B., Deuterium Isotope Effects in the Metabolism of Drugs and Xenobiotics: Implications for Drug Design, Adv. Drug Res., Academic Press, London, GB, vol. 14, Jan. 1, 1985, pp. 1-40.
Foster, A.B.; Deuterium isotope effects in studies of drug metabolism; Trends in Pharmacological Sciences (1984), 5 (12), 524-7.
Helfenbein, J. et. al.; Isotopic Effect Study of Propofol Deuteration on the Metabolism, Activity, and Toxicity of the Anesthetic; J. Med. Chem. 2002, 45, 5806-5808.
Lee, H. et. al.; Deuterium Magic Angle Spinning Studies of Substrates Bound to Cytochrome P450; Biochemistry 1999, 38, 10808-10813.
Mamada, K. et. al.; Pharmacokinetic Equivalence of Deuterium-Labeled and Unlabeled Phenytoin; Drug Metabolism and Disposition, 1986, 14(4), 509-11.
Nelson, SD et. al.; The Use of Deuterium Isotope Effect to Probe the Active Site Properties, Mechanism of Cytochrome P450-catalyzed Reactions, and Mechanisms of Metabolically Dependent Toxicity; Drug Metabolism and Disposition 31:1481-1498, 2003.
Nelson, SD et. al.; Primary and B-Secondary Deuterium Isotope Effects in N-Deethylation Reactions; Journal of Medicinal Chemistry, 1975, vol. 18, No. 11.
Pohl, L.R. et. al.; Determination of toxic pathways of metabolism by deuterium substitution; Drug Metabolism Reviews (1985), Volume Date 1984, 15(7), 1335-51.
Rampe, D. et. al.; Deuterated Analogs of verapamil and nifedipine. Synthesis and biological activity; Eur J Med Chem (1993) 28,259-263.
Baillie, Thomas, The Use of Stable Isotopes in Pharmaceutical Research, Pharmacological Reviews, 1981, 33(2), 81-132.
Browne, Thomas, Stable Isotope Techniques in Early Drug Development: An Economic Evaluation, J. Clin. Pharmacol., 1998, 38, 213-220.
Cherrah et al., Study of Deuterium Isotope Effects on Protein Binding by Gas Chromatography/Mass Spectrometry. Caffeine and Deuterated Isomers, Biomedical and Environmental Mass Spectrometry, 1987, 14, 653-657.
Dyck et al., Effects of Deuterium Substitution on the Catabolism of Beta-Phenethylamine: An In Vivo Study, J. Neurochem., 1986, 46(2), 399-404.
Goulette, Alain, Use of Deuterium-Labelled Elliptinium and Its Use in Metabolic Studies, Biomedical and Environmental Mass Spectrometry, 1988, 15, 243-247.
Haskins, N.J., The Application of Stable Isotopes in Biomedical Research, Biomedical Mass Spectrometry, 1982, 9(7), 269-277.
Honma et al., The Metabolism of Roxatidine Acetate Hydrochloride, Drug Metabolism and Disposition, 1987, 15(4), 551-559.
Pieiaszek et al., Moricizine Bioavailability Via Simultaneous, Dual, Stable Isotope Administration: Bioequivalence Implications, J. Clin. Pharmacol., 1999, 39, 817-825.
Tonn et al., Simultaneous Analysis of Diphenylhydramine and a Stable Isotope Analog (2H10) Diphenylhydramine Using Capillary Gas Chromatography With Mass Selective Detection in Biological Fluids From Chronically Instrumented Pregnant Ewes, Biomedical Mass Spectrometry, 1993, 22, 633-642.
Wolen et al., The Application of Stable Isotopes to Studies of Drug Bioavailibility and Bioequivalence, J. Clin. Pharmacol., 1986, 26, 419-424.
Rao et al., Cyclopropyl Modulators of P2Y12 Receptor, Auspex Pharmaceuticals, Inc., WO 2011017108 IPRP, Publication Date: Feb. 10, 2011.
Cannon et al., Comparison of ticagrelor with clopidogrel in patients with a planned invasive strategy for acute coronary syndromes (PLATO): a randomised double-blind study, 2010, www.thelancet.com, DOI:10.1016/S0140-6736(10) 60070-0.
Tantry et al., AZD6140, Expert Opin. Investig. Drugs, 2007, 16(2), 225-229.
Stone, Greg, Ticagrelor in ACS: redefining a new standard of care?, 2010, www.thelancet.com, DOI:10.1016/ 50140-6736(10)60070-0.
Springthorpe et al., From ATP to AZD6140: The discovery of an orally active reversible P2Y12 receptor antagonist for the prevention of thrombosis, Bioorganic & Medicinal Chemistry Letters, 2007, 17, 6013-6018.
Husted et al., Pharmacodynamics, pharmacokinetics, and safety of the oral reversible P2Y12 antagonist AZD6140 with aspirin in patients with atherosclerosis: a double-blind comparison to clopidogrel with aspirin, European Heart Journal, 2006, 27, 1038-1047.
Schomig, Albert, Ticagrelor—Is There Need for a New Player in the Antiplatelet-Therapy Field?, New Engl. J. Med., 2009, 361(11), 1108-1111.
Wallentin et al., Ticagrelor—Ticagrelor versus Clopidogrel in Patients with Acute Coronary Syndromes, New Engl. J. Med., 2009, 361(11), 1045-1057.
Angiolillo et al., Pharmacology of emerging novel platelet inhibitors, American Heart Journal, 2008, 156(2) Supp. 1, 10S-15S.
Owen et al., AZD6140, Drugs of the Future, 2007, 32(10), 845.
Yarnell, Heavy-Hydrogen Drugs Turn Heads, Again, http://pubs.acs.org/cen/science/87/8725scil.html, Jun. 22, 2009.
EP 2010806891—European Search Report, May 15, 2013.

* cited by examiner

CYCLOPROPYL MODULATORS OF P2Y12 RECEPTOR

This application claims the benefit of priority of U.S. provisional application No. 61/228,913, filed Jul. 27, 2009, the disclosure of which is hereby incorporated by reference as if written herein in its entirety.

Disclosed herein are new substituted cyclopropyl compounds, pharmaceutical compositions made thereof, and methods to modulate P2Y12 receptor activity in a subject are also provided for, for the treatment of disorders such as arterial thrombosis and coronary artery disease.

Ticagrelor (AR-C126532, AZD-6140, Brilinta®, CAS #274693-27-5), 3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1S,2S,3R,5S)-1,2-cyclopentanediol, is a P2Y12 receptor antagonist. Ticagrelor is currently under investigation for the treatment of arterial thrombosis (Tantry et al., *Exp. Opin. Invest. Drugs* 2007, 16(2), 225-229; Husted et al., *Eur. Heart J.* 2006, 27(9), 1038-1047; and WO 2000034283). Ticagrelor has also shown promise in treating coronary artery disease and other disorders related to platelet aggregation (Tantry et al., *Exp. Opin. Invest. Drugs* 2007, 16(2), 225-229; Husted et al., *Eur. Heart J.* 2006, 27(9), 1038-1047; and WO 2000034283).

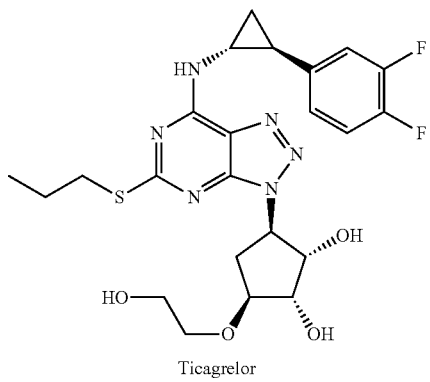 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

Ticagrelor

Ticagrelor is subject to CYP450-mediated oxidative metabolism, forming an active metabolite AR-C124910XX (Husted et al., *Eur. Heart J.* 2006, 27, 1038-1047). Adverse effects associated with ticagrelor include excessive bleeding.

Deuterium Kinetic Isotope Effect

In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k = Ae^{-E_{act}/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C—$^1H$ bond. If a C—$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C—$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects.

Deuterium ($^2H$ or D) is a stable and non-radioactive isotope of hydrogen which has approximately twice the mass of protium ($^1H$), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$, Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Ticagrelor is a P2Y12 receptor antagonist. The carbon-hydrogen bonds of ticagrelor contain a naturally occurring distribution of hydrogen isotopes, namely $^1$H or protium (about 99.9844%), $^2$H or deuterium (about 0.0156%), and $^3$H or tritium (in the range between about 0.5 and 67 tritium atoms per $10^{18}$ protium atoms). Increased levels of deuterium incorporation may produce a detectable Deuterium Kinetic Isotope Effect (DKIE) that could effect the pharmacokinetic, pharmacologic and/or toxicologic profiles of ticagrelor in comparison with ticagrelor having naturally occurring levels of deuterium.

Based on discoveries made in our laboratory, as well as considering the literature, ticagrelor is likely metabolized in humans at the 2-hydroxyethoxy group, the S-propyl group, and the cyclopropyl group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of ticagrelor and attenuate interpatient variability.

Novel compounds and pharmaceutical compositions, certain of which have been found to modulate P2Y12 receptor activity have been discovered, together with methods of synthesizing and using the compounds, including methods for the treatment of P2Y12 receptor-mediated disorders in a patient by administering the compounds as disclosed herein.

In certain embodiments of the present invention, compounds have structural Formula I:

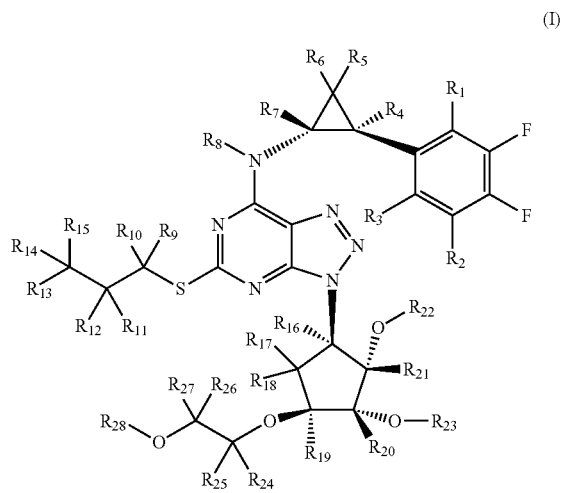

(I)

or a pharmaceutically acceptable salt thereof, wherein:
$R_1$-$R_{28}$ are independently selected from the group consisting of hydrogen and deuterium; and
at least one of $R_1$-$R_{28}$ is deuterium.

Certain compounds disclosed herein may possess useful P2Y12 receptor modulating activity, and may be used in the treatment or prophylaxis of a disorder in which P2Y12 receptors play an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for modulating P2Y12 receptor activity. Other embodiments provide methods for treating a P2Y12 receptor-mediated disorder in a patient in need of such treatment, comprising administering to said patient a therapeutically effective amount of a compound or composition according to the present invention. Also provided is the use of certain compounds disclosed herein for use in the manufacture of a medicament for the prevention or treatment of a disorder ameliorated by modulating P2Y12 receptor activity.

The compounds as disclosed herein may also contain less prevalent isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a", "an", and "the" may refer to plural articles unless specifically stated otherwise.

The term "about", as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule such as $R_1$-$R_{28}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S", depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat", "treating", and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent", "preventing", and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "P2Y12 receptor" refers to a G-protein coupled receptor located on the platelet membrane. The P2Y12 receptor (also known as P2T, P2YADP, or P2TAC) is primarily involved in mediating platelet aggregation/activation. The pharmacological characteristics of this receptor have been described, for example, by Humphries et al., *Br. J. Pharmacology* 1994, 113, 1057-1063; and Fagura et al., *Br. J. Pharmacology* 1998, 124, 157-164.

The term "P2Y12 receptor-mediated disorder", refers to a disorder that is characterized by abnormal P2Y12 receptor activity or excessive platelet aggregation, or normal platelet aggregation or normal P2Y12 receptor activity that when modulated ameliorates other abnormal biochemical processes. A P2Y12 receptor-mediated disorder may be completely or partially mediated by modulating P2Y12 receptor activity. In particular, a P2Y12 receptor-mediated disorder is one in which modulation of P2Y12 receptor activity results in some effect on the underlying disorder e.g., administration of a P2Y12 receptor modulator results in some improvement in at least some of the patients being treated.

The term "P2Y12 receptor modulator", refers to the ability of a compound disclosed herein to alter the function of P2Y12 receptors. A P2Y12 receptor modulator may activate the activity of a P2Y12 receptor, may activate or inhibit the activity of a P2Y12 receptor depending on the concentration of the compound exposed to the P2Y12 receptor, or may inhibit the activity of a P2Y12 receptor. Such activation or inhibition may be contingent on the occurrence of a specific event, such as activation of a signal transduction pathway, and/or may be manifest only in particular cell types. The term "P2Y12 receptor modulator", also refers to altering the function of a P2Y12 receptor by increasing or decreasing the probability that a complex forms between a P2Y12 receptor and a natural binding partner. A P2Y12 receptor modulator may increase the probability that such a complex forms between the P2Y12 receptor and the natural binding partner, may increase or decrease the probability that a complex forms between the P2Y12 receptor and the natural binding partner depending on the concentration of the compound exposed to the P2Y12 receptor, and or may decrease the probability that a complex forms between the P2Y12 receptor and the natural binding partner. In some embodiments, modulation of the P2Y12 receptor activity may be assessed using the method described in Husted et al., *Eur. Heart J.* 2006, 27(9), 1038-1047; WO 2000034283; WO 199905142.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier", "pharmaceutically acceptable excipient", "physiologically acceptable carrier", or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, Fla., 2004).

The terms "active ingredient", "active compound", and "active substance" refer to a compound, which is administered, alone or in combination with one or more pharmaceutically acceptable excipients or carriers, to a subject for treating, preventing, or ameliorating one or more symptoms of a disorder.

The terms "drug", "therapeutic agent", and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The compounds disclosed herein can exist as therapeutically acceptable salts. The term "pharmaceutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a P2Y12 receptor-mediated disorder comprising administering to a subject having or suspected of having such a disorder, a therapeutically effective amount of a compound as disclosed herein or a pharmaceutically acceptable salt, solvate, or prodrug thereof.

P2Y12 receptor-mediated disorders, include, but are not limited to, arterial thrombosis, coronary artery disease, myocardial infarction, stroke, atherosclerosis, acute coronary syndrome, peripheral artery occlusive disease, carotid, vertebral, or intracerebral artery stenosis, unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis, in other inflammatory conditions such as asthma, in which platelets and platelet-derived factors are implicated in the immunological disease process, and/or any disorder which can lessened, alleviated, or prevented by administering a P2Y12 receptor modulator.

In certain embodiments, a method of treating a P2Y12 receptor-mediated disorder comprises administering to the subject a therapeutically effective amount of a compound as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described by Li et al. *Rapid Communications in Mass Spectrometry* 2005, 19, 1943-1950; Butler, et al., *Drug Metab Rev* 2008, 40(*Suppl.* 3): Abst 280; Husted et al., *European Heart Journal* 2006, 27(9), 1038-1047; and any references cited therein and any modifications made thereof.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al., *British Journal of Clinical Pharmacology* 2000, 49, 343-351. The inhibition of the $MAO_A$ isoform is measured by the method of Weyler et al., *J. Biol Chem.* 1985, 260, 13199-13207. The inhibition of the $MAO_B$ isoform is measured by the method of Uebelhack et al., *Pharmacopsychiatry*, 1998, 31, 187-192.

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, bleeding time, platelet inhibition, inhibition of adenosine-5'-diphosphate-induced platelet aggregation as measured by optical aggregometry of platelet-rich plasma, reduced cardiovascular death, reduced myocardial infarction, reduced stroke, and reduced bleeding events (Tantry et al., *Exp. Opin. Invest. Drugs* 2007, 16(2), 225-229; Husted et al., *Eur. Heart J.* 2006, 27(9), 1038-1047; and WO 2000034283).

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.
Combination Therapy The compounds disclosed herein may also be combined or used in combination with other agents useful in the treatment of P2Y12 receptor-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more alpha adrenergic receptor antagonists, beta-adrenergic antagonists, angiotensin II receptor antagonists, angiotensin-converting enzyme inhibitors, anti-arrhythmics, antithrombotics, antiplatelet agents, calcium channel blockers, fibrates, and HMG-CoA reductase inhibitors.

In certain embodiments, the compounds disclosed herein can be combined with one or more alpha adrenergic receptor antagonists known in the art, including, but not limited to, abanoquil, adimolol, ajmalicine, alfuzosin, amosulalol, arotinolol, atiprosin, benoxathian, buflomedil, bunazosin, carvedilol, CI-926, corynanthine, dapiprazole, DL-017, domesticine, doxazosin, eugenodilol, fenspiride, GYKI-12,743, GYKI-16,084, indoramin, ketanserin, L-765,314, labetalol, mephendioxan, metazosin, monatepil, moxisylyte (thymoxamine), naftopidil, nantenine, neldazosin, nicergoline, niguldipine, pelanserin, phendioxan, phenoxybenzamine, phentolamine, piperoxan, prazosin, quinazosin, ritanserin, RS-97,078, SGB-1,534, silodosin, SL-89.0591, spiperone, talipexole, tamsulosin, terazosin, tibalosin, tiodazosin, tipentosin, tolazoline, trimazosin, upidosin, urapidil, zolertine, 1-PP, adimolol, atipamezole, BRL-44408, buflomedil, cirazoline, efaroxan, esmirtazapine, fluparoxan, GYKI-12,743, GYKI-16,084, idazoxan, mianserin, mirtazapine, MK-912, NAN-190, olanzapine, phentolamine, phenoxybenzamine, piperoxan, piribedil, rauwolscine, rotigotine, SB-269,970, setiptiline, spiroxatrine, sunepitron, tolazoline, and yohimbine.

In certain embodiments, the compounds disclosed herein can be combined with one or more beta-adrenergic antagonists, including, but not limited to, acebutolol, adaprolol, adimolol, afurolol, alprenolol, alprenoxime, amosulalol, ancarolol, arnolol, arotinolol, atenolol, befunolol, betaxolol, bevantolol, bisoprolol, bopindolol, bormetolol, bornaprolol, brefonalol, bucindolol, bucumolol, bufetolol, buftiralol, bufuralol, bunitrolol, bunolol, bupranolol, burocrolol, butaxamine, butidrine, butofilolol, capsinolol, carazolol, carpindolol, carteolol, carvedilol, celiprolol, cetamolol, cicloprolol, cinamolol, cloranolol, cyanopindolol, dalbraminol, dexpropranolol, diacetolol, dichloroisoprenaline, dihydroalprenolol, dilevalol, diprafenone, draquinolol, dropranolol, ecastolol, epanolol, ericolol, ersentilide, esatenolol, esmolol, esprolol, eugenodilol, exaprolol, falintolol, flestolol, flusoxolol, hydroxycarteolol, hydroxytertatolol, ICI-118,551, idropranolol, indenolol, indopanolol, iodocyanopindolol, iprocrolol, isoxaprolol, isamoltane, labetalol, landiolol, levobetaxolol, levobunolol, levocicloprolol, levomoprolol, medroxalol, mepindolol, metalol, metipranolol, metoprolol, moprolol, nadolol, nadoxolol, nafetolol, nebivolol, neraminol, nifenalol, nipradilol, oberadilol, oxprenolol, pacrinolol, pafenolol, pamatolol, pargolol, parodilol, penbutolol, penirolol, PhQA-33, pindolol, pirepolol, practolol, primidolol, procinolol, pronethalol, propafenone, propranolol, ridazolol, ronactolol, soquinolol, sotalol, spirendolol, SR 59230A, sulfinalol, TA-2005, talinolol, tazolol, teoprolol, tertatolol, terthianolol, tienoxolol, tilisolol, timolol, tiprenolol, tolamolol, toliprolol, tribendilol, trigevolol, xibenolol, and xipranolol.

In certain embodiments, the compounds disclosed herein can be combined with one or more angiotensin II receptor antagonists, including, but not limited to, candesartan, eprosartan, irbesartan, losartan, olmesartan, tasosartan, telmisartan, and valsartan.

In certain embodiments, the compounds disclosed herein can be combined with one or more angiotensin-converting enzyme inhibitors, including, but not limited to, captopril, enalapril, lisinopril, perindopril, ramipril, quinapril, benazepril, cilazapril, fosinopril, trandolapril, spirapril, delapril, moexipril, temocapril, zofenopril, and imidapril.

In certain embodiments, the compounds disclosed herein can be combined with one or more anti-arrhythmics, including, but not limited to quinidine, procainamide, disopyramide, sparteine, ajmaline, prajmaline, lorajmine, lidocaine, mexiletine, tocamide, aprindine, propafenone, flecamide, lorcamide, encamide, amiodarone, bretylium tosilate, bunaftine, dofetilide, ibutilidem, tedisamil, moracizine, and cibenzoline.

In certain embodiments, the compounds provided herein can be combined with one or more antithrombotics, including, but not limited to, dicoumarol, phenindione, warfarin, phenprocoumon, acenocoumarol, ethyl biscoumacetate, clorindione, diphenadione, tioclomarol, heparin, antithrombin III, dalteparin, enoxaparin, nadroparin, parnaparin, reviparin, danaparoid, tinzaparin, sulodexide, bemiparin, ditazole, cloricromen, picotamide, clopidogrel, ticlopidine, acetylsalicylic acid, dipyridamole, carbasalate calcium, epoprostenol, indobufen, iloprost, abciximab, aloxiprin, eptifibatide, tirofiban, triflusal, beraprost, treprostinil, prasugrel, streptokinase, alteplase, urokinase, fibrinolysin, brinase, reteplase, saruplase, ancrod, drotrecogin alfa (activated), tenecteplase, protein C, desirudin, lepirudin, argatroban, melagatran, ximelagatran, bivalirudin, dabigatran etexilate, defibrotide, dermatan sulfate, fondaparinux, and rivaroxaban.

In certain embodiments, the compounds provided herein can be combined with one or more antiplatelet agents, including, but not limited to, abciximab, eptifibatide, tirofiban, clopidogrel, prasugrel, ticlopidine, ticagrelor, beraprost, prostacyclin, iloprost, treprostinil, acetylsalicylic acid, aloxiprin, carbasalate calcium, indobufen, dipyridamole, picotamide, terutroban, cilostazol, dipyridamole, triflusal, cloricromen, and ditazole.

In certain embodiments, the compounds disclosed herein can be combined with one or more beta-adrenergic antagonists, including, but not limited to, acebutolol, adaprolol, adimolol, afurolol, alprenolol, alprenoxime, amosulalol, ancarolol, arnolol, arotinolol, atenolol, befunolol, betaxolol, bevantolol, bisoprolol, bopindolol, bormetolol, bornaprolol, brefonalol, bucindolol, bucumolol, bufetolol, buftiralol, bufuralol, bunitrolol, bunolol, bupranolol, burocrolol, butaxamine, butidrine, butofilolol, capsinolol, carazolol, carpindolol, carteolol, carvedilol, celiprolol, cetamolol, cicloprolol, cinamolol, cloranolol, cyanopindolol, dalbraminol, dexpropranolol, diacetolol, dichloroisoprenaline, dihydroalprenolol, dilevalol, diprafenone, draquinolol, dropranolol, ecastolol, epanolol, ericolol, ersentilide, esatenolol, esmolol, esprolol, eugenodilol, exaprolol, falintolol, flestolol, flusoxolol, hydroxycarteolol, hydroxytertatolol, ICI-118,551, idropranolol, indenolol, indopanolol, iodocyanopindolol, iprocrolol, isoxaprolol, isamoltane, labetalol, landiolol, levobetaxolol, levobunolol, levocicloprolol, levomoprolol, medroxalol, mepindolol, metalol, metipranolol, metoprolol, moprolol, nadolol, nadoxolol, nafetolol, nebivolol, neraminol, nifenalol, nipradilol, oberadilol, oxprenolol, pacrinolol, pafenolol, pamatolol, pargolol, parodilol, penbutolol, penirolol, PhQA-33, pindolol, pirepolol, practolol, primidolol, procinolol, pronethalol, propafenone, propranolol, ridazolol, ronactolol, soquinolol, sotalol, spirendolol, SR 59230A, sulfinalol, TA-2005, talinolol, tazolol, teoprolol, tertatolol, terthianolol, tienoxolol, tilisolol, timolol, tiprenolol, tolamolol, toliprolol, tribendilol, trigevolol, xibenolol, and xipranolol.

In certain embodiments, the compounds disclosed herein can be combined with one or more calcium channel blockers, including, but not limited to amlodipine, felodipine, isradipine, nicardipine, nifedipine, nimodipine, nisoldipine, nitrendipine, lacidipine, nilvadipine, manidipine, barnidipine, lercanidipine, cilnidipine, benidipine, mibefradil, verapamil, gallopamil, diltiazem, fendiline, bepridil, lidoflazine, and perhexiline.

In certain embodiments, the compounds provided herein can be combined with one or more fibrates, including, but not limited to, clofibrate, bezafibrate, aluminium clofibrate, gemfibrozil, fenofibrate, simfibrate, ronifibrate, ciprofibrate, etofibrate, and clofibride.

In certain embodiments, the compounds disclosed herein can be combined with one or more HMG-CoA reductase inhibitors, including, but not limited to, atorvastatin, cerivastatin, fluvastatin, lovastatin, mevastatin, pitavastatin, pravastatin, rosuvastatin, and simvastatin.

The compounds disclosed herein can also be administered in combination with other classes of compounds, including, but not limited to, decongestant treatments; antitussive treatments; mucolytic treatments; expectorant treatments; antiallergic non-steroidal treatments; steroidal drugs; antihistamine treatments; leukotriene receptor antagonists; phosphodiesterase inhibitors; CYP3A inhibitors; CYP3A inducers; protease inhibitors; antifugal agents; antibacterials; antimycobacterial agents; sepsis treatments; steroidal drugs; non-steroidal anti-inflammatory agents, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; squalene synthetase inhibitors; bile acid sequestrants, such as questran; niacin; anti-atherosclerotic agents, such as ACAT inhibitors; MTP Inhibitors; potassium channel activators; alpha-muscarinic agents; beta-muscarinic agents, such as carvedilol and metoprolol; diuretics, such as chlorothlazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating P2Y12 receptor-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of P2Y12 receptor-mediated disorders.

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in Shireman et al., *Tetrahedron Letters* 2000, 41, 9537-9540; *Bioorganic & Medicinal Chemistry Letters* 2007, 17, 6013-6018; US 20030148888 and WO 2010030224; WO 2000034283; WO 2001092262; WO 2001092263; WO 199905142, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

Scheme I
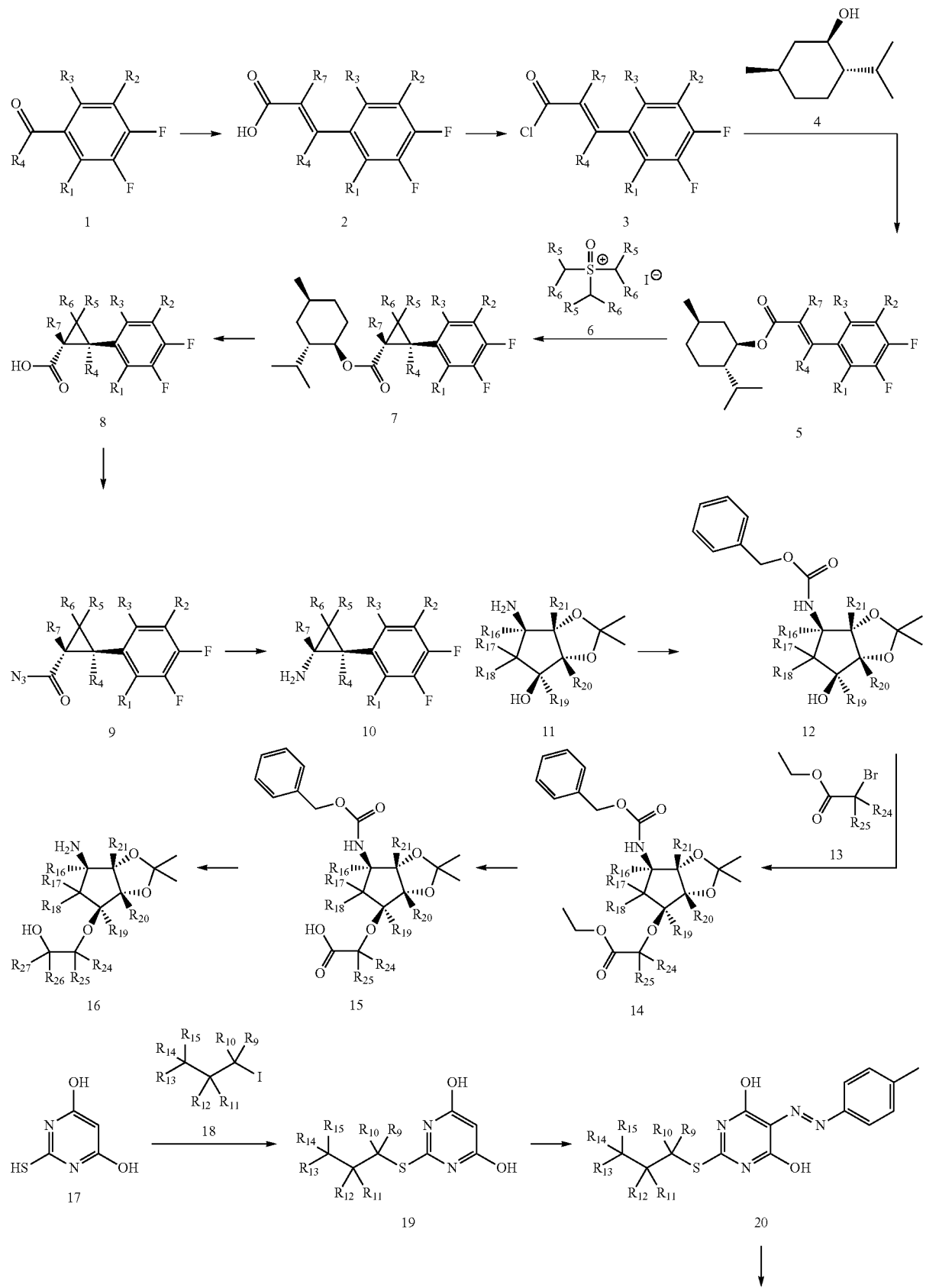

-continued

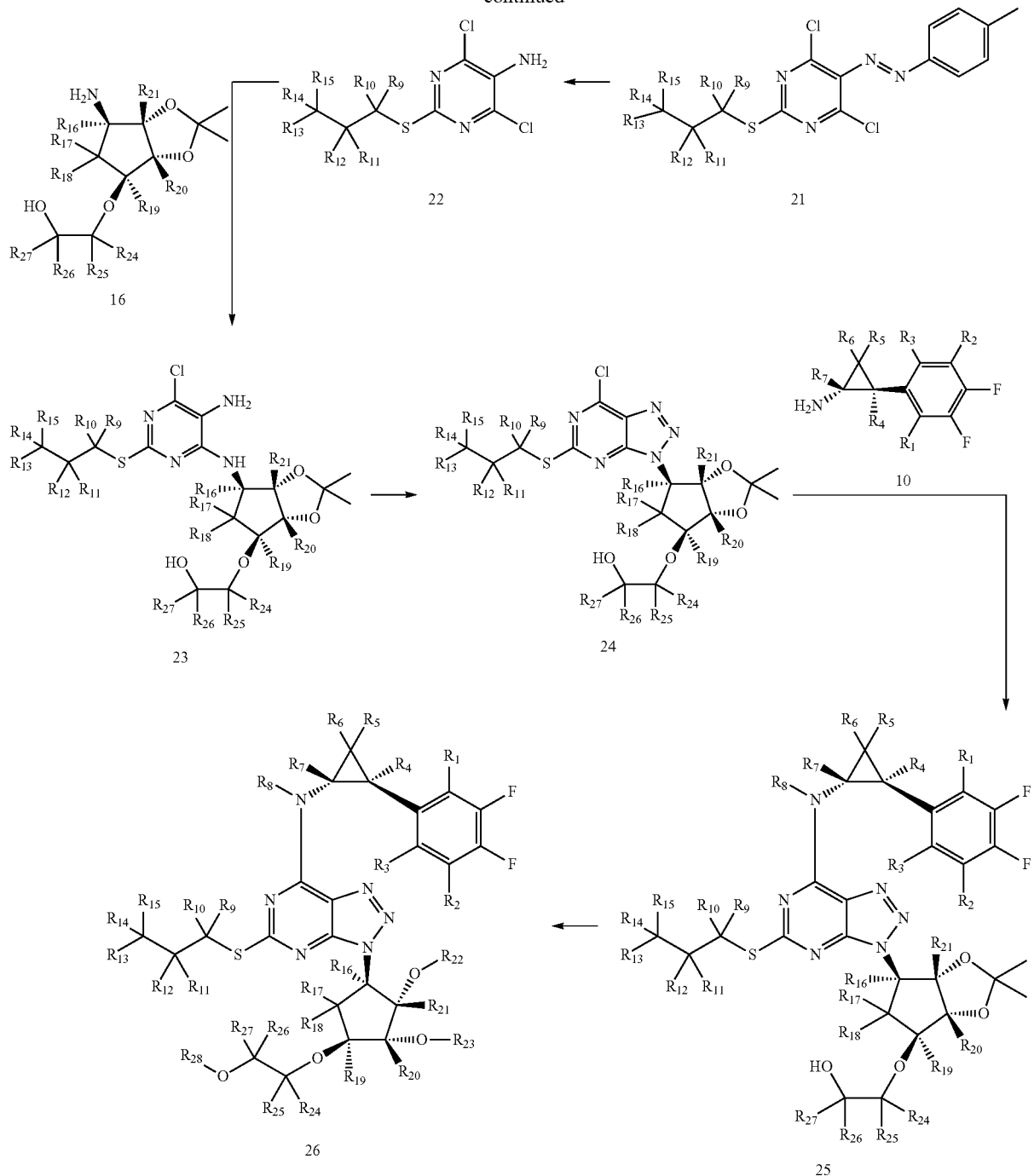

Compound 1 is treated with malonic acid in the presence of an appropriate base, such as piperidine, in an appropriate solvent, such as pyridine, to give compound 2. Compound 2 is reacted with an appropriate chlorinating agent, such as thionyl chloride, in the presence of an appropriate base, such as pyridine, in an appropriate solvent, such as toluene, to give compound 3. Compound 3 is reacted with compound 4 in the presence of an appropriate base, such as pyridine, in an appropriate solvent, such as toluene, to give compound 5. Compound 5 is reacted with compound 6, in the presence of an appropriate base, such as sodium hydroxide, in an appropriate solvent, such as an appropriate mixture of dimethyl sulfoxide and water, to give compound 7. Compound 7 is reacted with an appropriate hydroxide base, such as sodium hydroxide, in an appropriate solvent, such as an appropriate mixture of dimethyl sulfoxide and water, to give compound 8. Compound 8 is reacted with an appropriate chlorinating agent, such as thionyl chloride, in an appropriate solvent, such as toluene, to give an acyl cholide intermediate which is then reacted with an appropriate azide source, such as sodium azide, in the presence of an appropriate base, such as sodium carbonate, in the presence of an appropriate phase-transfer catalyst, such as tetrabutylammonium bromide, to give compound 9. Compound 9 is reacted at an elevated temperature in an appropriate solvent, such as toluene, to give compound 10. Compound 11 is reacted with an appropriate amine protecting reagent, such as benzyl chloroformate, in the presence of an appropriate base, such as potassium carbonate, in an appropriate solvent, such as 4-methyl-2-pentanone, to give compound 12. Compound 12 is reacted with compound 13 in the presence of an appropriate base, such as potassium tert-butoxide, in an appropriate solvent, such as tetrahydrofuran, to give compound 14. Compound 14 is treated with an appropriate reducing reagent, such as lithium borohydride, in an appropriate solvent, such as tetrahydrofuran, to give compound 15. Compound 15 is treated with an appropriate deprotecting reagent, such as a combination of hydrogen gas and palladium on carbon, in an appropriate solvent, such as ethanol, to give compound 16. Compound 17 is reacted with compound 18 in the presence of an appropriate base, such as sodium hydroxide, in an appropriate solvent, such as an appropriate mixture of water and 1-methyl-2-pyrrolidinone, to give compound 19. Compound 19 is reacted with an appropriate base, such as sodium hydroxide, and then reacted with an aromatic amine, such as para-toluidine, in the presence of an appropriate nitrite salt, such as sodium nitrite, in the presence of an appropriate acid, such as hydrochloric acid, in an appropriate solvent, such as water, to give compound 20. Compound 20 is reacted with an appropriate chlorinating agent, such as phosphorous oxychloride, in an appropriate solvent, such as toluene, to give compound 21. Compound 21 is reacted with an appropriate reducing agent, such as a hydrogen gas, in the presence of an appropriate catalyst, such as platinum on carbon, in an appropriate solvent, such as 2-propanol, to give compound 22. Compound 22 is reacted with compound 16, in the presence of an appropriate base, such as triethylamine, in an appropriate solvent, such as ethanol, to give compound 23. Compound 23 is reacted with an appropriate nitrite salt, such as sodium nitrite, in the presence of an appropriate acid, such as acetic acid, in an appropriate solvent, such as water, to give compound 24. Compound 24 is reacted with compound 10 in the presence of an appropriate base, such as triethylamine, in an appropriate solvent, such as acetonitrile, to give compound 25. Compound 25 is treated with an appropriate ketal deprotecting reagent, such as hydrochloric acid, in an appropriate solvent, such as a combination of water and methanol, to give a compound 26 of Formula I.

Deuterium can be incorporated to different positions synthetically, according to the synthetic procedures as shown in Scheme I, by using appropriate deuterated intermediates. For example, to introduce deuterium at one or more positions of $R_1$-$R_4$, compound 1 with the corresponding deuterium substitutions can be used. To introduce deuterium at $R_7$, malonic acid with the corresponding deuterium substitutions can be used. To introduce deuterium at one or more positions of $R_5$-$R_6$, compound 6 with the corresponding deuterium substitutions can be used. To introduce deuterium at one or more positions of $R_{16}$-$R_{21}$, compound 11 with the corresponding deuterium substitutions can be used. To introduce deuterium at one or more positions of $R_{24}$-$R_{25}$, compound 13 with the corresponding deuterium substitutions can be used. To introduce deuterium at one or more positions of $R_{26}$-$R_{27}$, lithium borodeuteride can be used. To introduce deuterium at one or more positions of $R_9$-$R_{15}$, compound 18 with the corresponding deuterium substitutions can be used.

Deuterium can be incorporated to various positions having an exchangeable proton, such as the amine N—H and hydroxyl O—Hs, via proton-deuterium equilibrium exchange. For example, to introduce deuterium at $R_8$, $R_{22}$-$R_{23}$, and $R_{28}$, this proton may be replaced with deuterium selectively or non-selectively through a proton-deuterium exchange method known in the art.

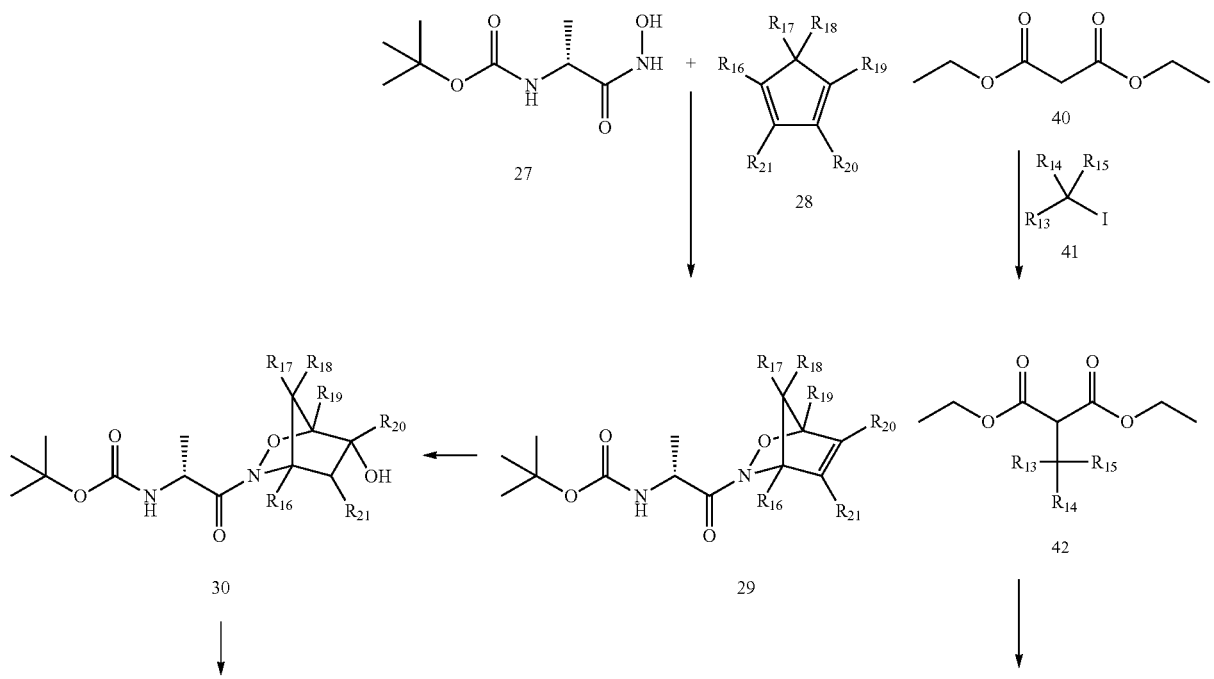

25
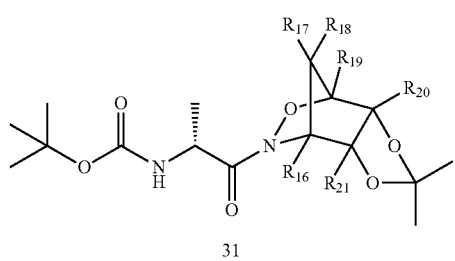
31
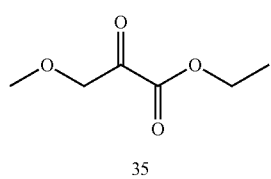
35
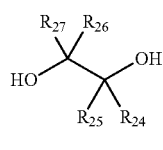
36
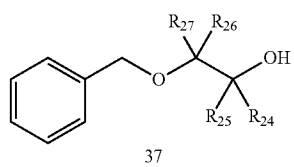
37 → 38
-continued
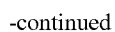
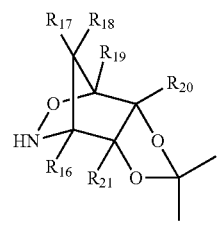
32
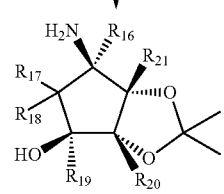
33
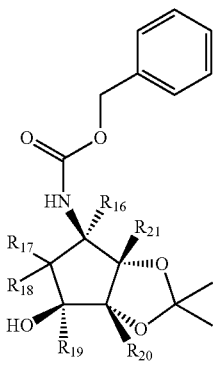
34
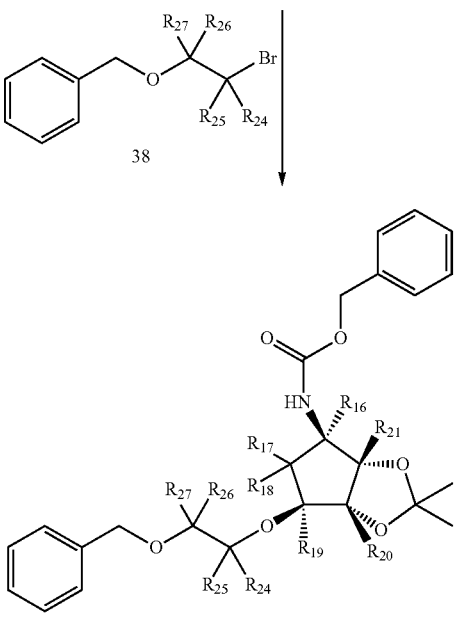
39
26
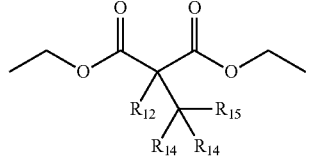
43
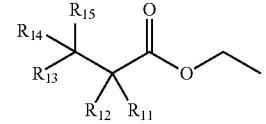
44
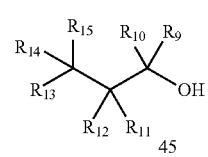
45
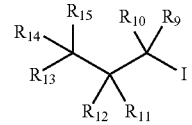
18
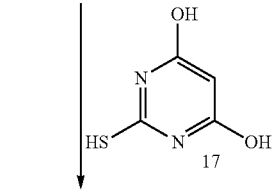
17
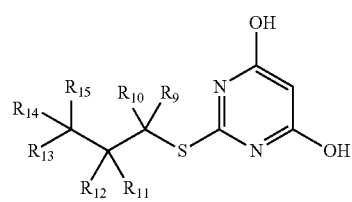
19

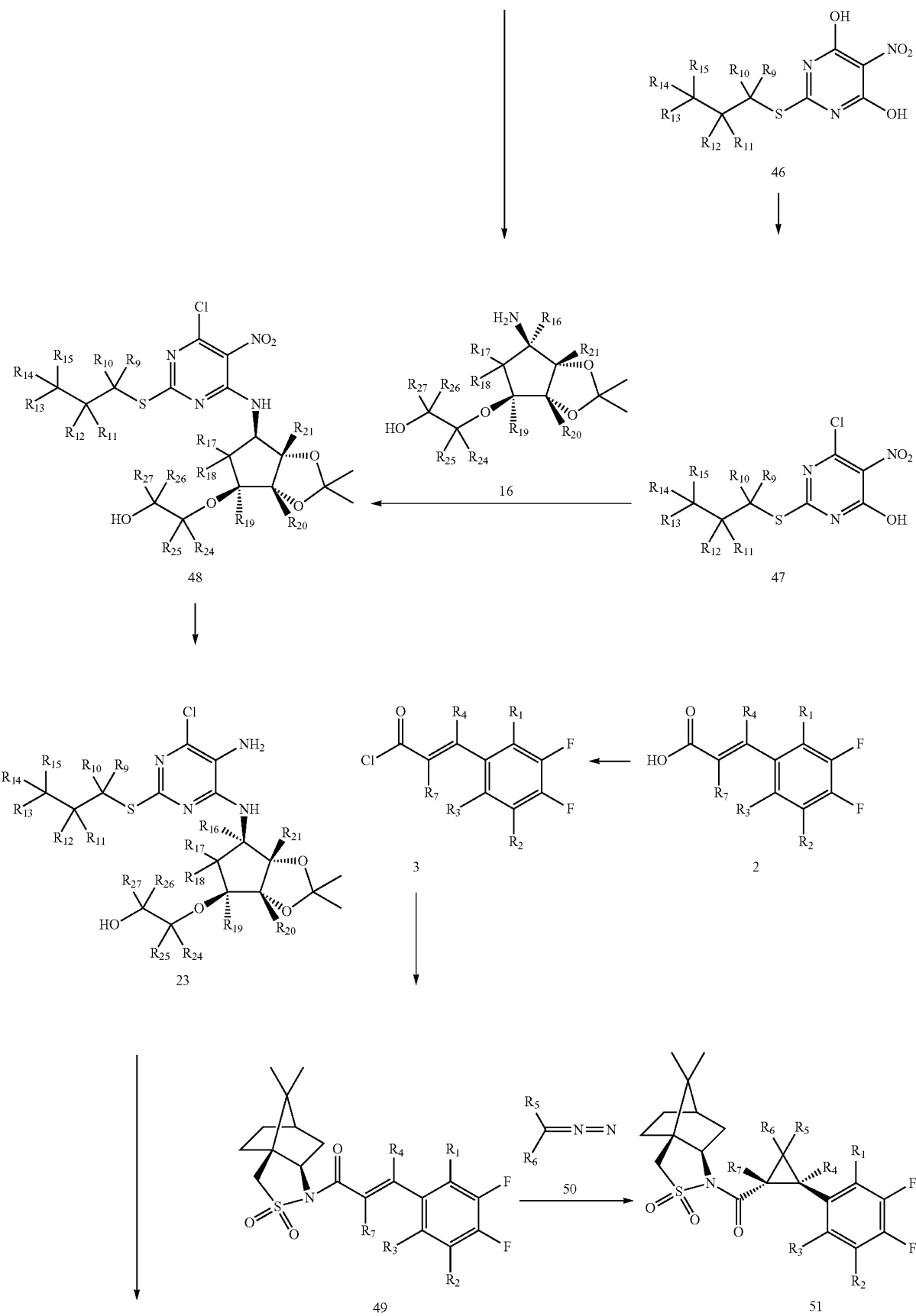

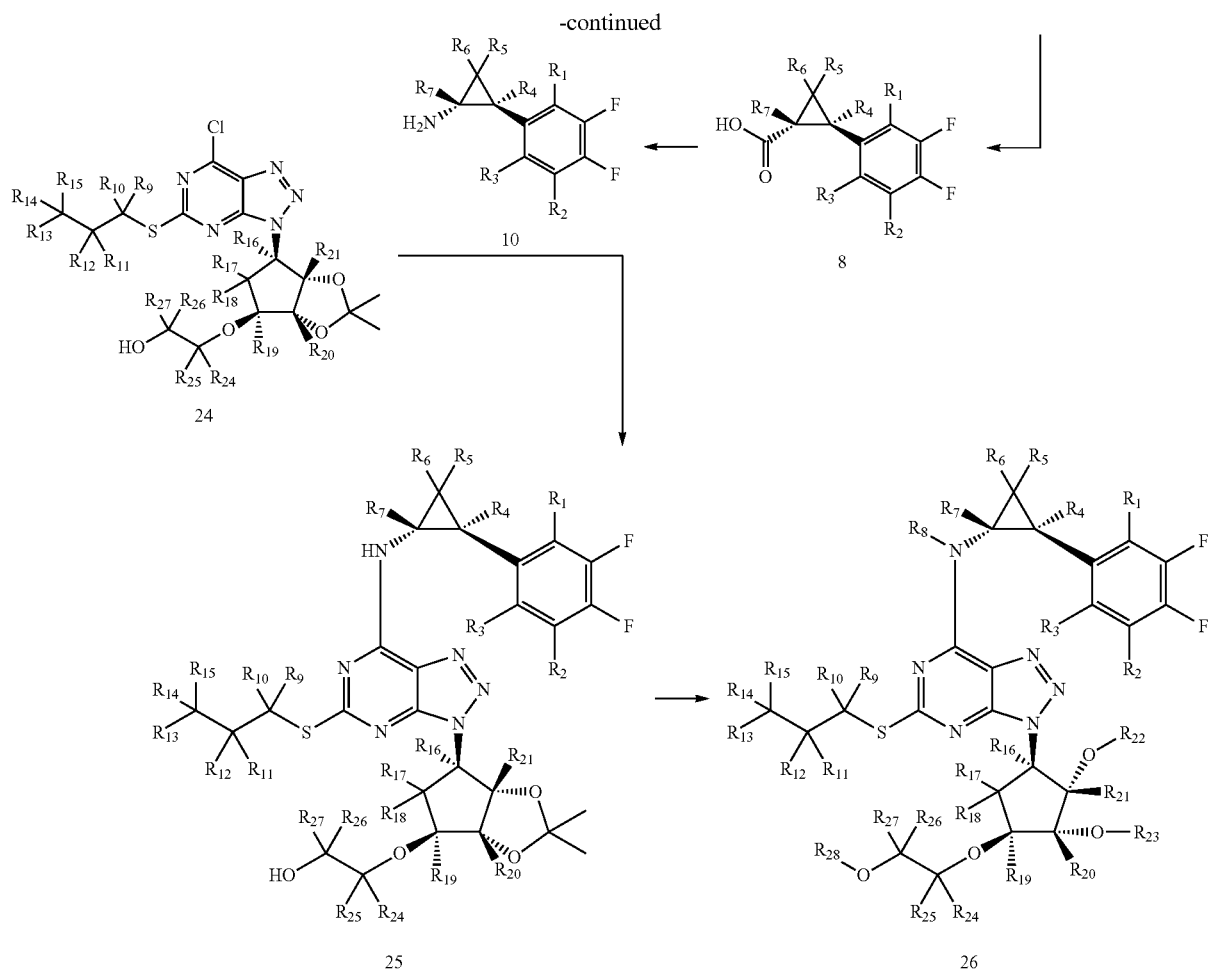

Compound 27 is reacted with compound 28 in the presence of an appropriate oxidant, such as a combination of oxalyl chloride, dimethyl sulfoxide, and triethylamine, in an appropriate solvent, such as a combination of dichloromethane and dimethyl sulfoxide, to give compound 29. Compound 29 is reacted with an appropriate oxidizing agent, such as a combination of osmium tetroxide and N-methylmorpholine N-oxide, in an appropriate solvent, such as a combination of water and tetrahydrofuran, to give compound 30. Compound 30 is reacted with an appropriate 1,2-dihydroxy protecting group, such as 2,2-dimethoxypropane, in the presence of an appropriate acid, such as p-toluenesulfonic acid, to give compound 31. Compound 31 is reacted with an appropriate reducing agent, such as sodium borohydride, in an appropriate solvent, such as methanol, to give compound 32. Compound 32 is treated with an appropriate reducing agent, such as a combination of hydrogen gas and palladium on carbon, in an appropriate solvent, such as methanol, to give compound 33. Compound 33 is reacted with an appropriate amine protecting reagent, such as benzyl chloroformate, in the presence of an appropriate base, such as potassium carbonate, in an appropriate solvent, such as a combination of water and tetrahydrofuran, to give compound 34. Compound 35 is treated with an appropriate reducing reagent, such as lithium aluminum hydride, in an appropriate solvent, such as tetrahydrofuran, to give compound 36. Compound 36 is reacted with an appropriate alcohol protecting reagent, such as benzyl bromide, in the presence of an appropriate base, such as silver oxide, in an appropriate solvent, such as dichloromethane, to give compound 37. Compound 37 is reacted with an appropriate brominating agent, such as a combination of N-bromosuccinimide and triphenylphosphine, in an appropriate solvent, such as tetrahydrofuran, to give compound 38. Compound 34 is reacted with compound 38 in the presence of an appropriate base, such as sodium hydride, in an appropriate solvent, such as dimethylformamide, to give compound 39. Compound 39 is treated with an appropriate deprotecting reagent, such as a combination of hydrogen gas and palladium on carbon, in an appropriate solvent, such as methanol, to give compound 16. Compound 40 is reacted with compound 41 in the presence of an appropriate base, such as sodium ethoxide, in an appropriate solvent, such as ethanol, to give compound 42. Compound 42 is reacted with an appropriate base, such as triethylamine, at an elevated temperature, in an appropriate solvent, such as methanol or d$_4$-methanol, to give compound 43. Compound 43 is reacted with an appropriate decarboxylating catalyst, such as sodium chloride, in an appropriate solvent, such as a combination of water and dimethylsulfoxide, to give compound 44. Compound 44 is treated with an appropriate reducing reagent, such as lithium aluminum hydride, in an appropriate solvent, such as diethyl ether, to give compound 45. Compound 45 is treated with an appropriate iodinating reagent, such as hydroiodic acid, to give compound 18. Compound 18 is reacted with compound 17 in the presence of an appropriate base, such as sodium hydroxide, in an appropriate solvent, such as an appropriate mixture of water and 1-methyl-2-pyrrolidinone, to give compound 19. Compound 19 is reacted with an appropriate nitrating agent, such as nitric acid, to give compound 46. Compound 46 is reacted with an appropriate chlorinating agent, such as phosphorous oxychloride, in the presence of an appropriate base, such as N,N-diethylbenzenamine, to give compound 47. Compound 47 is reacted with compound 16 in an appropriate solvent, such as tetrahydrofuran, to give compound 48. Compound 48 is treated with an appropriate reducing reagent, such as a combination of iron and acetic acid, in an appropriate solvent, such as a mixture of ethanol and water, to give compound 23. Compound 23 is reacted with an appropriate nitrite salt, such as sodium nitrite, in the presence of an appropriate acid, such as acetic acid, in an appropriate solvent, such as a combination of toluene and water, to give compound 24. Compound 2 is reacted with an appropriate chlorinating agent, such as oxalyl chloride, in the presence of an appropriate catalyst, such as dimethylformamide, in an appropriate solvent, such as dichloromethane, to give compound 3. Compound 3 is reacted with an appropriate chiral auxiliary, such as (2R)-bornane-10,2-sultam, in the presence of an appropriate base, such as triethylamine, in an appropriate solvent, such as dichloromethane, to give compound 49. Compound 49 is reacted with compound 50, in the presence of an appropriate catalyst, such as palladium (II) acetate, in an appropriate solvent, such as an appropriate mixture of diethyl ether and dichloromethane, to give compound 51. Compound 51 is reacted with an appropriate base, such as lithium hydroxide, in an appropriate solvent, such as an appropriate mixture of tetrahydrofuran and water, to give compound 8. Compound 8 is reacted with an appropriate acyl azide-forming reagent, such as diphenylphosphoryl azide, in the presence of an appropriate base, such as triethylamine, at elevated temperature, in an appropriate solvent, such as toluene, to give compound 10. Compound 24 is reacted with compound 10 in the presence of an appropriate base, such as diisopropylethylamine, in an appropriate solvent, such as dichloromethane, to give compound 25. Compound 25 is treated with an appropriate ketal deprotecting reagent, such as hydrochloric acid, in an appropriate solvent, such as a combination of water and methanol, to give a compound 26 of Formula I.

Deuterium can be incorporated to different positions synthetically, according to the synthetic procedures as shown in Scheme I, by using appropriate deuterated intermediates. For example, to introduce deuterium at one or more positions of $R_{16}$-$R_{21}$, compound 28 with the corresponding deuterium substitutions can be used. To introduce deuterium at $R_{13}$-$R_{15}$, compound 41 with the corresponding deuterium substitutions can be used. To introduce deuterium at $R_{11}$, deuterium oxide and/or $d_6$-deuterium oxide can be used. To introduce deuterium at $R_{12}$, $d_4$-methanol can be used. To introduce deuterium at one or more positions of $R_9$-$R_{10}$ or $R_{24}$-$R_{27}$, lithium aluminum deuteride can be used. To introduce deuterium at one or more positions of $R_1$-$R_4$ and $R_7$, compound 2 with the corresponding deuterium substitutions can be used. To introduce deuterium at one or more positions of $R_5$-$R_6$, compound 50 with the corresponding deuterium substitutions can be used.

Deuterium can be incorporated to various positions having an exchangeable proton, such as the amine N—H and hydroxyl O—Hs, via proton-deuterium equilibrium exchange. For example, to introduce deuterium at $R_8$, $R_{22}$-$R_{23}$, and $R_{28}$, this proton may be replaced with deuterium selectively or non-selectively through a proton-deuterium exchange method known in the art.

The invention is further illustrated by the following examples. All IUPAC names were generated using CambridgeSoft's ChemDraw 10.0.

EXAMPLE 1

(1S,2S,3R,5S)-3-(7-((1R,2S)-2-(3,4-difluorophenyl)cyclopropylamino)-5-(propylthio)-3H-[1,2,3]-triazolo[4,5-d]pyrimidin-3-yl)-5-(2-hydroxyethoxy)cyclopentane-1,2-diol (ticagrelor)

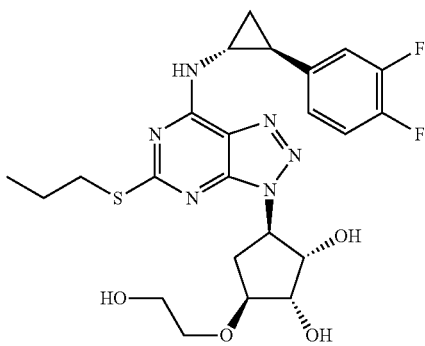 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

Step 1

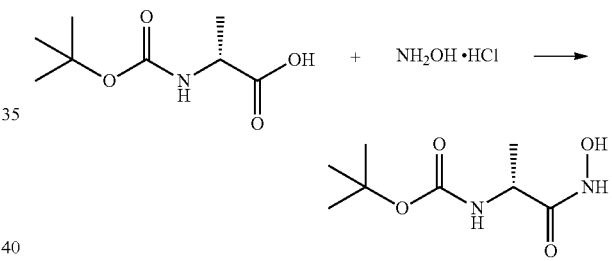

(R)-tert-Butyl 1-(hydroxyamino)-1-oxopropan-2-ylcarbamate

At about 0° C., isopropyl chloroformate (86.05 g, 702.16 mmol, 1.00 equiv.) was added dropwise, over a period of 60 minutes, to a stirred mixture of (S)-2-(tert-butoxycarbonylamino)propanoic acid (118 g, 623.65 mmol, 1.00 equiv.), tetrahydrofuran (500 mL), and triethylamine (63.63 g, 628.82 mmol, 1.00 equiv.). The resulting mixture was then stirred at about 0° C. for about 2 hours, and then the solids were removed by filtration. The resulting filtrate was then added to a hydroxylamine solution (formed by first stirring a mixture of sodium hydroxide (37.6 g, 940.00 mmol, 1.50 equiv.), methanol (500 mL), and hydroxylamine hydrochloride (65 g, 935.39 mmol, 1.50 equiv) at about 0° C. for about 2 hours, and then removing the resulting solids by filtration). The resulting mixture was stirred at about 0° C. for about 2 hours, the solids were removed by filtration, and the resulting filtrate was concentrated in vacuo. The resulting residue was purified by silica gel column chromatography (ethyl acetate/petroleum ether (1:1)) to give the title product as a white solid (70 g; yield=55%). $^1$H NMR (300 MHz, CDCl$_3$) δ: 5.18 (b, 1H), 4.21 (m, 1H), 2.06 (s, 1H), 1.46 (s, 9H), 1.40 (d, J=7.2 Hz, 3H).

Step 2

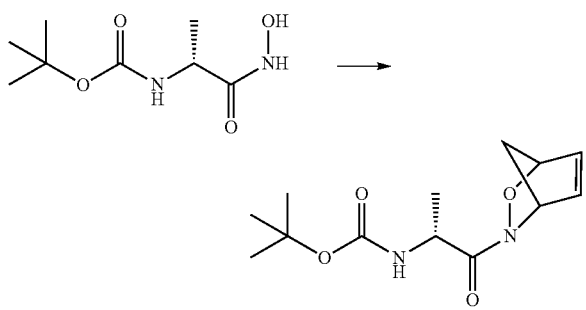

tert-Butyl-(R)-1-(3-oxa-2-aza-bicyclo[2.2.1]hept-5-en-2-yl)-1-oxopropan-2-ylcarbamate At about −78° C. and under an atmosphere of nitrogen, oxalyl dichloride (30.43 g, 239.74 mmol, 4.00 equiv.) was added dropwise, over a period of 20 minutes, to stirred solution of dimethylsulfoxide (28.1 g, 359.66 mmol, 6.00 equiv.) in dichloromethane (200 mL). To this mixture was added dropwise, over a period of about 10 minutes, a solution of (R)-tert-butyl 1-(hydroxyamino)-1-oxopropan-2-ylcarbamate (12.24 g, 59.94 mmol, 1.00 equiv.) and cyclopenta-1,3-diene (4.15 g, 62.78 mmol, 1.05 equiv.) in a mixture of dichloromethane/dimethylsulfoxide (5:1) (60 mL). The resulting mixture was stirred for at about −78° C. for about 30 minutes, and then triethylamine (66.8 mL) was added. The resulting mixture was washed with 1M hydrochloric acid (2×200 mL), and extracted with dichloromethane (3×100 mL). After the organic layers were combined, the organic phase was washed with 10% sodium bicarbonate (2×200 mL), dried over anhydrous sodium sulfate, and concentrated in vacuo. The resulting residue was purified by silica gel column chromatography (ethyl acetate/petroleum ether (1:10)) to give the desired product as a white solid (8.6 g; yield=53%). $^1$H NMR (300 MHz, CDCl$_3$) δ: 6.54 (s, 1H), 6.39 (m, 1H), 5.22-5.34 (m, 3H), 4.51 (m, 1H), 2.02 (d, J=8.4 Hz, 1H), 1.86 (d, J=8.7 Hz, 1H), 1.43 (s, 9H), 1.09 (m, 3H).

Step 3

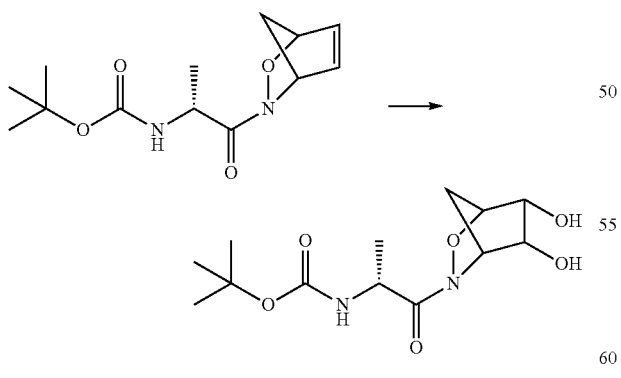

tert-Butyl(R)-1-(5,6-dihydroxy-3-oxa-2-aza-bicyclo[2.2.1]heptan-2-yl)-1-oxopropan-2-ylcarbamate A solution of tert-butyl-(R)-1-(3-oxa-2-aza-bicyclo[2.2.1]hept-5-en-2-yl)-1-oxopropan-2-ylcarbamate (27.3 g, 101.75 mmol, 1.00 equiv.) in teterahydrofuran:water (5:1) (600 mL), osmium tetroxide (230 mg, 0.90 mmol, 0.01 equiv.), and N-methylmorpholine-N-oxide (25.26 g, 215.62 mmol, 2.10 equiv.) was stirred at about 20° C. for about 50 minutes. After adding sodium thiolsulfate (22 g), the resulting solution was extracted with ethyl acetate (3×200 mL) and the organic layers combined. The organic phase was washed with a saturated sodium bicarbonate solution (1×250 mL) and then concentrated in vacuo to give the desired product as a yellow liquid (30.1 g; yield=98%). $^1$H NMR (300 MHz, CDCl$_3$) δ: 5.29 (b, 1H), 4.36-4.74 (m, 3H), 3.76-4.09 (m, 4H), 2.67 (m, 1H), 1.90 (m, 1H), 1.43 (s, 9H), 1.30 (d, J=6.9 Hz, 3H).

Step 4

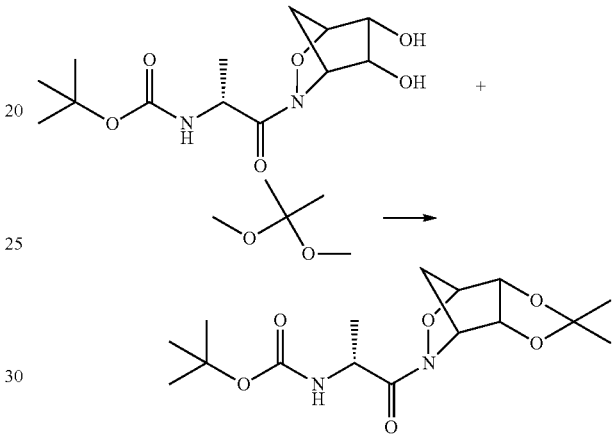

(2-(4,4-Dimethyl-3,5,8-trioxa-9-aza-tricyclo[5.2.1.0$^{2,b}$]dec-9-yl)-1-methyl-2-oxo-ethyl]-carbamic acid tert-butyl ester A solution of tert-butyl(R)-1-(5,6-dihydroxy-3-oxa-2-aza-bicyclo[2.2.1]heptan-2-yl)-1-oxopropan-2-ylcarbamate (30.1 g, 99.56 mmol, 1.00 equiv.) in 2,2-dimethoxypropane (600 mL) and p-toluenesulfonic acid (1.1 g, 6.39 mmol, 0.06 equiv.) was stirred at about 22° C. for about 50 minutes. After adding a saturated solution of sodium bicarbonate (450 mL), the mixture was extracted with ethyl acetate (3×300 mL). The organic layers were combined and concentrated in vacuo to give the title product as a white solid (33.5 g; yield=98%). $^1$H NMR (300 MHz, CDCl$_3$) δ: 5.22 (b, 1H), 4.89 (s, 1H), 4.70 (s, 1H), 4.61 (b, 1H), 4.33 (s, 2H), 2.24 (d, J=11.4 Hz, 1H), 1.82 (m, 1H), 1.52 (s, 3H), 1.46 (s, 9H), 1.32 (d, J=6.9 Hz, 3H), 1.27 (s, 3H).

Step 5

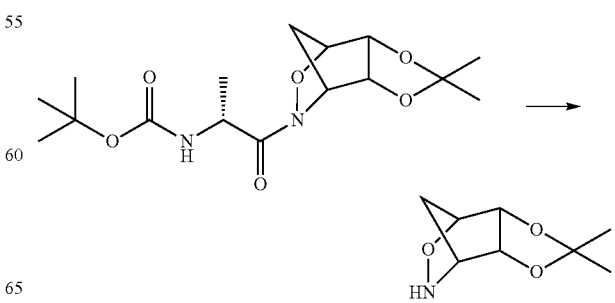

4,4-Dimethyl-3,5,8-trioxa-9-aza-tricyclo[5.2.1.0$^{2,6}$]decane

A mixture of [2-(4,4-dimethyl-3,5,8-trioxa-9-aza-tricyclo [5.2.1.0$^{2,6}$]dec-9-yl)-1-methyl-2-oxo-ethyl]-carbamic acid tert-butyl ester (33.5 g, 97.84 mmol, 1.00 equiv.), methanol (500 mL), and sodium borohydride (14.67 g, 388.10 mmol, 4.00 equiv) was stirred at about 20° C. for about 50 minutes. The pH value of the mixture was then adjusted to 3 by adding 1M hydrochloric acid. After extracting the mixture with ethyl acetate (200 mL), the aqueous layers were combined and the pH was adjusted to 10 by adding a 10% sodium bicarbonate solution. Standard extractive workup with ethyl acetate (3×300 mL) gave the title product as a white solid (16.7 g; yield=99.8%). $^1$H NMR (300 MHz, CDCl$_3$) δ: 4.80 (b, 1H), 4.69 (s, 1H), 4.29 (d, J=5.4 Hz, 1H), 4.22 (d, J=5.4 Hz, 1H), 3.77 (s, 1H), 2.28 (d, J=11.1 Hz, 1H), 1.65 (d, J=11.4 Hz, 1H), 1.50 (s, 3H), 1.27 (s, 3H).
Step 6

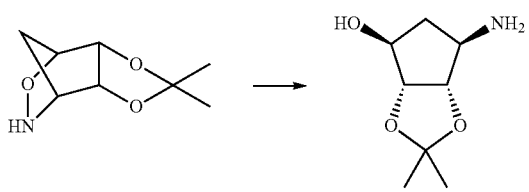

(3aR,4S,6R,6aS)-6-amino-2,2-dimethyl-tetrahydro-3aH-cyclopenta[d][1,3]dioxol-4-ol Under a pressurized hydrogen atmosphere (3 atm), a suspension of 4,4-dimethyl-3,5,8-trioxa-9-aza-tricyclo[5.2.1.0$^{2,6}$]decane (16.7 g, 97.55 mmol, 1.00 equiv.), 10% palladium on carbon (1.67 g), and methanol (250 mL) was stirred at about 20° C. for about 60 minutes. After filtering the solution, the resulting filtrate was concentrated in vacuo to give the title product as a white solid (16.8 g; yield=99%). MS: m/z=174 (MH)$^+$.
Step 7

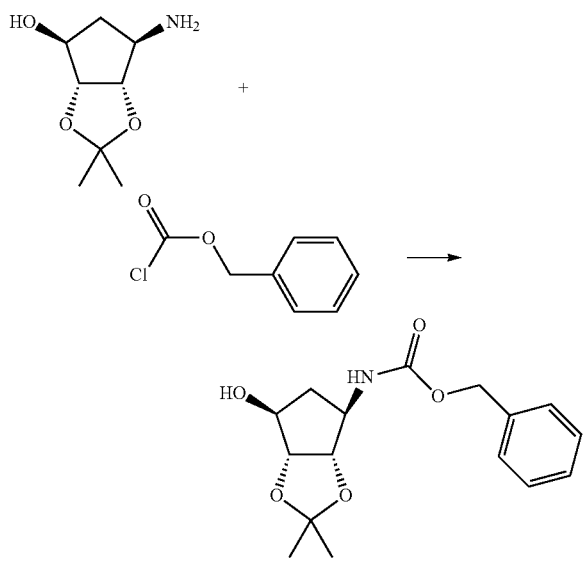

Benzyl 3aS,4R,6S,6aR)-6-hydroxy-2,2-dimethyl-tetrahydro-3aH-cyclopenta[d][1,3]dioxol-4-ylcarbamate At about 0° C., benzyl carbonochloridate (18.4 g, 107.86 mmol, 1.05 equiv.) was added to the solution of (3aR,4S,6R,6aS)-6-amino-2,2-dimethyl-tetrahydro-3aH-cyclopenta[d][1,3]dioxol-4-ol (17.0 g, 98.15 mmol, 1.00 equiv.) and sodium carbonate (20.8 g, 196.24 mmol, 2.00 equiv) in tetrahydrofuran:water (5:1) (600 mL). Standard extractive workup with ethyl acetate (3×200 mL) gave the title product as a white solid (20.5 g; yield=68%). $^1$H NMR (300 MHz, CDCl$_3$) δ: 7.30-7.39 (m, 5H), 5.20 (s, 2H), 4.60 (d, J=5.4 Hz, 1H), 4.50 (d, J=5.4 Hz, 1H), 4.27 (s, 1H), 4.19 (d, J=5.7 Hz 1H), 2.26 (m, 1H), 1.71 (d, J=14.4 Hz, 1H), 1.47 (s, 3H), 1.28 (s, 3H).
Step 8

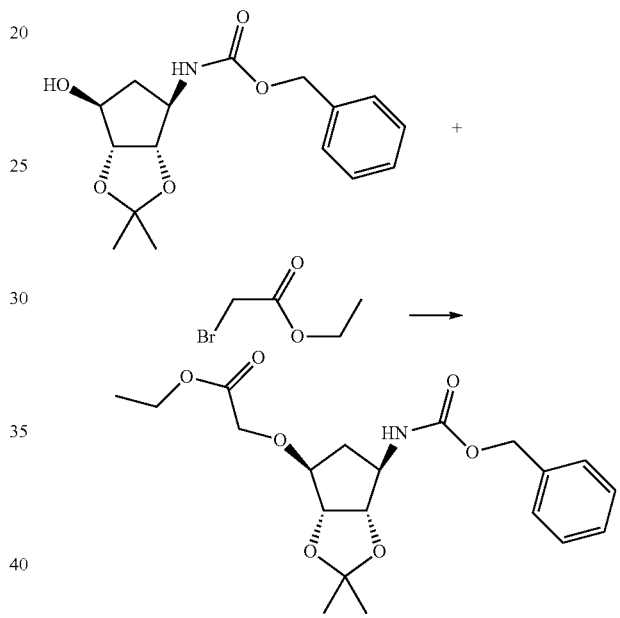

Ethyl 2-3aR,4S,6R,6aS)-6-(benzylcarbonyl)-2,2-dimethyl-tetrahydro-3aH-cyclopenta[d][1,3]dioxol-4-yloxy)acetate Benzyl (3aS,4R,6S,6aR)-6-hydroxy-2,2-dimethyl-tetrahydro-3aH-cyclopenta[d][1,3]dioxol-4-ylcarbamate (12.29 g, 39.99 mmol, 1.00 equiv.) was added to a solution of sodium hydride (70%) (1.44 g, 60.00 mmol, 1.05 equiv.) in dimethylformamide (200 mL). The solution was stirred at about −30° C. for about 30 minutes, and then ethyl 2-bromoacetate (7.68 g, 45.99 mmol, 1.20 equiv) was added. The resulting solution was stirred at ambient temperature for about 5.5 hours, and then water was added (500 mL). Following standard extractive workup with ethyl acetate (3×200 mL), the resulting residue was purified by silica gel column chromatography (ethyl acetate: petroleum ether (1:10)) to afford the title product as a colorless solid (0.9 g; yield=69%). $^1$H NMR (300 MHz, CD$_3$OD) δ: 7.30-7.35 (m, 5H), 5.07 (s, 2H), 4.60 (d, J=5.7 Hz, 1H), 4.51 (d, J=5.7 Hz, 1H), 4.12-4.29 (q, J=16.5 Hz, 2H), 4.10-4.22 (q, J=7.2 Hz, 2H), 4.00 (d, J=5.7 Hz, 1H), 3.92 (J=4.3 Hz, 1H), 2.17-2.19 (m, 1H), 1.84 (d, J=14.7 Hz, 1H), 1.38 (s, 3H), 1.26 (s, 3H), 1.11-1.22 (t, J=7.2 Hz, 3H).

Step 9

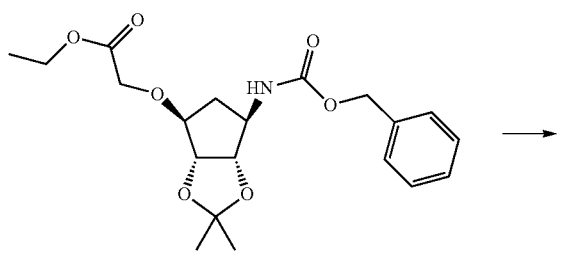

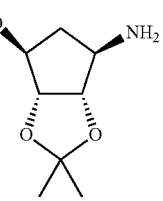

Ethyl 2-3aR,4S,6R,6aS)-6-amino-2,2-dimethyl-tetrahydro-3aH-cyclopenta[d][1,3]dioxol-4-yloxy)acetate Under an atmosphere of hydrogen, a suspension of ethyl 2-((3 aR,4S,6R,6aS)-6-(benzyloxycarbonyl)-2,2-dimethyl-tetrahydro-3 aH-cyclopenta[d][1,3]dioxol-4-yloxy)acetate (150 mg, 0.38 mmol, 30.00 equiv.) and 10% palladium on carbon (16 mg, 0.15 mmol, 1.00 equiv) in methanol (10 mL) was stirred at ambient temperature for about 80 minutes. After filtering, the resulting filtrate was concentrated in vacuo to give the title product as a yellow solid (80 mg; yield=82%). $^1$H NMR (300 MHz, CDCl$_3$) 4.64 (s, 1H), 4.42 (s, 1H), 4.08-4.20 (m, 4H), 3.87 (s, 1H), 3.31 (s, 1H), 2.17 (m, 1H), 1.76 (m, 1H), 1.36 (s, 3H), 1.21-1.29 (m, 6H).

Step 10

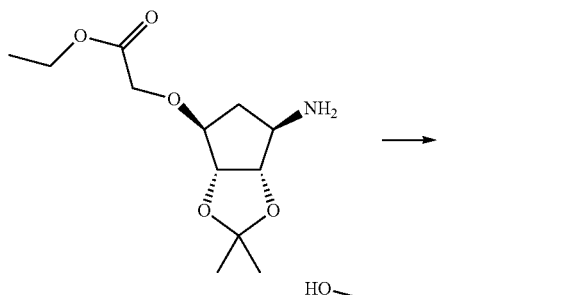

2-((3aR,4S,6R,6aS)-6-amino-2,2-dimethyl-tetrahydro-3aH-cyclopenta[d][1,3]dioxol-4-yloxy)ethanol A solution of ethyl 2-((3aR,4S,6R,6aS)-6-amino-2,2-dimethyl-tetrahydro-3aH-cyclopenta[d][1,3]dioxol-4-yloxy)acetate (4.2 g, 16.2 mmol, 1.00 equiv.) in dry tetrahydrofuran (50 mL) was slowly added to a suspension of lithium aluminum hydride (1.23 g, 32.4 mmol, 2.00 equiv.) in tetrahydrofuran (50 mL). The mixture was heated at reflux for about 1 hour, and then water was added (2 mL). After the solids were collected by filtration, the solids were washed with tetrahydrofuran (50 mL) and then dried in vacuo to give the title product as a yellow oil (2.3 g, 65%). MS: m/z=218 (MH)$^+$.

Step 11

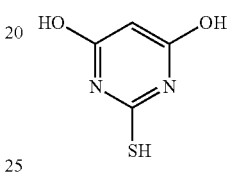

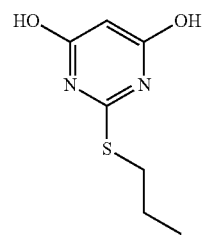

2-(Propylthio)pyrimidine-4,6-diol

A solution of 2-mercaptopyrimidine-4,6-diol (25 g, 173.61 mmol, 1.00 equiv.), sodium hydroxide (15.8 g, 395.00 mmol, 2.27 equiv.), 1-methylpyrrolidin-3-one (50 mL), and 1-iodopropane (30.6 g, 180.00 mmol, 1.05 equiv.) dissolved in water (60 mL) was stirred at ambient temperature for about 48 hours. The pH value of the solution was adjusted to 2-3 by adding hydrochloric acid. The solids were then collected by filtration to give the product as an off-white solid (35 g; (crude)). $^1$H NMR (300 MHz, DMSO-d$_6$) δ: 11.78 (b, 1H), 10.30 (b, 1H), 5.13 (s, 1H), 3.07 (t, J=7.2 Hz, 2H), 1.58-1.70 (m, 2H), 0.96 (t, J=7.2 Hz, 2H).

Step 12

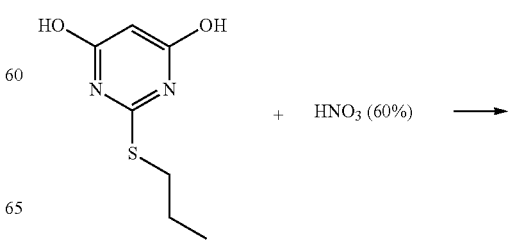

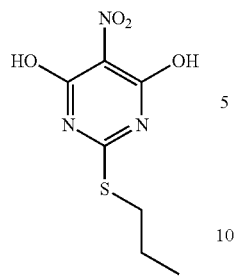

5-Nitro-2-(propylthio)pyrimidine-4,6-diol

A solution of 2-(propylthio)pyrimidine-4,6-diol (3 g, 16.11 mmol, 1.00 equiv.) in nitric acid (65%) (10 mL) was stirred at ambient temperature for about 2 hours. After adding water (10 mL), the mixture was stirred at about 0° C. for about 30 minutes. The resulting solids were collected by filtration to afford the title product as a yellow solid (1.8 g; yield=48%). $^1$H NMR (300 MHz, DMSO-d$_6$) δ: 3.17 (t, J=7.2 Hz, 2H), 1.62-1.75 (m, 2H), 0.95-1.02, (t, J=7.2 Hz, 3H).

Step 13

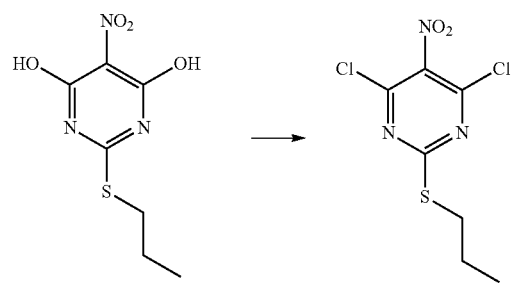

4,6-Dichloro-5-nitro-2-(propylthio)pyrimidine

A solution of 5-nitro-2-(propylthio)pyrimidine-4,6-diol (1.8 g, 6.71 mmol, 1.00 equiv.), phosphoryl chloride (15 mL) and N,N-diethylbenzenamine (2 mL) was stirred at reflux for about 3 hours in an oil bath. After cooling the mixture to about 20° C. with a water/ice bath, the mixture was concentrated in vacuo. The resulting residue was purified by silica gel column chromatography (ethyl acetate/petroleum ether (1:100)) to give the title product as a yellow oil (1.1 g; yield=61%). $^1$H NMR (300 MHz, CDCl$_3$) δ: 3.15 (t, J=7.2 Hz, 2H), 1.73-1.87 (m, 2H), 1.07-1.13 (J=7.2 Hz, 3H).

Step 14

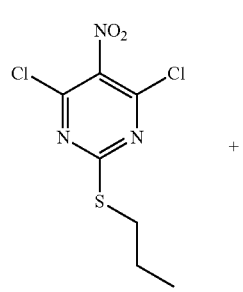 +

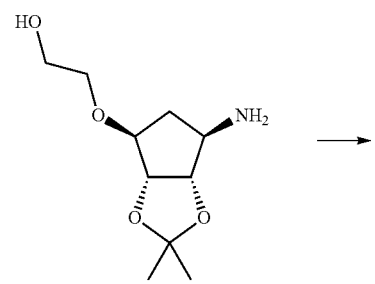

2-((3aR,4S,6R,6aS)-6-(6-Chloro-5-nitro-2-(propylthio)pyrimidin-4-ylamino)-2,2-dimethyl-tetrahydro-3aH-cyclopenta[d][1,3]dioxol-4-yloxy)ethanol A solution of 4,6-dichloro-5-nitro-2-(propylthio)pyrimidine (1.07 g, 3.99 mmol, 1.00 equiv.), and 2-((3aR,4S,6R,6aS)-6-amino-2,2-dimethyl-tetrahydro-3aH-cyclopenta[d][1,3]dioxol-4-yloxy)ethanol (570 mg, 4.41 mmol, 1.20 equiv.) in tetrahydrofuran (20 mL) was stirred at 0-10° C. for about 2 hours and then water (20 mL) was added. Standard extractive workup with ethyl acetate (3×20 mL) afforded the title product as a yellow oil (800 mg; yield=45%). $^1$H NMR (300 MHz, CDCl$_3$) δ: 8.65 (b, 1H), 4.66-4.76 (m, 2H), 4.56 (m, 1H), 3.99 (d, J=7.5 Hz, 1H), 3.70-3.87 (m, 3H), 3.64-3.67 (m, 1H), 3.07-3.20 (m, 2H), 2.34 (m, 1H), 1.97 (m, 1H), 1.76-1.82 (m, 2H), 1.46 (s, 3H), 1.27 (s, 3H), 1.07 (t, J=7.5 Hz, 3H).

Step 15

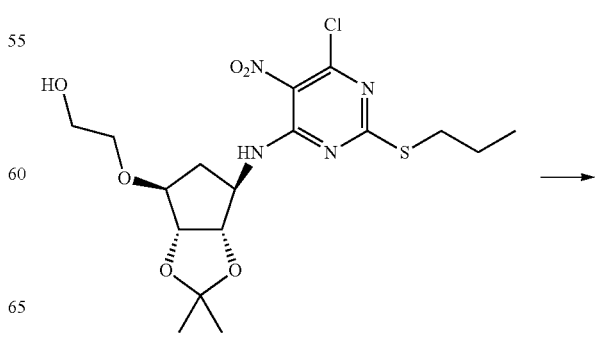

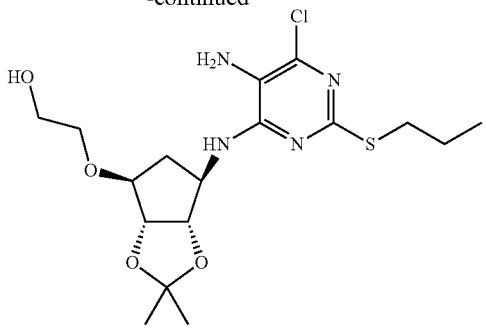

2-((3aR,4S,6R,6aS)-6-(5-Amino-6-chloro-2-(propylthio)pyrimidin-4-ylamino)-2,2-dimethyl-tetrahydro-3aH-cyclopenta[d][1,3]dioxol-4-yloxy)ethanol A suspension of 2-((3aR,4S,6R,6aS)-6-(6-chloro-5-nitro-2-(propylthio)pyrimidin-4-ylamino)-2,2-dimethyl-tetrahydro-3aH-cyclopenta[d][1,3]dioxol-4-yloxy)ethanol (800 mg, 1.78 mmol, 1.00 equiv.), iron powder (800 mg, 14.29 mmol, 8.00 equiv.), acetic acid (860 mg, 14.33 mmol, 8.00 equiv.) and water/ethanol (10 mL) was stirred at about 60° C. for about 20 minutes in an oil bath. After the solids were removed by filtration, the resulting filtrate was extracted with dichloromethane (3×10 mL). The organic layers were combined, dried over anhydrous sodium sulfate, and concentrated in vacuo to give the title product as a yellow oil (780 mg; yield=93%). MS: m/z=419 (MH)$^+$.

Step 16

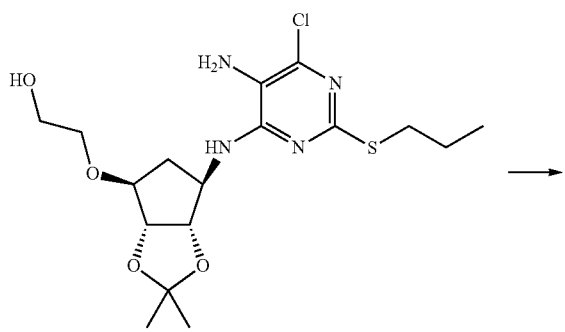

2-((3aR,4S,6R,6aS)-6-(7-Chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol A solution of sodium nitrite (148 mg, 2.14 mmol, 1.12 equiv.) in water (1 mL) was added to a solution of 2-((3aR, 4S,6R,6aS)-6-(5-amino-6-chloro-2-(propylthio)pyrimidin-4-ylamino)-2,2-dimethyl-tetrahydro-3aH-cyclopenta[d][1,3]dioxol-4-yloxy)ethanol (800 mg, 1.91 mmol, 1.00 equiv.) and acetic acid (680 mg, 11.33 mmol, 5.90 equiv.) in toluene (9 mL). The resulting solution was stirred at about 20° C. for about 30 minutes, and then the pH value of the solution was adjusted to 8-9 by adding potassium carbonate. Following standard extractive workup with ethyl acetate (3×10 mL), the resulting residue was purified by silica gel column (ethyl acetate/petroleum ether (1:10)) to give the title product as a yellow oil (370 mg; yield=45%). $^1$H NMR (300 MHz, CDCl$_3$) δ: 5.54-5.56 (q, J$_1$=2.4 Hz, J$_2$=6.3 Hz, 1H), 5.21-5.25 (m, 1H), 4.90 (d, J=6.3 Hz, 1H), 4.05-4.09 (m, 1H), 3.50-3.66 (m, 4H), 3.23 (t, J=7.5 Hz, 2H), 2.68-2.72 (m, 1H), 2.58 (m, 1H), 1.81-1.89 (m, 2H), 1.57 (s, 3H), 1.39 (s, 3H), 1.12, (t, J=7.5 Hz, 3H).

Step 17

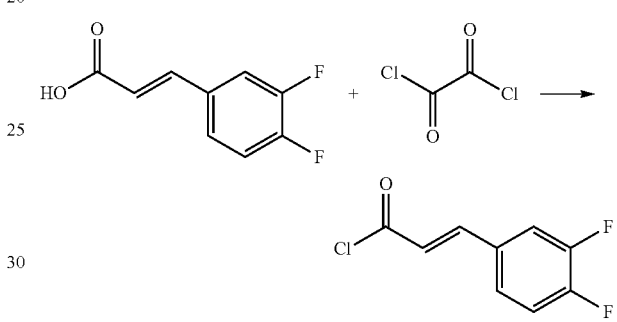

3-(3,4-Difluoro-phenyl)-acryloyl chloride

At 0-5° C., oxalyl dichloride (25.7 g, 202.36 mmol, 3.00 equiv.) was added to a mixture of (E)-3-(3,4-difluorophenyl) acrylic acid (12.4 g, 67.38 mmol, 1.00 equiv.), N,N-dimethylformamide (1 mL), and dichloromethane (150 mL). The solution was stirred at ambient temperature for about 2 hours, and then concentrated in vacuo to give the title product, which was used in the next step without any further purification.

Step 17

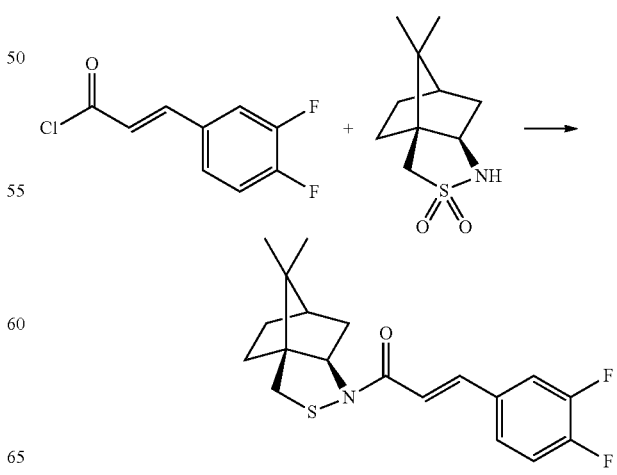

[3aS-[1(E),3a,6,7a]]-1-[3-(3,4-Difluorophenyl)-1-oxo-2-propenyl]-hexahydro-8,8-dimethyl-3H-3a,6-methano-2,1-benzisothiazole-2,2-dioxide At 0-5° C., a solution of 3-(3,4-difluoro-phenyl)-acryloyl chloride in dichloromethane (30 mL) was added to a mixture of (2R)-bornane-10,2-sultam (14.5 g, 67.35 mmol, 1.00 equiv), triethylamine (20.4 g, 201.98 mmol, 3.00 equiv), and dichloromethane (120 mL). The resulting solution was stirred at ambient temperature for about 3 hours and then water (40 mL) was added. Standard extractive workup with dichloromethane (2×40 mL) gave the title product as an off-white solid (18.5 g; yield=72%). $^1$H NMR (300 MHz, CDCl$_3$) δ: 7.68 (d, J=15.6 Hz, 1H), 7.15-7.45 (m, 3H), 7.19 (d, J=15.6 Hz, 1H), 4.00 (m, 1H), 3.55 (q, J$_1$=13.8 Hz, J$_2$=24.0 Hz), 2.18 (m, 2H), 1.93 (m, 2H), 1.37-1.48 (m, 2H), 1.22 (s, 3H), 0.96 (s, 3H).

Step 18

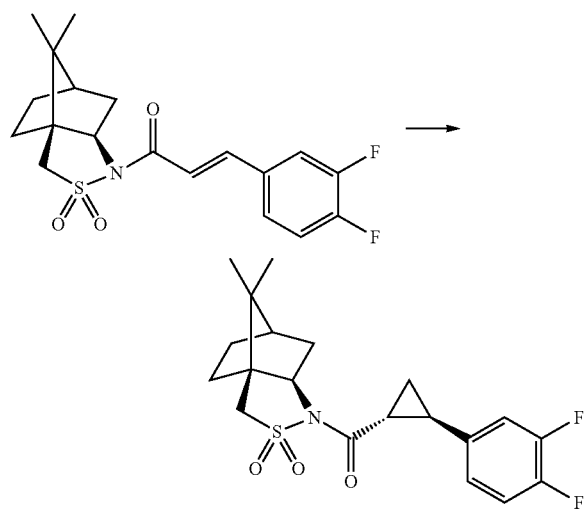

[3aS-[1(1R,2R),3a,6,7a]]-1-[[2-(3,4-Difluorophenyl)cyclopropyl]carbonyl]-hexahydro-8,8-dimethyl-3H-3a,6-methano-2,1-benzisothiazole-2,2-dioxide At 0-5° C., 1-methyl-1-nitrosourea (39.1 g, 379.61 mmol, 2.50 equiv.) was added in portions to a mixture of 50% aqueous sodium hydroxide (150 mL) and ethyl ether (300 mL). After the solid was dissolved, the aqueous phase was removed. At 0-5° C., a solution of [3aS-[1(E),3a,6,7a]]-1-[3-(3,4-difluorophenyl)-1-oxo-2-propenyl]-hexahydro-8,8-dimethyl-3H-3a,6-methano-2,1-benzisothiazole-2,2-dioxide (48.2 g, 126.51 mmol, 1.00 equiv.), palladium(II) acetate (200 mg, 1.04 mmol) in dichloromethane (300 mL) was then added to the mixture. The mixture was stirred at ambient temperature for about 1 hour, acetic acid (100 mL) was added, and then water (500 mL) was added. Standard extractive workup with dichloromethane (2×100 mL) afforded the title product as a light-yellow oil (48 g; yield=80%). $^1$H NMR (300 MHz, CDCl$_3$) δ: 6.97-7.09 (m, 3H), 3.91-3.95 (m, 1H), 3.44-3.57 (q, J$_1$=13.8 Hz, J$_2$=24.9 Hz), 2.56 (m, 2H), 2.15 (m, 2H), 1.90-1.95 (m, 3H), 1.76-1.82 (m, 1H), 1.22-1.47 (m, 2H), 1.20 (s, 3H), 1.00 (s, 3H).

Step 19

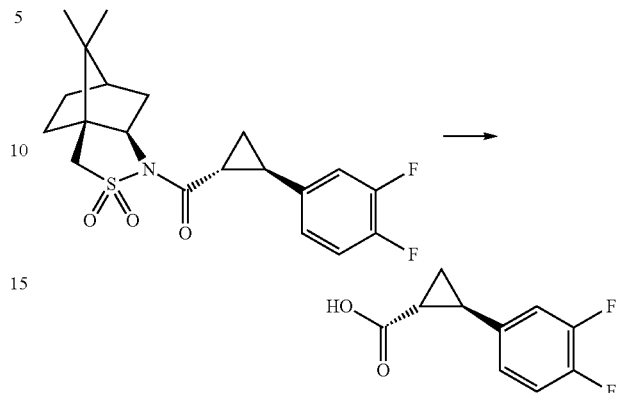

(1R,2R)-2-(3,4-Difluorophenyl)cyclopropanecarboxylic acid

A mixture of [3aS-[1(1R,2R),3a,6,7a]]-1-[[2-(3,4-difluorophenyl)cyclopropyl]carbonyl]-hexahydro-8,8-dimethyl-3H-3a,6-methano-2,1-benzisothiazole-2,2-dioxide (48 g, 121.52 mmol, 1.00 equiv.) in 10% lithium hydroxide (200 mL) and tetrahydrofuran (200 mL) was stirred at about 50° C. for about 0.5 hours. The mixture was cooled to ambient temperature, and washed ether (2×100 mL). The pH value of the aqueous layer was adjusted to 3 by adding 12N hydrochloric acid. Following standard extractive workup with ether (3×200 mL), the crude residue was purified by silica gel column chromatography (ethyl acetate/petroleum ether (1:4)) to give the title product as a white solid (16.0 g; yield=66%). $^1$H NMR (300 MHz, CDCl$_3$) δ: 7.05-7.14 (m, 1H), 6.85-6.96 (m, 2H), 2.54-2.60 (m, 1H), 1.84-1.90 (m, 1H), 1.65-1.72 (m, 1H), 1.30-1.40 (m, 1H).

Step 20

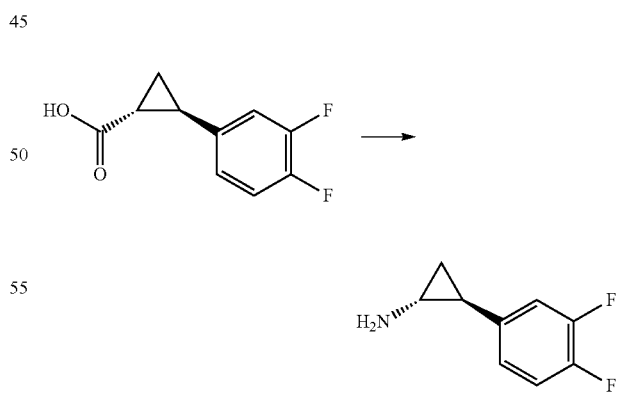

(1R,2S)-2-(3,4-Difluorophenyl)cyclopropanamine

A solution of (1R,2R)-2-(3,4-difluorophenyl)cyclopropanecarboxylic acid (8.0 g, 40.40 mmol, 1.00 equiv.), diphenylphosphoryl azide (11.2 g, 40.73 mmol, 1.00 equiv.), triethylamine (6.2 g, 61.39 mmol, 1.50 equiv.) in toluene (60 mL) was heated at reflux for about 1 hour and then refluxing 6N hydrogen chloride was added. The mixture was kept at reflux for 16 hours, and then cooled to ambient temperature. The resulting mixture was concentrated in vacuo, and the resulting residue was dissolved in water/ether (1:1) 200 mL). Following standard extractive workup with ether (3×100 mL), the resulting residue was purified by silica gel column chromatography (ethyl acetate/petroleum ether (1:4~1:0)) to give the title product as a light-brown solid (6.2 g; yield=91%). $^1$H NMR (300 MHz, CDCl$_3$) δ: 6.98-7.07 (m, 1H), 6.72-6.81 (m, 2H), 2.40 (m, 1H), 1.82-1.87 (m, 1H), 1.05-1.11 (m, 1H), 0.85-0.96 (m, 1H).

Step 21

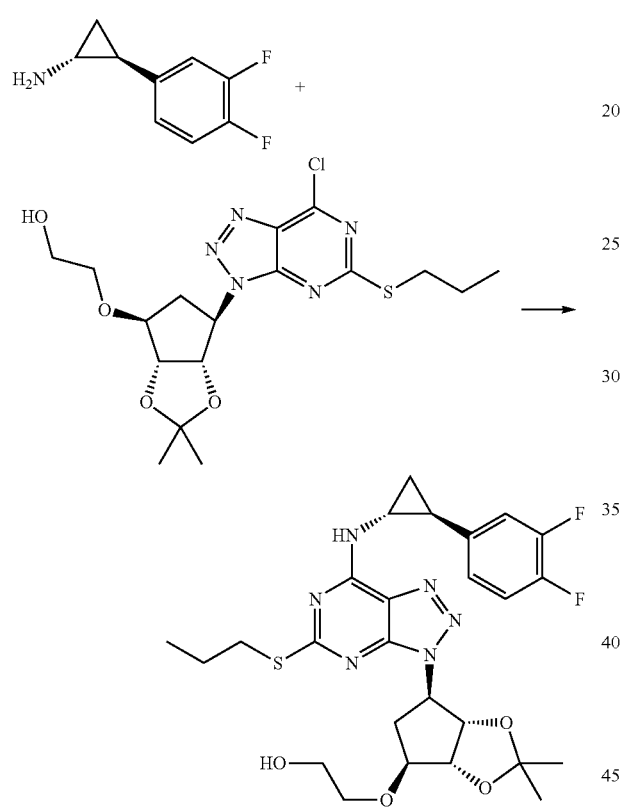

2-((3aR,4S,6R,6aS)-6-(7-((1R,2S)-2-(3,4-Difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol A solution of 2-((3aR,4S,6R,6aS)-6-(7-chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol (370 mg, 0.86 mmol, 1.00 equiv) (15 mL), (1R,2S)-2-(3,4-difluorophenyl)cyclopropanamine (145.6 mg, 0.86 mmol, 1.00 equiv.) and N,N-diisopropylethylamine (155.7 mg, 1.21 mmol, 1.20 equiv.) in dichloromethane was stirred at ambient temperature for about 16 hours, and then water (10 mL) was added. Standard extractive workup with dichloromethane (3×10 mL) gave the title product as a yellow oil (450 mg; yield=93%). m/z=563 (MH)$^+$.

Step 22

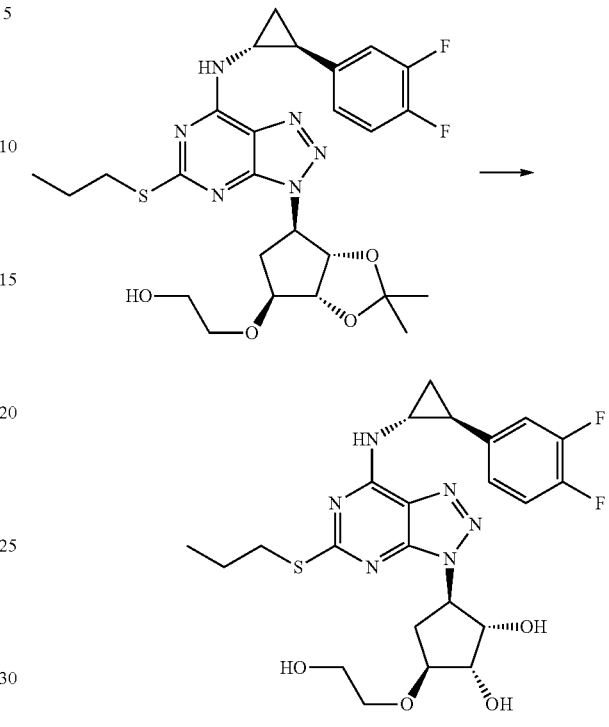

(1S,2S,3R,5S)-3-(7-((1R,2S)-2-(3,4-difluorophenyl)cyclopropylamino)-5-(propylthio)-3H-[1,2,3]triazolo[4,5-d]pyrimidin-3-yl)-5-(2-hydroxyethoxy)cyclopentane-1,2 diol (ticagrelor-d$_0$)

A solution of 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol (450 mg, 0.80 mmol, 1.00 equiv.) in methanol (4 mL) and 12N hydrochloric acid (1.5 mL) was stirred at ambient temperature for about 3 hours. The pH value of the solution was adjusted to 8-9 by adding potassium carbonate. Following standard extractive workup with ethyl acetate (3×20 mL), the resulting crude residue was purified by silica gel column chromatography (dichloromethane/methanol (50:1)) to give a semi-crude product (200 mg; yield=48%). The semi-crude product, which contained about 5% of other diastereoisomers, was then further purified by chiral-prep HPLC (column: Chiralpak IA2×25 cm, 5 umChiral-P(IA)004IA00CJ-MB003) to afford the title compound (100 mg). [α]$_D^{24.1}$-43.2° (c, 0.2 g/100 mL in MeOH). LC-MS: m/z=523.0 (MH)$^+$, Retention time: 1.58 minute. $^1$H NMR (300 MHz, CD$_3$OD) δ: 7.08-7.23 (m, 3H), 5.13 (q, 1H), 4.75-4.79 (m, 1H), 4.17-4.20 (m, 1H), 3.91-3.95 (m, 1H), 3.63-3.73 (m, 4H), 3.06-3.26 (m, 2H), 2.90-3.00 (m, 1H), 2.70-2.80 (m, 1H), 2.05-2.29 (m, 2H), 1.60-1.88 (m, 2H), 1.38-1.59 (m, 2H), 0.94 (t, J=7.5 Hz, 3H).

EXAMPLE 2

(1S,2S,3R,5S)-3-(7-((1R,2S)-2-(3,4-difluorophenyl)cyclopropylamino)-5-(propylthio)-3H-[1,2,3]-triazolo[4,5-d]pyrimidin-3-yl)-5-(2-hydroxy-d₄-ethoxy)cyclopentane-1,2-diol (ticagrelor-d₄)

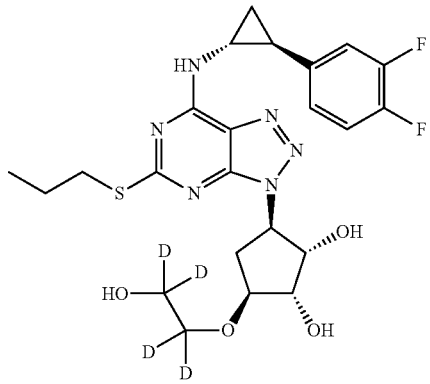 [SMILES: [2H]C([2H])(O)C([2H])([2H])O[C@H]1C[C@@H](n2nnc3c(N[C@@H]4C[C@H]4c4ccc(F)c(F)c4)nc(SCCC)nc32)[C@H](O)[C@@H]1O]

Step 1

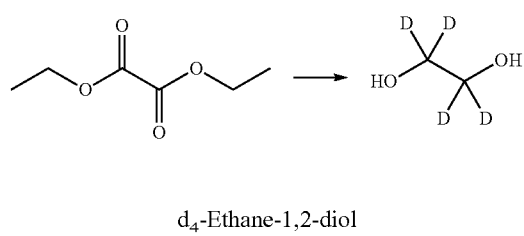

d₄-Ethane-1,2-diol

A solution of diethyloxalate (6.5 g, 44.48 mmol, 1.00 equiv.) in dry tetrahydrofuran (100 mL) was slowly added to a slurry of lithium aluminum deuteride (1.87 g, 44.48 mmol, 1.00 equiv) in tetrahydrofuran (100 mL). The mixture was heated at reflux for about 3 hours, and then water (4 mL) was added. The solids were removed by filtration, and the resulting filtrate was then washed with tetrahydrofuran (100 mL). The solvent was removed in vacuo to give the title product as a colorless oil (2.1 g; yield=71%).

Step 2

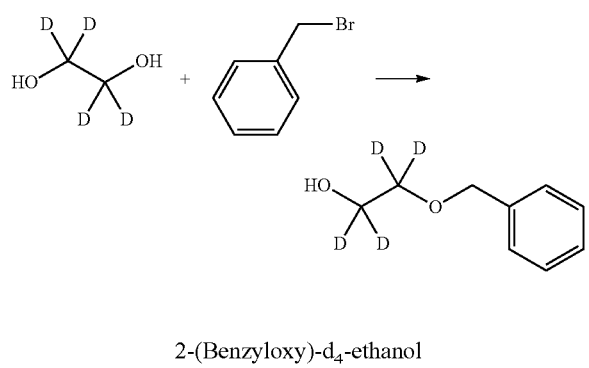

2-(Benzyloxy)-d₄-ethanol

Silver oxide (11.05 g, 47.72 mmol, 1.50 equiv.), and benzylbromide (5.98 g, 34.99 mmol, 1.10 equiv.) were added to a stirred solution of d₄-ethane-1,2-diol (2.1 g, 31.81 mmol, 1.00 equiv.) in dichloromethane (40 mL). The mixture was stirred at ambient temperature for about 16 hours, and then filtered through a small pad of silica gel. Following standard extractive workup with ethyl acetate, the crude residue was purified by silica gel column chromatography (ethyl acetate: petroleum ether (1:10)) to give the title product as a colorless oil (2.85 g; yield=57%). ¹H NMR (300 MHz, CDCl₃) δ: 7.29-7.42 (m, 5H), 4.59 (s, 2H).

Step 3

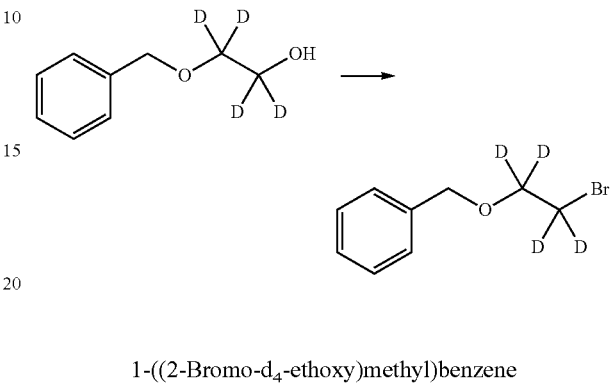

1-((2-Bromo-d₄-ethoxy)methyl)benzene

At about −20° C., triphenylphosphine (5.73 g, 21.87 mmol, 1.20 equiv.) was added in portions, over a period of 15 minutes, to a solution of d₄-2-(benzyloxy)ethanol (2.85 g, 18.24 mmol, 1.00 equiv), and N-bromosuccinimide (4.85 g, 27.25 mmol, 1.50 equiv.) in tetrahydrofuran (80 mL). The resulting solution was stirred at 15-25° C. for about 30 minutes. Following standard extractive workup with ethyl acetate, the resulting crude residue was purified by silica gel column chromatography (ethyl acetate/petroleum ether (1:5)) to give the title product as a colorless liquid (2.64 g; yield=66%). ¹H NMR (300 MHz, CDCl₃) δ: 7.31-7.40 (m, 5H), 4.62 (s, 2H)

Step 4

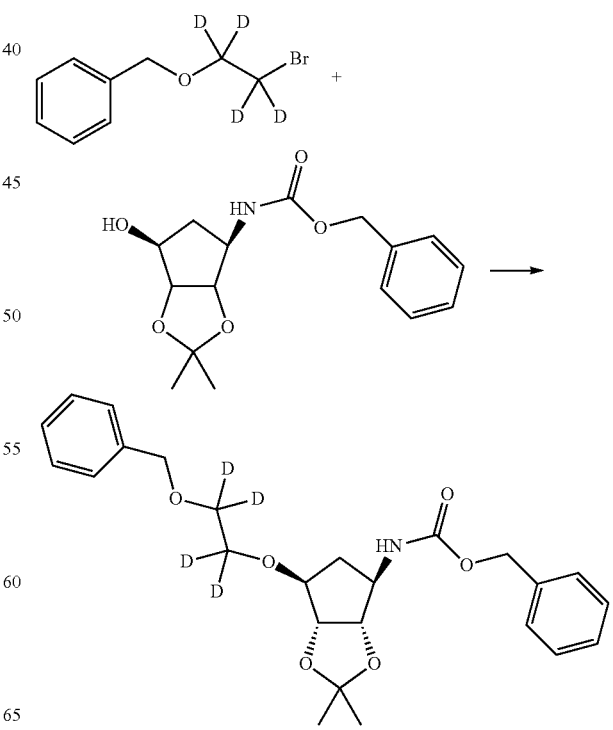

Benzyl (3aS,4R,6S,6aR)-6-(2-(benzyloxy)-d₄-ethoxy)-2,2-dimethyl-tetrahydro-3aH-cyclopenta[d][1,3]dioxol-4-ylcarbamate At about −10° C., benzyl (3aS,4R,6S,6aR)-6-hydroxy-2,2-dimethyl-tetrahydro-3aH-cyclopenta[d][1,3]dioxol-4-yl-carbamate (3.25 g, 10.57 mmol, 1.00 equiv.) was added to a solution of 70% sodium hydride (0.38 g, 11.11 mmol, 1.05 equiv.) in N,N-dimethylformamide (50 mL). The solution was stirred at about −10° C. for about 30 minutes, and then 1-((2-bromo-d₄-ethoxy)methyl)benzene (2.64 g, 12.04 mmol, 1.14 equiv.) was added. The resulting solution was stirred at ambient temperature for about 24 hours, and then water (50 mL) was added. Following standard extractive workup with ethyl acetate (3×50 mL), the resulting crude product was purified by silica gel column chromatography (ethyl acetate:petroleum ether (1:10)) to give title product as a colorless solid (2.25 g; yield=48%).

Step 5

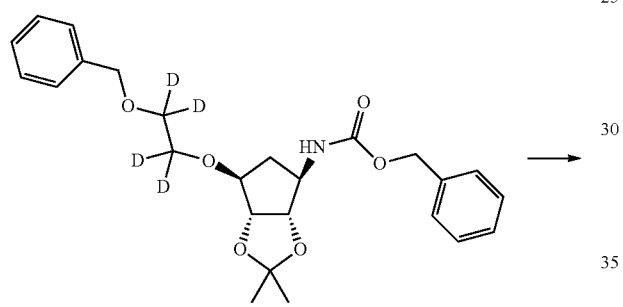

2-((3aR,4S,6R,6aS)-6-Amino-2,2-dimethyl-tetrahydro-3aH-cyclopenta[d][1,3]dioxol-4-yloxy)-d₄-ethanol Under an atmosphere of hydrogen, a suspension of benzyl (3aS,4R,6S,6aR)-6-(2-(benzyloxy)-d₄-ethoxy)-2,2-dimethyl-tetrahydro-3aH-cyclopenta[d][1,3]dioxol-4-ylcarbamate (2.25 g, 5 mmol, 3.30 equiv.), 10% palladium on carbon (1.6 g, 1.5 mmol, 1.00 equiv.), and methanol (50 mL) was stirred at ambient temperature for about 10 hours. The suspension was filtered, and the resulting filtrate was concentrated in vacuo to give the title product as a yellow solid (0.95 g; yield=86%). MS: m/z=222 (MH)⁺.

Step 6

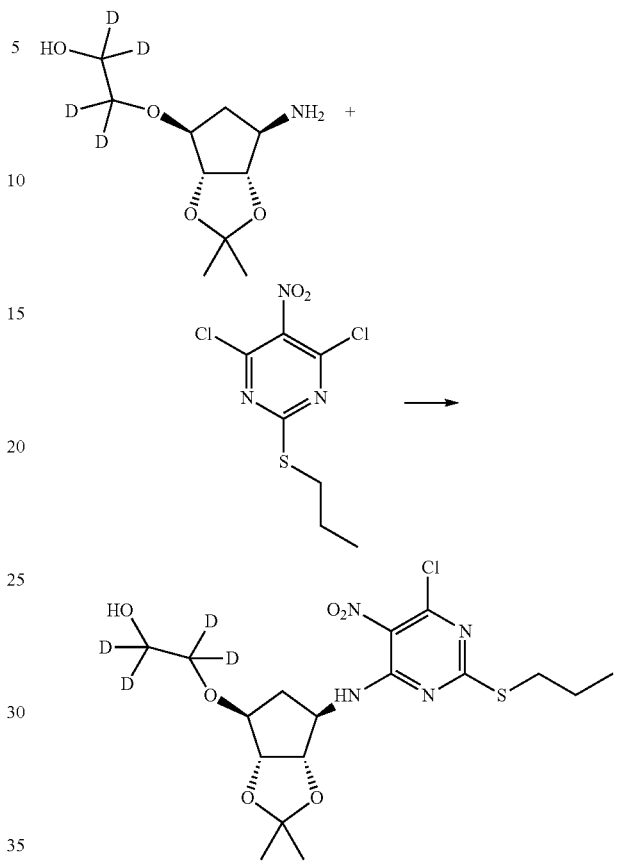

2-((3aR,4S,6R,6aS)-6-(6-Chloro-5-nitro-2-(propylthio)pyrimidin-4-ylamino)-2,2-dimethyl-tetrahydro-3aH-cyclopenta[d][1,3]dioxol-4-yloxy)-d₄-ethanol The procedure of Example 1, Step 14 was followed, but substituting 2-((3aR,4S,6R,6aS)-6-amino-2,2-dimethyl-tetrahydro-3aH-cyclopenta[d][1,3]dioxol-4-yloxy)-d₄-ethanol for 2-((3aR,4S,6R,6aS)-6-amino-2,2-dimethyl-tetrahydro-3aH-cyclopenta[d][1,3]dioxol-4-yloxy)ethanol. The title product was isolated as a yellow oil (680 mg; yield=47.39%). ¹H NMR (300 MHz, CDCl₃) δ: 8.66 (b, 1H), 4.65-4.76 (m, 2H), 4.56 (m, 1H), 3.99 (d, J=7.5 Hz, 1H), 3.07-3.21 (m, 2H), 2.34 (m, 1H), 1.98 (m, 1H), 1.77-1.82 (m, 2H), 1.46 (s, 3H), 1.27 (s, 3H), 1.06 (t, J=7.5 Hz, 3H).

Step 7

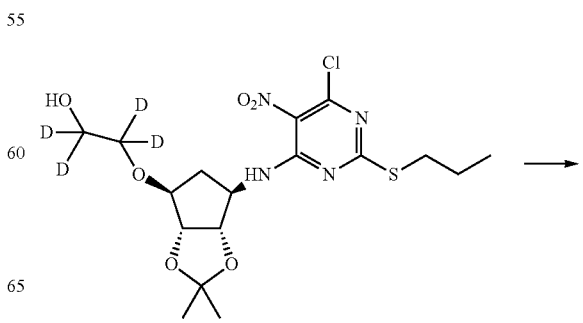

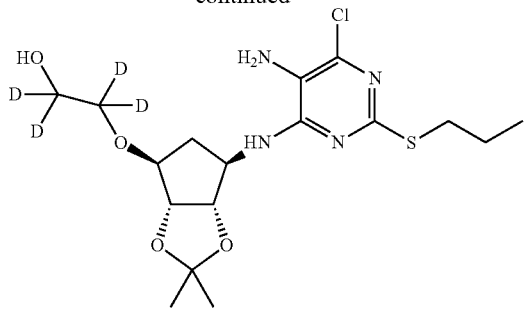

2-((3aR,4S,6R,6aS)-6-(5-Amino-6-chloro-2-(propylthio)pyrimidin-4-ylamino)-2,2-dimethyl-tetrahydro-3aH-cyclopenta[d][1,3]dioxol-4-yloxy)-d₄-ethanol The procedure of Example 1, Step 15 was followed, but substituting 2-((3aR,4S,6R,6aS)-6-(6-chloro-5-nitro-2-(propylthio)pyrimidin-4-ylamino)-2,2-dimethyl-tetrahydro-3aH-cyclopenta[d][1,3]dioxol-4-yloxy)-d₄-ethanol for 2-((3aR,4S,6R,6aS)-6-(6-chloro-5-nitro-2-(propylthio)pyrimidin-4-ylamino)-2,2-dimethyl-tetrahydro-3aH-cyclopenta[d][1,3]dioxol-4-yloxy)ethanol. The title product was isolated as a yellow oil (700 mg (crude)). MS: m/z=423 (MH)⁺.

Step 8

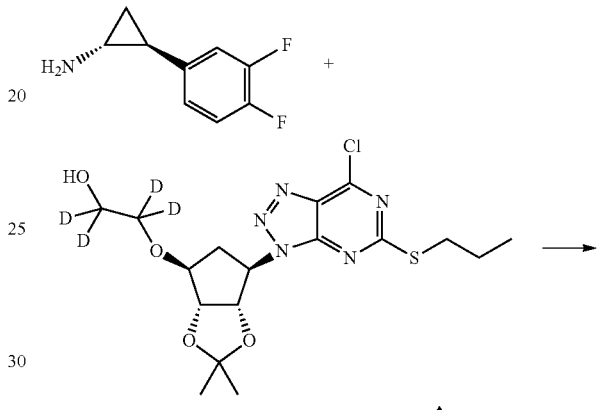

2-((3aR,4S,6R,6aS)-6-(7-Chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)-d₄-ethanol The procedure of Example 1, Step 16 was followed but substituting 2-((3aR,4S,6R,6aS)-6-(5-amino-6-chloro-2-(propylthio)pyrimidin-4-ylamino)-2,2-dimethyl-tetrahydro-3aH-cyclopenta[d][1,3]dioxol-4-yloxy)-d₄-ethanol for 2-((3aR,4S,6R,6aS)-6-(5-amino-6-chloro-2-(propylthio)pyrimidin-4-ylamino)-2,2-dimethyl-tetrahydro-3aH-cyclopenta[d][1,3]dioxol-4-yloxy)ethanol. The title product was isolated as a yellow oil (800 mg; (crude)). ¹H NMR (300 MHz, CDCl₃) δ: 5.53-5.57 (q, J₁=2.4 Hz, J₂=6.3 Hz, 1H), 5.22-5.25 (m, 1H), 4.91 (d, J=6.3 Hz, 1H), 4.05-4.09 (m, 1H), 3.25 (t, J=7.5 Hz, 2H), 2.68-2.72 (m, 1H), 2.57 (m, 1H), 1.81-1.88 (m, 2H), 1.57 (s, 3H), 1.39 (s, 3H), 1.11, (t, J=7.5 Hz, 3H).

Step 9

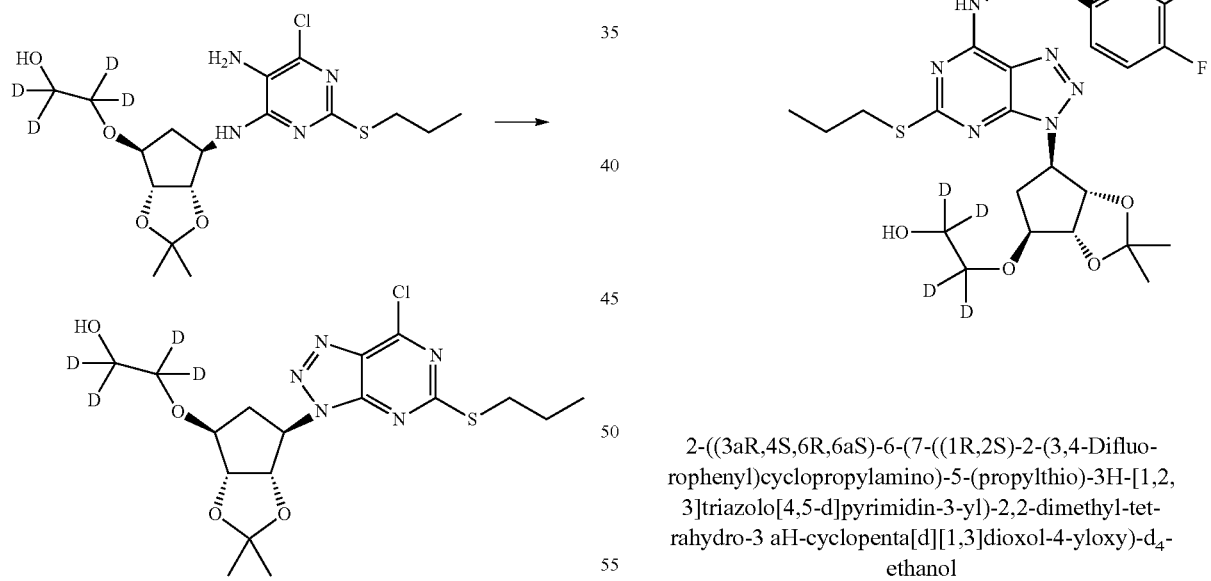

2-((3aR,4S,6R,6aS)-6-(7-((1R,2S)-2-(3,4-Difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)-d₄-ethanol The procedure of Example 1, Step 21 was followed but substituting 2-((3aR,4S,6R,6aS)-6-(7-chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)-d₄-ethanol for 2-((3aR,4S,6R,6aS)-6-(7-chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was isolated as a yellow oil (450 mg; yield=43%). MS: m/z=567 (MH)⁺.

Step 10

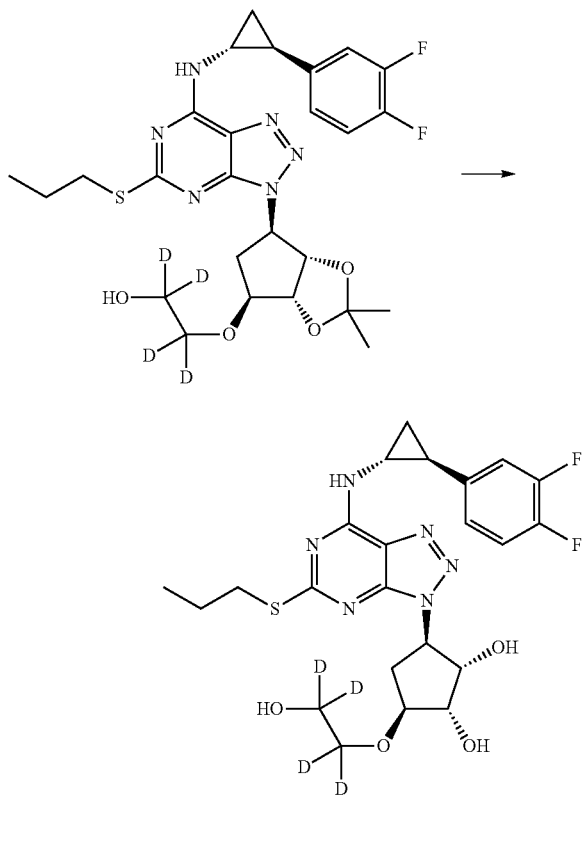

(1S,2S,3R,5S)-3-(7-((1R,2S)-2-(3,4-Difluorophenyl)cyclopropylamino)-5-(propylthio)-3H-[1,2,3]triazolo[4,5-d]pyrimidin-3-yl)-5-(2-hydroxy-d4-(ethoxy)cyclopentane-1,2-diol (ticagrelor-d4)

The procedure of Example 1, Step 22 was followed but substituting 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)-d4-ethanol for 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was first isolated as an semi-pure off-white solid (300 mg) that was then further purified by chiral-prep HPLC (column: Chiralpak IA2×25 cm, 5 umChiral-P(IA)004IA00CJ-MB003) to give the title compound as a nearly pure product (210 mg; yield=50%). $[\alpha]_D^{24.1}$ -19.0° (c, 0.1 g/100 mL in MeOH). LC-MS: m/z=527.0 (MH)$^+$, Retention time: 1.58 minute. $^1$H NMR (300 MHz, CD$_3$OD) δ: 7.09-7.24 (m, 3H), 5.14 (q, 1H), 4.75-4.80 (m, 1H), 4.17-4.20 (m, 1H), 3.90-3.95 (m, 1H), 3.06-3.26 (m, 2H), 2.90-3.00 (m, 1H), 2.70-2.81 (m, 1H), 2.05-2.30 (m, 2H), 1.61-1.88 (m, 2H), 1.38-1.59 (m, 2H), 0.94 (t, J=7.5 Hz, 3H).

EXAMPLE 3

(1S,2S,3R,5S)-3-(7-((1R,2S)-2-(3,4-Difluorophenyl)cyclopropylamino)-5-(d7-propylthio)-3H-[1,2,3]-triazolo[4,5-d]pyrimidin-3-yl)-5-(2-hydroxyethoxy)cyclopentane-1,2-diol (ticagrelor-d7)

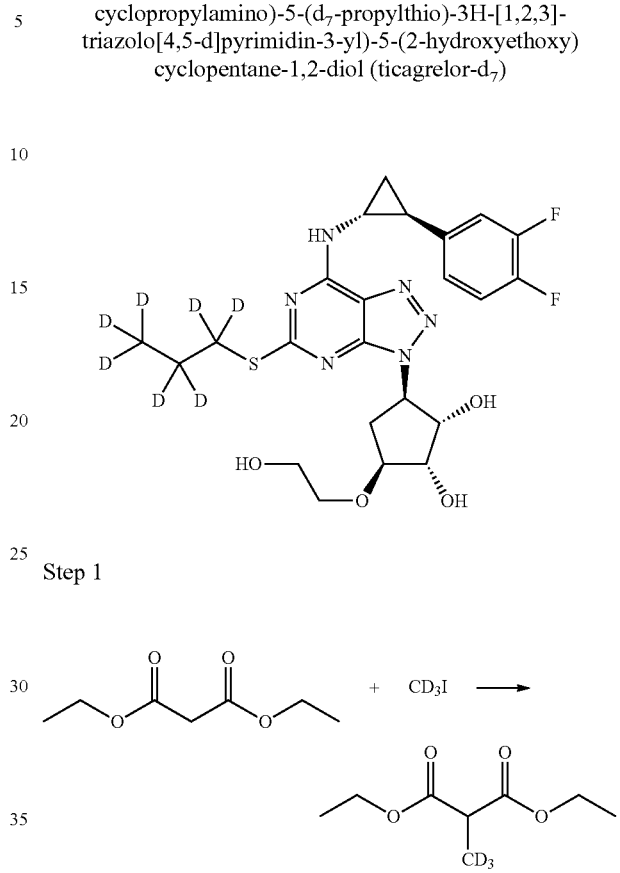

Step 1

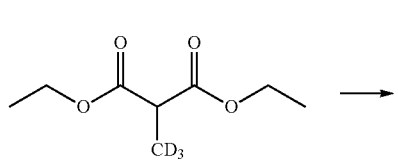

d3-Diethyl 2-methylmalonate

Sodium metal (7.59 g, 330.00 mmol, 1.05 equiv.) was slowly added to ethanol (500 mL) and stirred at ambient temperature until all the sodium metal was consumed. At about 0° C., diethyl malonate (50 g, 312.50 mmol, 1.00 equiv.) was added dropwise, over a period of 30 minutes, to the stirred solution. At about 0° C., iodomethane-d$_3$ (47.85 g, 330.00 mmol, 1.05 equiv) was then added dropwise, over a period of about 2 hours, to the stirred solution. The solution was stirred at ambient temperature for about 3 hours and then concentrated in vacuo. After adding water (500 mL), standard extractive workup with ethyl acetate (3×300 mL) afforded the title product as a light yellow liquid (48 g; yield=87%). $^1$H NMR (300 MHz, CDCl$_3$) δ: 4.15 (q, J=7.2 Hz, 2H), 2.30 (s, 1H), 1.28 (t, J=7.2 Hz, 3H).

Step 2

-continued

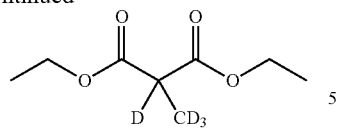

d₄-Diethyl 2-methylmalonate

A solution of d₃-diethyl 2-methylmalonate (48 g, 271.19 mmol, 1.00 equiv.) and triethylamine (27.4 g, 271.29 mmol, 1.00 equiv.) in d₄-methanol (240 mL) was stirred at about 25° C. for about 16 hours. The resulting mixture was then concentrated in vacuo to give the title product as a light yellow liquid (48 g; yield=99%). ¹H NMR (300 MHz, CDCl₃) δ: 4.16 (q, J=7.2 Hz, 2H), 1.29 (t, J=7.2 Hz, 3H).
Step 3

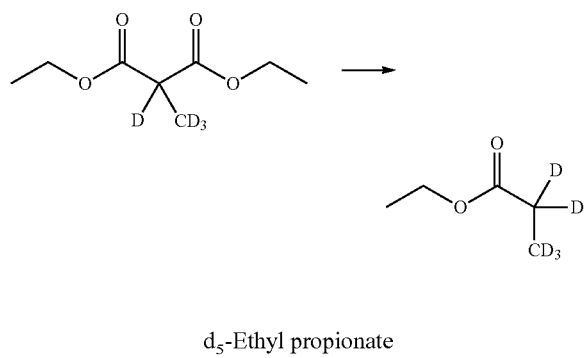

d₅-Ethyl propionate

A mixture of d₄-diethyl 2-methylmalonate (42 g, 235.69 mmol, 1.00 equiv.), sodium chloride (27.5 g, 470.57 mmol, 2.00 equiv.), deuterium oxide (4.8 g, 240.00 mmol, 1.00 equiv.) and dimethylsulfoxide-d₆ (200 mL) was stirred at 150-160° C. for about 3 hours. The solvent was then removed by distillation. Standard extractive workup with ethyl ether (250 mL) gave the title product, which was used in the next step without further purification (15 g; yield=59%), ¹H NMR (300 MHz, CDCl₃) δ: 4.13 (q, J=7.2 Hz, 2H), 1.25 (t, J=7.2 Hz, 3H).
Step 4

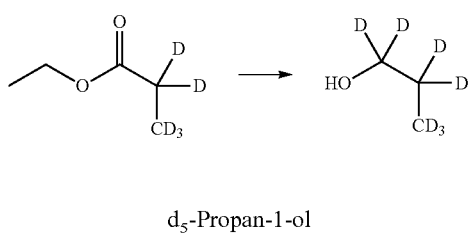

d₅-Propan-1-ol

At 0-5° C., lithium aluminum deuteride (5.8 g, 138.10 mmol, 0.80 equiv.) was added to a solution of d₅-ethyl propionate (18.6 g, 173.83 mmol, 1.00 equiv.) in ethyl ether (200 mL). The resulting solution was stirred at ambient temperature for about 3 hours, and then deuterium oxide (50 mL) was added. The solution was stirred at ambient temperature for about 1 hour, and then the pH value of the solution was adjusted to 4-5 by adding 10% sulfuric acid. The crude product was purified by distillation. The fraction collected was at 70-88° C. to give the title product (19.8 g; (crude, contained water and ethanol)) as a colorless liquid, which was used in the next step without more purification.
Step 5

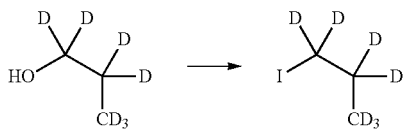

d₇-1-Iodopropane

A solution of d₅-propan-1-ol (19.8 g, 295.52 mmol, 1.00 equiv.) in 45% hydroiodic acid (180 mL) was heated at reflux for about 17 hours. The organic phase was separated and washed with sodium sulfate (1×10 mL) and brine (1×10 mL). The resulting crude product was then purified by distillation (1 atm). The fraction collected was at 95-101° C. to give the title product as a colorless liquid (5.1 g; yield=26%).
Step 6

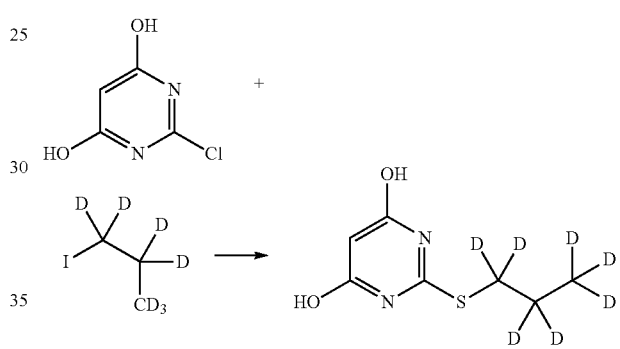

2-(d₇-Propylthio)pyrimidine-4,6-diol

The procedure of Example 1, Step 11, was followed but substituting d₇-1-iodopropane for 1-iodopropane. The title product was isolated as an off-white solid (3.5 g; yield=64%).
Step 7

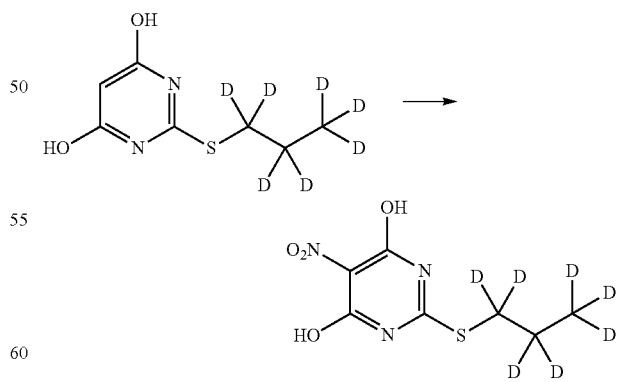

5-Nitro-2-(d₇-propylthio)pyrimidine-4,6-diol

The procedure of Example 1, Step 12 was followed, but substituting 2-(propyl-d₇-thio)pyrimidine-4,6-diol for 2-(propylthio)pyrimidine-4,6-diol. The title product was isolated as a yellow solid (3.2 g; yield=51%).
Step 8

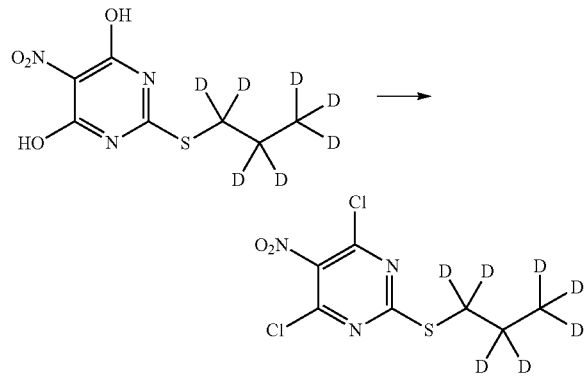

4,6-Dichloro-5-nitro-2-(d₇-propylthio)pyrimidine

The procedure of Example 1, Step 13 was followed, but substituting 5-nitro-2-(d₇-propylthio)pyrimidine-4,6-diol for 5-nitro-2-(propylthio)pyrimidine-4,6-diol. The title product was isolated as a yellow oil (1.8 g; yield=49%).
Step 9

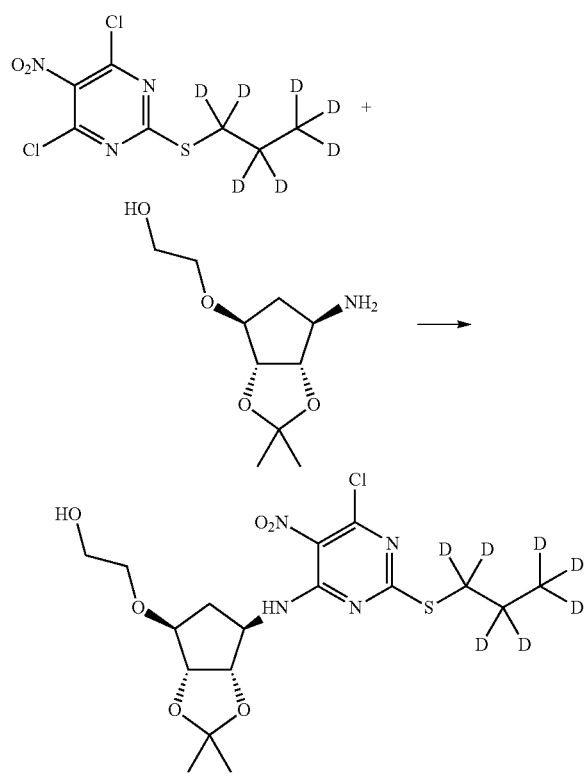

2-((3aR,4S,6R,6aS)-6-(6-Chloro-5-nitro-2-(d₇-propylthio)-pyrimidin-4-ylamino)-2,2-dimethyl-tetrahydro-3aH-cyclopenta[d][1,3]dioxol-4-yloxy)ethanol The procedure of Example 1, Step 14 was followed, but substituting 4,6-dichloro-5-nitro-2-(d₇-propylthio)pyrimi-dine for 4,6-dichloro-5-nitro-2-(propylthio)pyrimidine. The title product was isolated as a yellow oil (800 mg; yield=57%). ¹H NMR (300 MHz, CDCl₃) δ: 8.66 (b, 1H), 4.66-4.77 (m, 2H), 4.56 (m, 1H), 3.99 (d, J=7.5 Hz, 1H), 3.71-3.87 (m, 3H), 3.64-3.66 (m, 1H), 2.33 (m, 1H), 1.97 (m, 1H), 1.45 (s, 3H), 1.26 (s, 3H).
Step 10

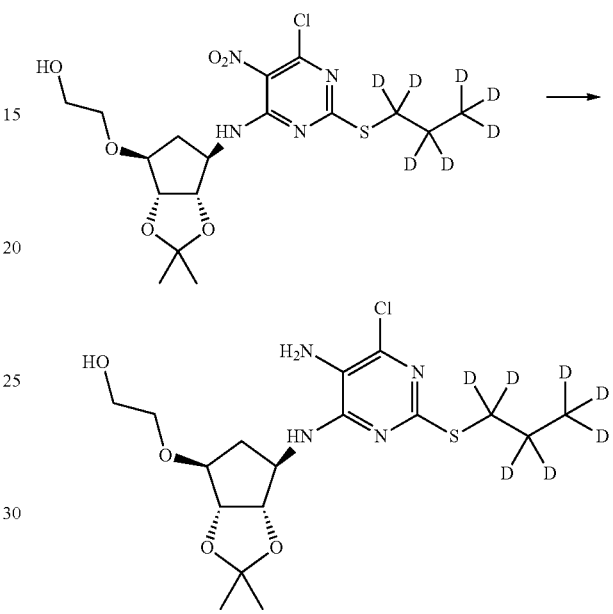

2-((3aR,4S,6R,6aS)-6-(5-Amino-6-chloro-2-(d₇-propylthio)pyrimidin-4-ylamino)-2,2-dimethyl-tetrahydro-3aH-cyclopenta[d][1,3]dioxol-4-yloxy)ethanol The procedure of Example 1, Step 15 was followed, but substituting 2-((3aR,4S,6R,6aS)-6-(6-chloro-5-nitro-2-(d₇-propylthio)pyrimidin-4-ylamino)-2,2-dimethyl-tetrahydro-3aH-cyclopenta[d][1,3]dioxol-4-yloxy)ethanol for 2-((3aR, 4S,6R,6aS)-6-(6-chloro-5-nitro-2-(propylthio)pyrimidin-4-ylamino)-2,2-dimethyl-tetrahydro-3aH-cyclopenta[d][1,3] dioxol-4-yloxy)ethanol. The title product was isolated as a yellow oil (700 g; yield=93%).
Step 11

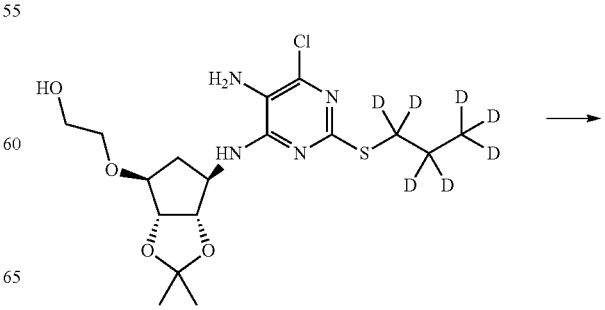

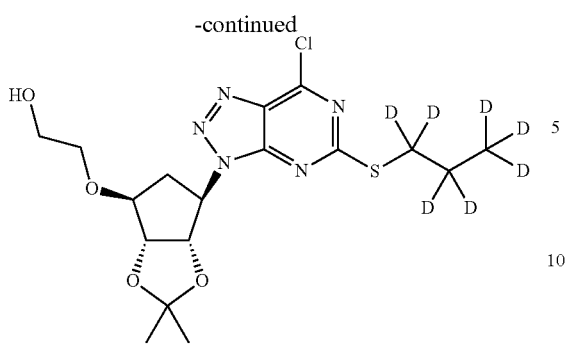

2-((3aR,4S,6R,6aS)-6-(7-Chloro-5-(d₇-propylthio)-
3H-[1,2,3]triazolo[4,5-d]pyrimidin-3-yl)-2,2-dimethyl-tetrahydro-3 aH-cyclopenta[d][1,3]dioxol-4-yloxy)ethanol The procedure of Example 1, Step 16 was followed, but substituting 2-((3aR,4S,6R,6aS)-6-(5-amino-6-chloro-2-(d₇-propylthio)pyrimidin-4-ylamino)-2,2-dimethyl-tetrahydro-3 aH-cyclopenta[d][1,3]dioxol-4-yloxy)ethanol for 2-((3aR,4S,6R,6aS)-6-(5-amino-6-chloro-2-(propylthio)pyrimidin-4-ylamino)-2,2-dimethyl-tetrahydro-3aH-cyclopenta[d][1,3]dioxol-4-yloxy)ethanol. The title product was isolated as a yellow oil (320 mg; yield=45%). ¹H NMR (300 MHz, CDCl₃) δ: 5.54-5.57 (q, J₁=2.4 Hz, J₂=6.3 Hz, 1H), 5.21-5.25 (m, 1H), 4.91 (d, J=6.3 Hz, 1H), 4.05-4.08 (m, 1H), 3.50-3.65 (m, 4H), 2.68-2.72 (m, 1H), 2.58 (m, 1H), 1.57 (s, 3H), 1.38 (s, 3H).

Step 12

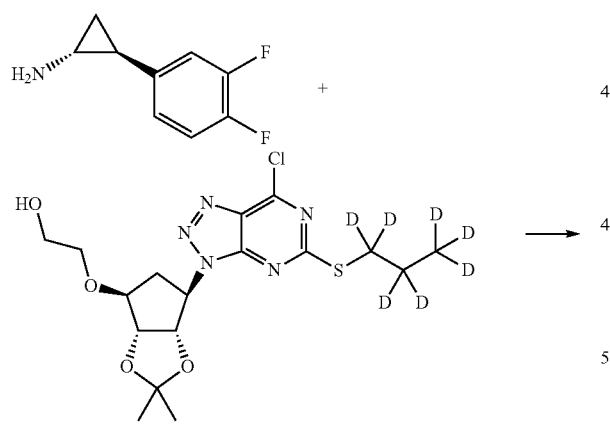

2-((3aR,4S,6R,6aS)-6-(7-((1R,2S)-2-(3,4-Difluorophenyl)cyclopropylamino)-5-(d₇-propylthio)-3H-[1,2,3]triazolo[4,5-d]pyrimidin-3-yl)-2,2-dimethyl-tetrahydro-3 aH-cyclopenta[d][1,3]dioxol-4-yloxy)ethanol The procedure of Example 1, Step 21 was followed, but substituting 2-((3aR,4S,6R,6aS)-6-(7-chloro-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol for 2-((3aR,4S,6R,6aS)-6-(7-chloro-5-(d₇-propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was isolated as a yellow oil (600 mg; yield=58%).

Step 13

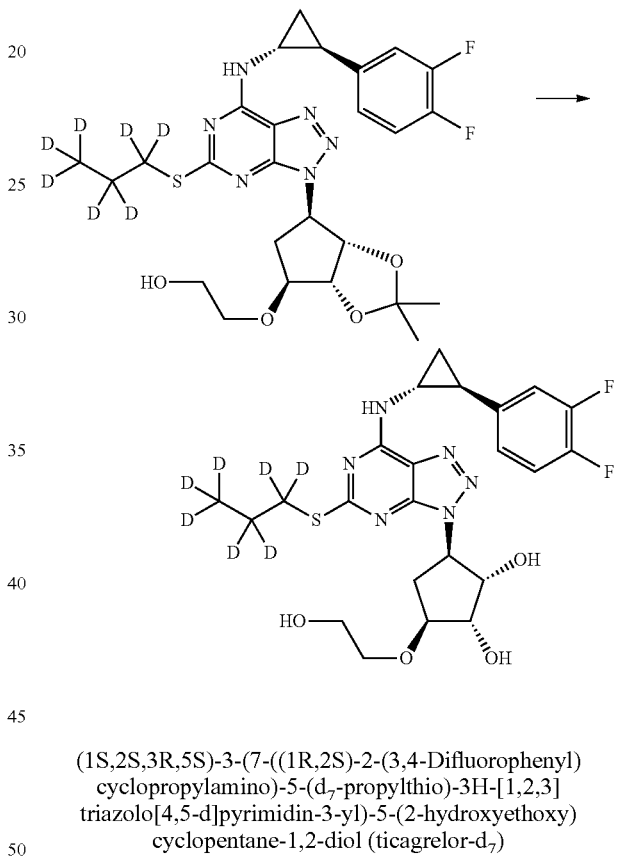

(1S,2S,3R,5S)-3-(7-((1R,2S)-2-(3,4-Difluorophenyl)cyclopropylamino)-5-(d₇-propylthio)-3H-[1,2,3]triazolo[4,5-d]pyrimidin-3-yl)-5-(2-hydroxyethoxy)cyclopentane-1,2-diol (ticagrelor-d₇)

The procedure of Example 1, Step 22 was followed, but substituting 2-((3aR,4S,6R,6aS)-6-(7-((1R,2S)-2-(3,4-difluorophenyl)cyclopropylamino)-5-(d₇-propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol for 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was isolated as a semi pure off-white solid (350 mg) that was further purified by chiral-prep HPLC (column: Chiralpak IA2×25 cm, 5 umChiral-P(IA)004IA00CJ-MB003) to give the nearly pure product (220 mg; yield=40%). $[\alpha]_D^{26.3}$ -26.8° (c, 0.31 g/100 mL in MeOH). LC-MS: m/z=530.0 (MH)⁺, Retention time: 1.58 minute. ¹H NMR (300 MHz, CD₃OD) δ: 7.08-7.23 (m, 3H), 5.13 (q, 1H), 4.75-4.79 (m, 1H), 4.17-4.20 (m, 1H), 3.91-3.95 (m, 1H), 3.63-3.73 (m, 4H), 3.14 (m, 1H), 2.70-2.80 (m, 1H), 2.15-2.29 (m, 2H), 1.38-1.50 (m, 2H).

EXAMPLE 4

(1S,2S,3R,5S)-3-(7-((1R,2S)-2-(3,4-difluorophenyl)cyclopropylamino)-5-($d_7$-propylthio)-3H-[1,2,3]-triazolo[4,5-d]pyrimidin-3-yl)-5-(2-hydroxy-$d_4$-ethoxy)cyclopentane-1,2-diol (ticagrelor-$d_{11}$)

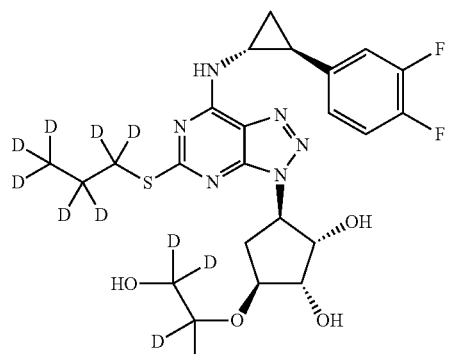

Step 1

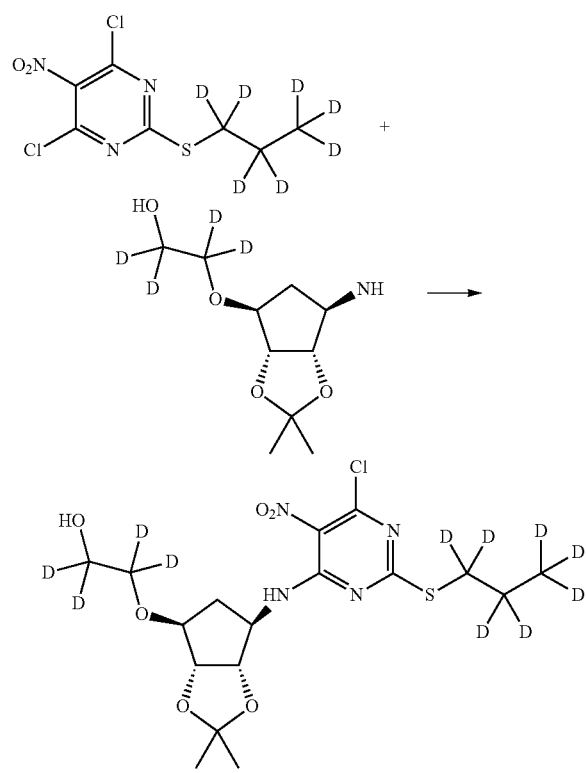

2-((3aR,4S,6R,6aS)-6-(6-Chloro-5-nitro-2-($d_7$-propylthio)pyrimidin-4-ylamino)-2,2-dimethyl-tetrahydro-3aH-cyclopenta[d][1,3]dioxol-4-yloxy)-$d_4$-ethanol The procedure of Example 3, Step 9 was followed, but substituting 2-((3aR,4S,6R,6aS)-6-amino-2,2-dimethyl-tetrahydro-3aH-cyclopenta[d][1,3]dioxol-4-yloxy)-$d_4$-ethanol for 2-((3aR,4S,6R,6aS)-6-amino-2,2-dimethyl-tetrahydro-3aH-cyclopenta[d][1,3]dioxol-4-yloxy)ethanol. The title product was isolated as a yellow oil (800 mg; yield=57%). $^1$H NMR (300 MHz, CDCl$_3$) δ: 8.65 (b, 1H), 4.66-4.77 (m, 2H), 4.56 (m, 1H), 3.99 (d, J=7.5 Hz, 1H), 2.34 (m, 1H), 1.98 (m, 1H), 1.45 (s, 3H), 1.27 (s, 3H).

Step 2

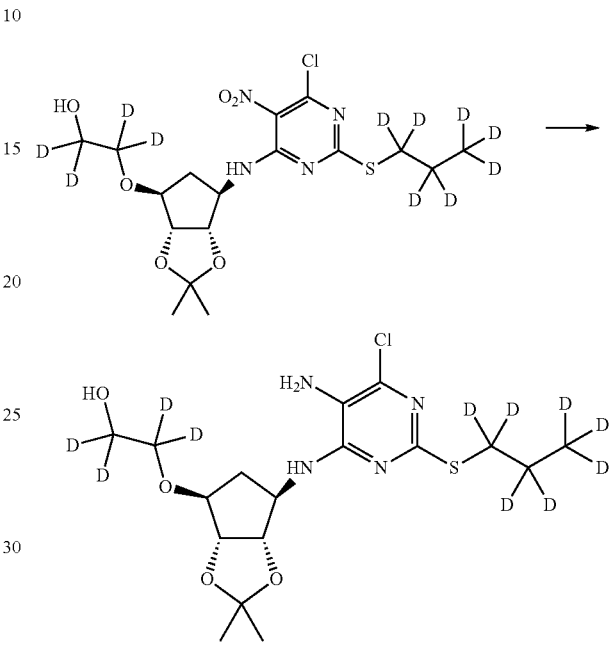

$d_{11}$-2-((3aR,4S,6R,6aS)-6-(5-Amino-6-chloro-2-($d_7$-propylthio)pyrimidin-4-ylamino)-2,2-dimethyl-tetrahydro-3aH-cyclopenta[d][1,3]dioxol-4-yloxy)-$d_4$-ethanol The procedure of Example 3, Step 10 was followed, but substituting 2-((3aR,4S,6R,6aS)-6-(6-chloro-5-nitro-2-($d_7$-propylthio)pyrimidin-4-ylamino)-2,2-dimethyl-tetrahydro-3aH-cyclopenta[d][1,3]dioxol-4-yloxy)-$d_4$-ethanol for 2-((3aR,4S,6R,6aS)-6-(6-chloro-5-nitro-2-($d_7$-propylthio)pyrimidin-4-ylamino)-2,2-dimethyl-tetrahydro-3aH-cyclopenta[d][1,3]dioxol-4-yloxy)ethanol. The title product was isolated as a yellow oil (560 mg; yield=81%).

Step 3

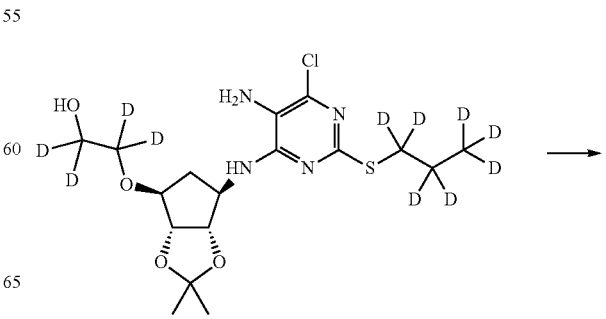

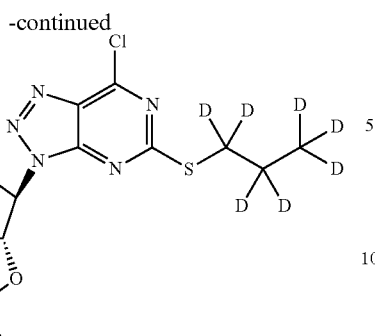

2-((3aR,4S,6R,6aS)-6-(7-chloro-5-(propyl-d₇-thio)-3H-[1,2,3]triazolo[4,5-d]pyrimidin-3-yl)-2,2-dimethyl-tetrahydro-3aH-cyclopenta[d][1,3]dioxol-4-yloxy)-d4-ethanol The procedure of Example 3, Step 11 was followed, but substituting 2-((3aR,4S,6R,6aS)-6-(5-amino-6-chloro-2-(d₇-propylthio)pyrimidin-4-ylamino)-2,2-dimethyl-tetrahydro-3aH-cyclopenta[d][1,3]dioxol-4-yloxy)-d₄-ethanol for 2-((3aR,4S,6R,6aS)-6-(5-amino-6-chloro-2-(d₇-propylthio)pyrimidin-4-ylamino)-2,2-dimethyl-tetrahydro-3aH-cyclopenta[d][1,3]dioxol-4-yloxy)ethanol. The title product was isolated as a yellow oil (460 mg; yield=80%). ¹H NMR (300 MHz, CDCl₃) δ: 5.54-5.58 (q, J₁=2.4 Hz, J₂=6.3 Hz, 1H), 5.21-5.25 (m, 1H), 4.92 (d, J=6.3 Hz, 1H), 4.06-4.09 (m, 1H), 2.67-2.73 (m, 1H), 2.58 (m, 1H), 1.57 (s, 3H), 1.38 (s, 3H).

Step 4

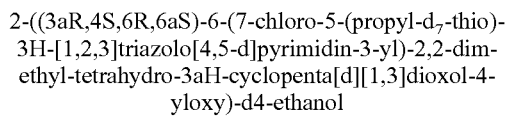

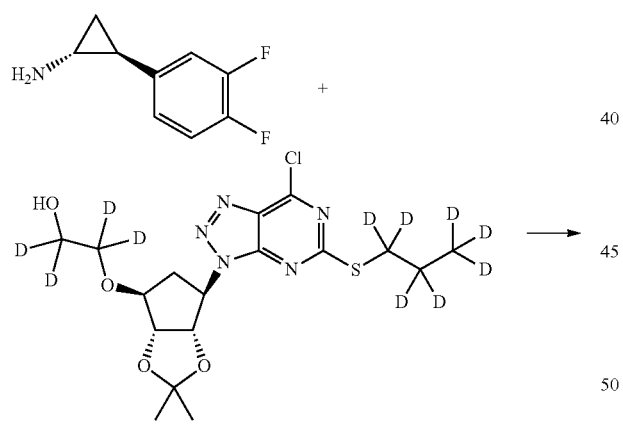

2-((3aR,4S,6R,6aS)-6-(7-((1R,2S)-2-(3,4-difluorophenyl)cyclopropylamino)-5-(d₇-propylthio)-3H-[1,2,3]triazolo[4,5-d]pyrimidin-3-yl)-2,2-dimethyl-tetrahydro-3 aH-cyclopenta[d][1,3]dioxol-4-yloxy)-d₄-ethanol The procedure of Example 3, Step 12 was followed, but substituting 2-((3aR,4S,6R,6aS)-6-(7-chloro-5-(propyl-d₇-thio)-3H-[1,2,3]triazolo[4,5-d]pyrimidin-3-yl)-2,2-dimethyl-tetrahydro-3aH-cyclopenta[d][1,3]dioxol-4-yloxy)-d₄-ethanol for 2-((3aR,4S,6R,6aS)-6-(7-chloro-5-(propyl-d₇-thio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was isolated as a yellow oil (400 mg; yield=67%).

Step 5

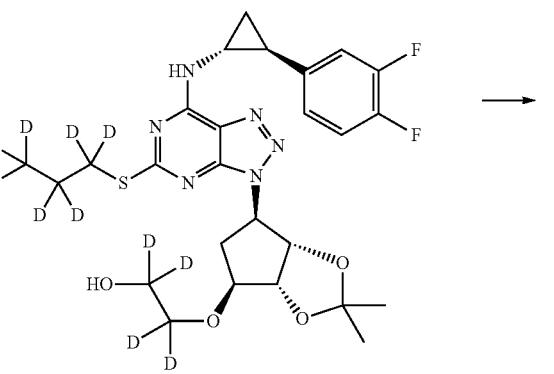

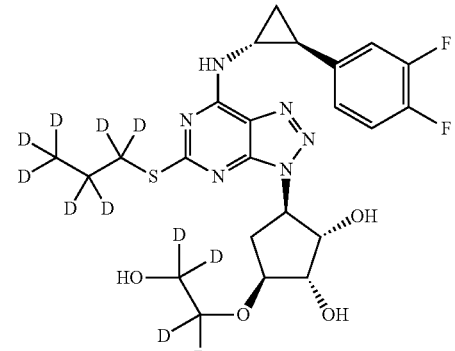

(1S,2S,3R,5S)-3-(7-((1R,2S)-2-(3,4-difluorophenyl)cyclopropylamino)-5-(propylthio)-3H-[1,2,3]triazolo[4,5-d]pyrimidin-3-yl)-5-(2-hydroxyethoxy)cyclopentane-1,2-diol (ticagrelor-d₁₁)

The procedure of Example 3, Step 13 was followed, but substituting 2-((3aR,4S,6R,6aS)-6-(7-((1R,2S)-2-(3,4-difluorophenyl)cyclopropylamino)-5-(d₇-propylthio)-3H-[1,2,3]triazolo[4,5-d]pyrimidin-3-yl)-2,2-dimethyl-tetrahydro-3aH-cyclopenta[d][1,3]dioxol-4-yloxy)-d₄-ethanol for 2-((3aR,4S,6R,6aS)-6-(7-((1R,2S)-2-(3,4-difluorophenyl)cyclopropylamino)-5-(d₇-propylthio)-3H-[1,2,3]triazolo[4,5-d]pyrimidin-3-yl)-2,2-dimethyl-tetrahydro-3aH-cyclopenta[d][1,3]dioxol-4-yloxy)ethanol. The title product was isolated as an semi-pure off-white solid (350 mg) that was further purified by chiral-prep-HPLC (column: Chiralpak IA2×25 cm, 5 umChiral-P(IA)004IA00CJ-MB003) to give pure product 260 mg (70%). [α]$_D^{26.1}$-23.2° (c, 0.21 g/100 mL in MeOH). LC-MS: m/z=534.0 (MH)⁺, Retention time: 1.58 minute. $^1$H NMR (300 MHz, CD$_3$OD) δ: 7.09-7.26 (m, 3H), 5.14 (q, 1H), 4.75-4.79 (m, 1H), 4.17-4.20 (m, 1H), 3.91-3.95 (m, 1H), 3.14 (m, 1H), 2.76-2.84 (m, 1H), 2.15-2.29 (m, 2H), 1.43-1.51 (m, 2H).
The following compounds can generally be made using the methods described above. It is expected that these compounds when made will have activity similar to those described in the examples above.
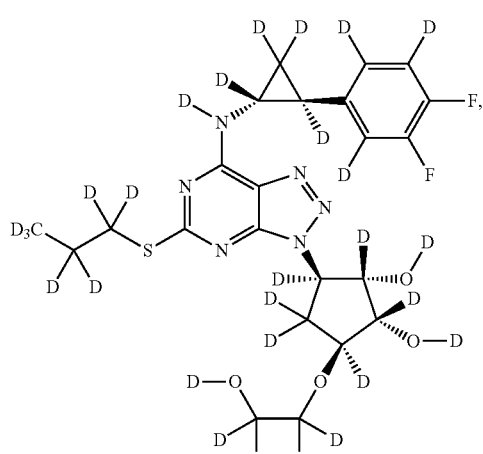
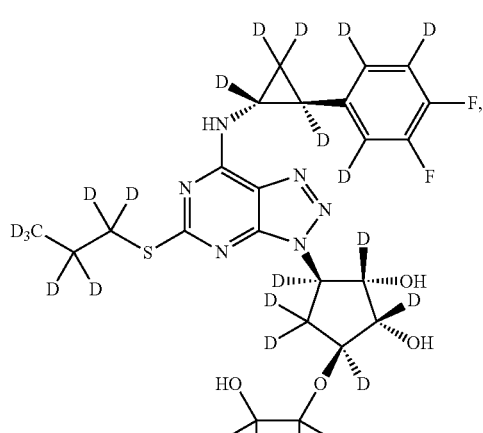
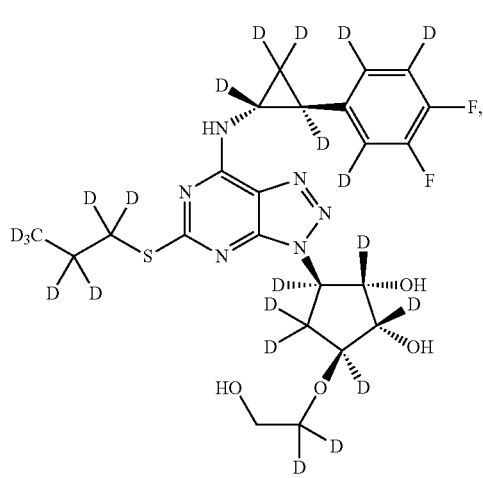
-continued
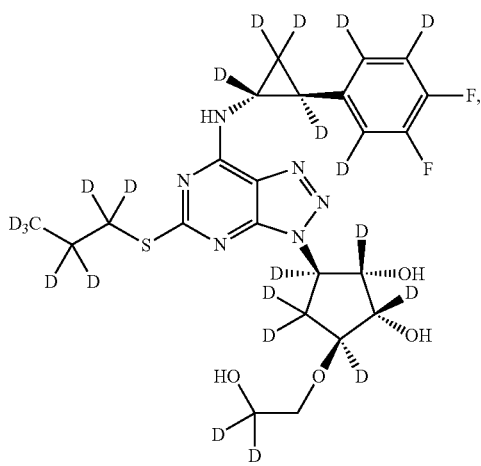
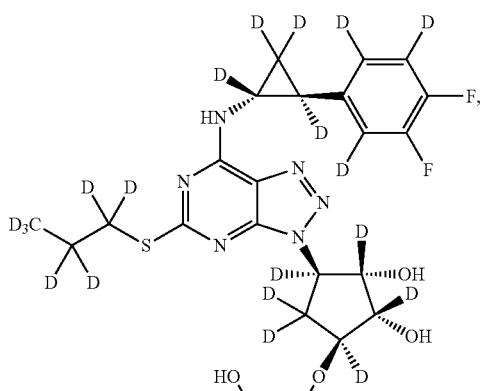
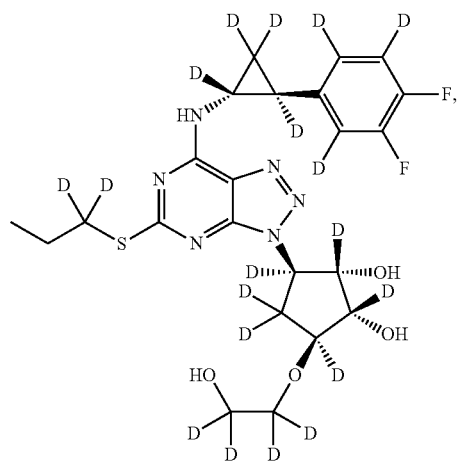

-continued
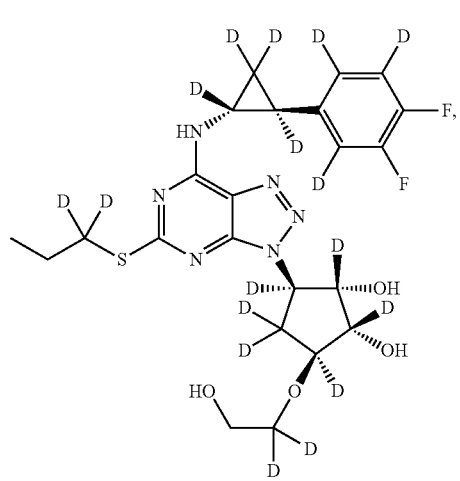
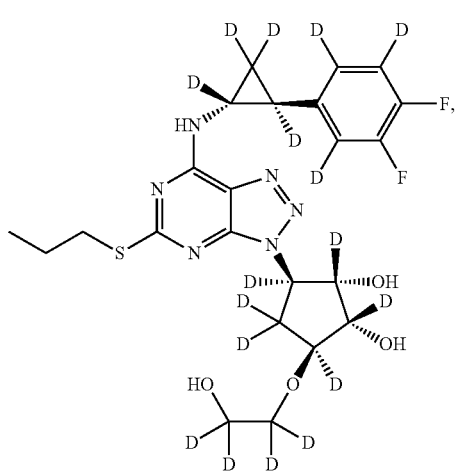
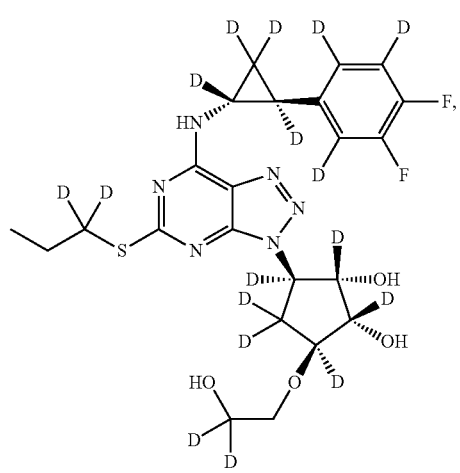
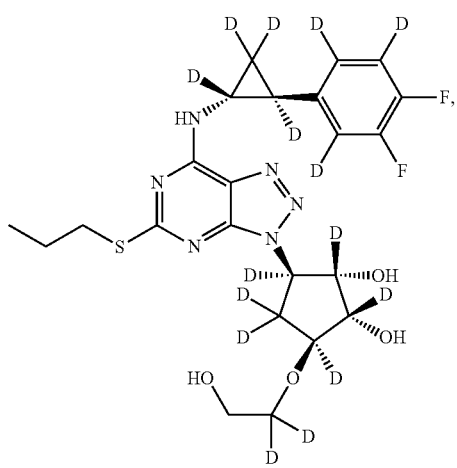
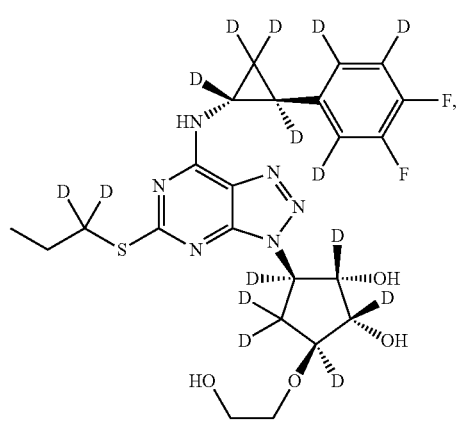
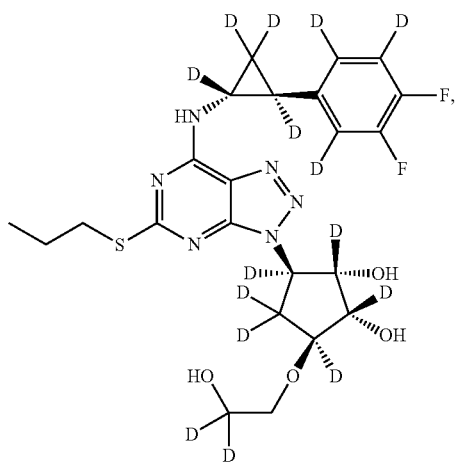

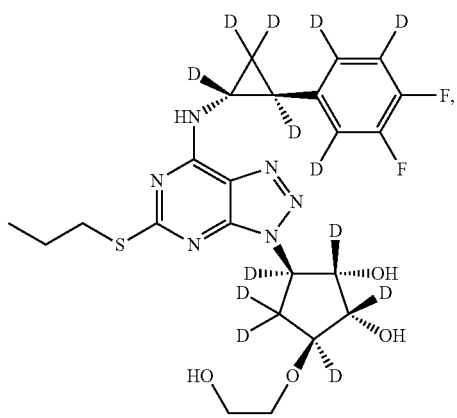
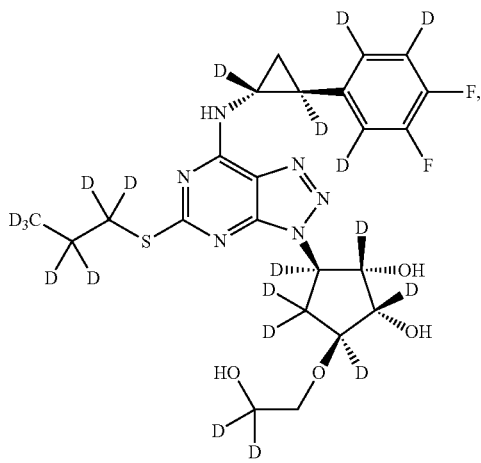
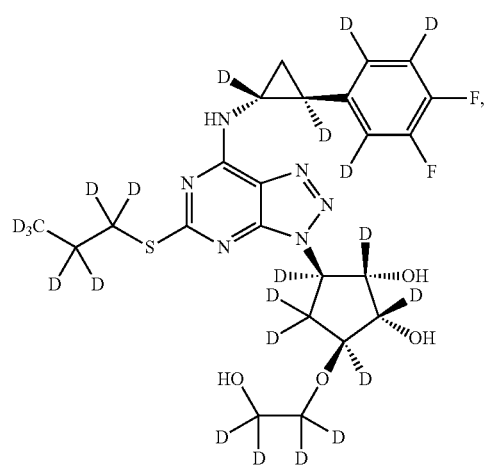
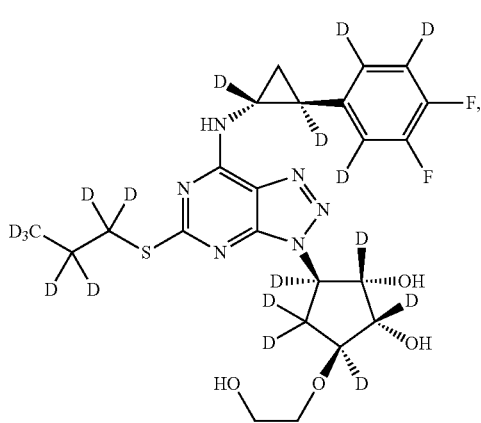
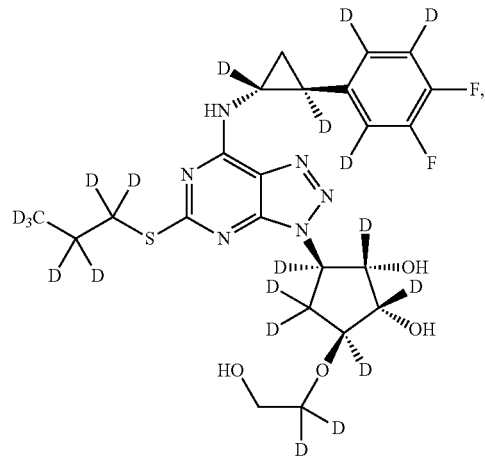
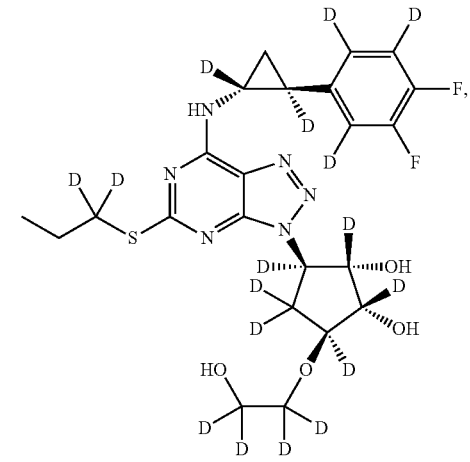

-continued
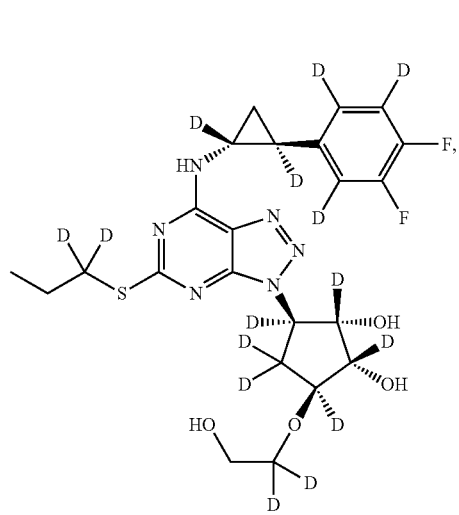
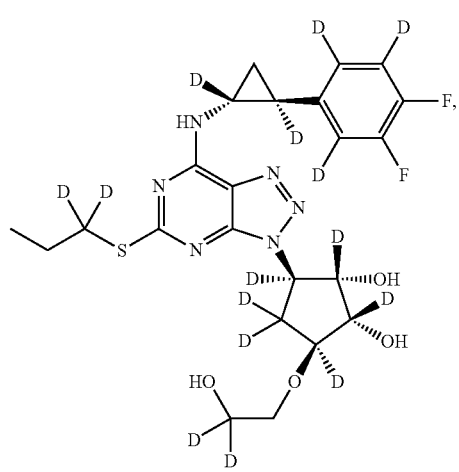
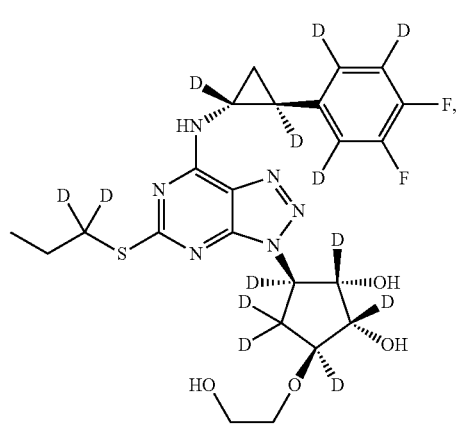
-continued
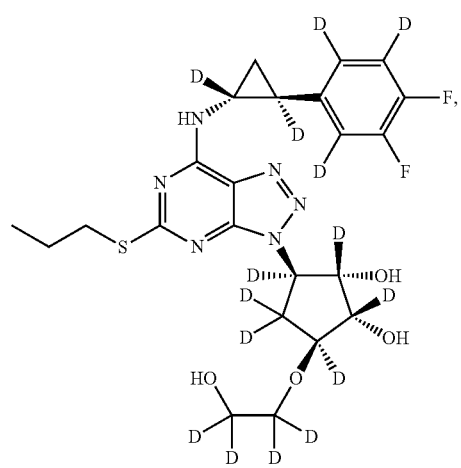
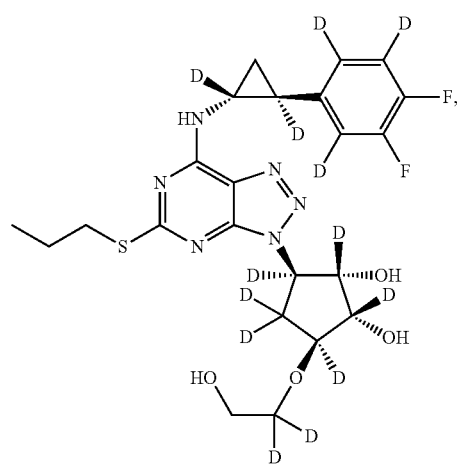
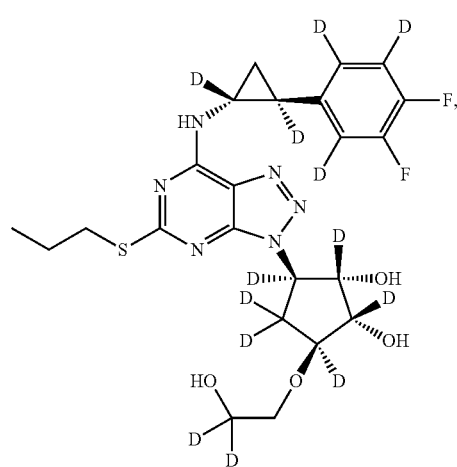

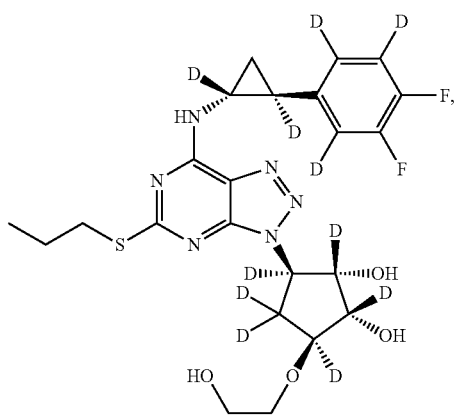
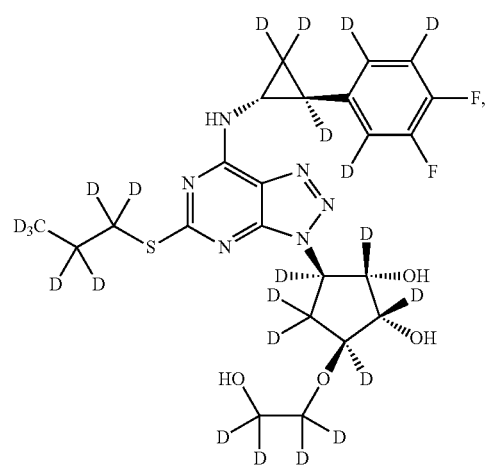
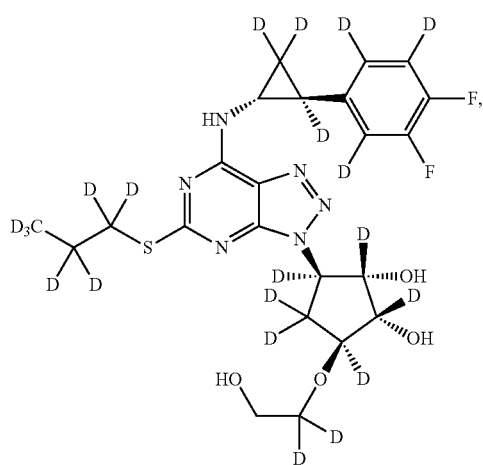
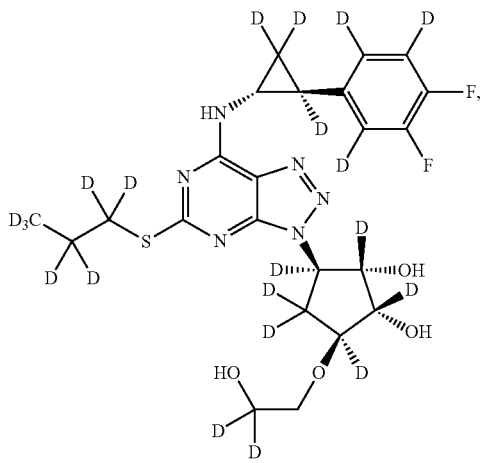
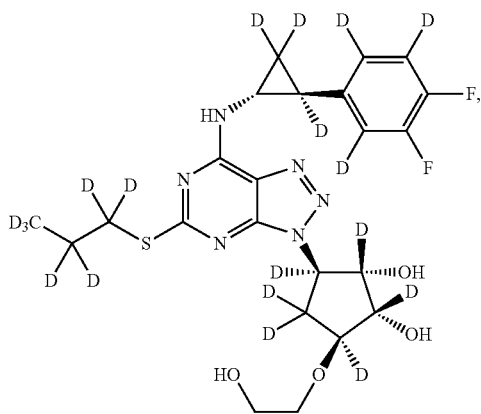
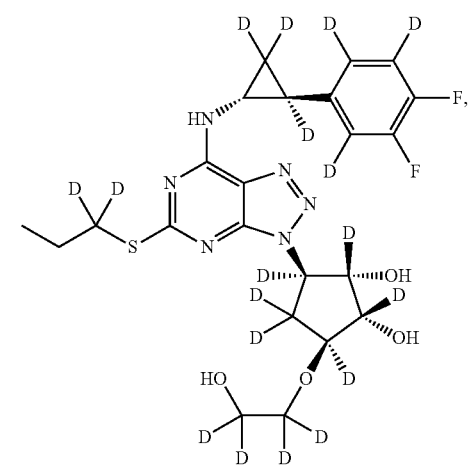

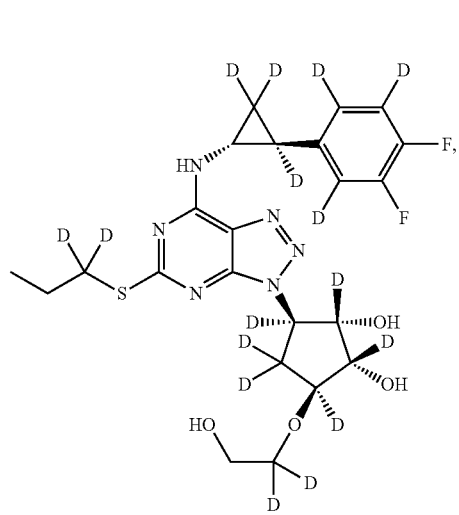
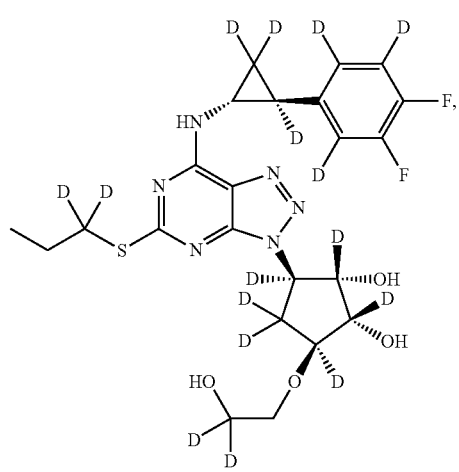
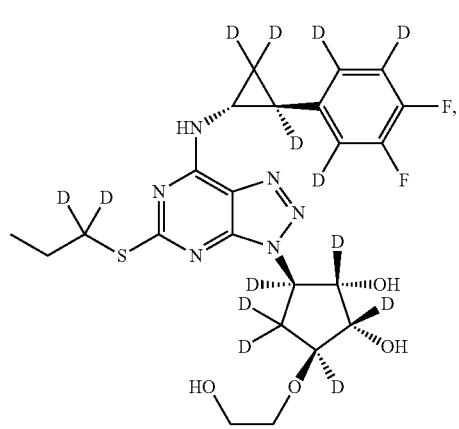
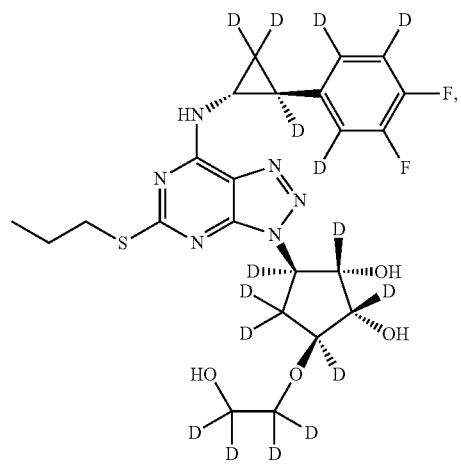
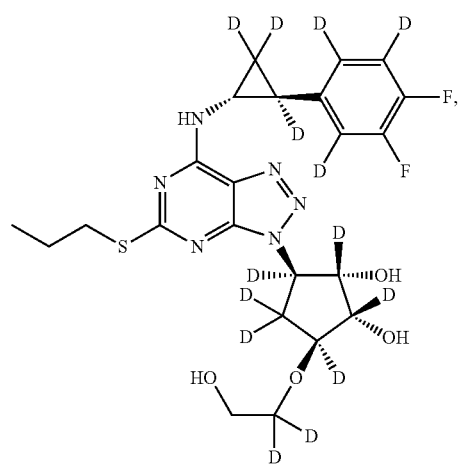
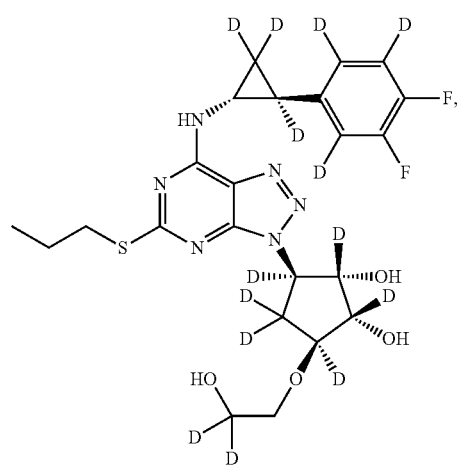

77
-continued
78
-continued
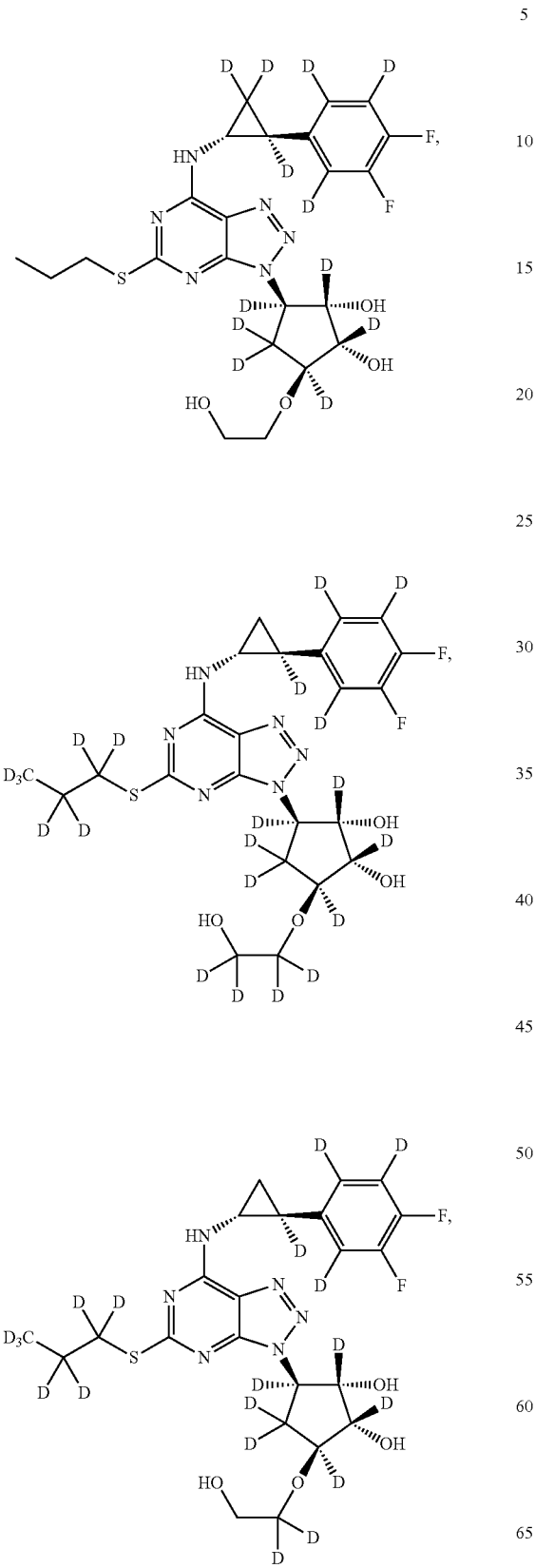
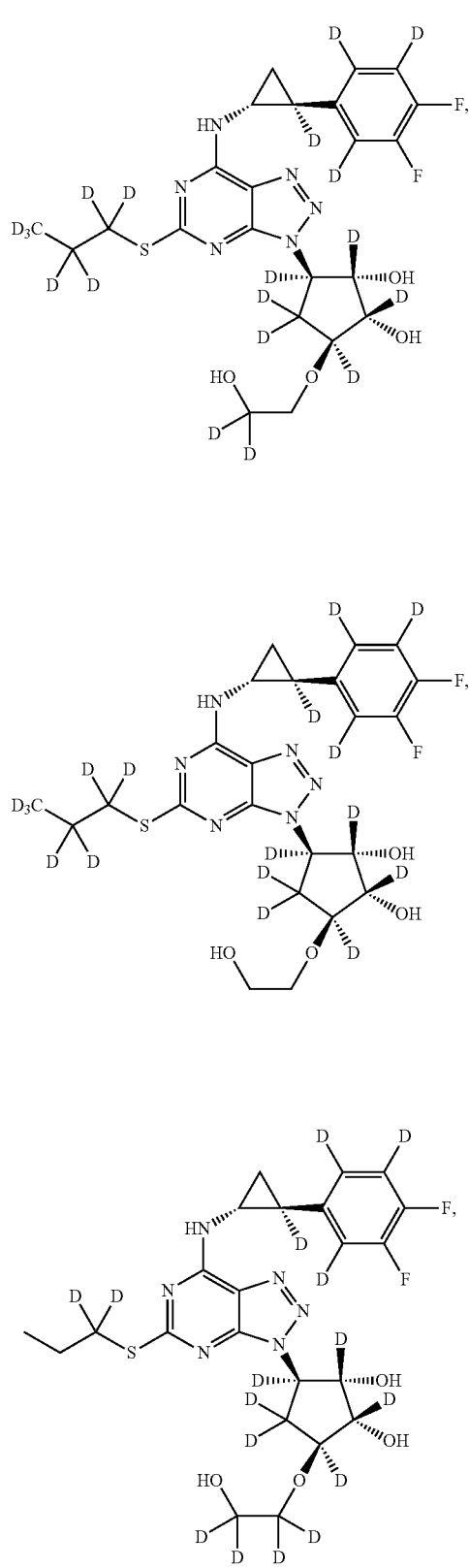

-continued
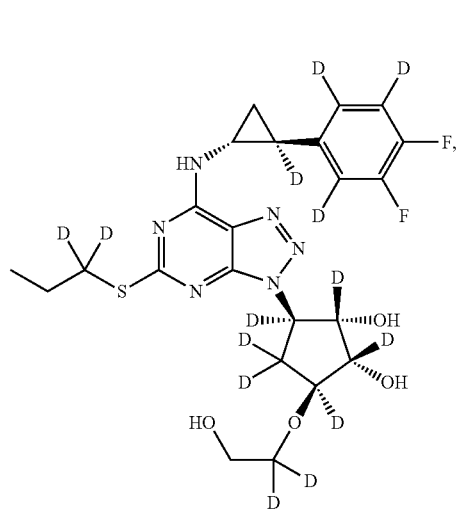
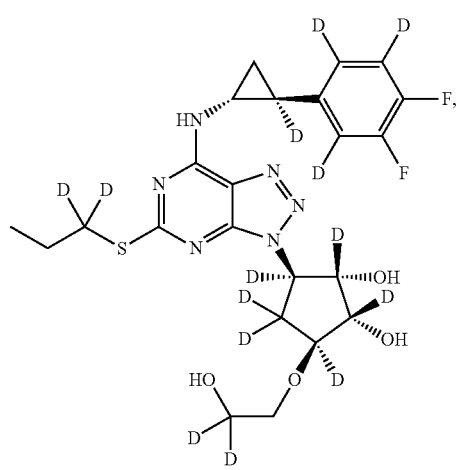
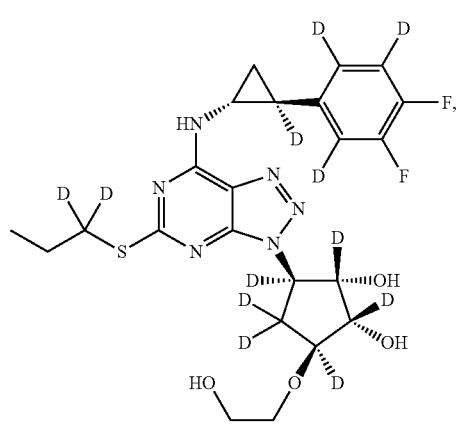 [SMILES: [2H]c1c([2H])c([C@]2([2H])C[C@H]2Nc2nc(SC([2H])([2H])CC)nc3c2nnn3[C@]2([2H])C([2H])([2H])[C@]([2H])(OCCO)[C@@]([2H])(O)[C@@]2([2H])O)c([2H])c(F)c1F]
-continued
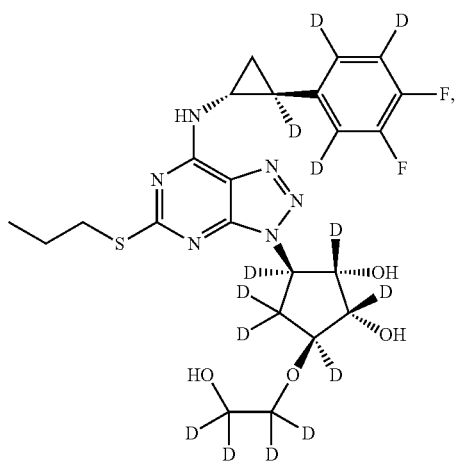
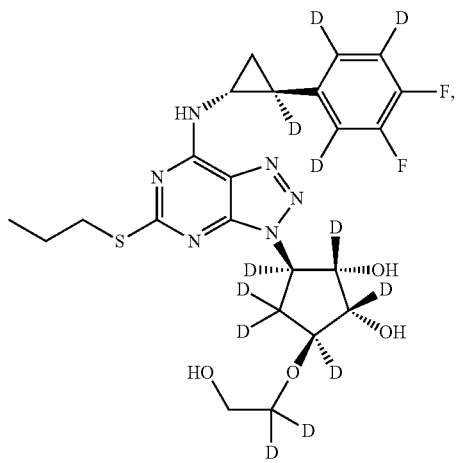
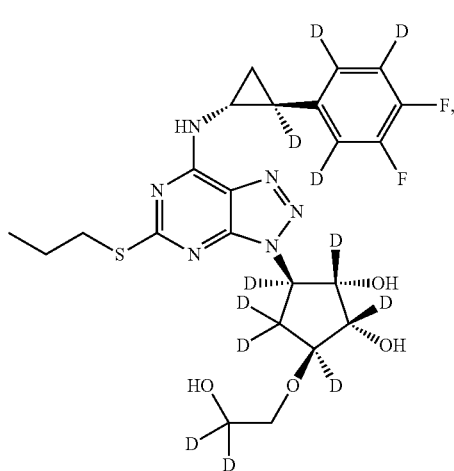

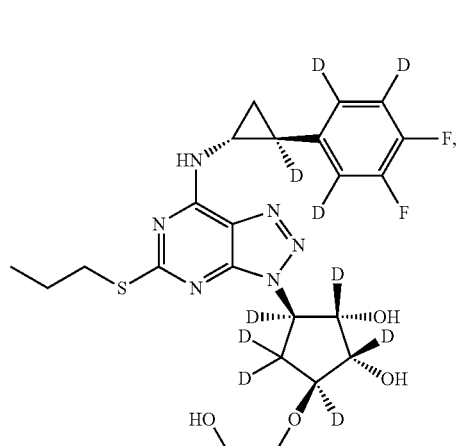
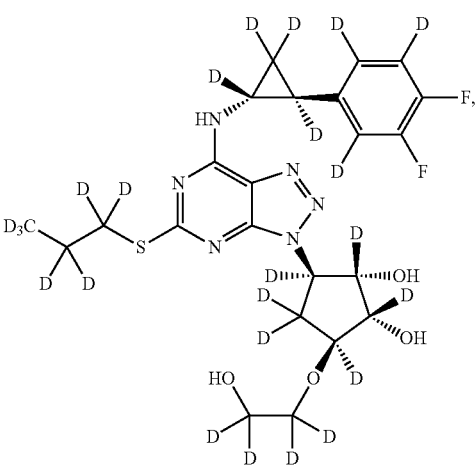
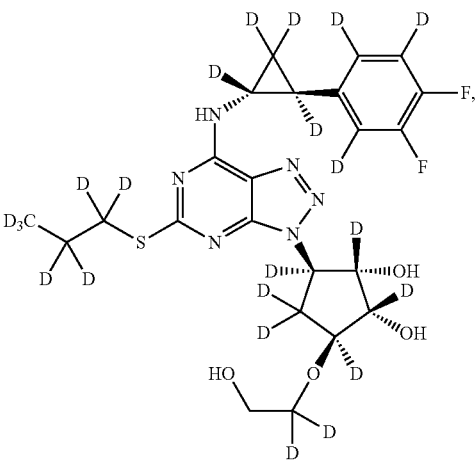
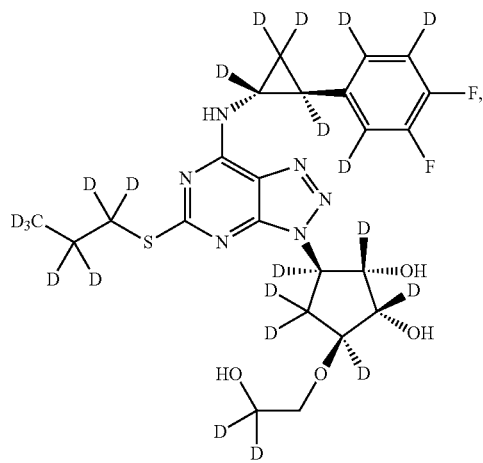
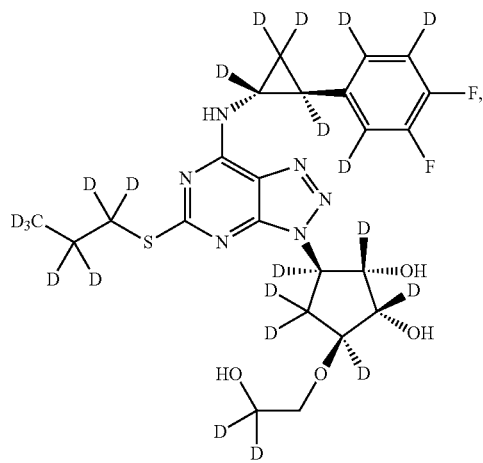
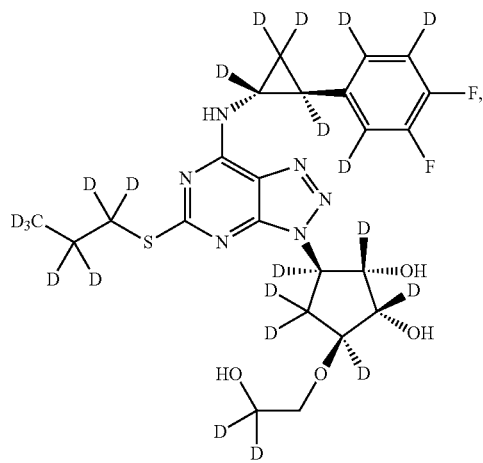

-continued
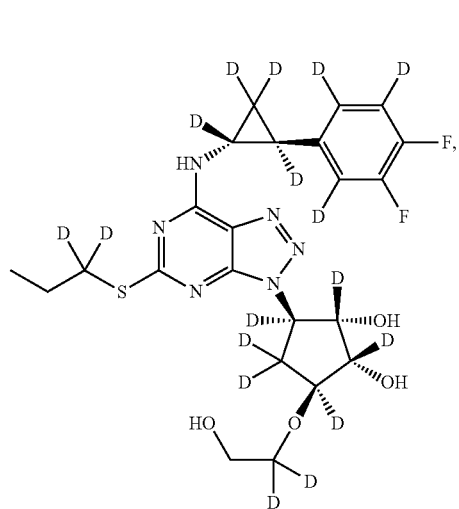
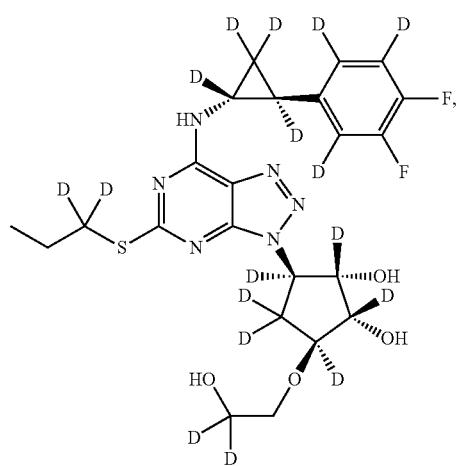
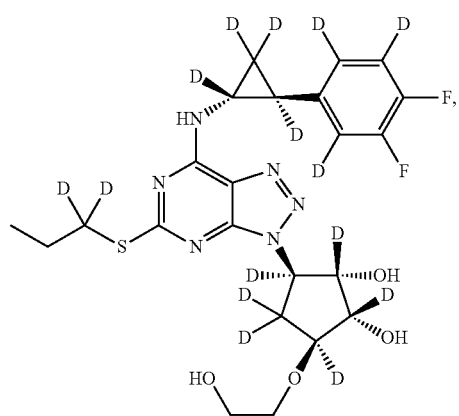
-continued
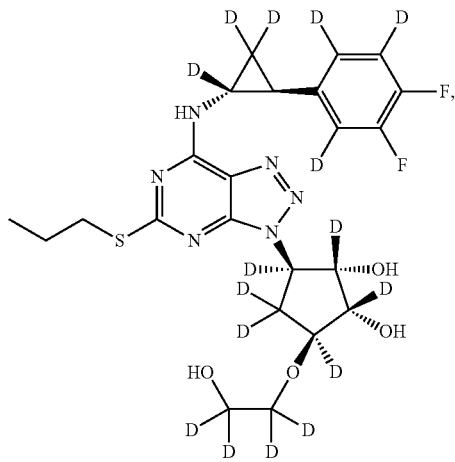
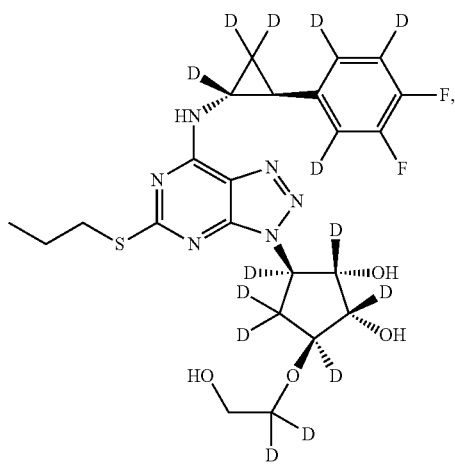
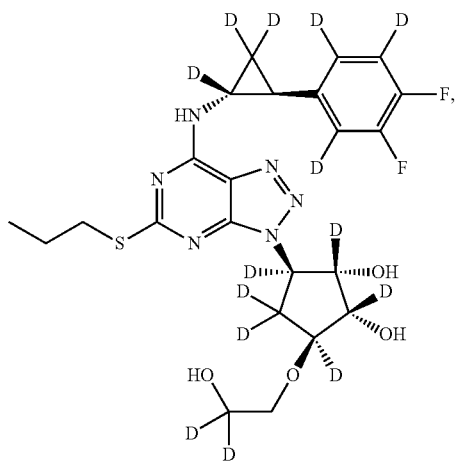

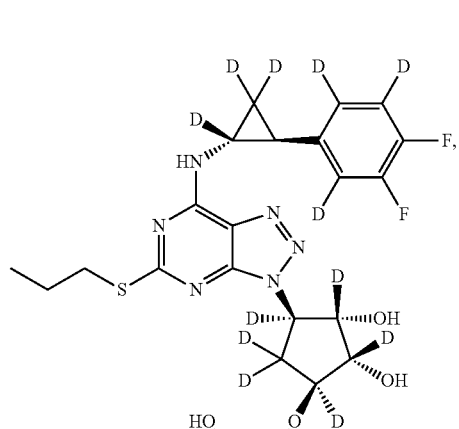
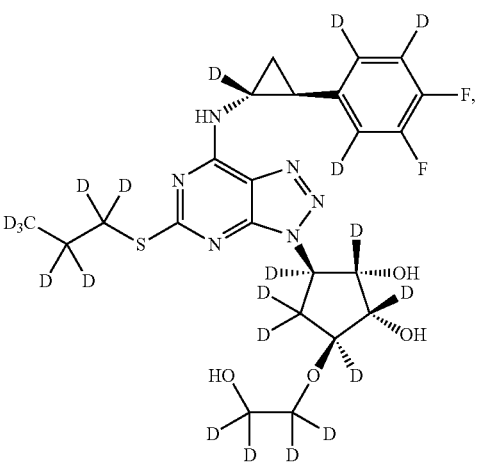
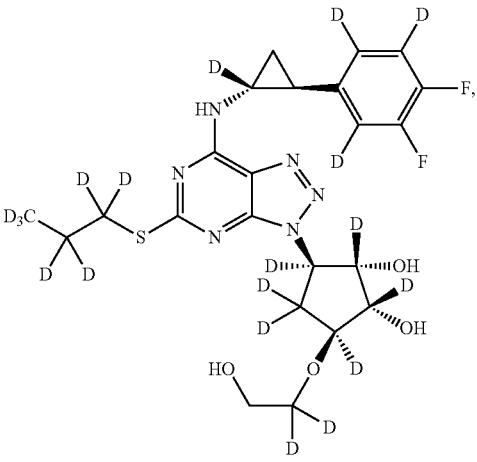
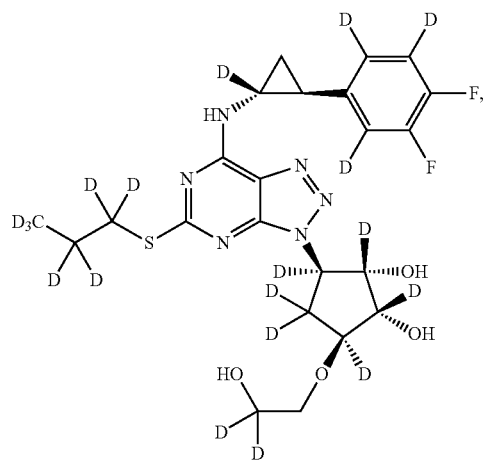
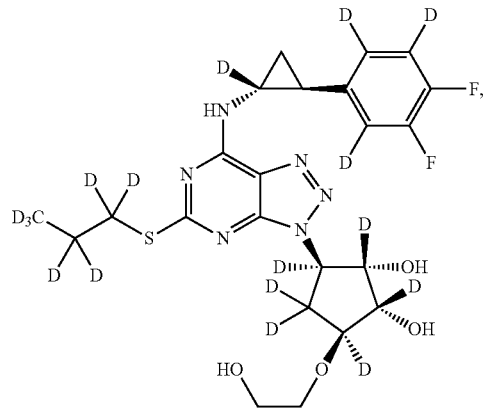
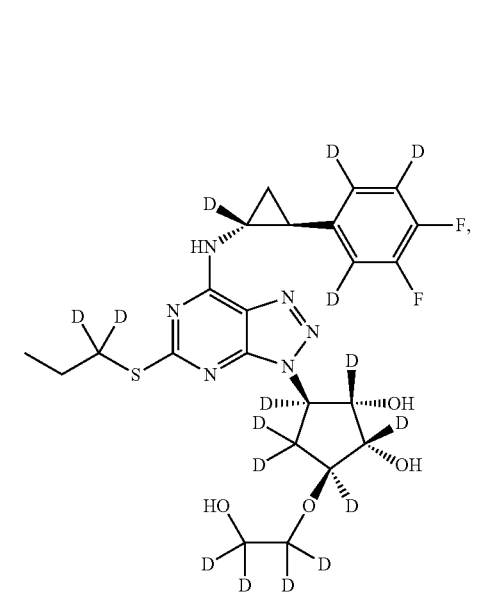

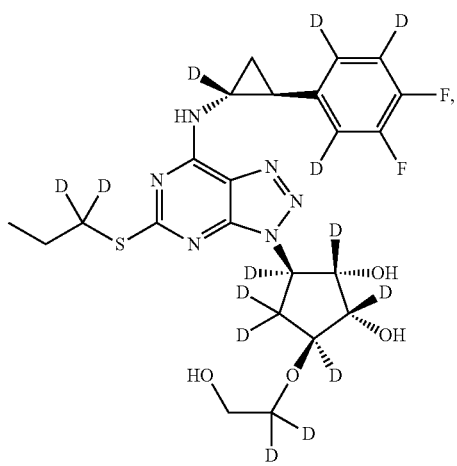
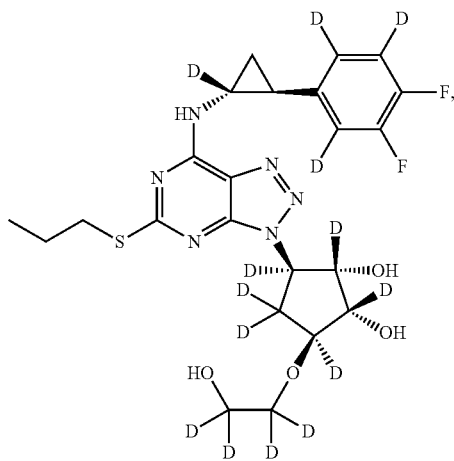
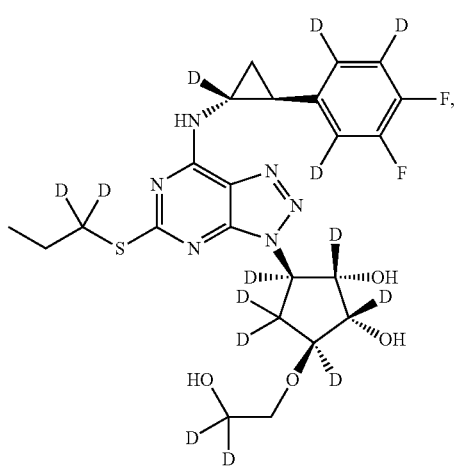
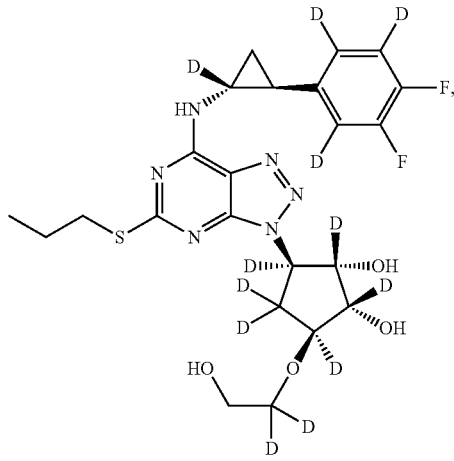
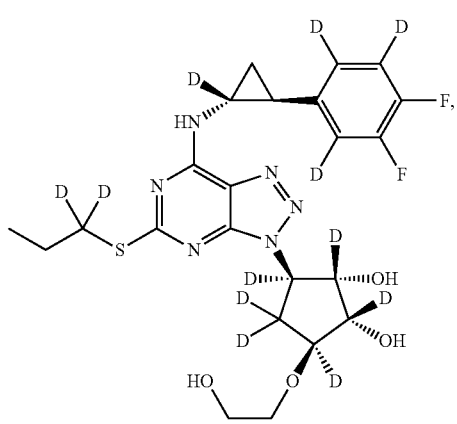
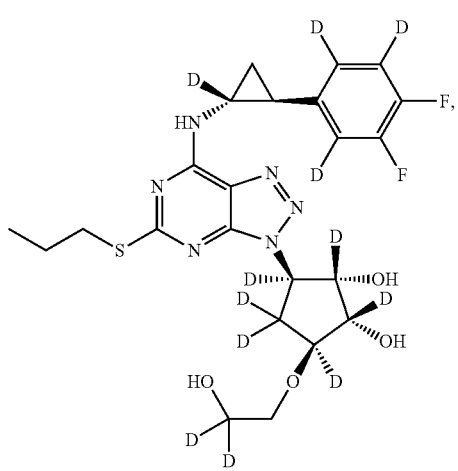

89
-continued
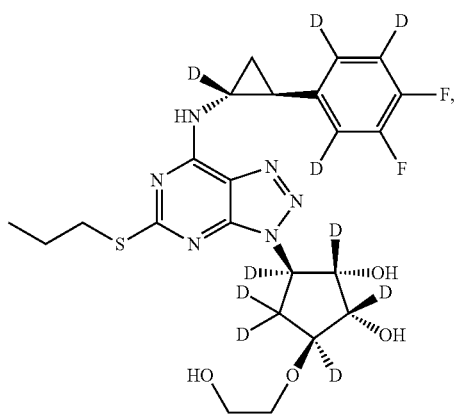
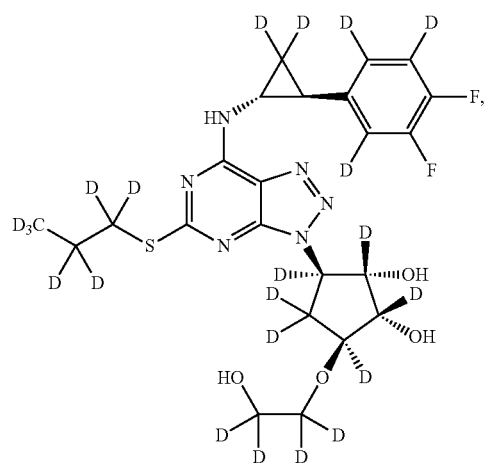
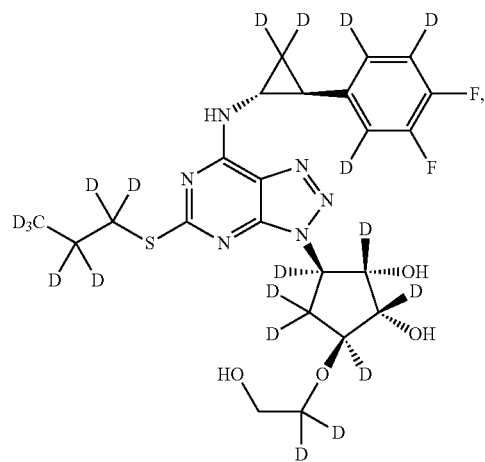
90
-continued
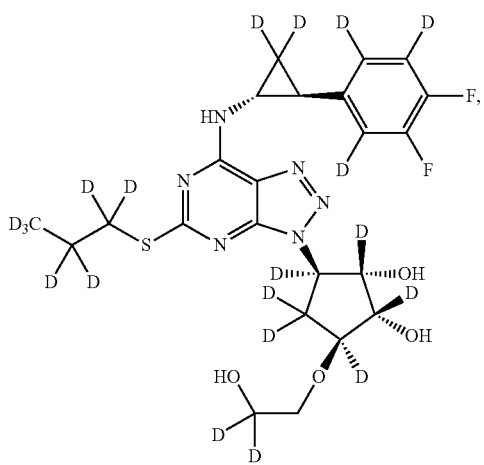
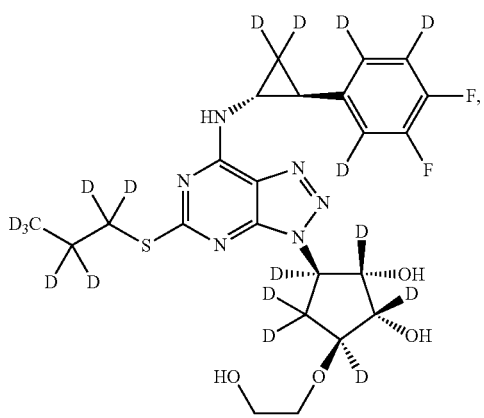
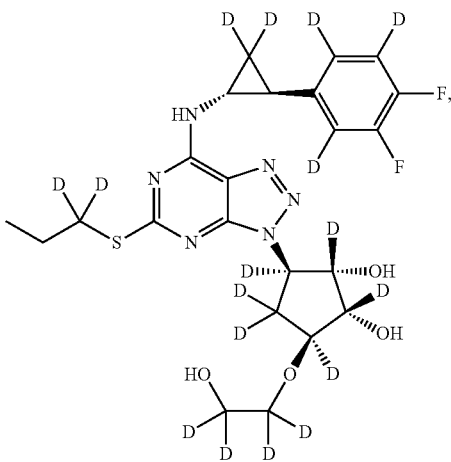

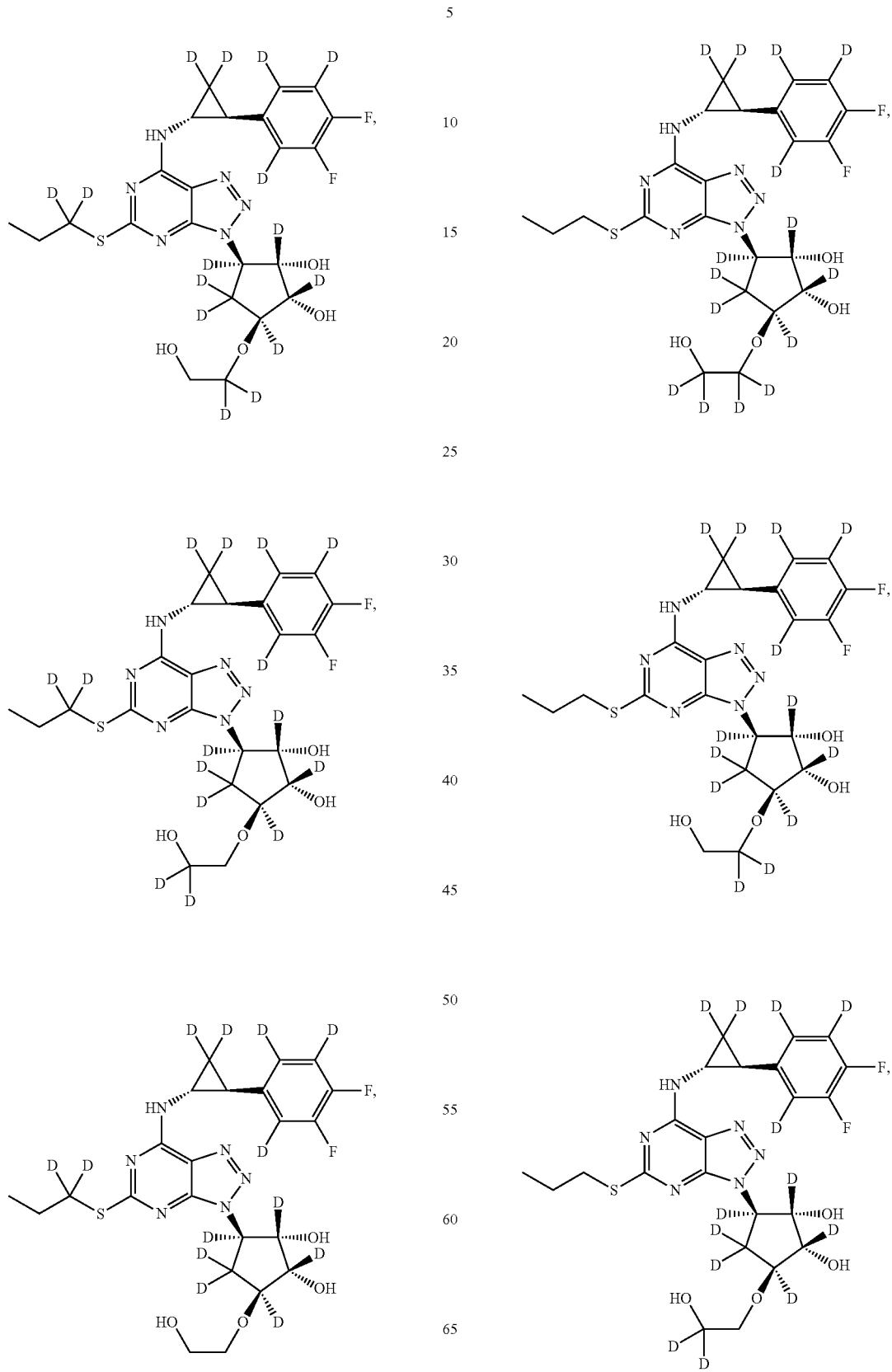

93
-continued
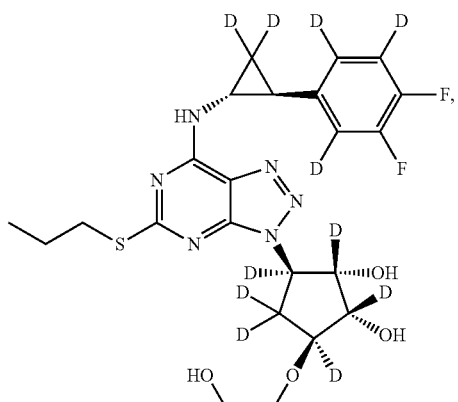
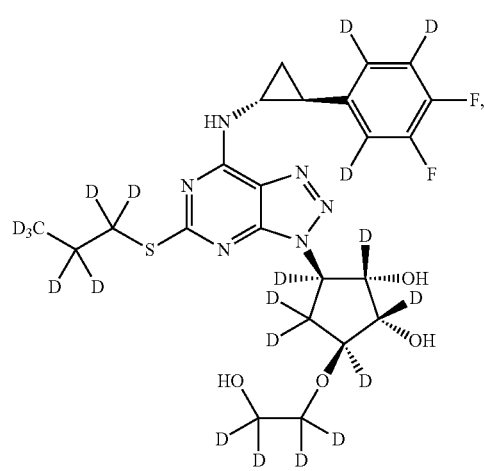
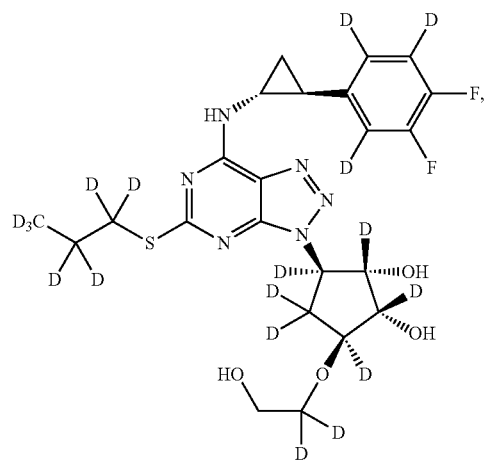
94
-continued
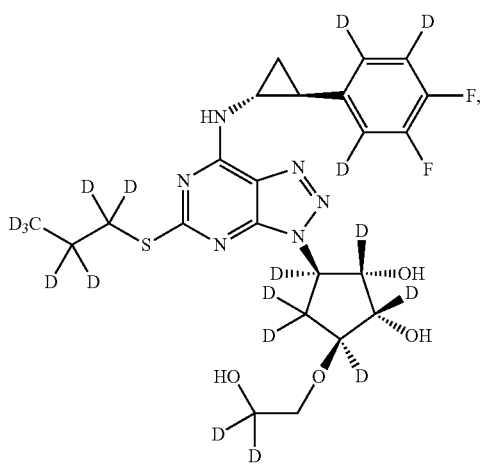
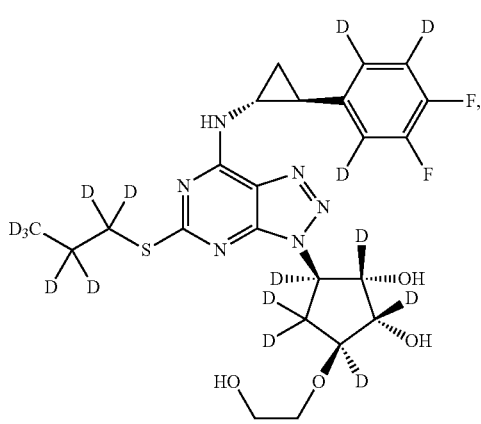
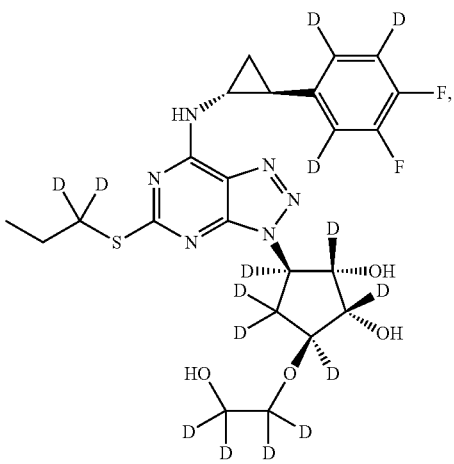

95
-continued
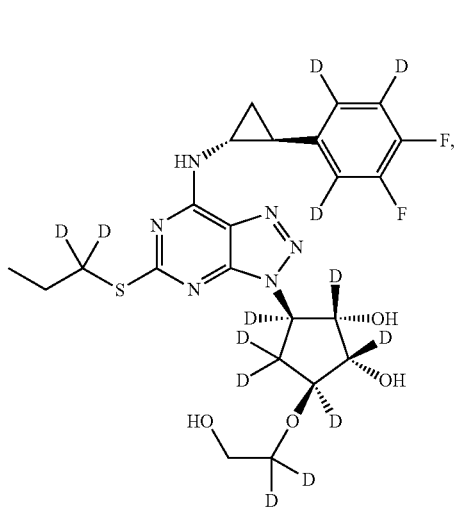
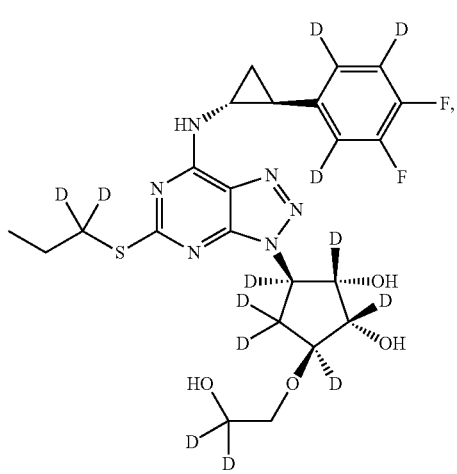
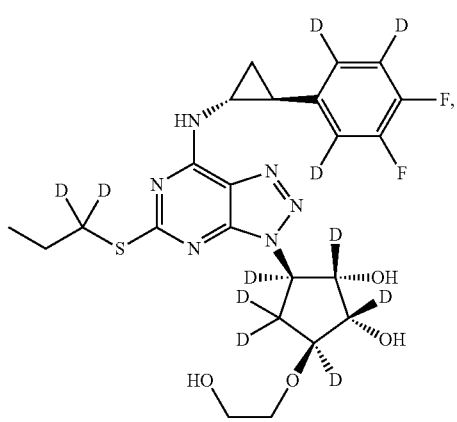
96
-continued
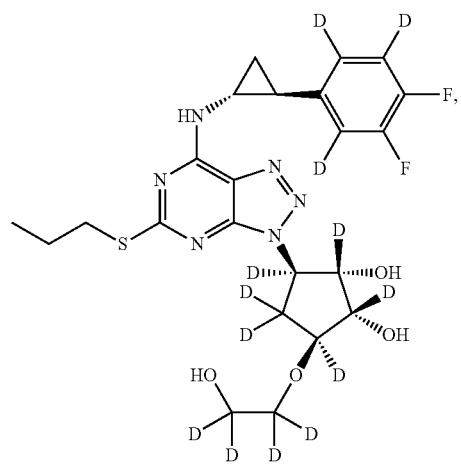
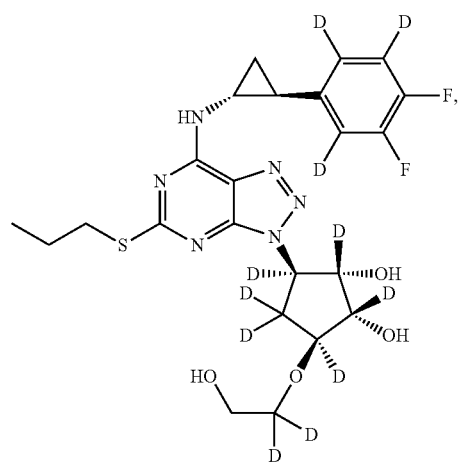
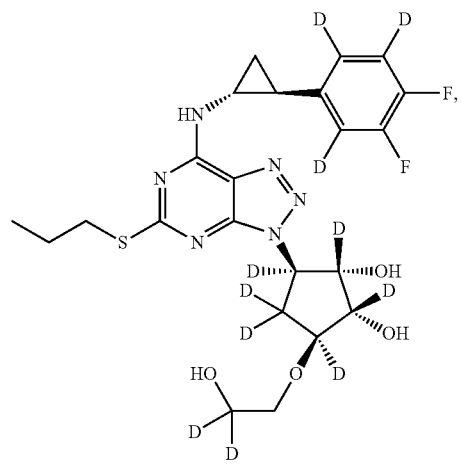

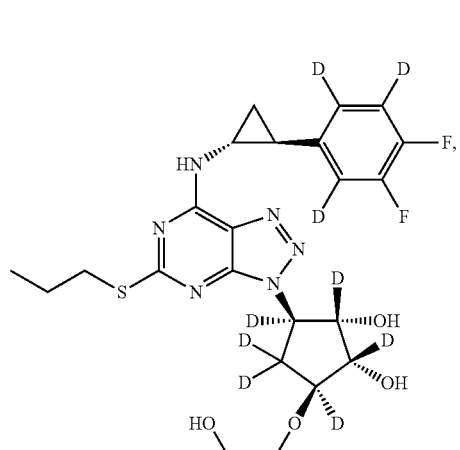
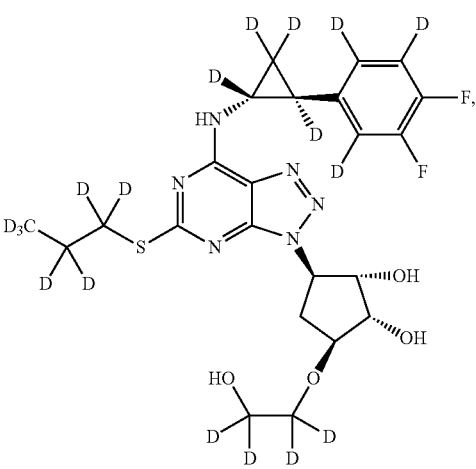
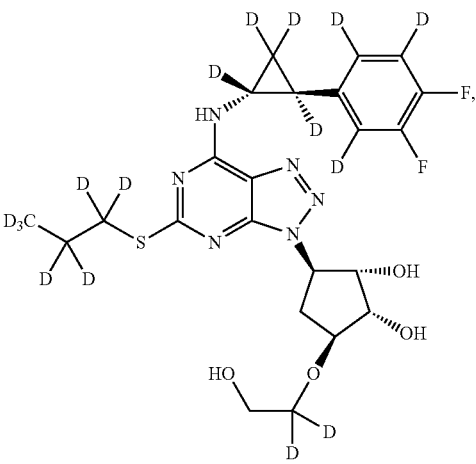
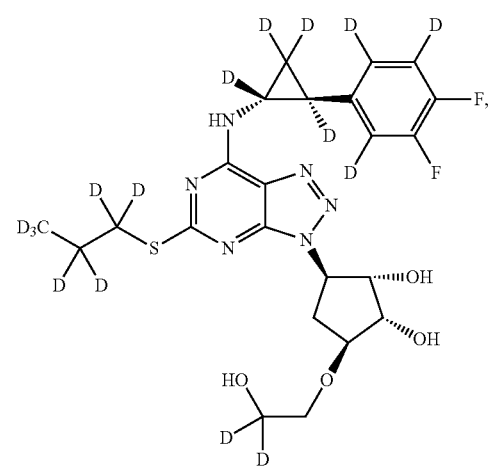
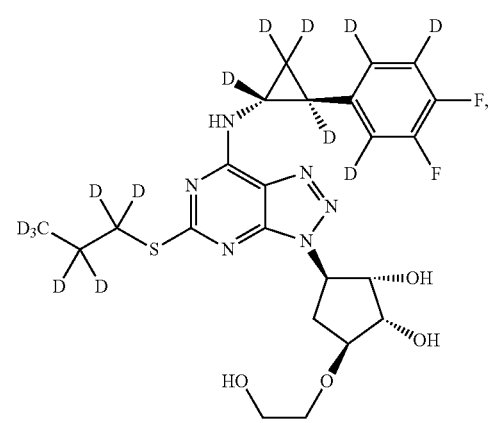
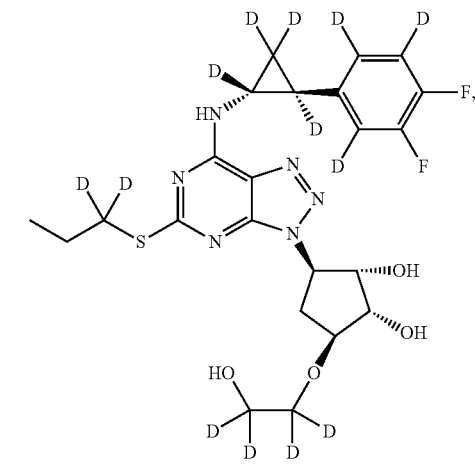

99
-continued
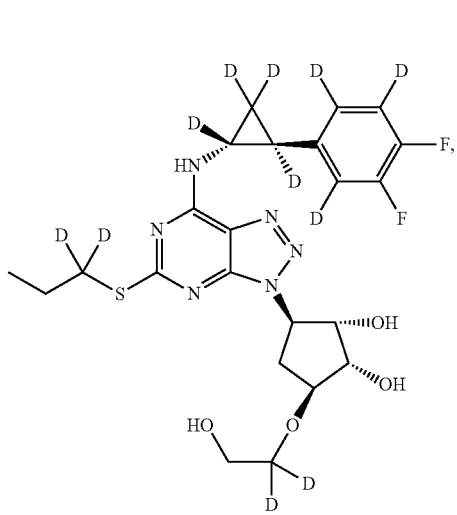
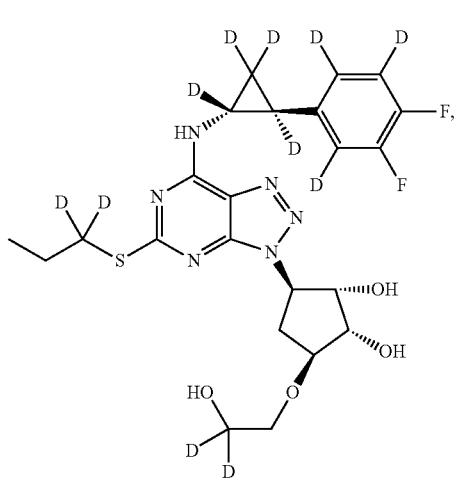
100
-continued
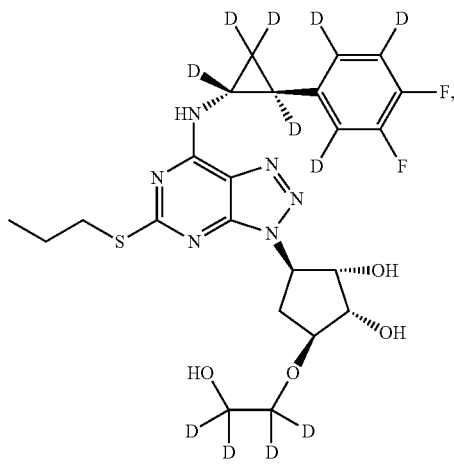
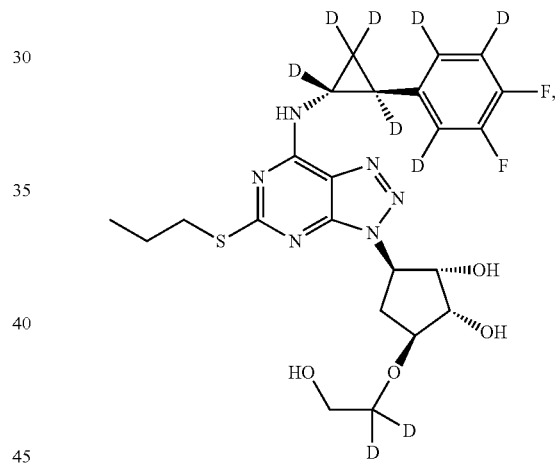
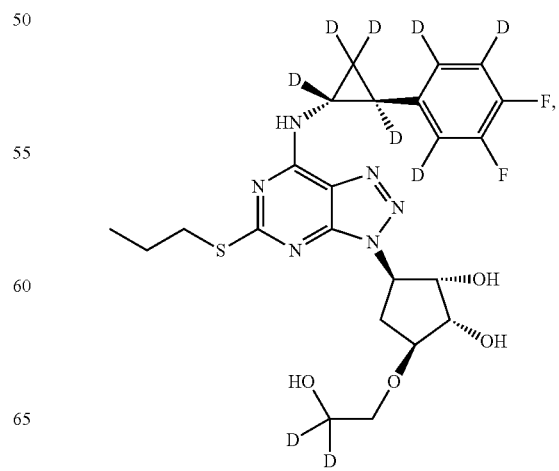

101
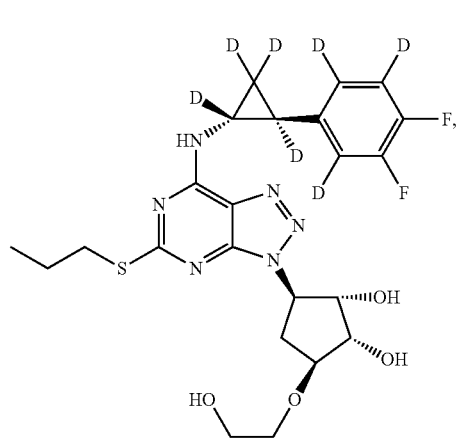
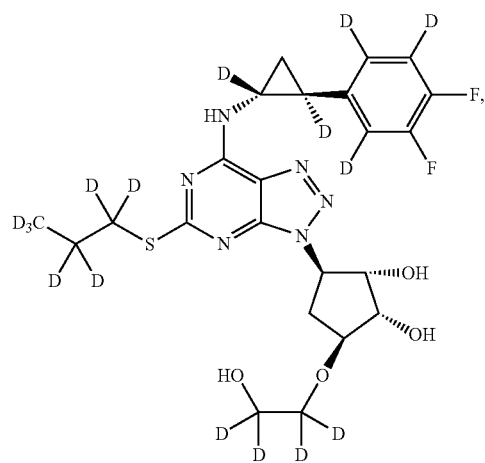
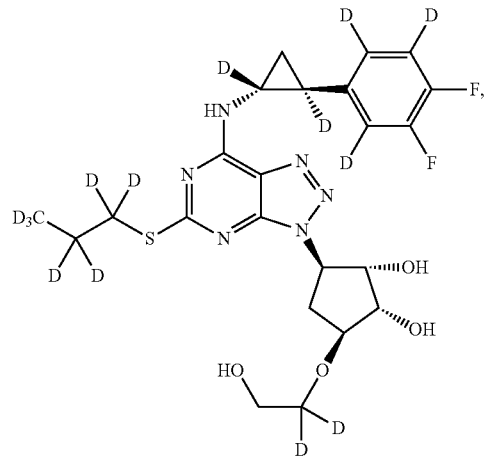
102
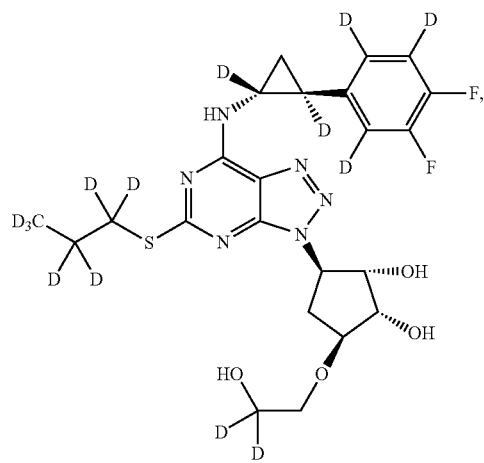
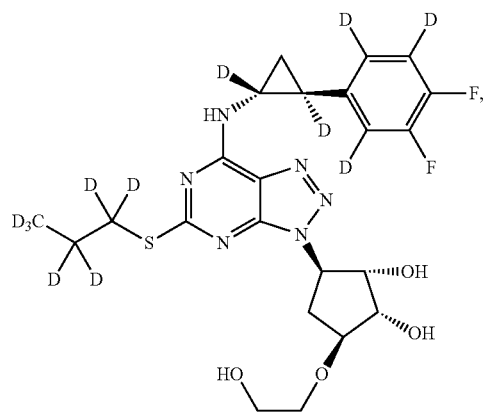
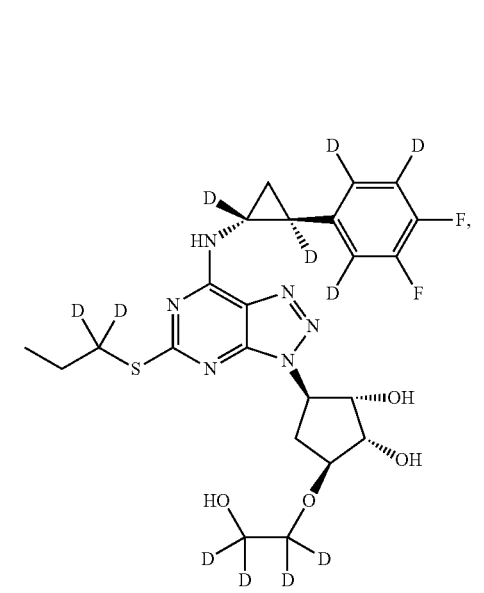

103
-continued
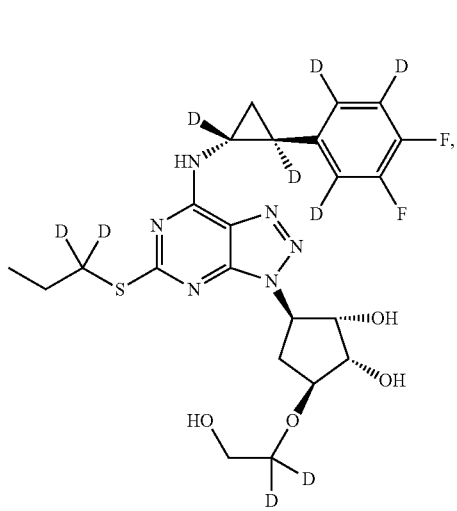
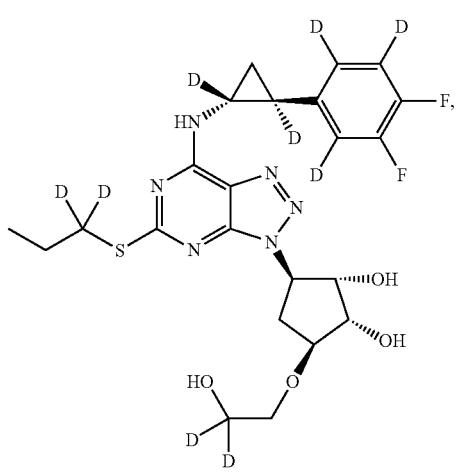
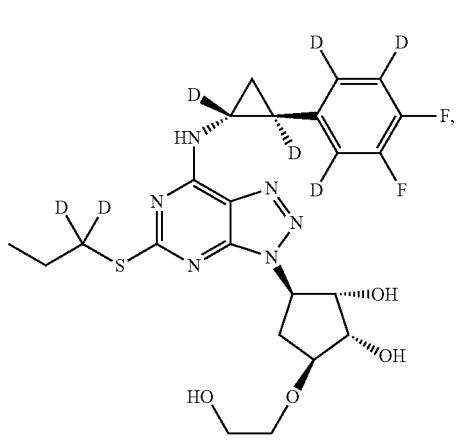
104
-continued
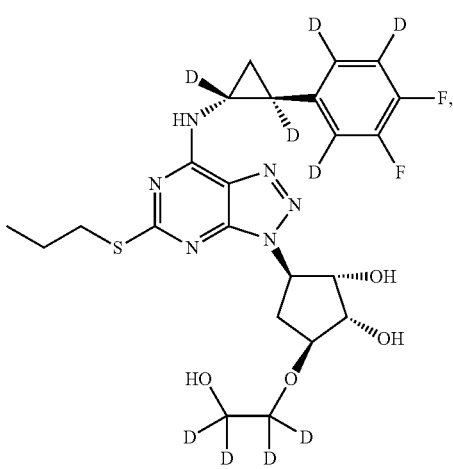
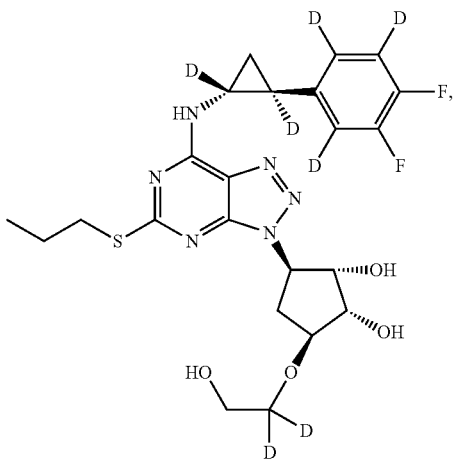
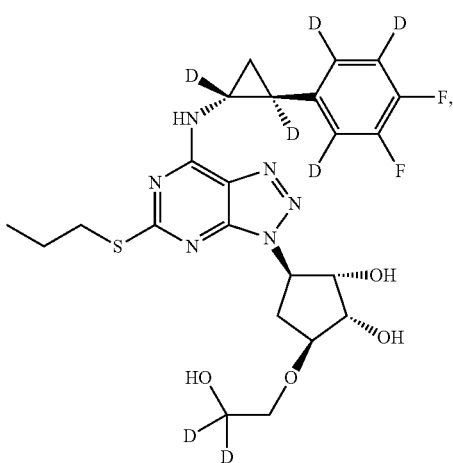

105
-continued
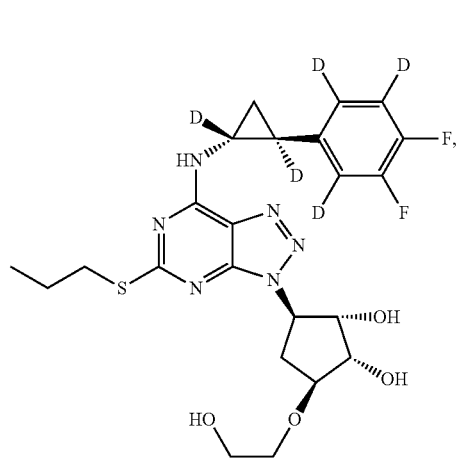
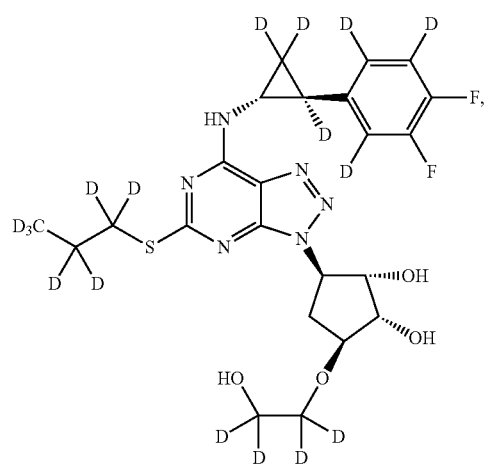
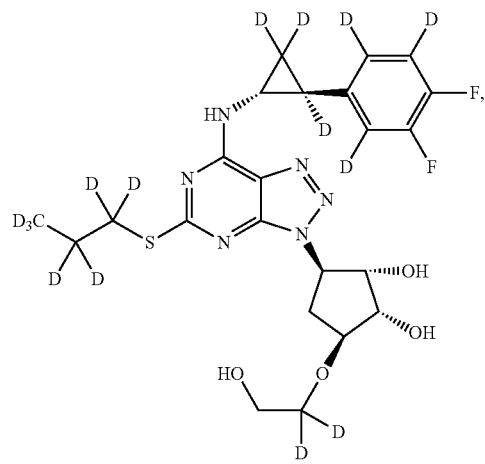
106
-continued
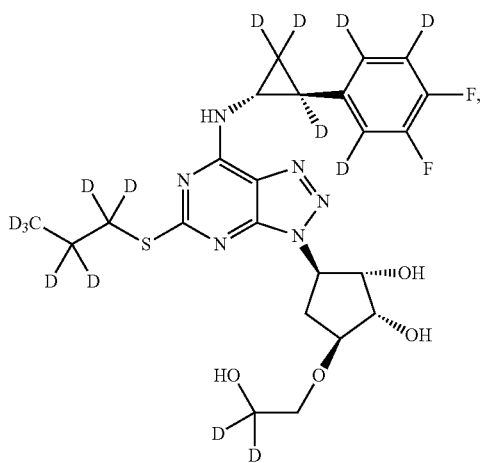
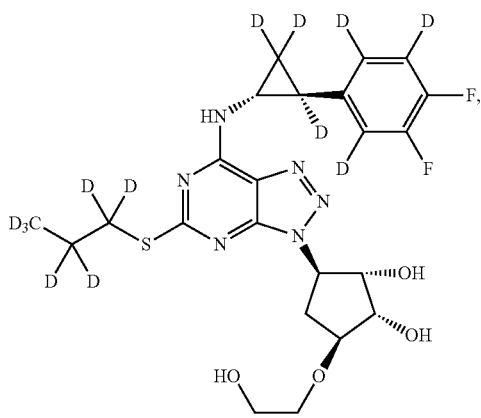
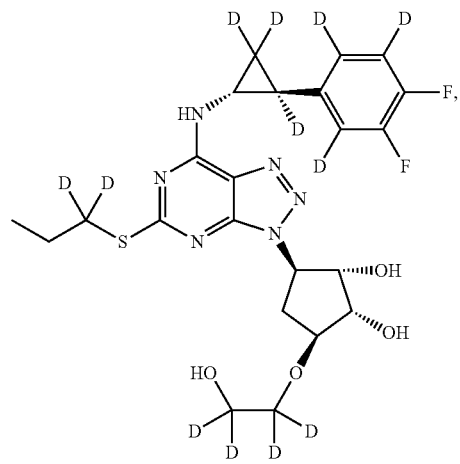

107
-continued
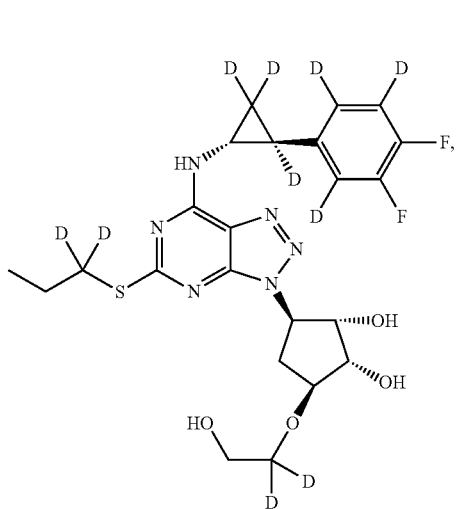
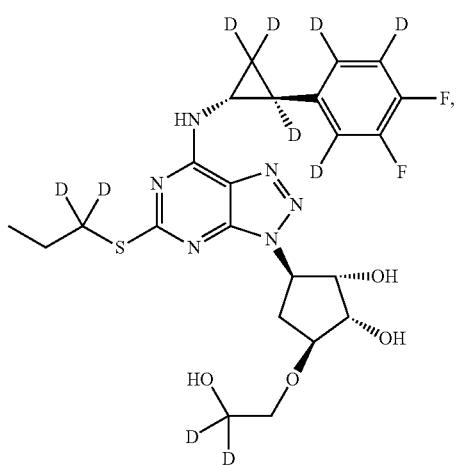
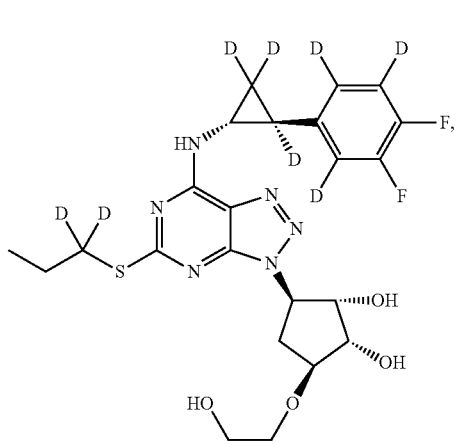
108
-continued
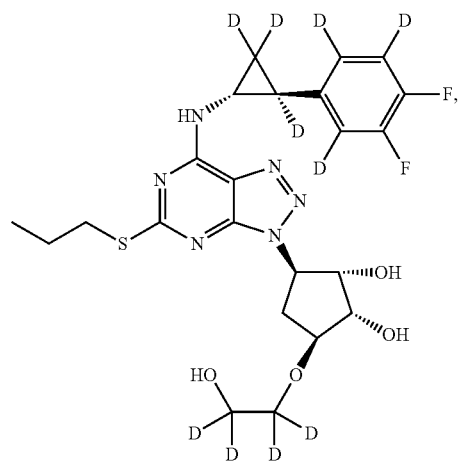
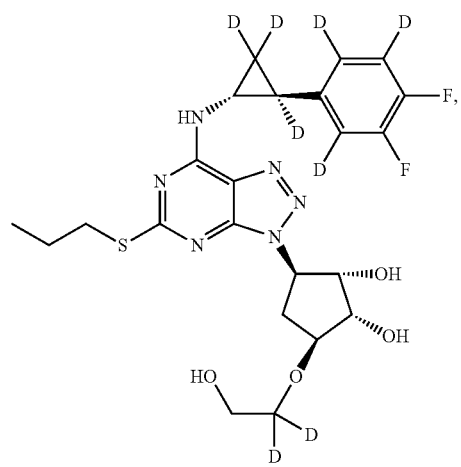
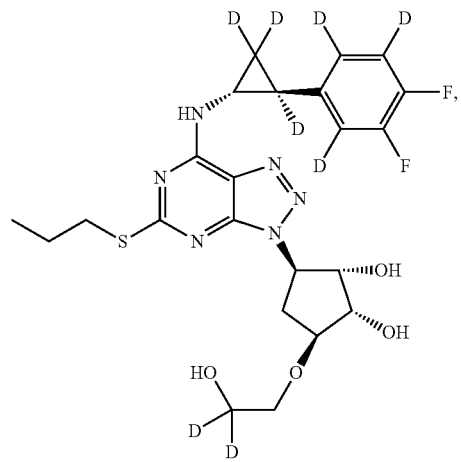

109
-continued
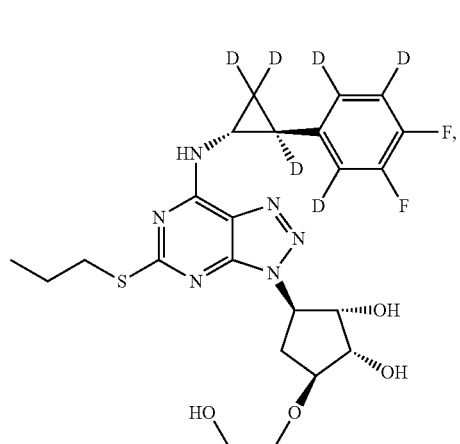
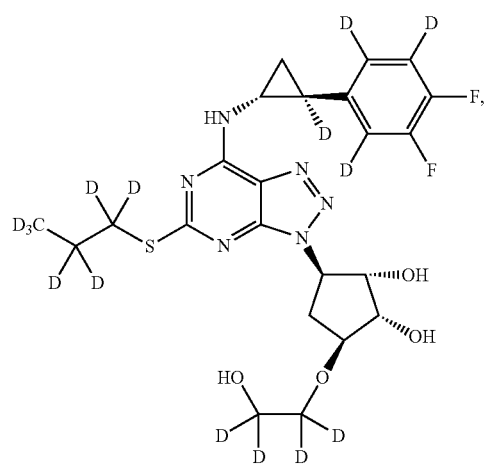
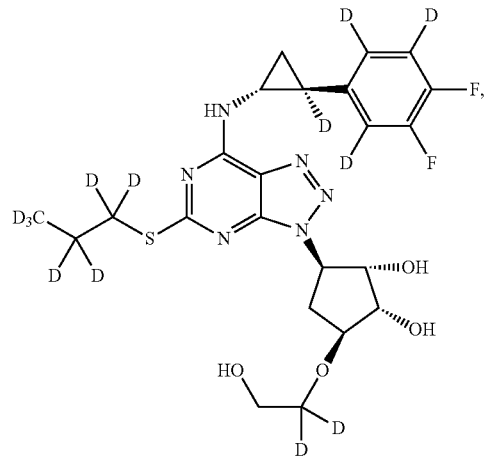
110
-continued
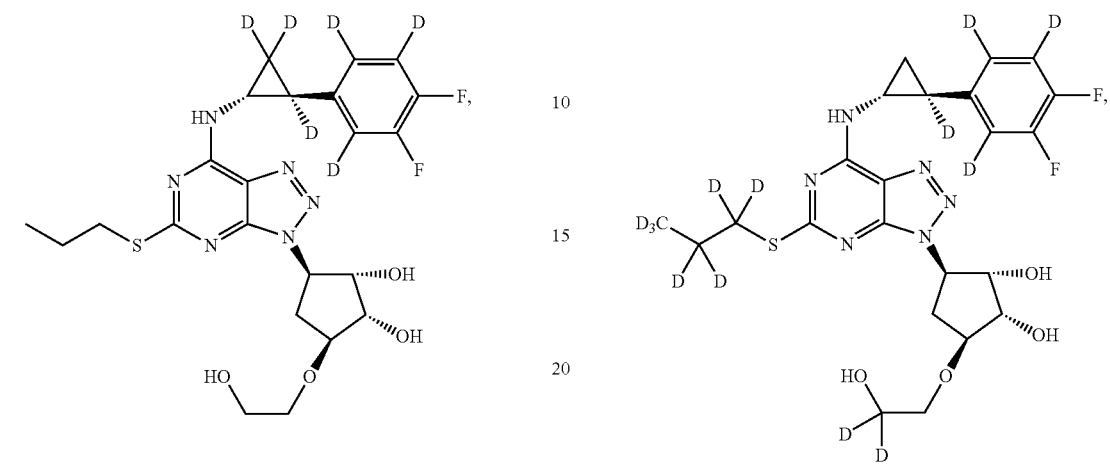
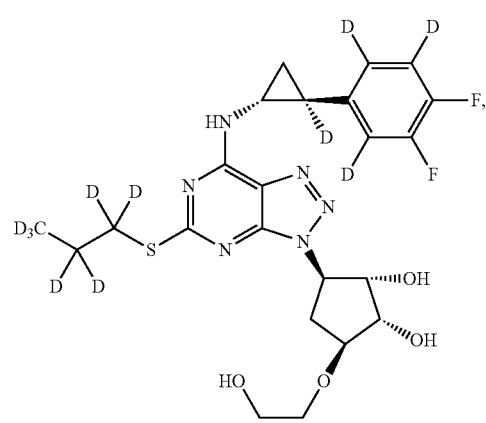
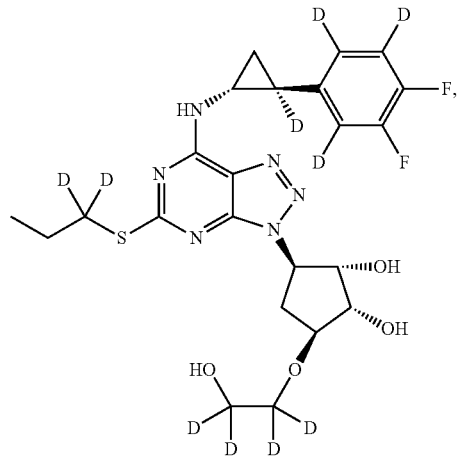

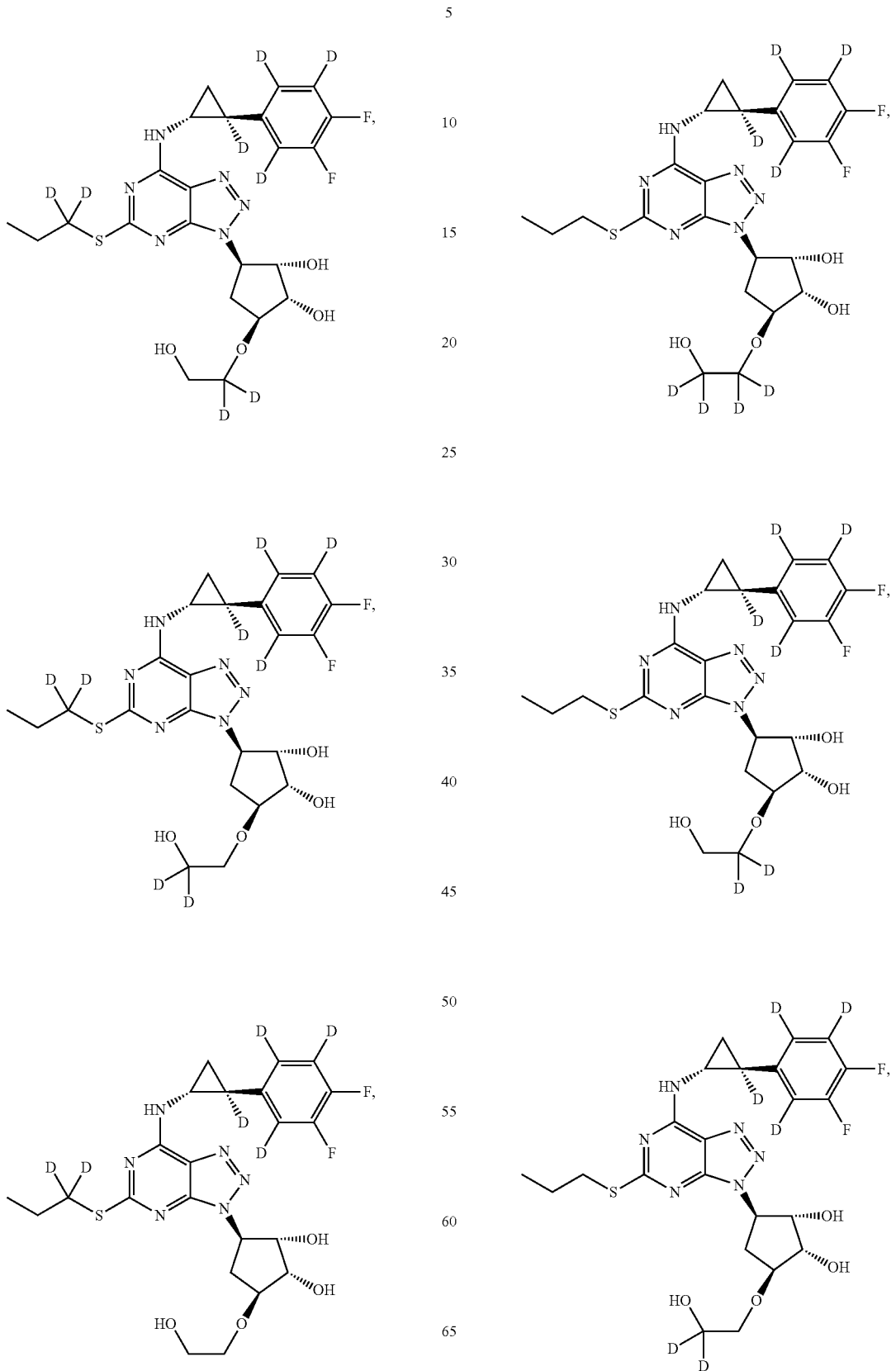

113
-continued
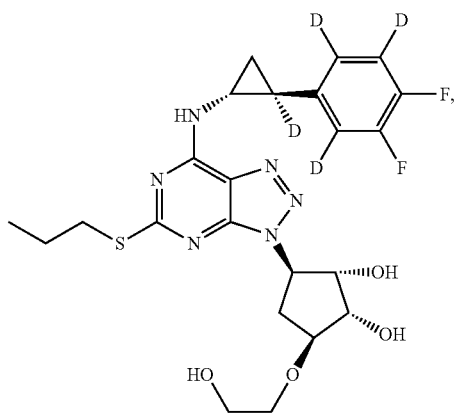
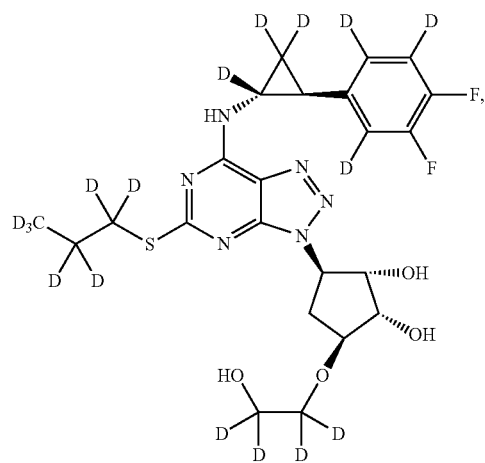
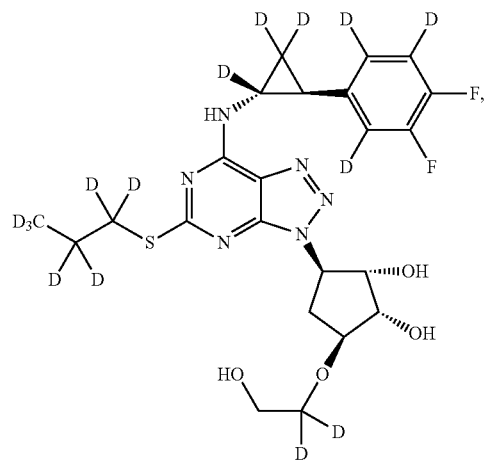
114
-continued
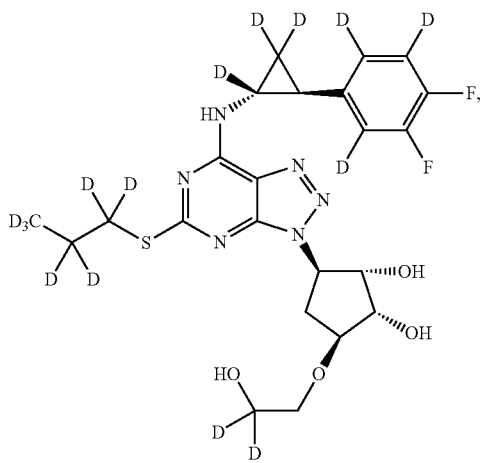
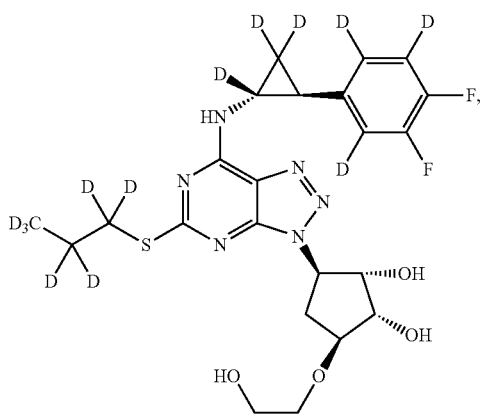
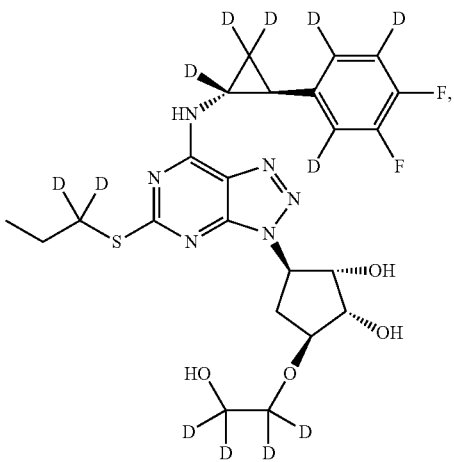

115
-continued
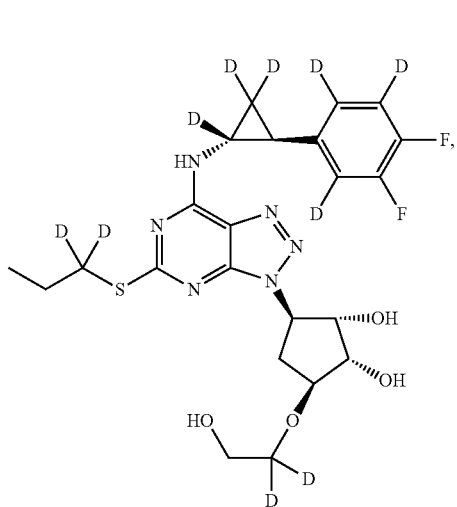
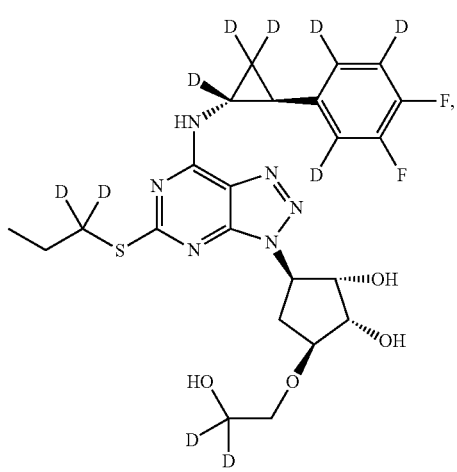
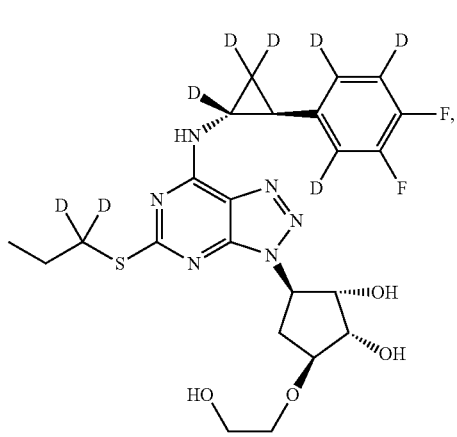
116
-continued
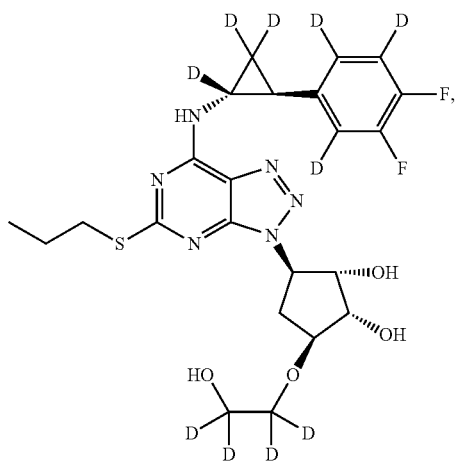
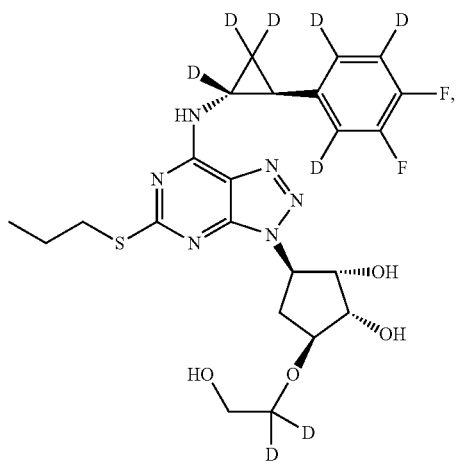
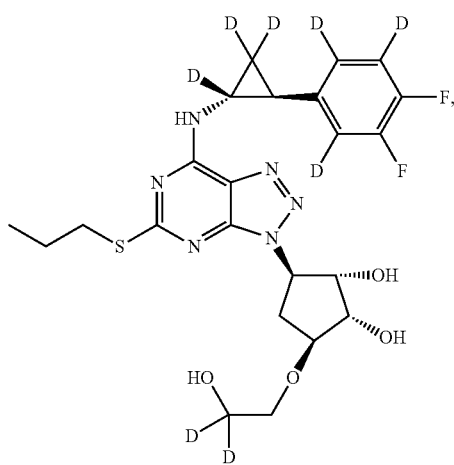

117
-continued
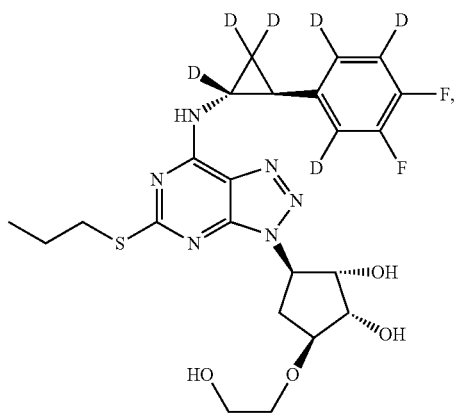
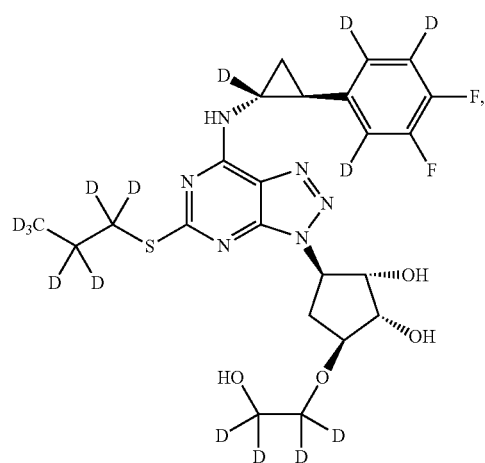
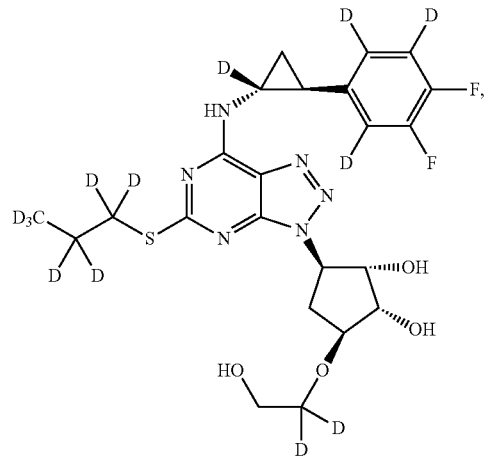
118
-continued
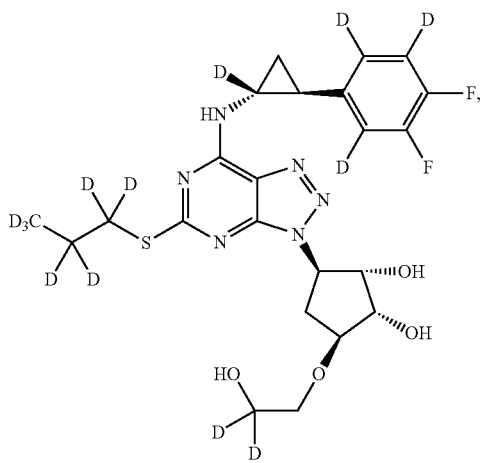
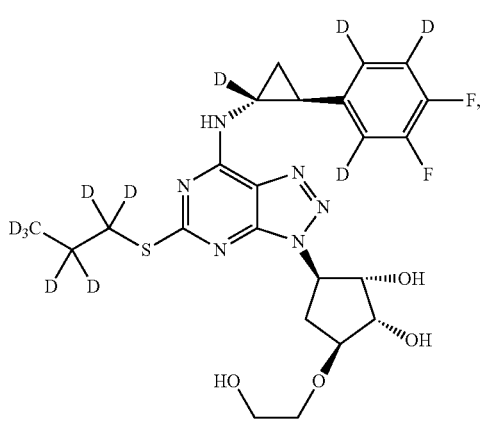
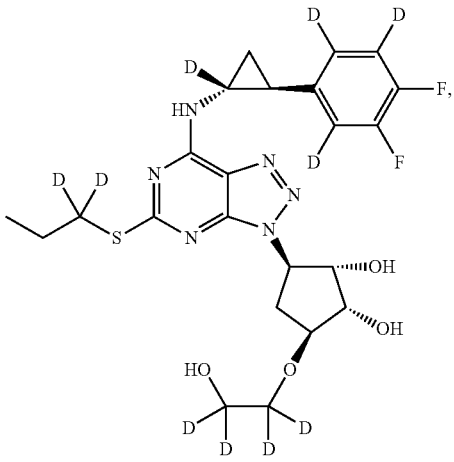

119
-continued
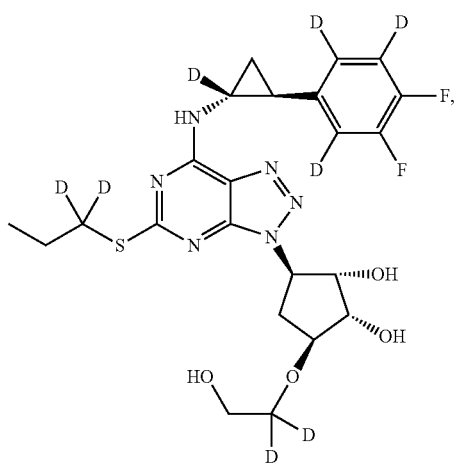
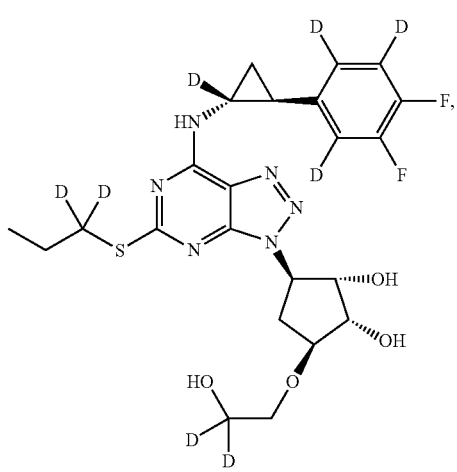
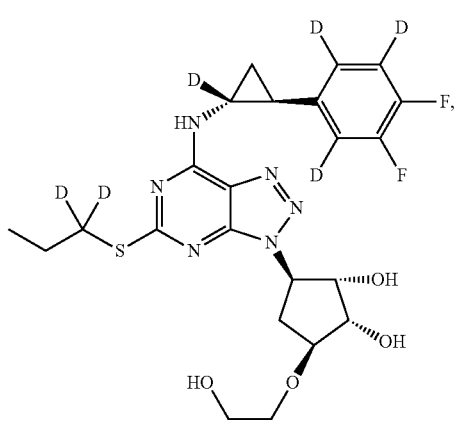
120
-continued
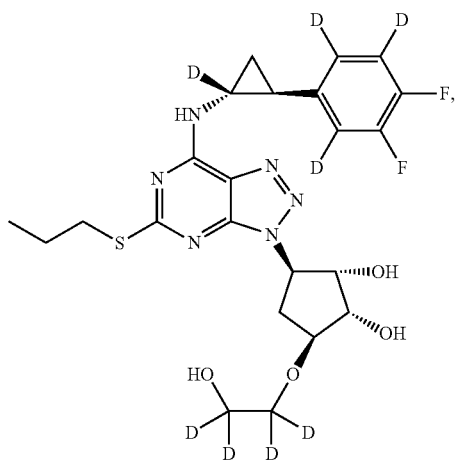
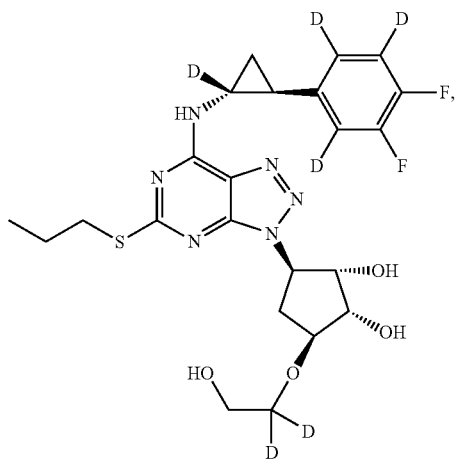
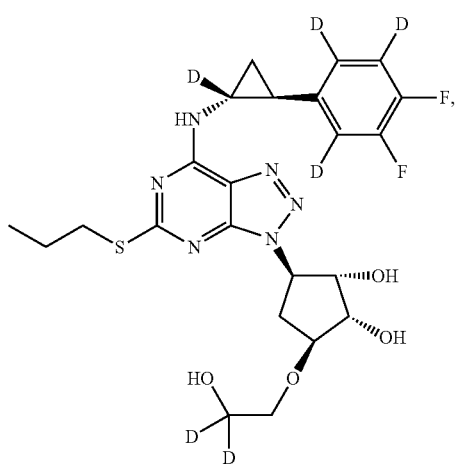

121
-continued
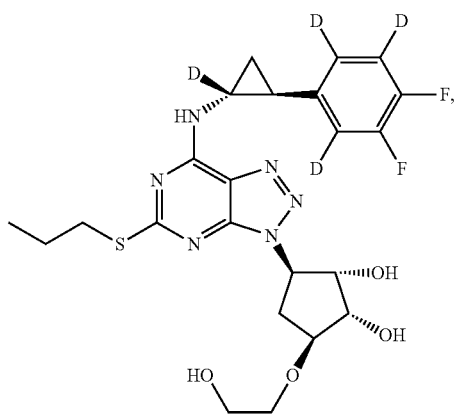
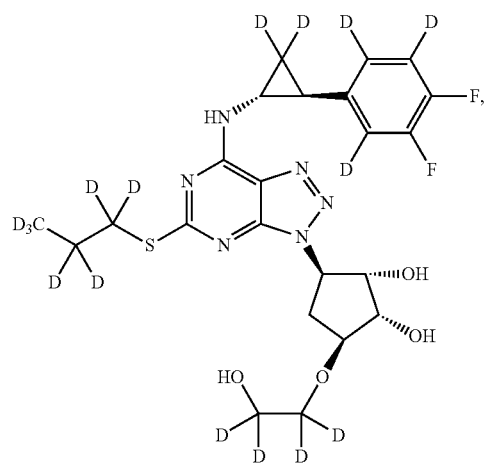
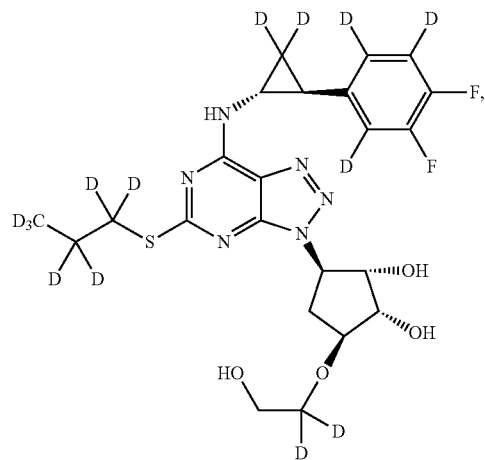
122
-continued
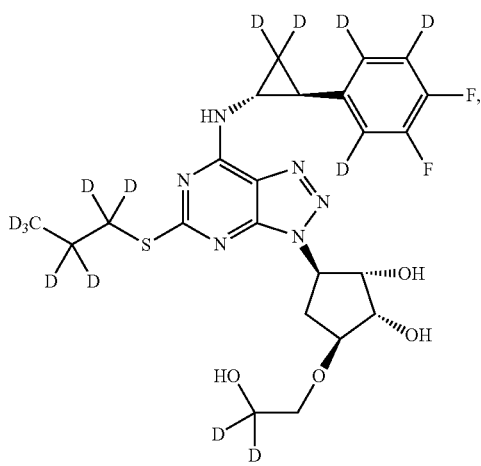
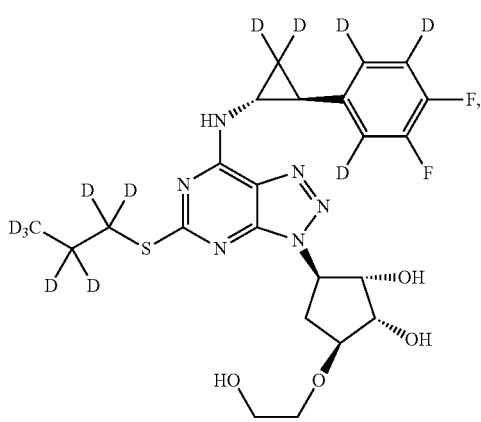
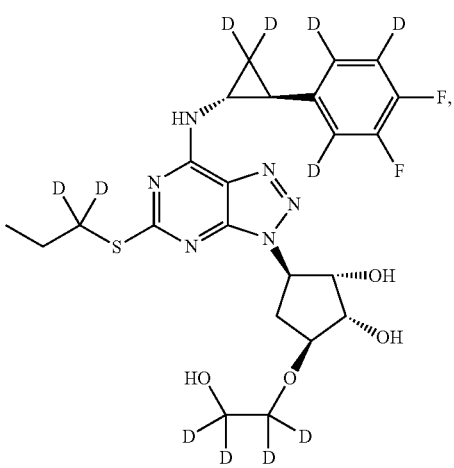

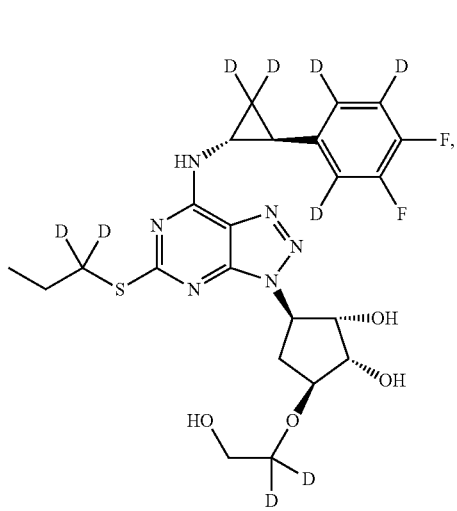
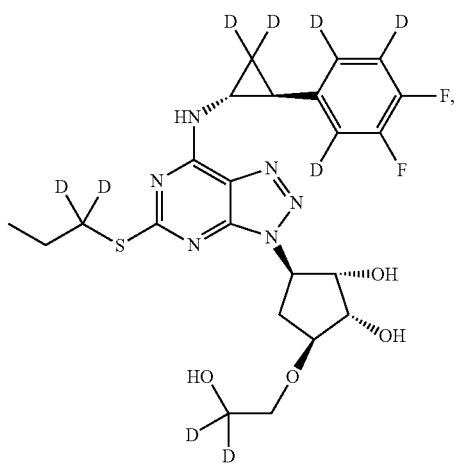
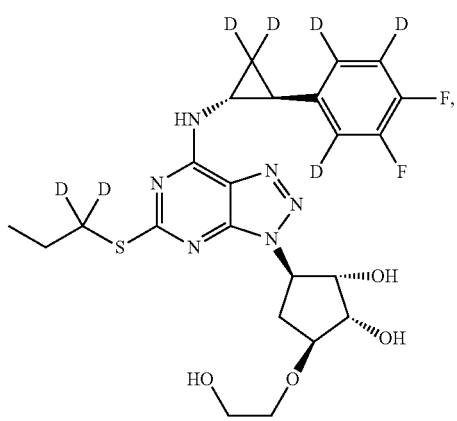
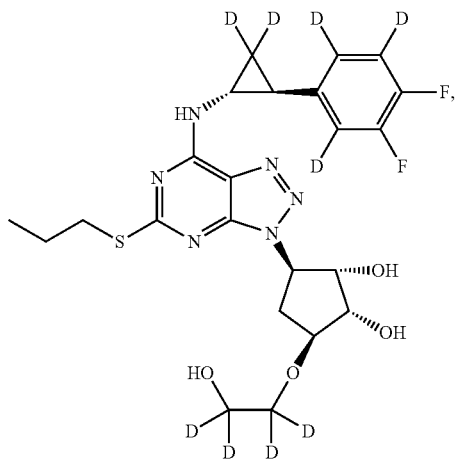
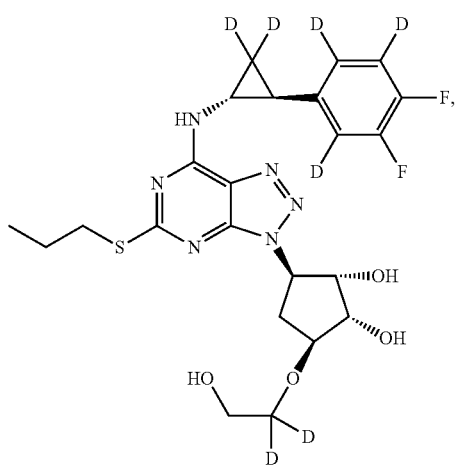
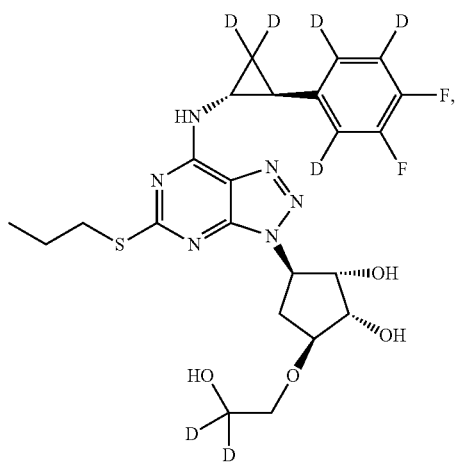

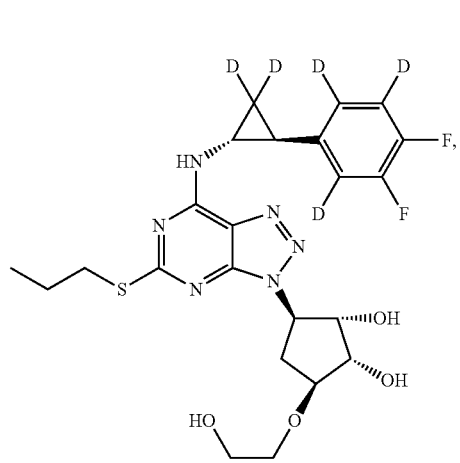
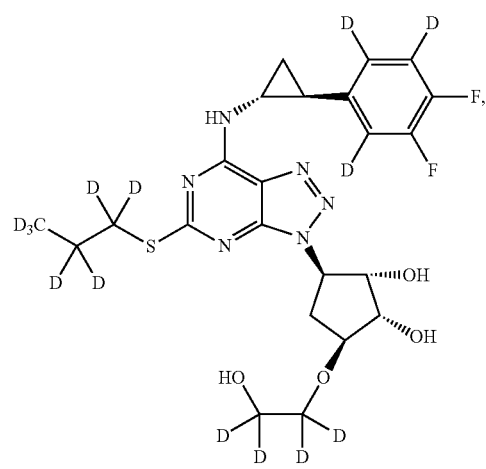
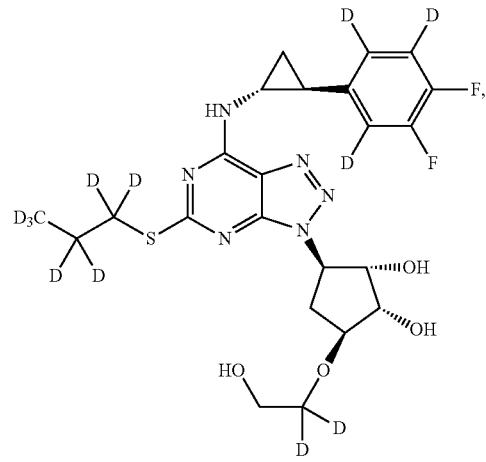
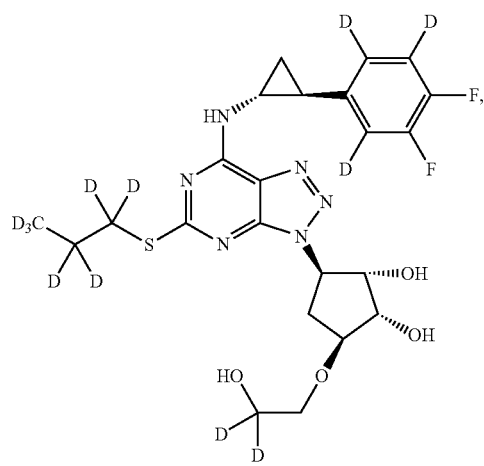
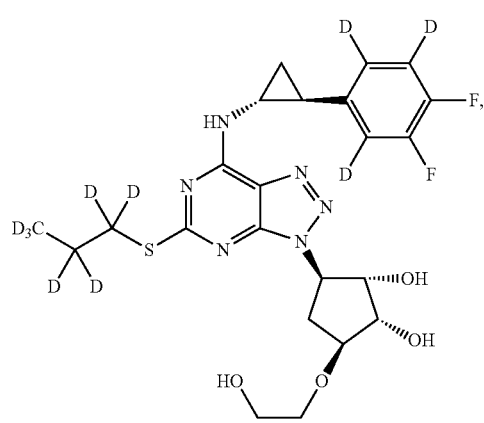
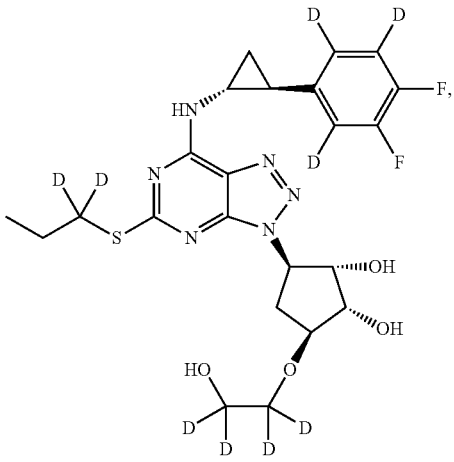

127
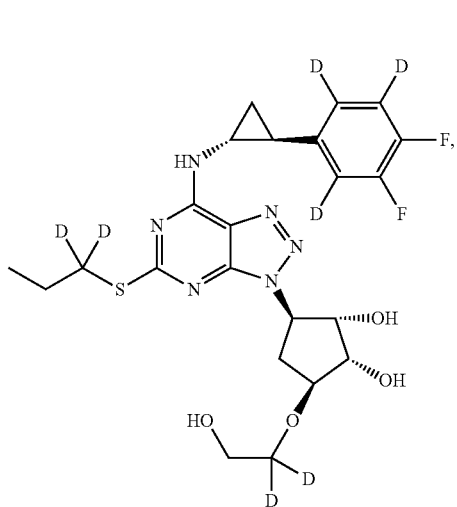
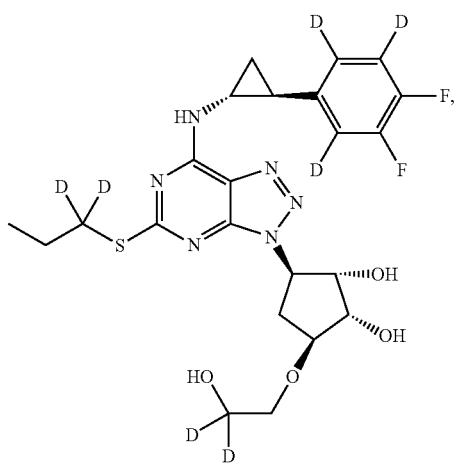
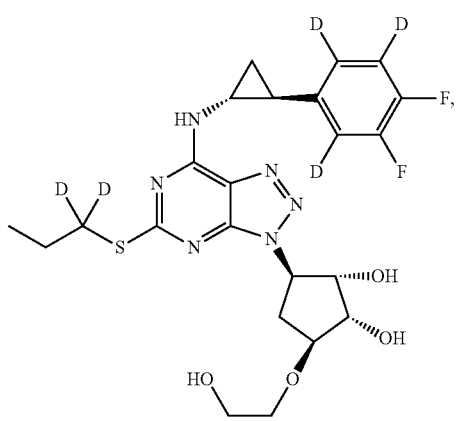
128
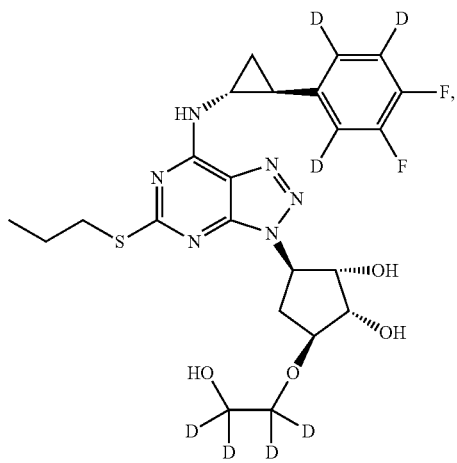
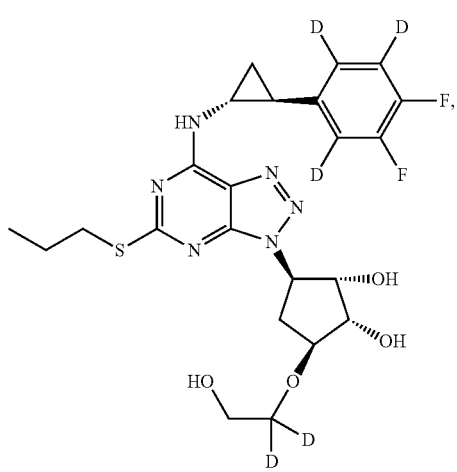
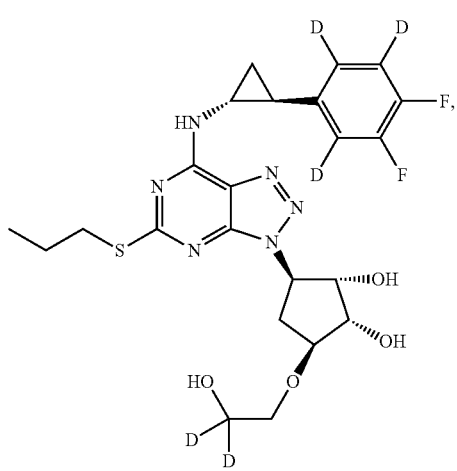

129
-continued
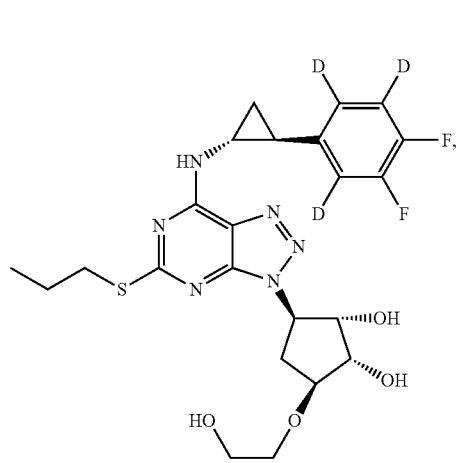
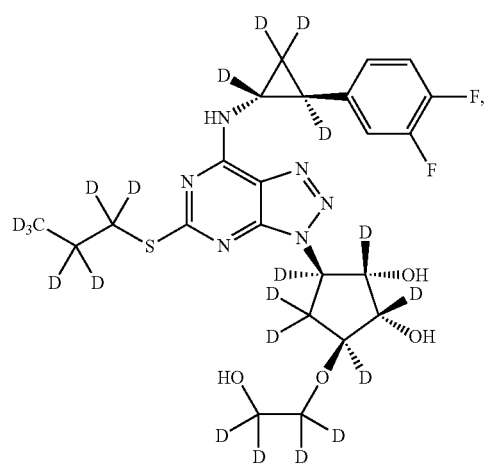
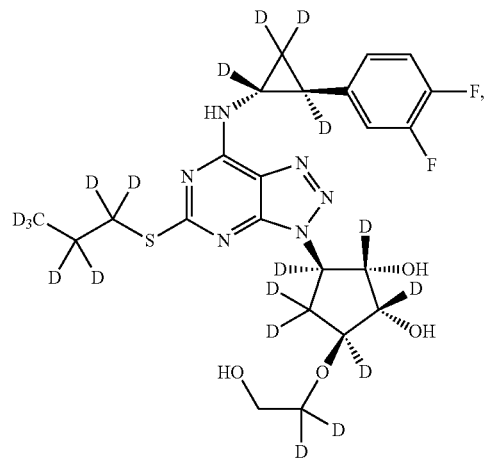
130
-continued
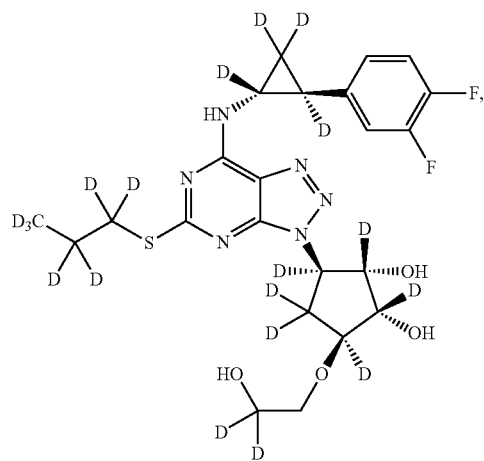
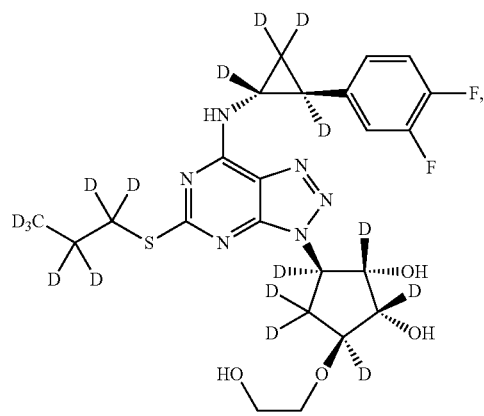
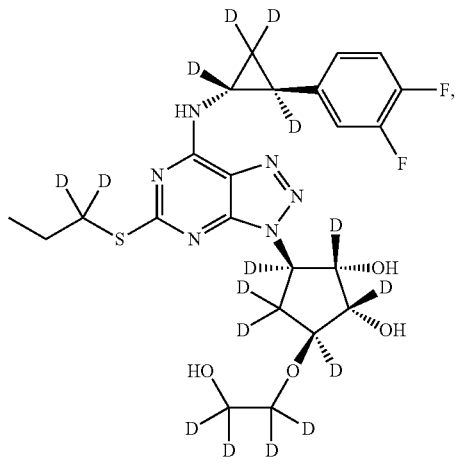

131
-continued
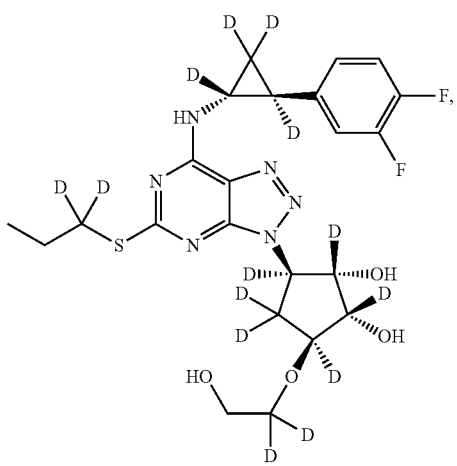
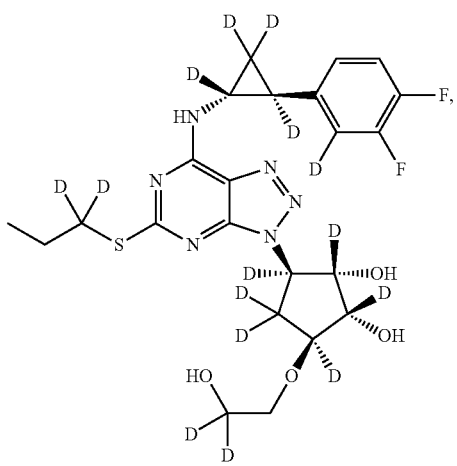
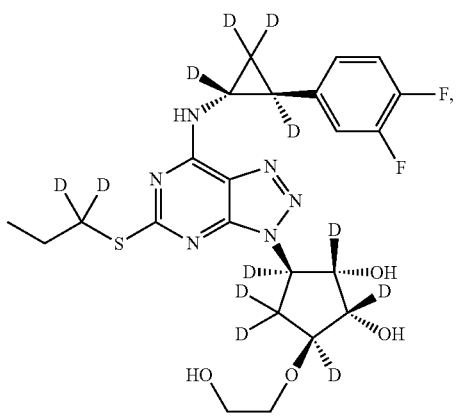
132
-continued
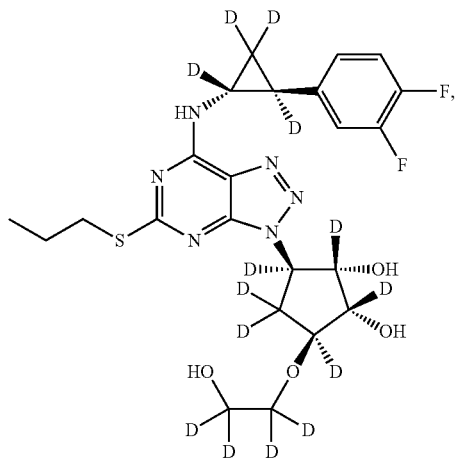
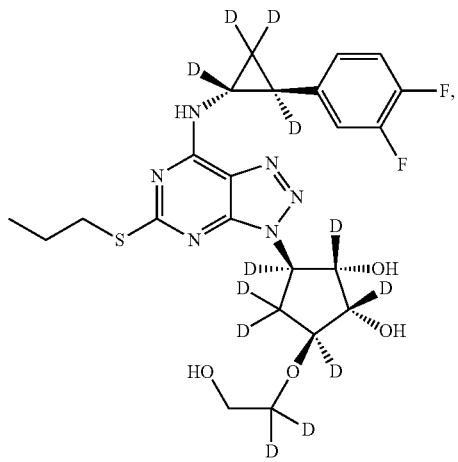
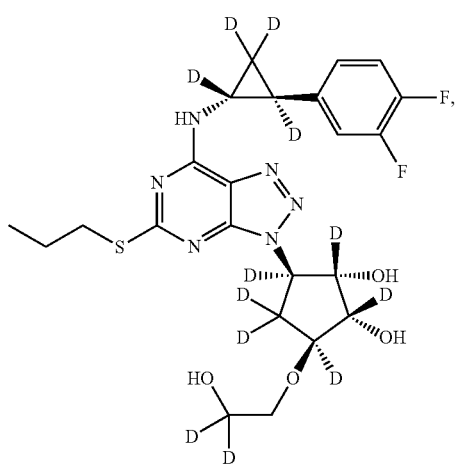

133
-continued
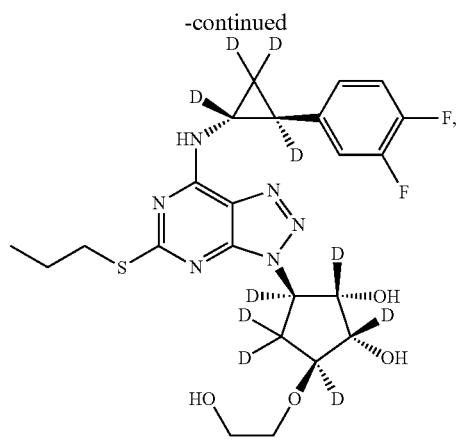
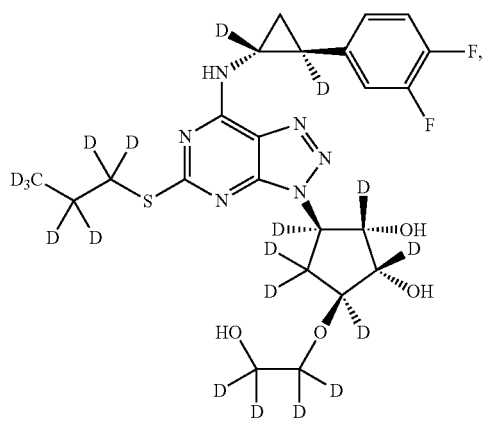
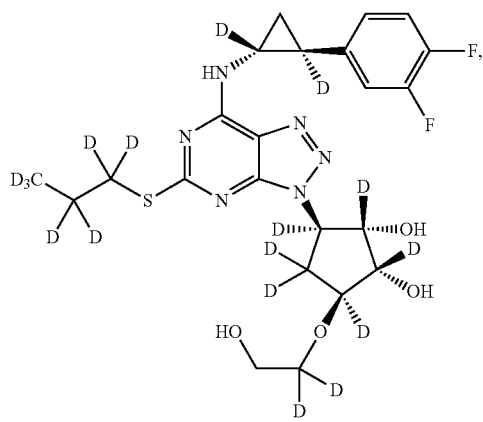
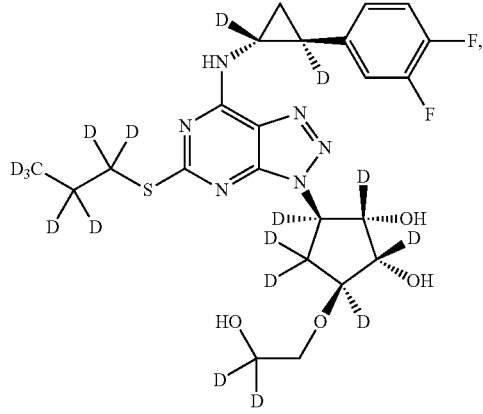
134
-continued
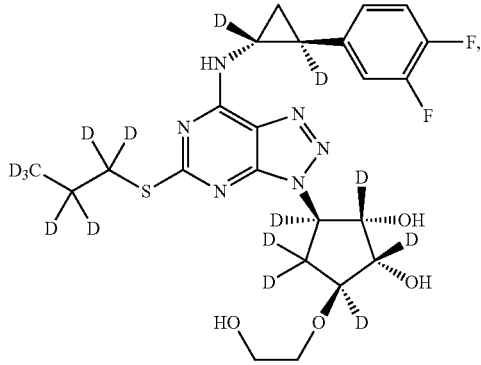
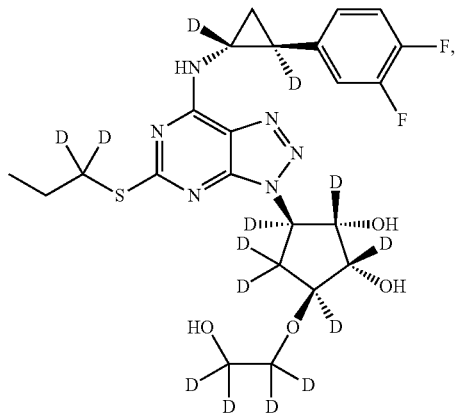
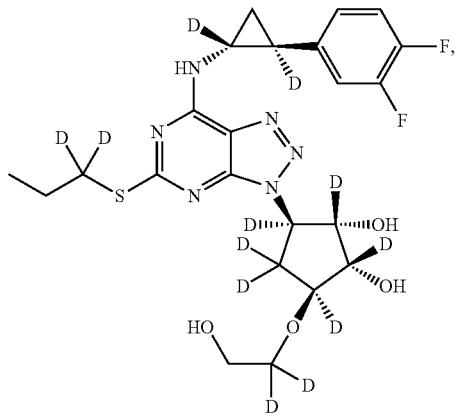
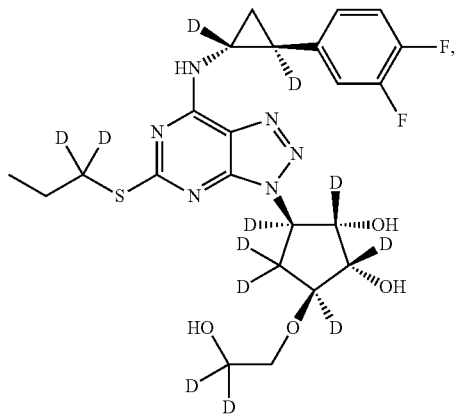

135
-continued
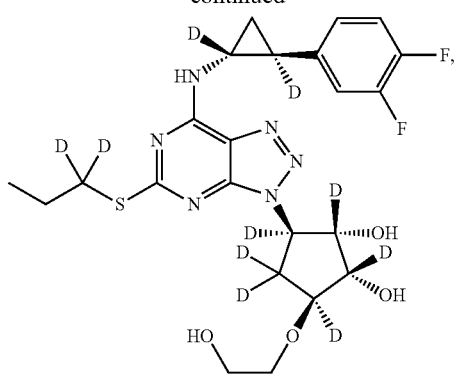
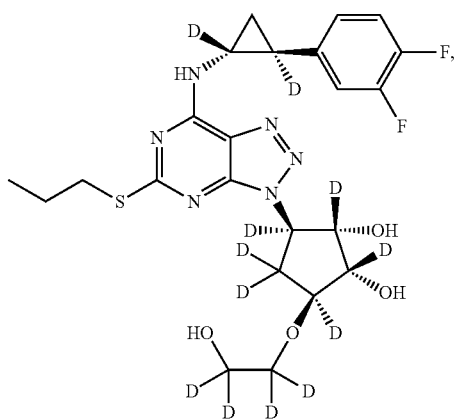
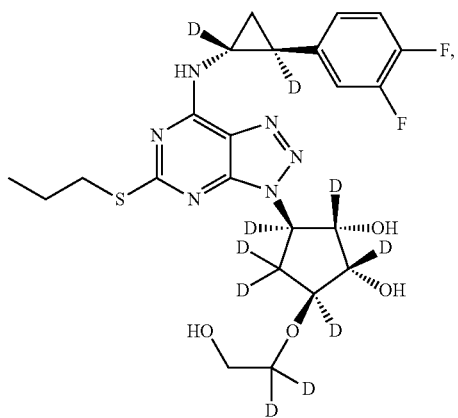
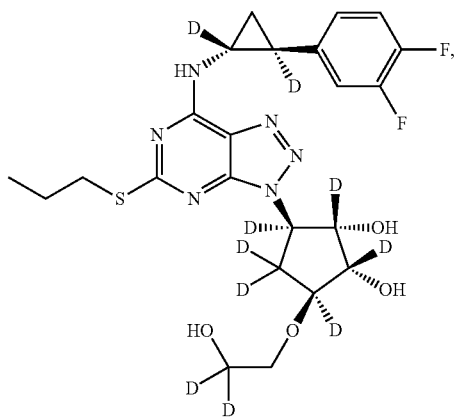
136
-continued
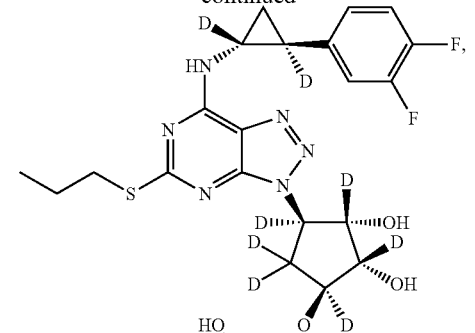
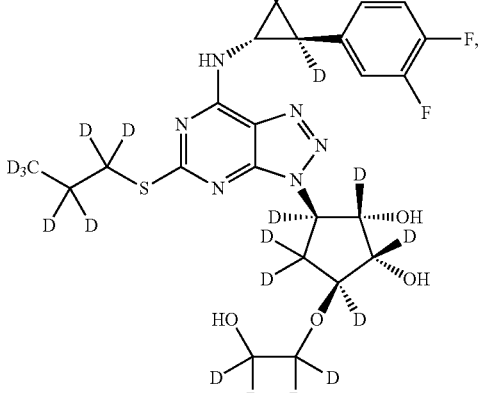
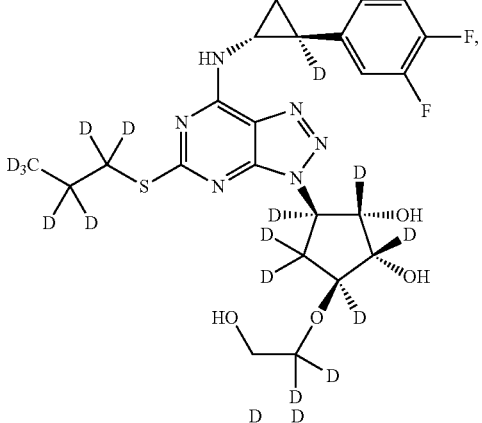
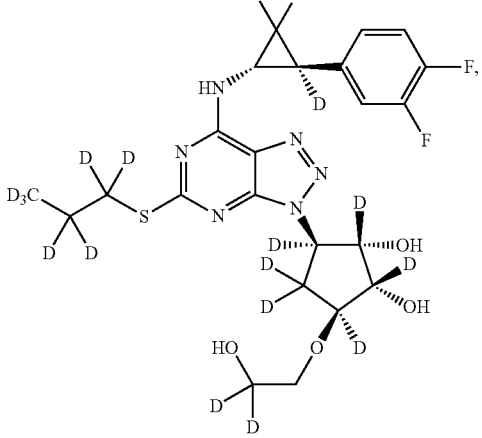

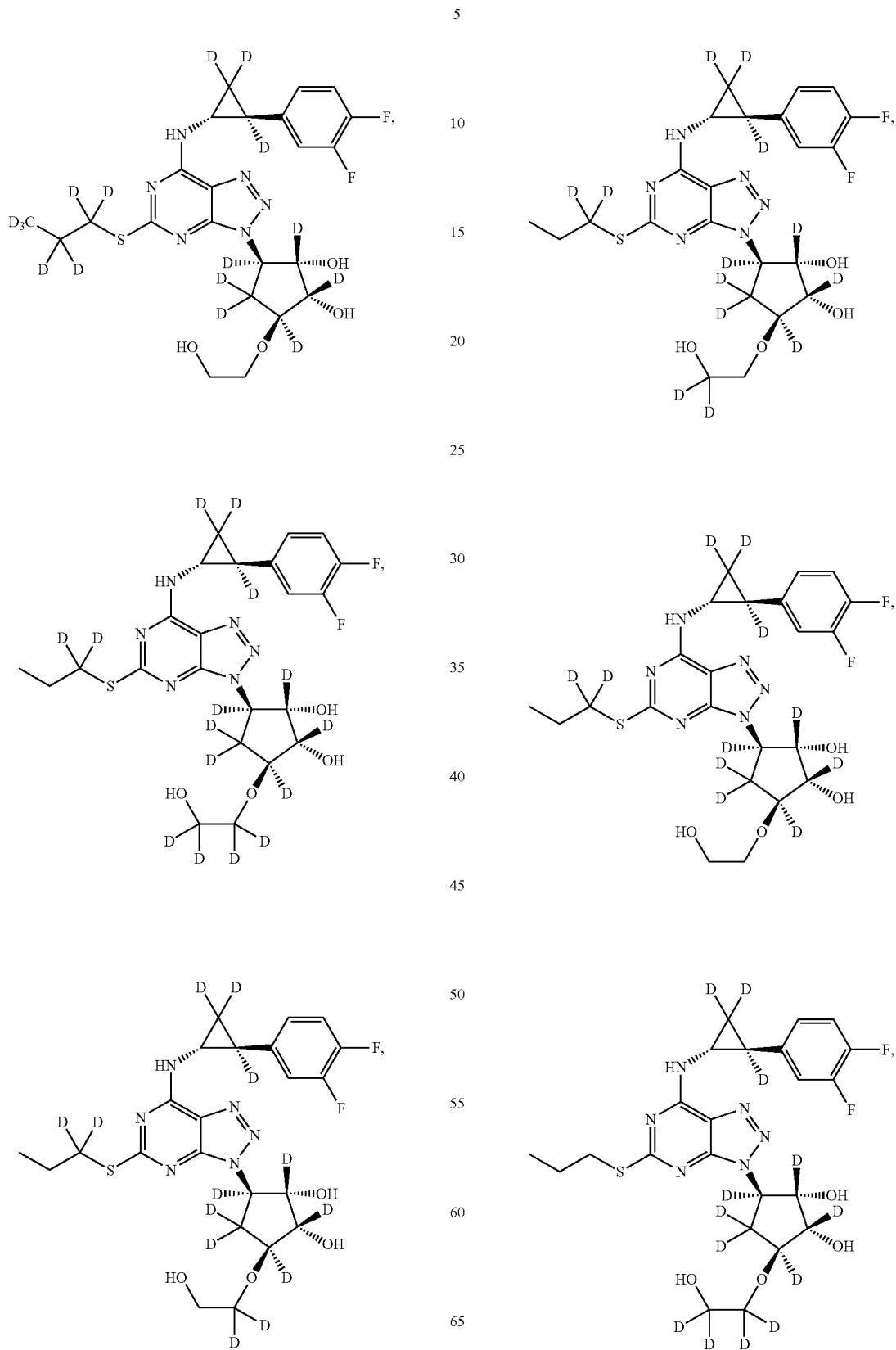

139
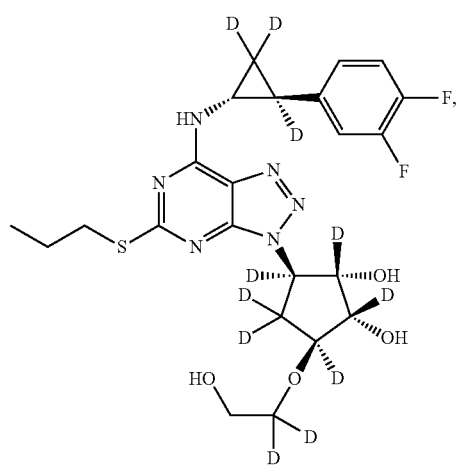
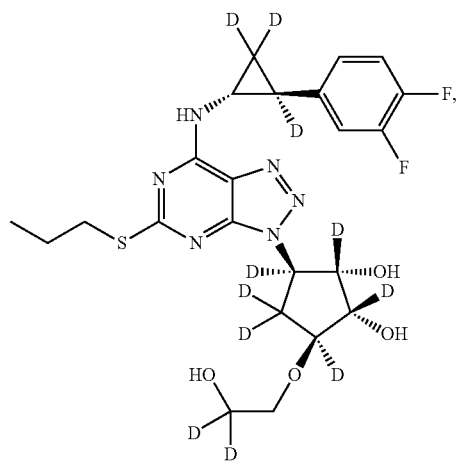
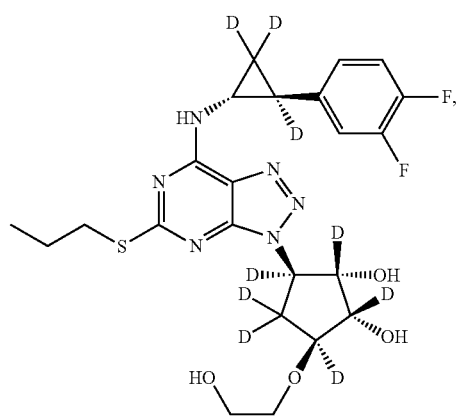
140
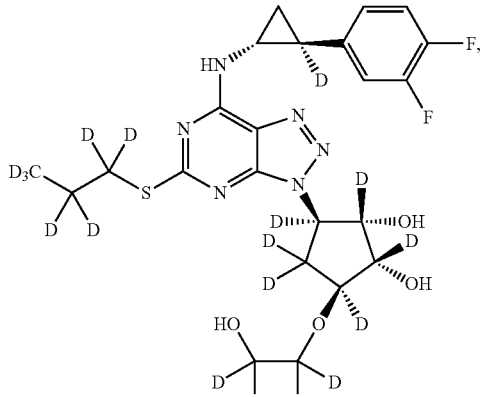
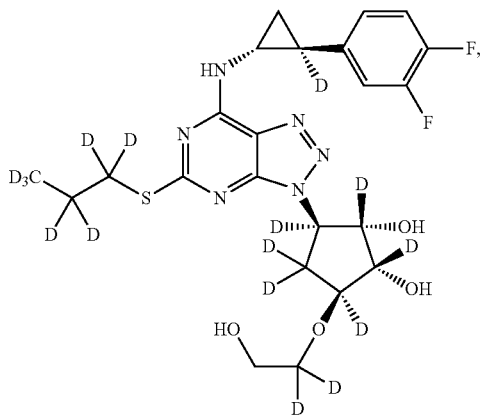
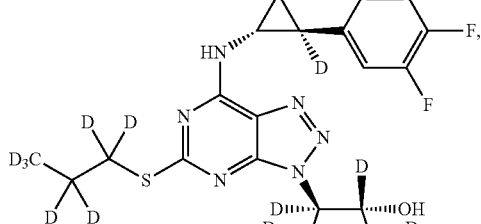
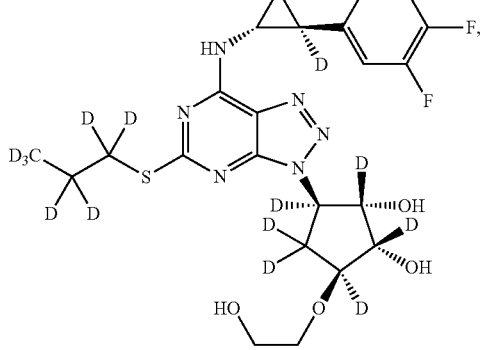

141
-continued
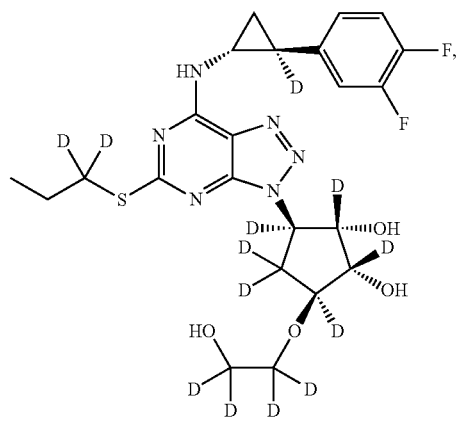
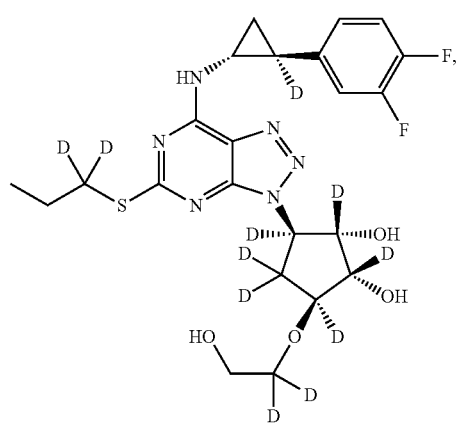
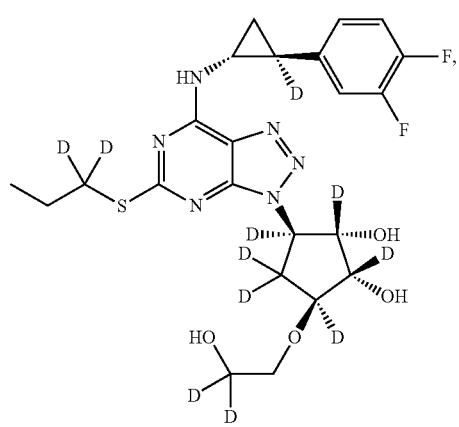
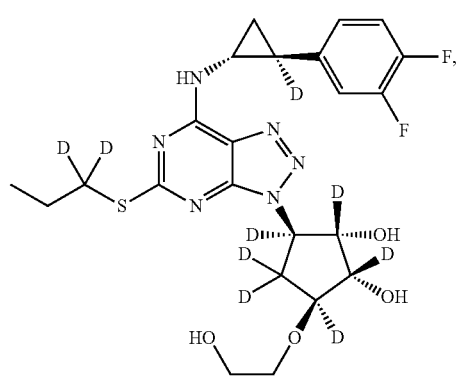
142
-continued
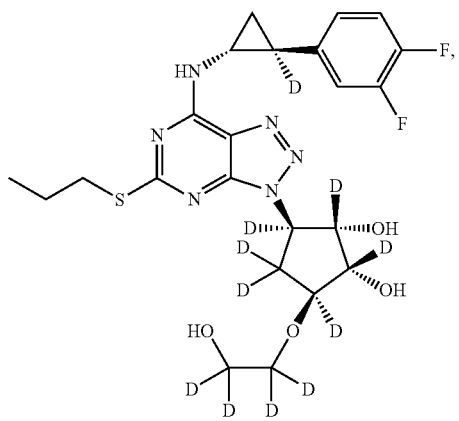
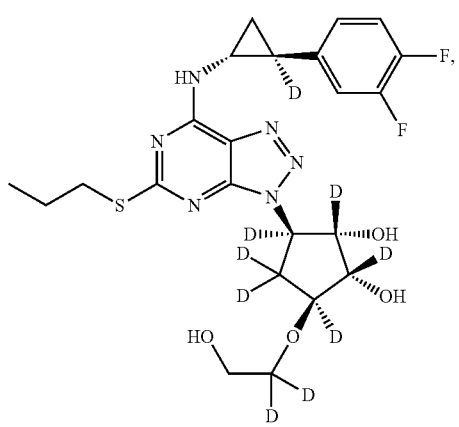
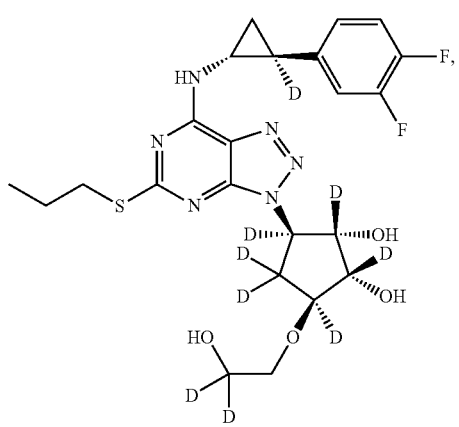
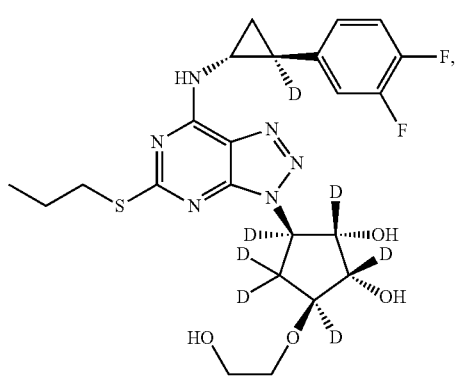

143
-continued
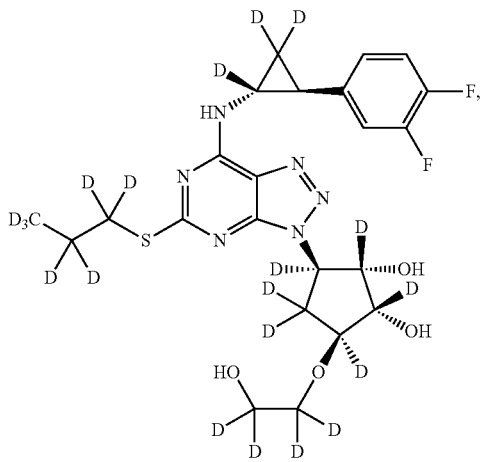
144
-continued
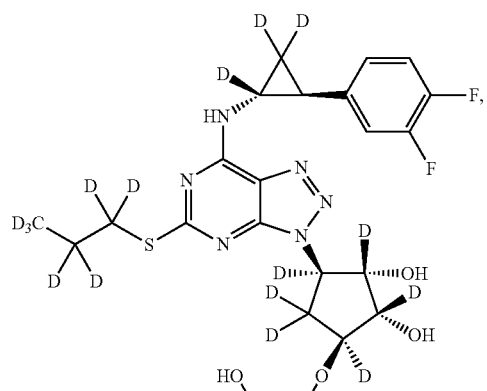
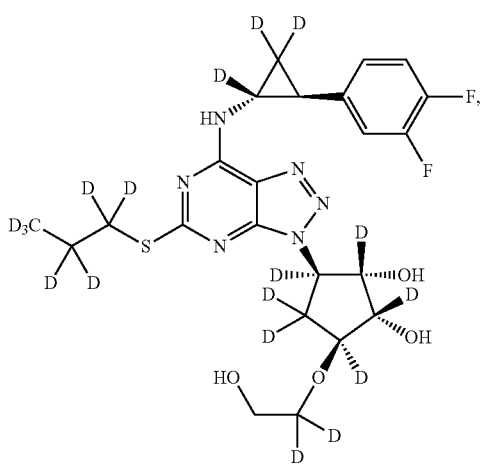
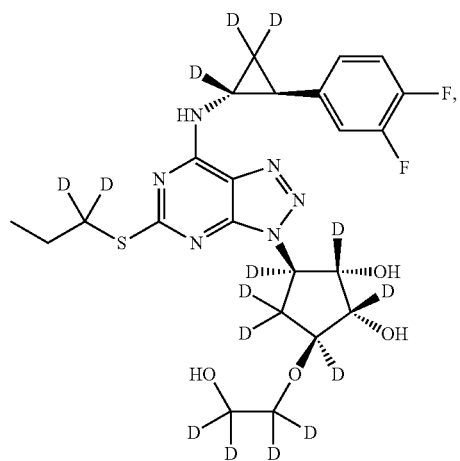
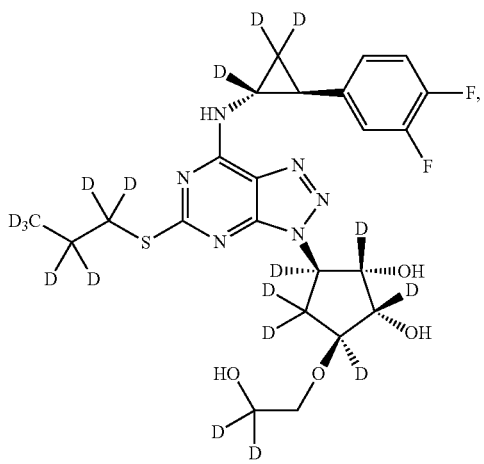
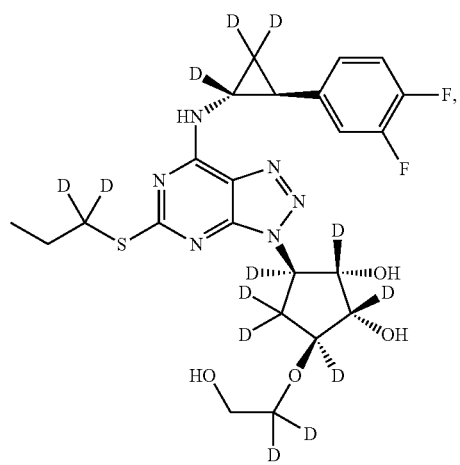

145
-continued
146
-continued
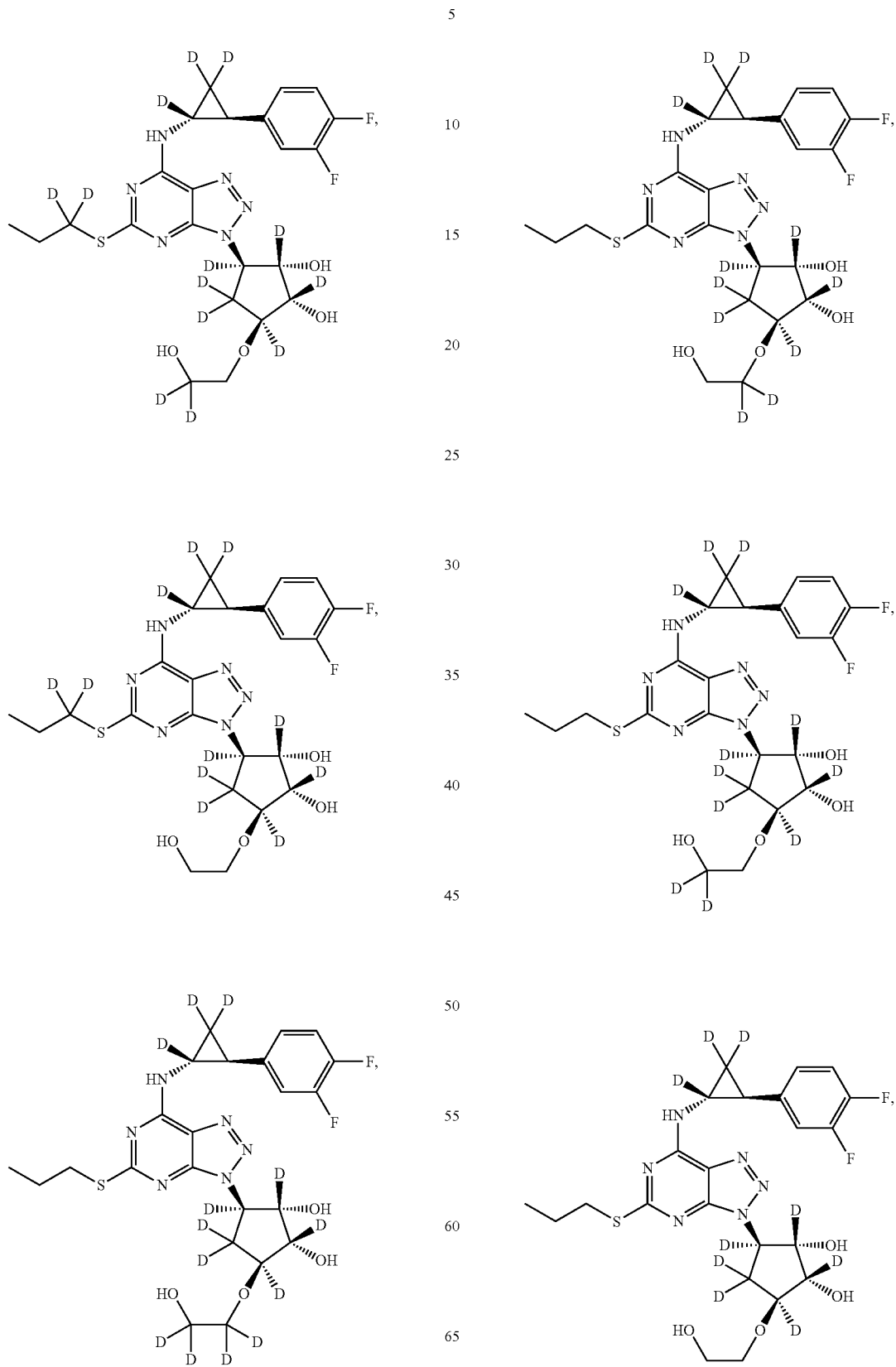

-continued
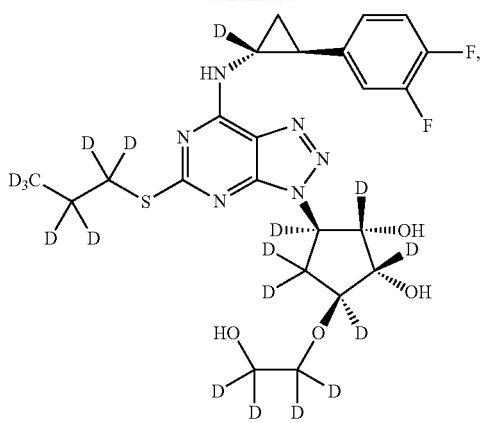
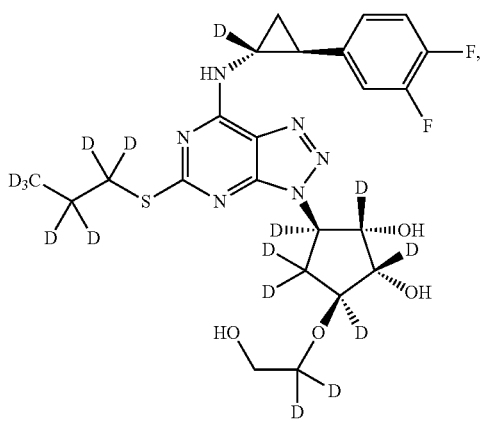
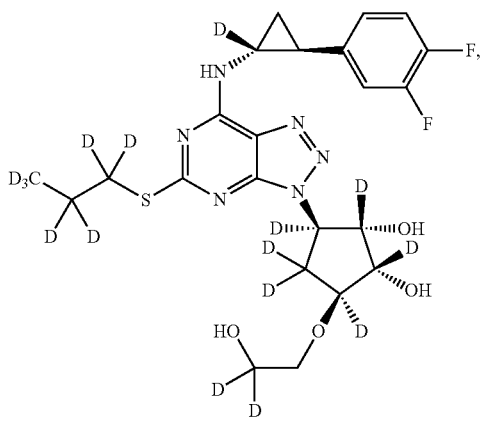
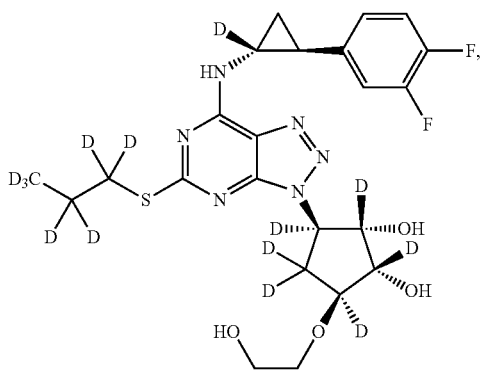
-continued
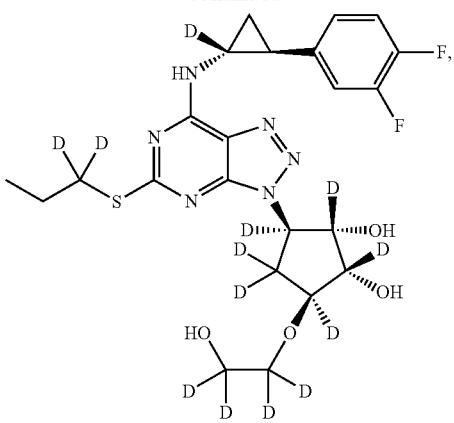
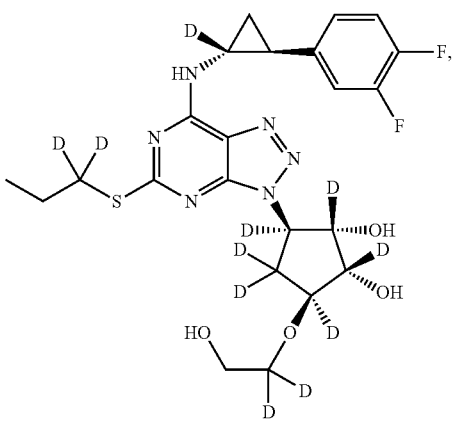
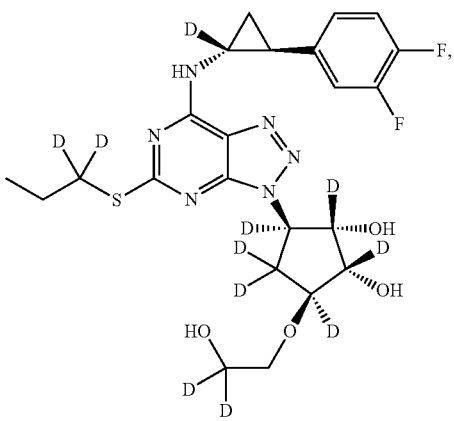
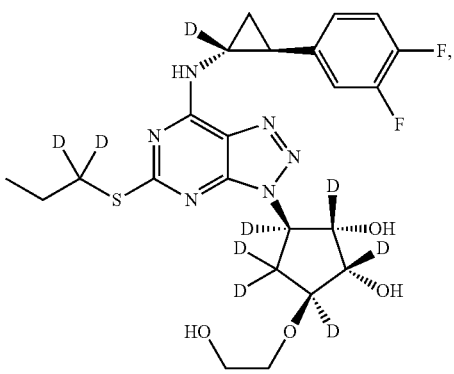

-continued
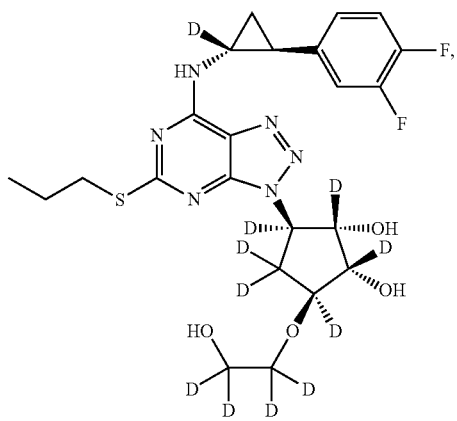
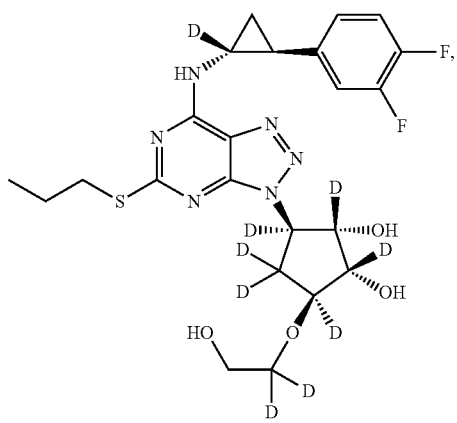
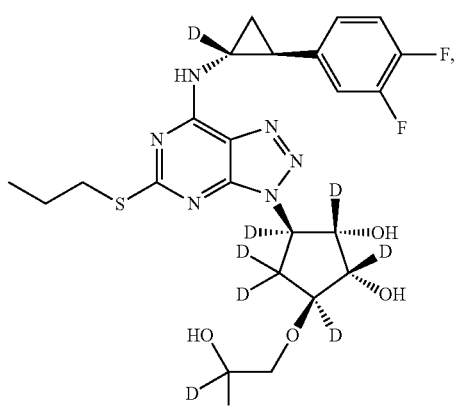
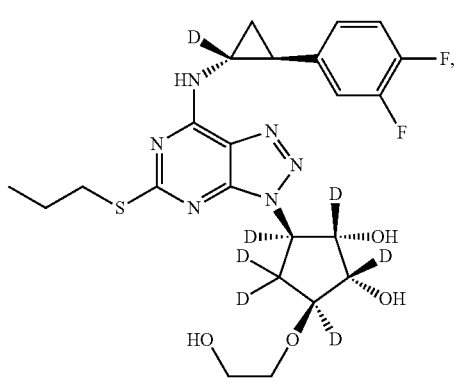
-continued
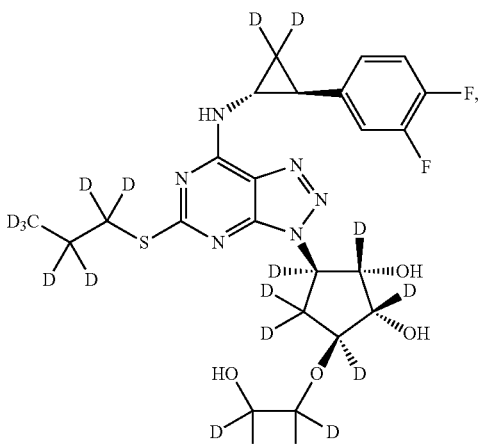
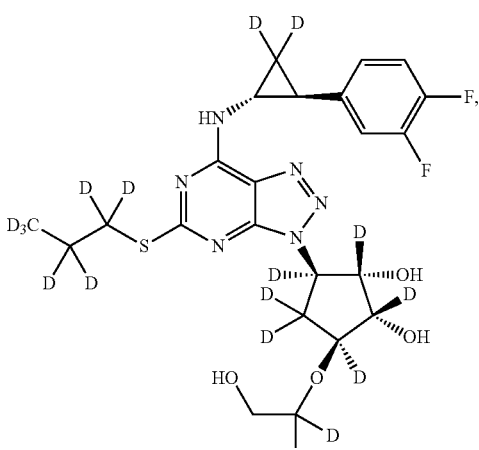
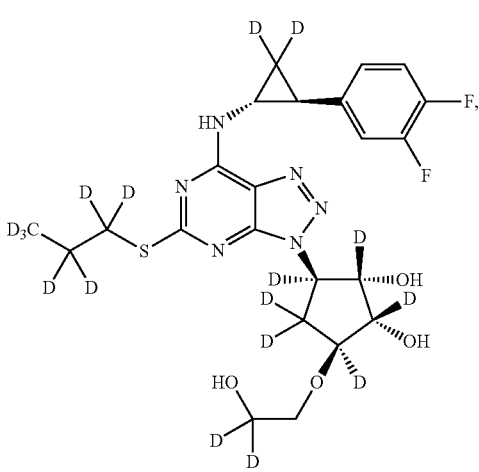

151
-continued
152
-continued
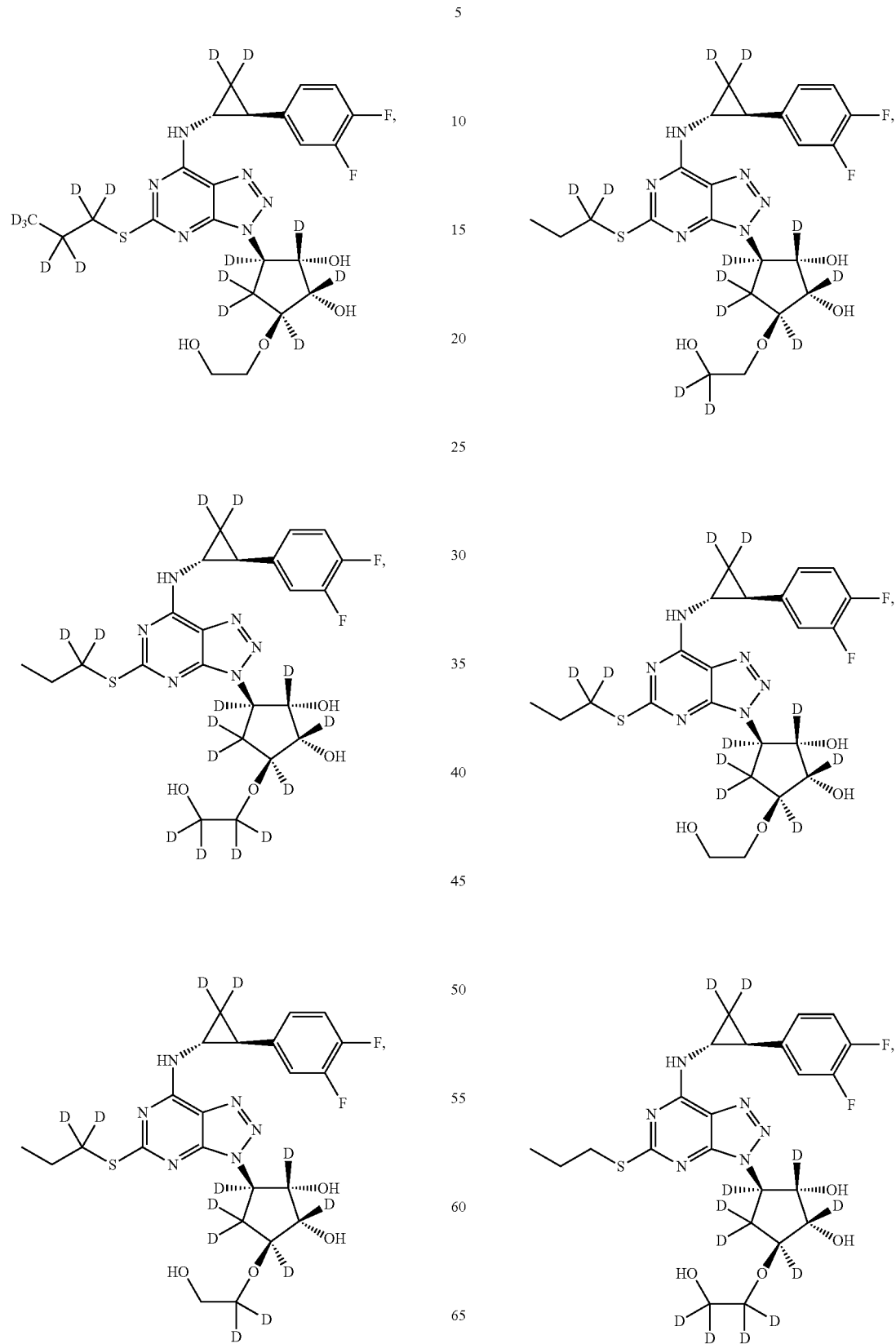

153
-continued
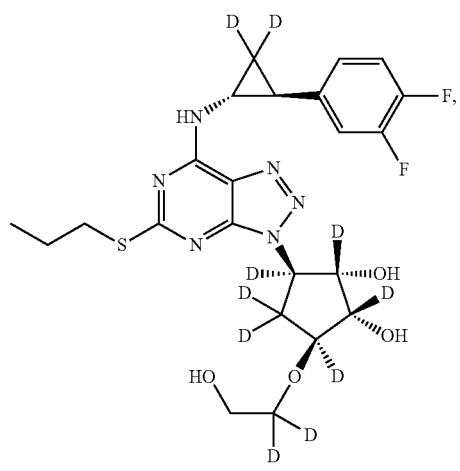
154
-continued
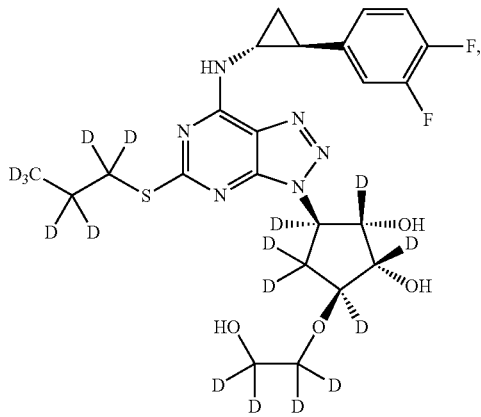
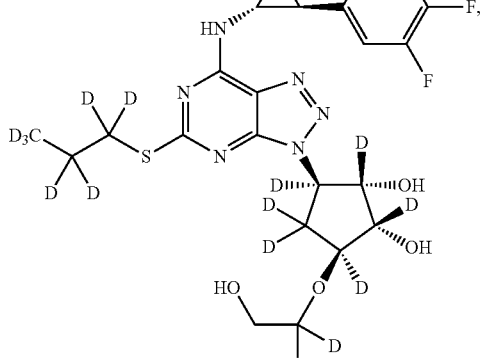
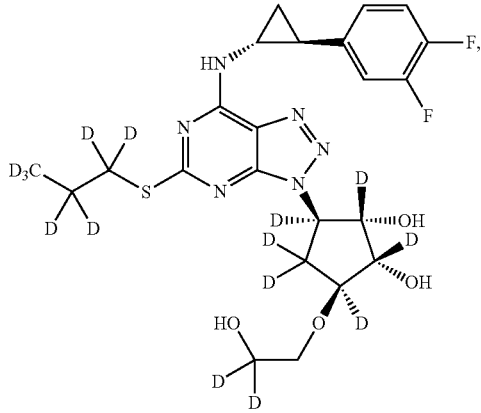
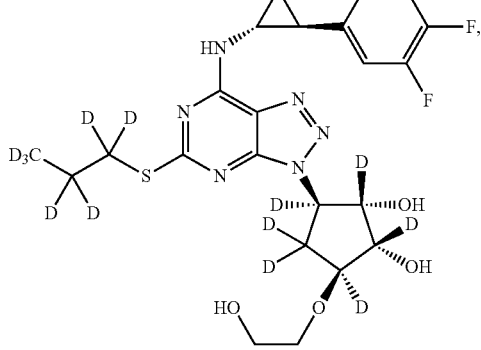

155
-continued
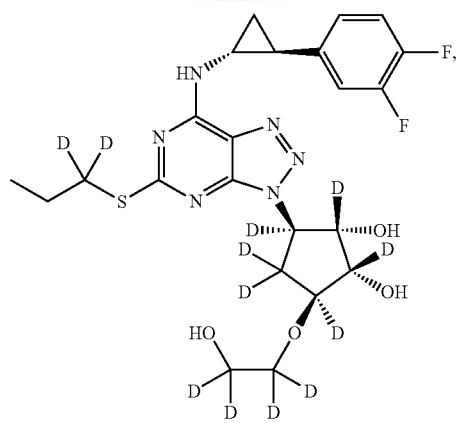
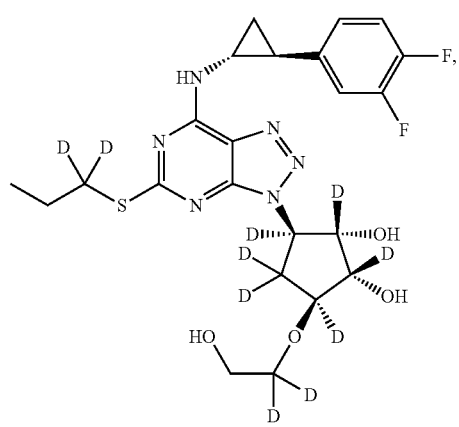
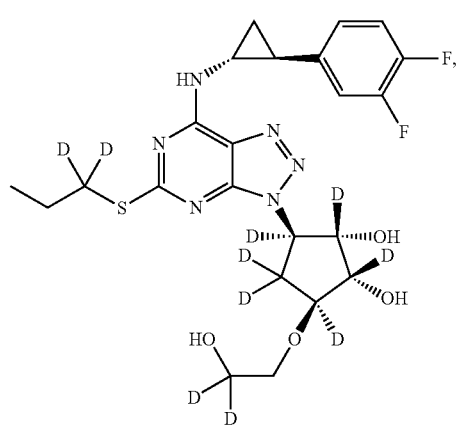
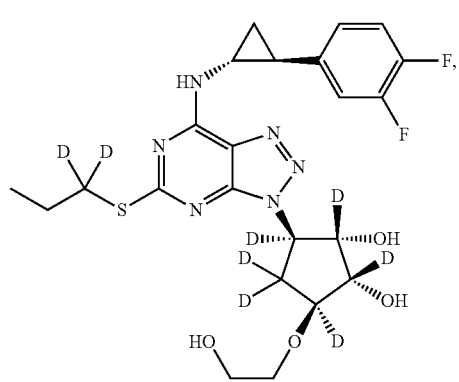
156
-continued
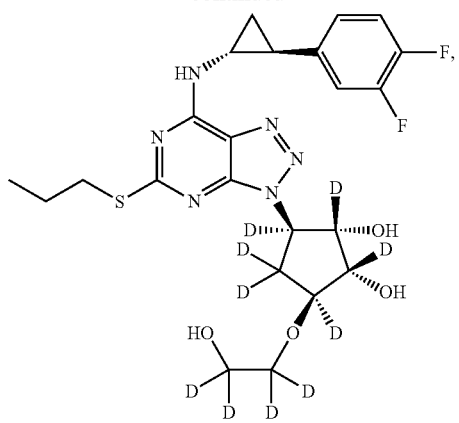
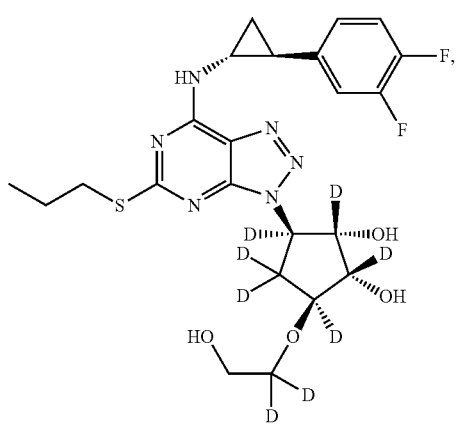
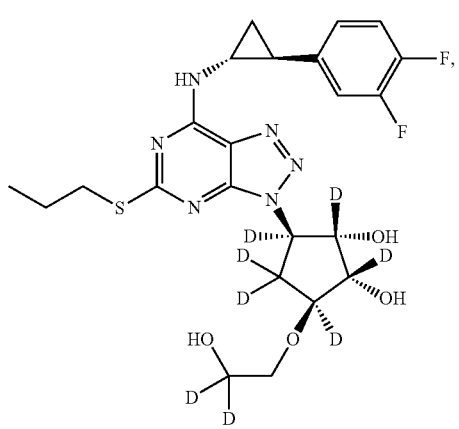
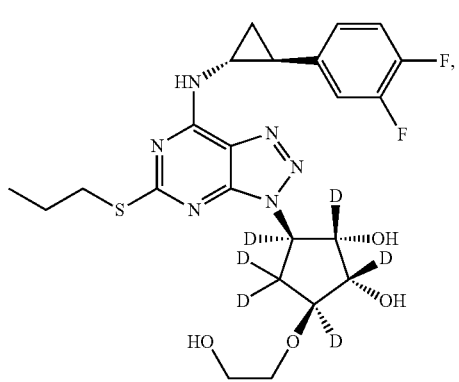

157
-continued
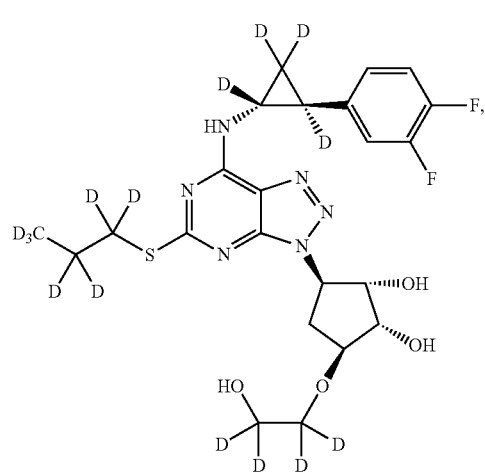
158
-continued
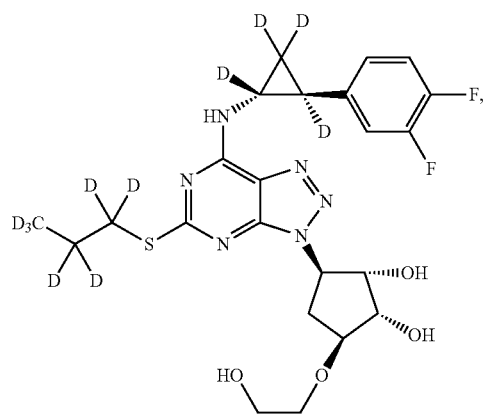
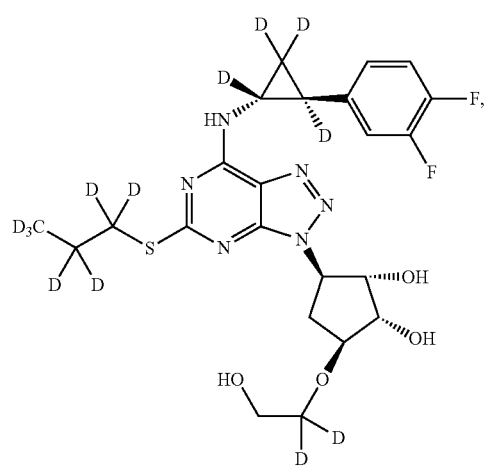
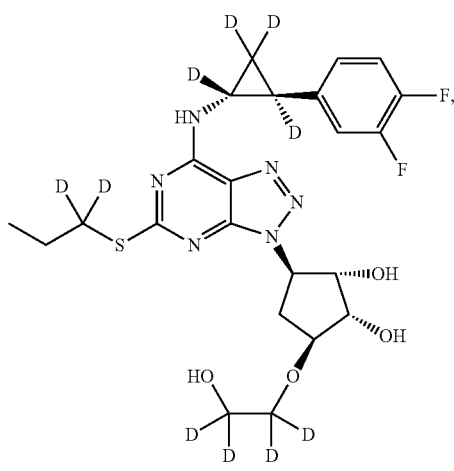
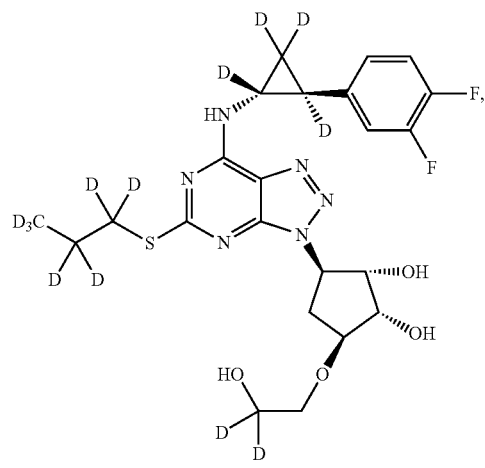
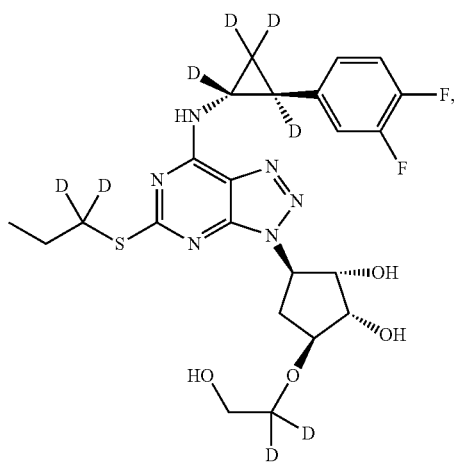

159
-continued
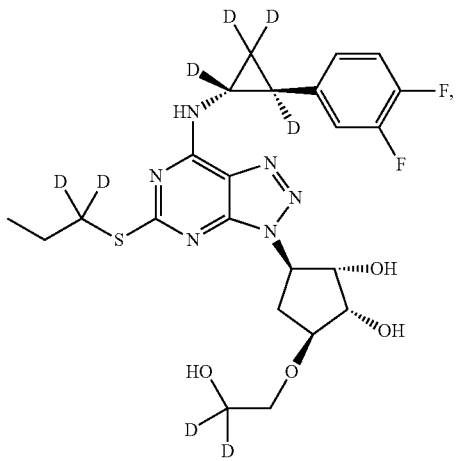
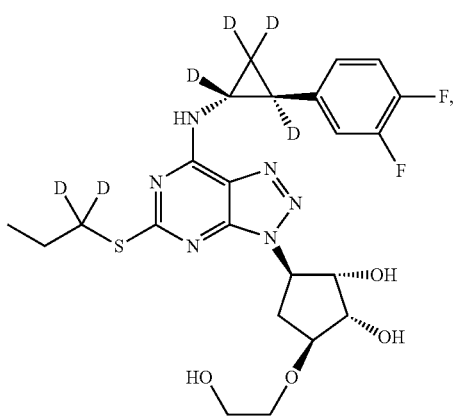
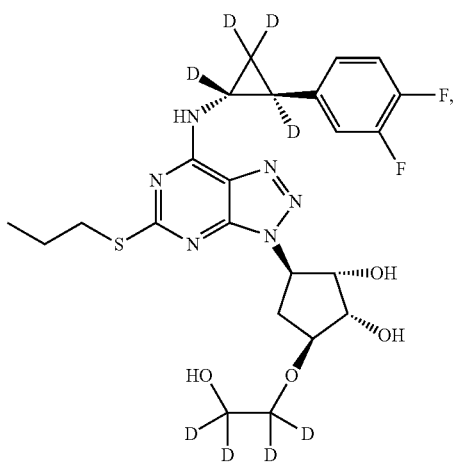
160
-continued
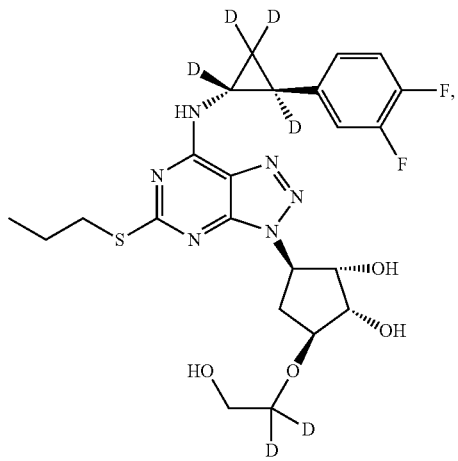
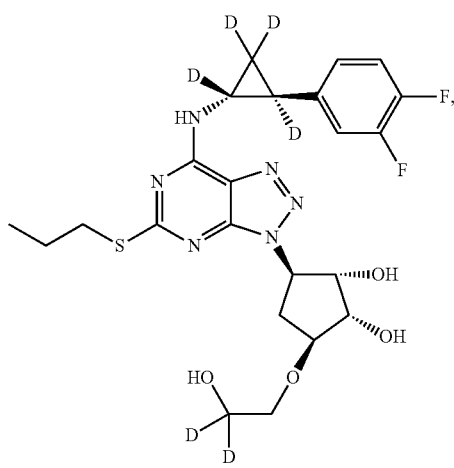
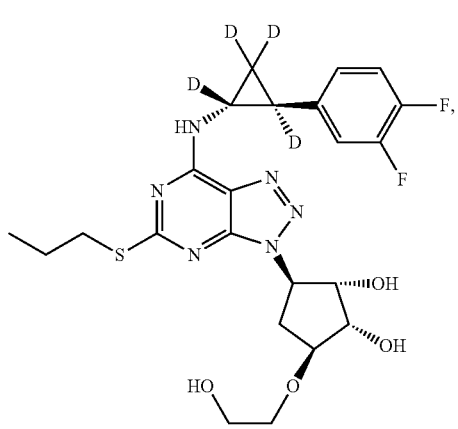

161
-continued
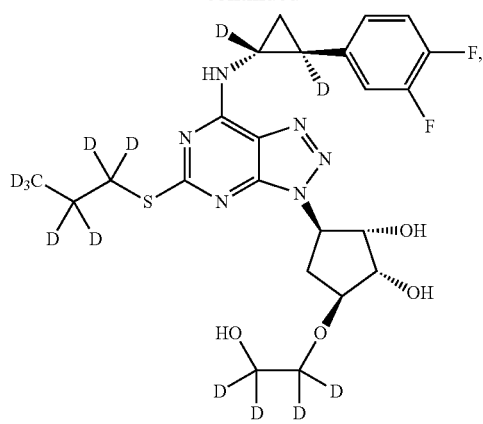
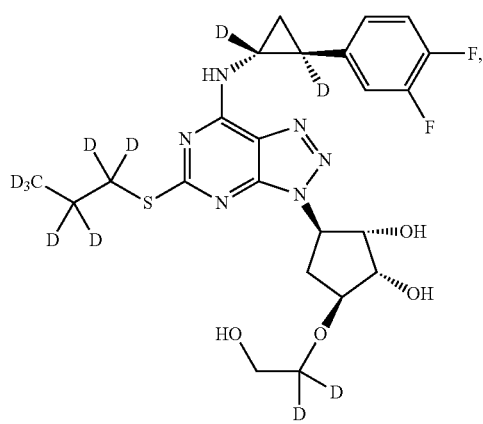
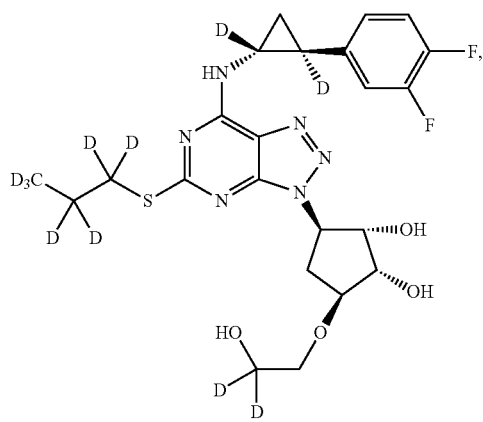
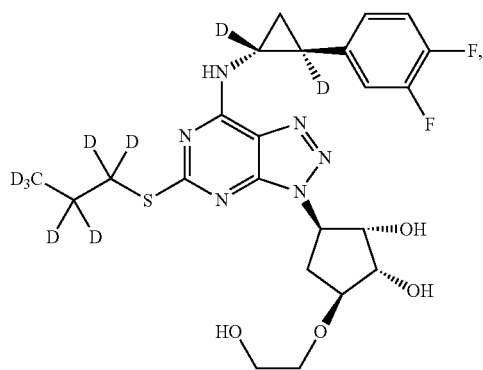
162
-continued
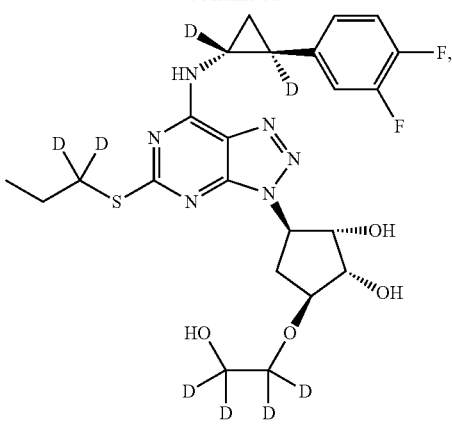
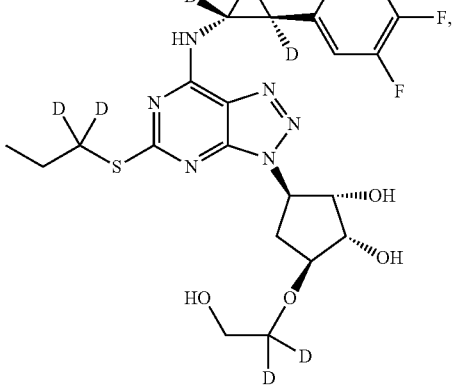
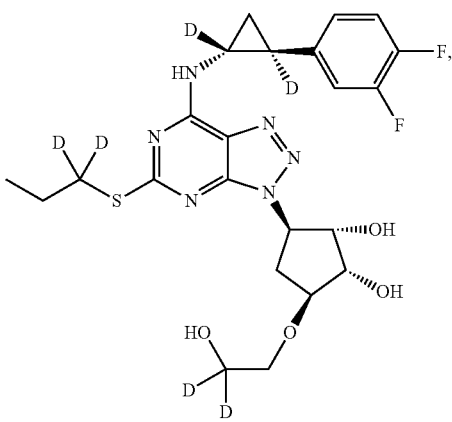
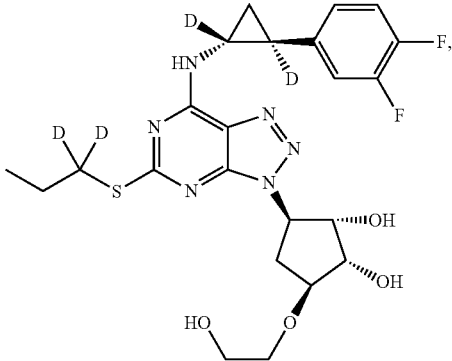

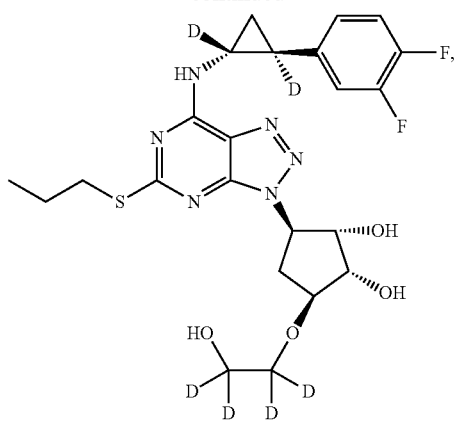
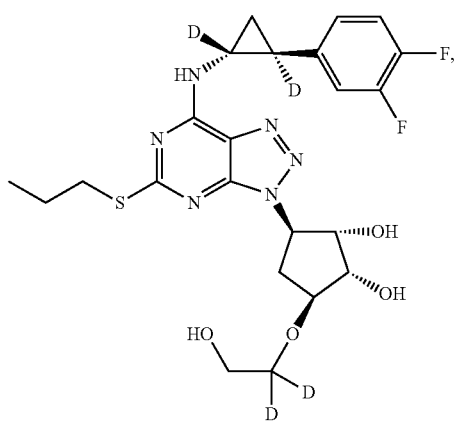
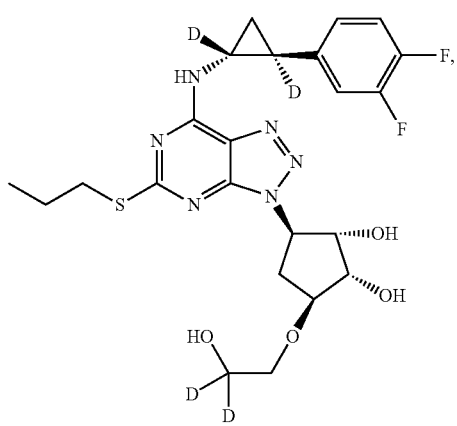
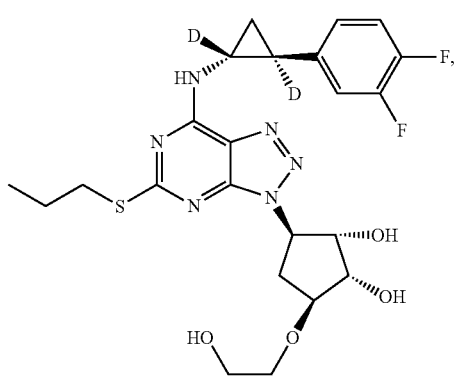
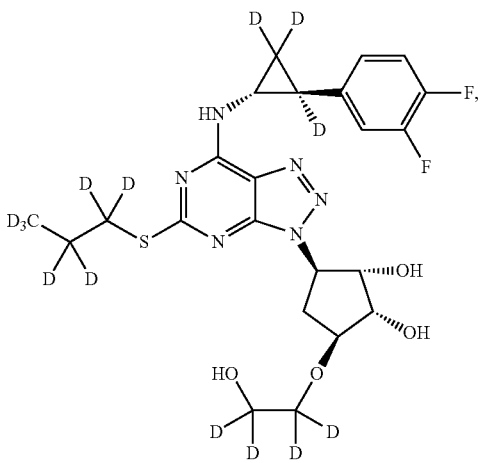
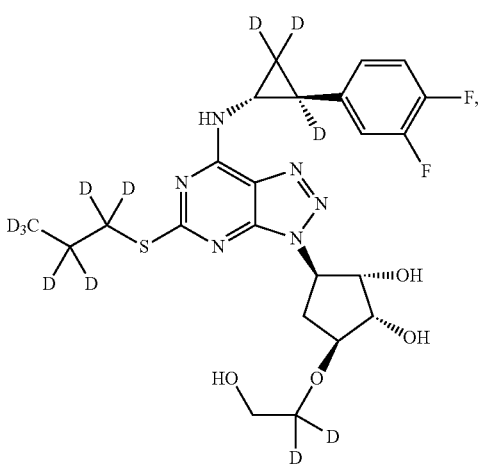
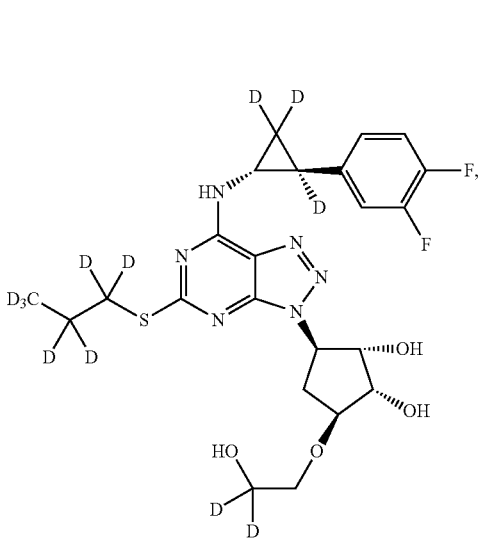

165
-continued
166
-continued
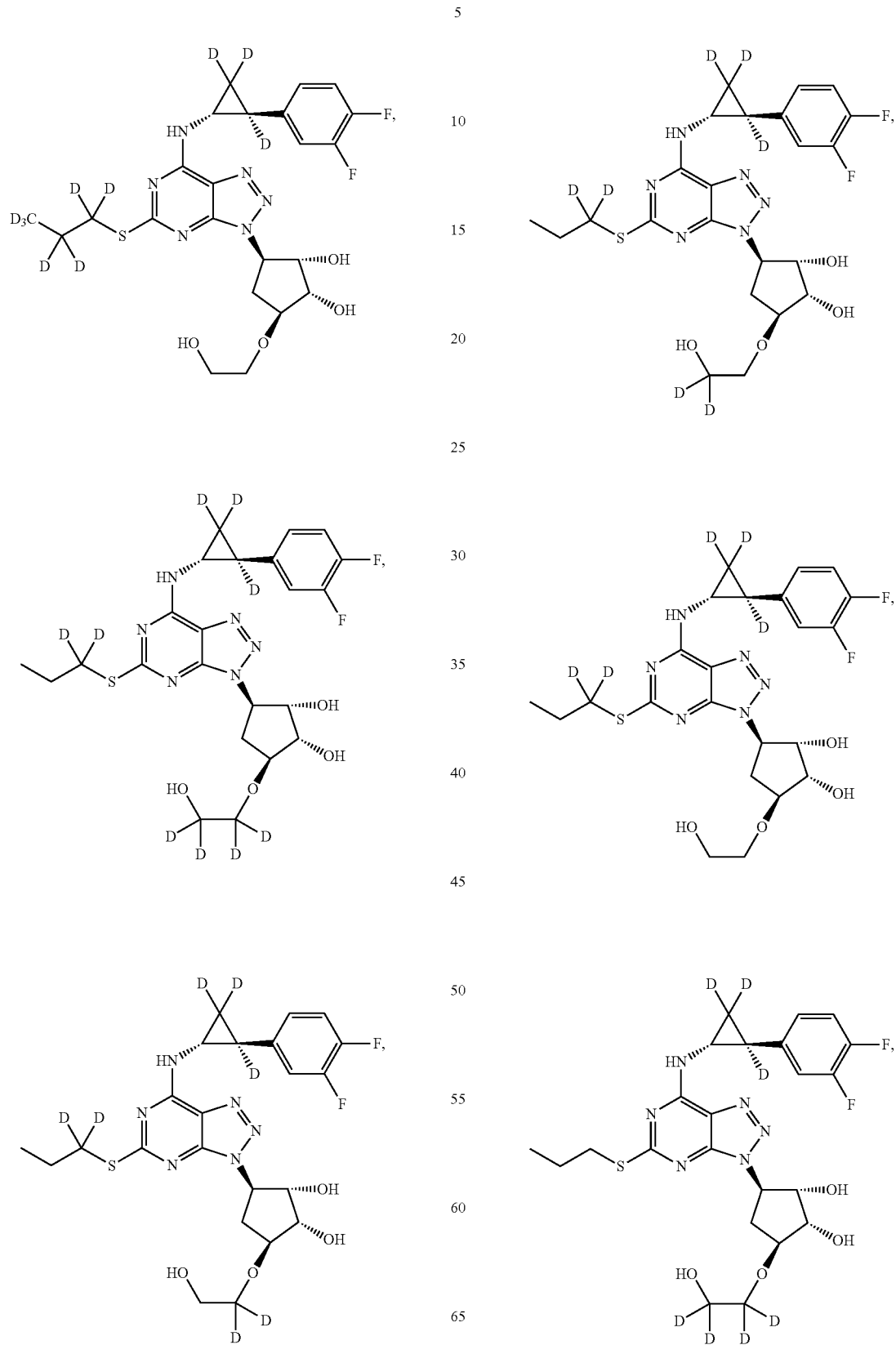

-continued
167
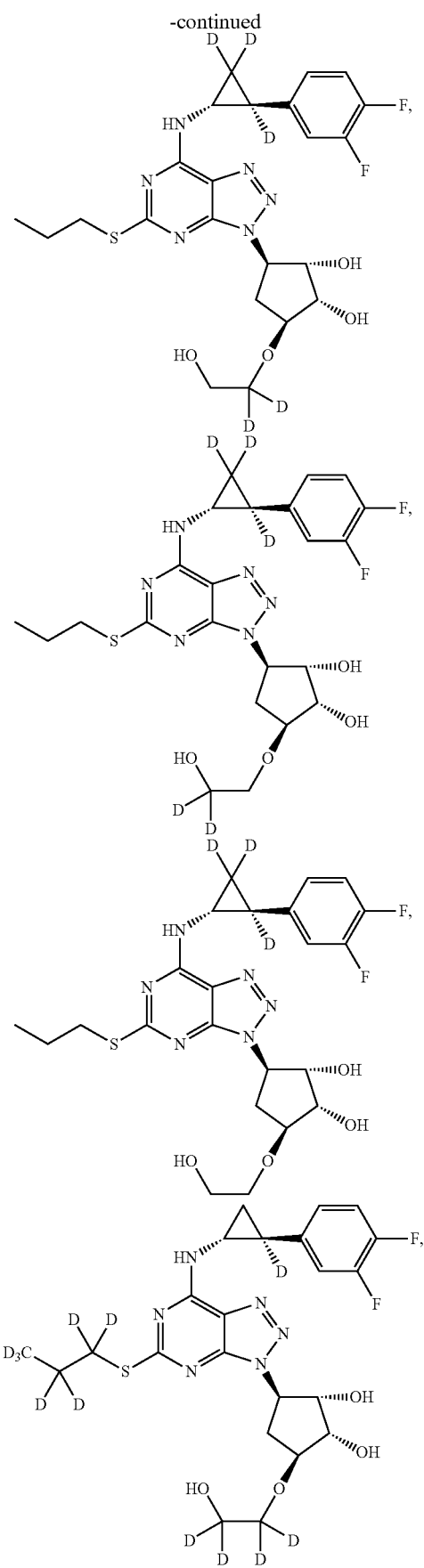
168
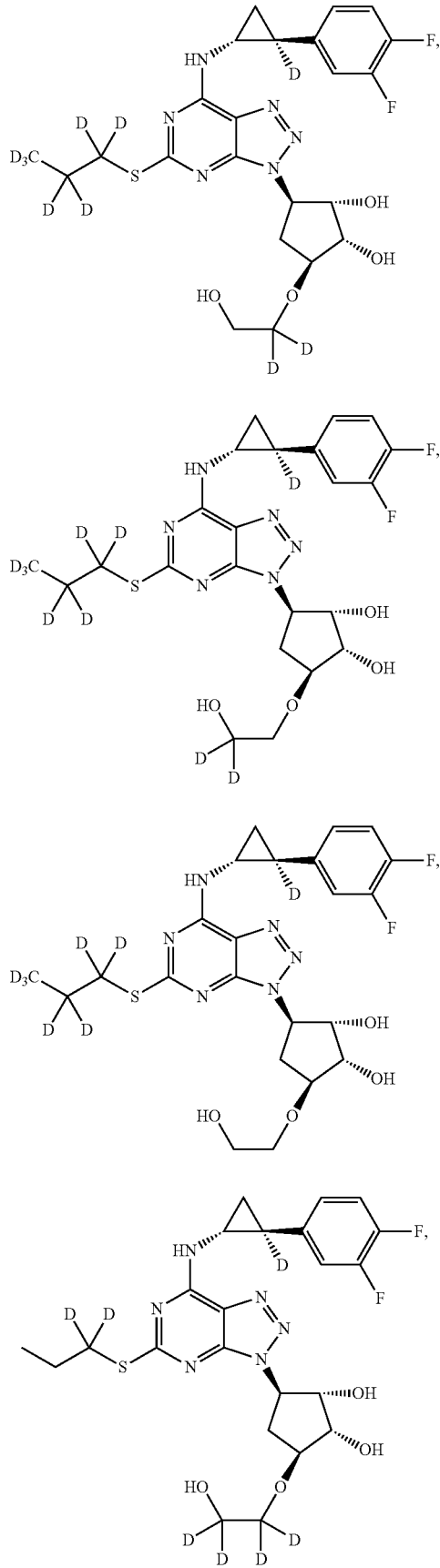

169
-continued
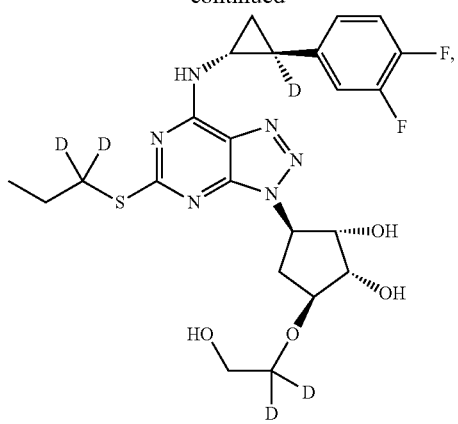
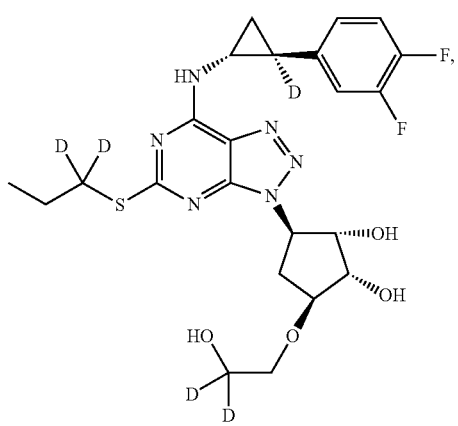
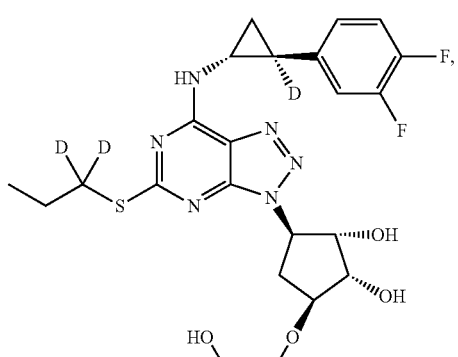
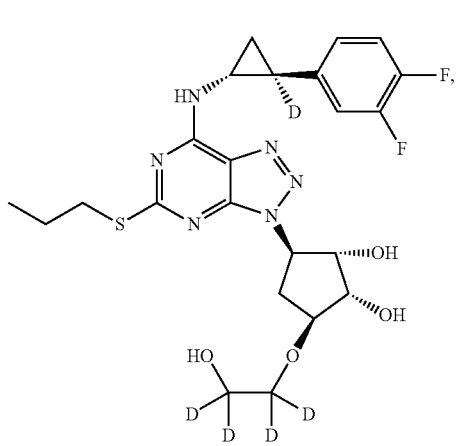
170
-continued
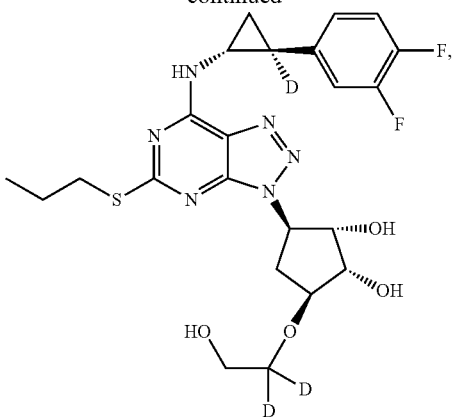
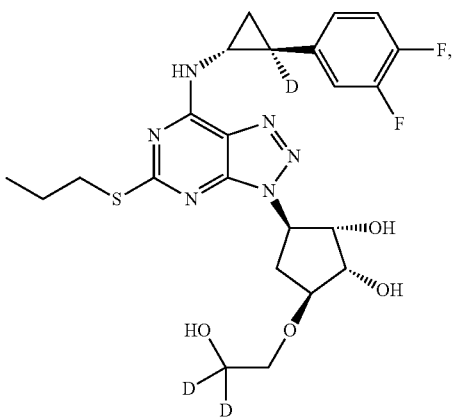
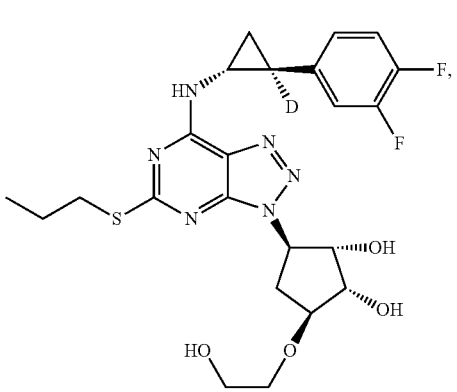
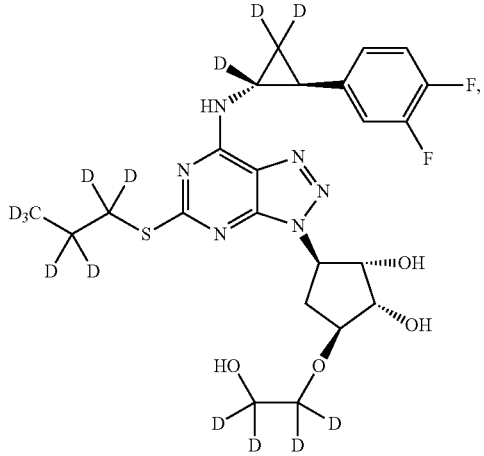

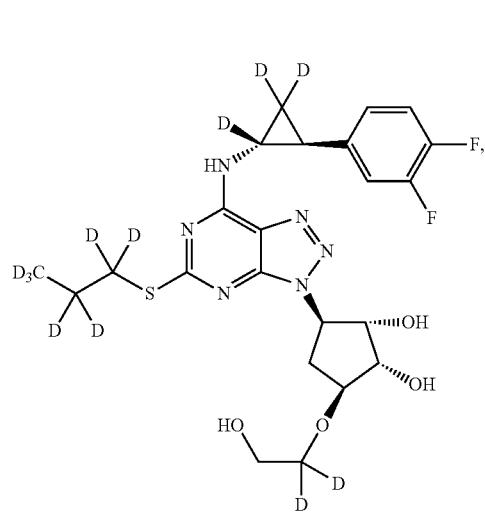
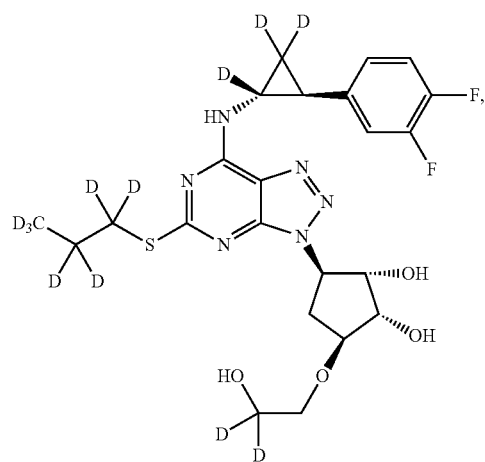
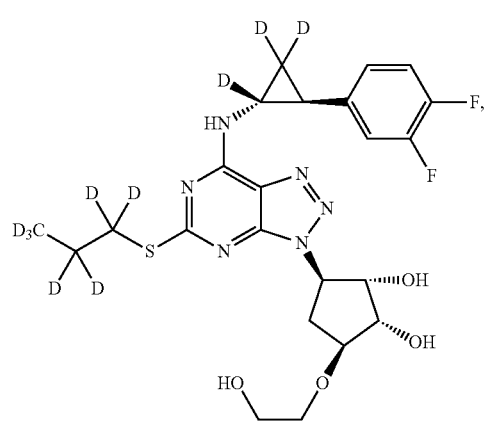
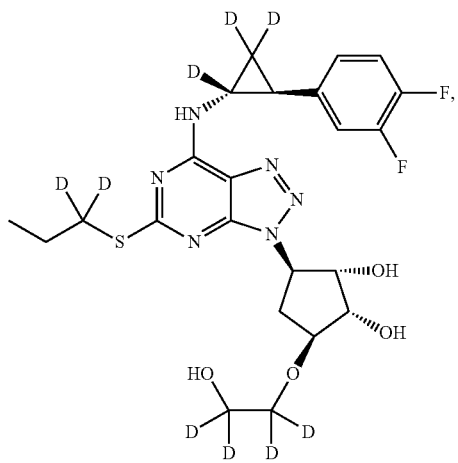
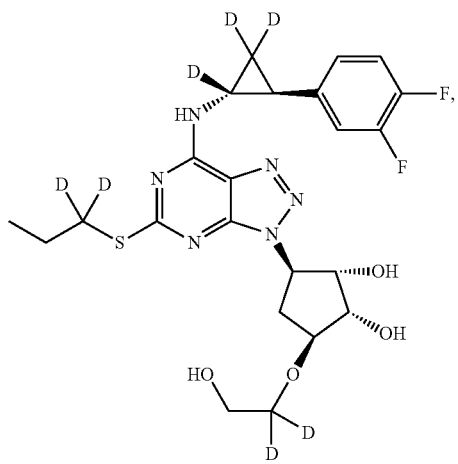
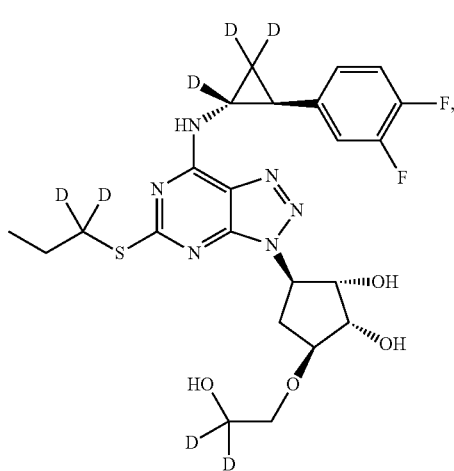

173
-continued
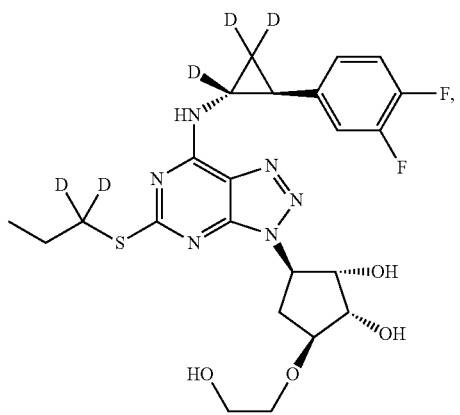
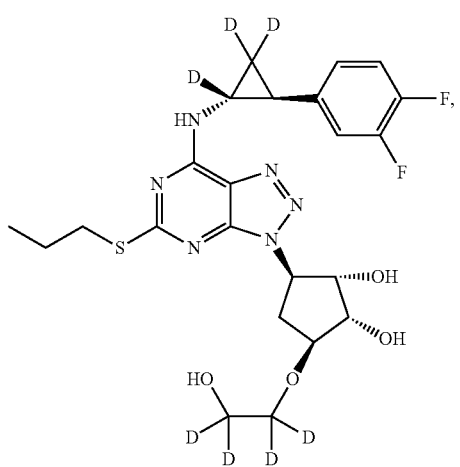
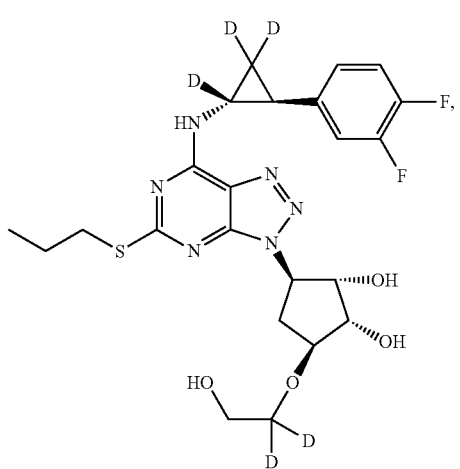
174
-continued
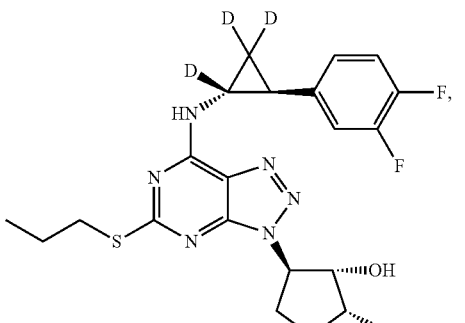
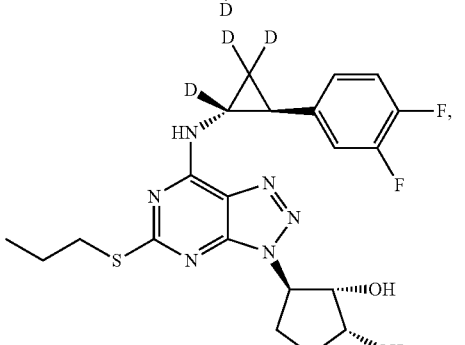
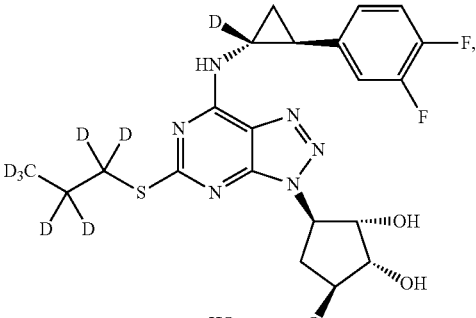
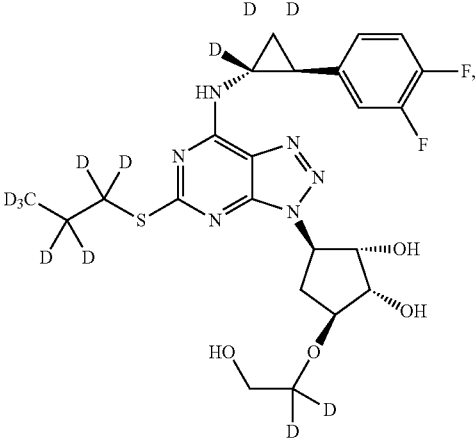

175
-continued
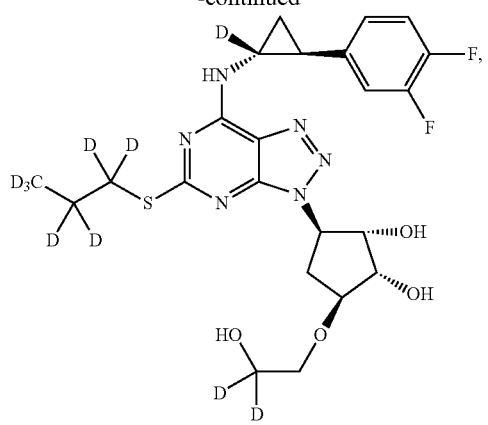
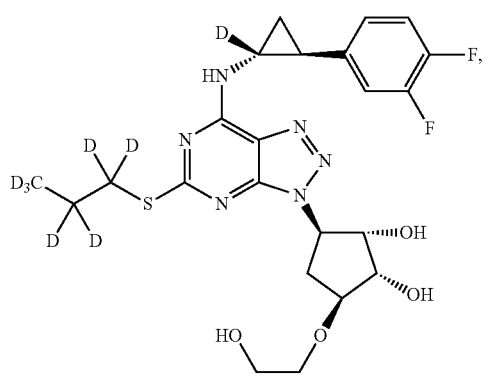
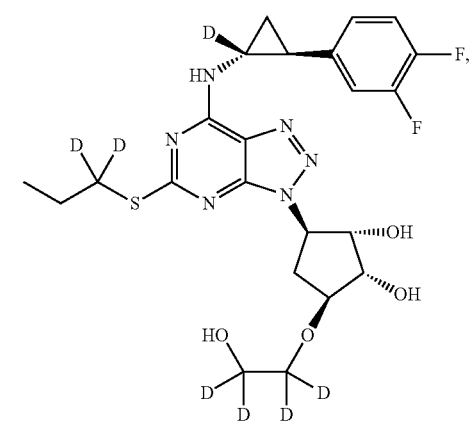
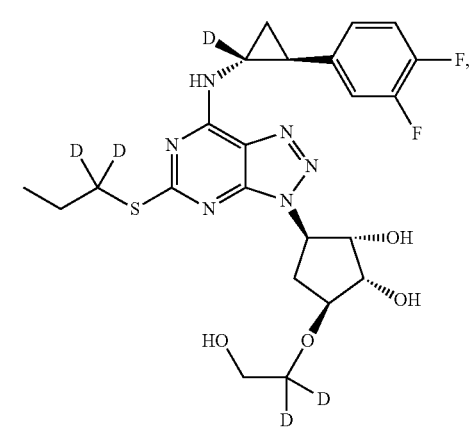
176
-continued
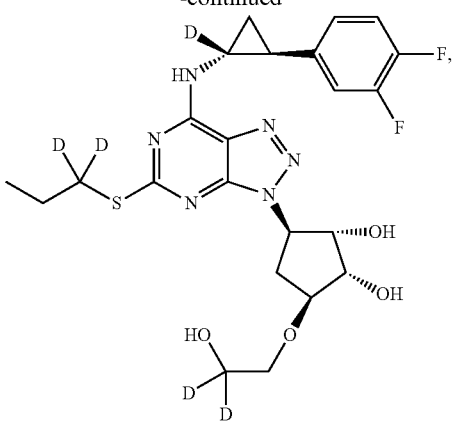
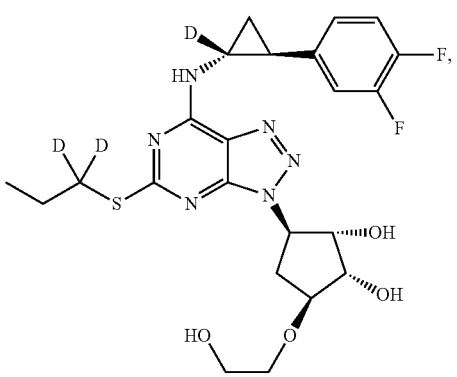
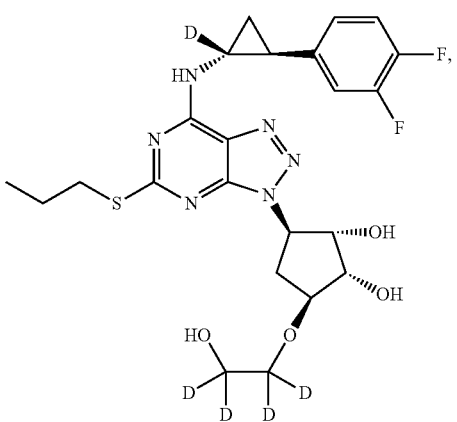
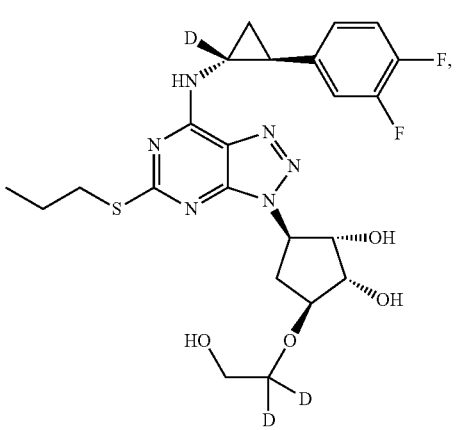

177
-continued
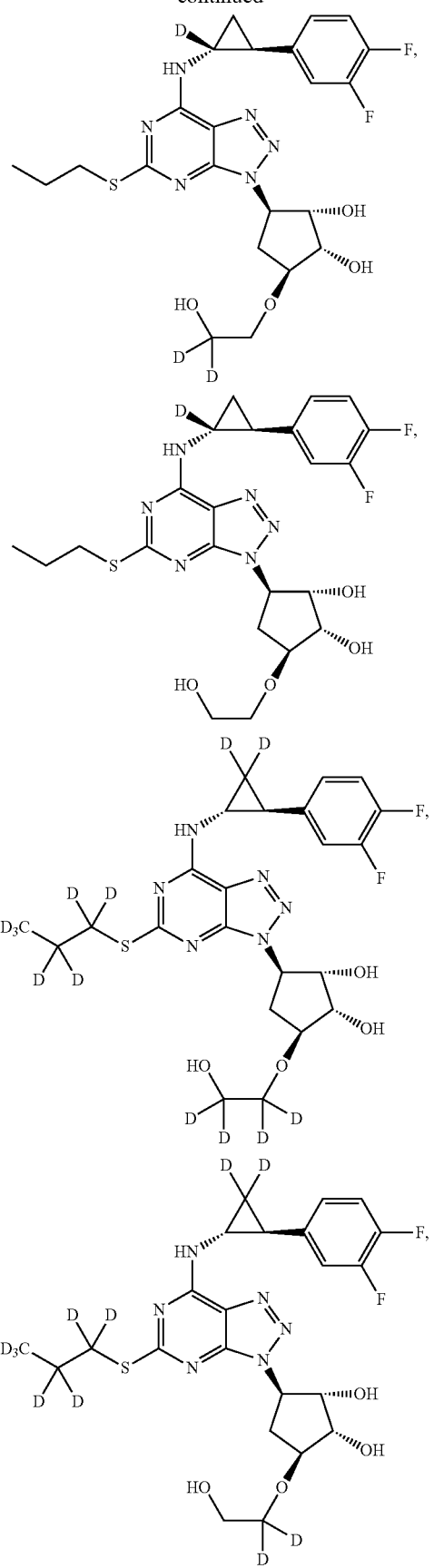
178
-continued
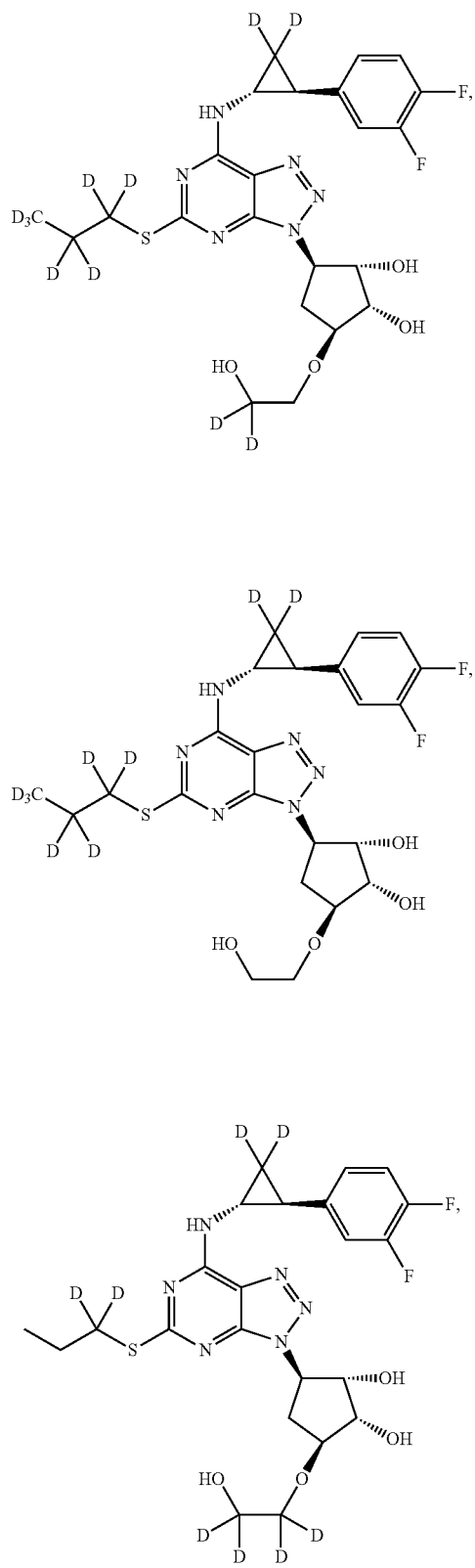

179
-continued
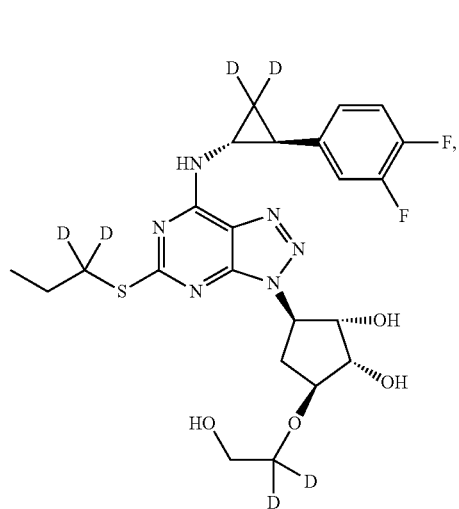
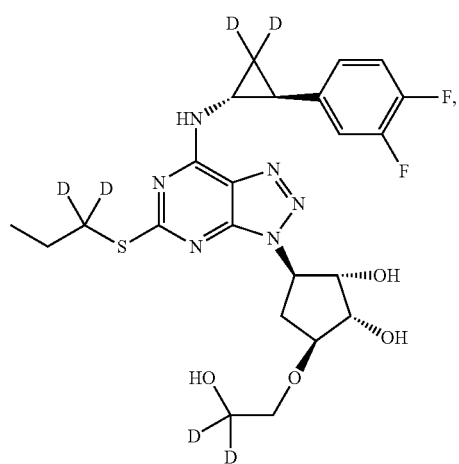
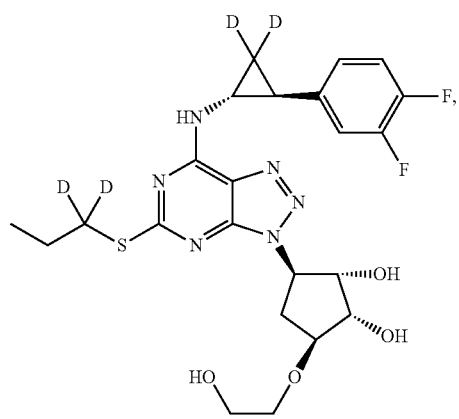
180
-continued
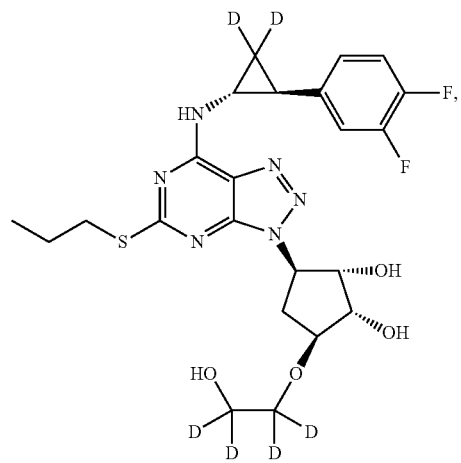
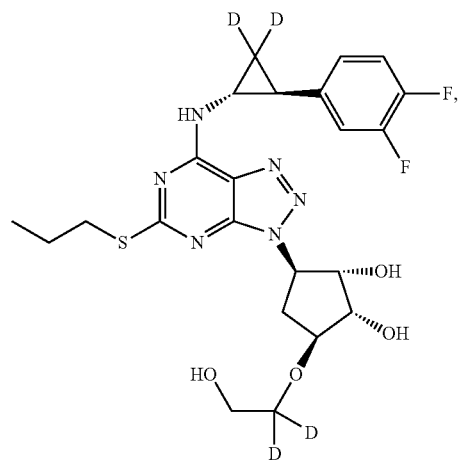
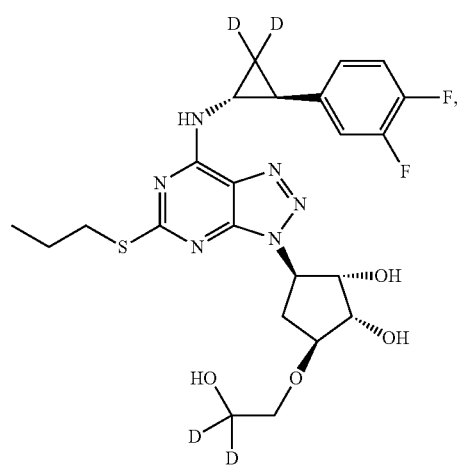

181
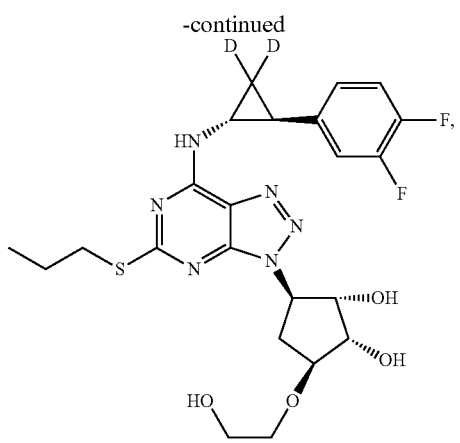
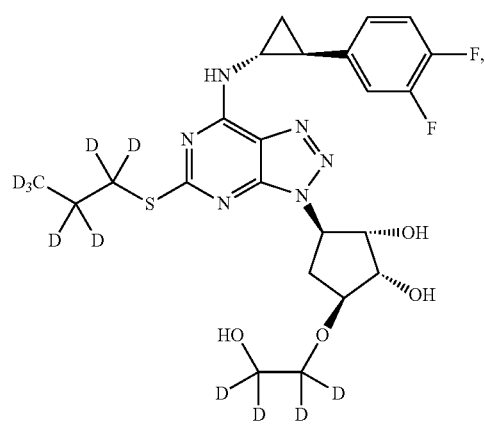
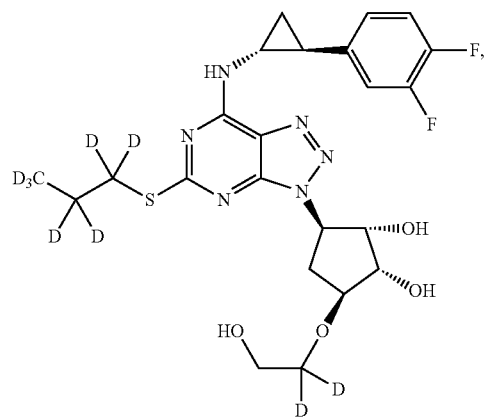
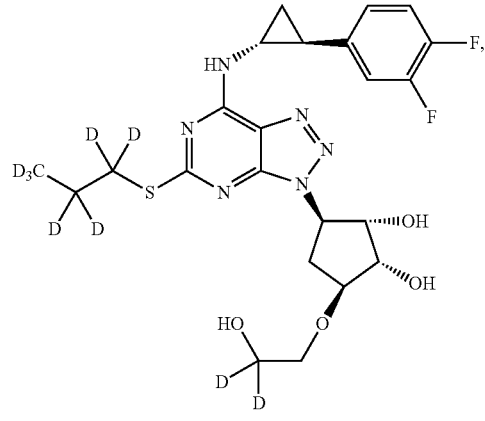
182
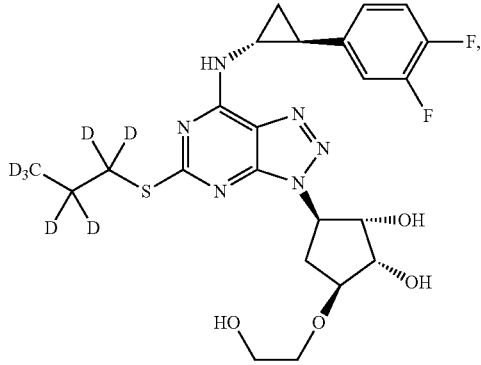
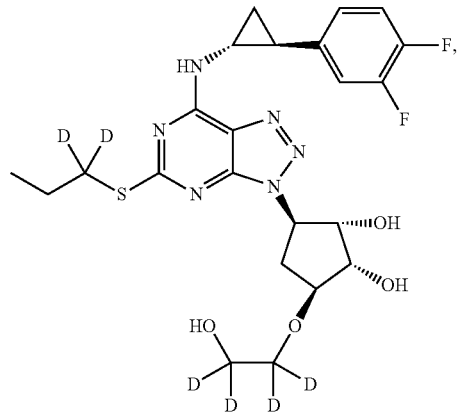
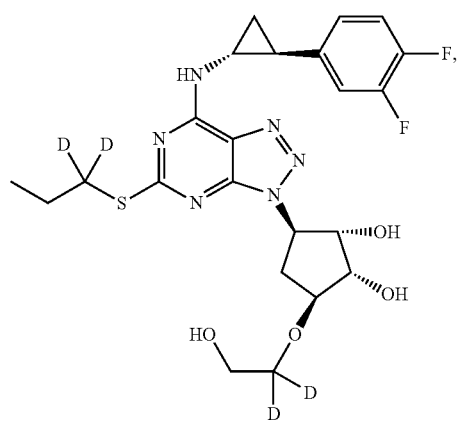
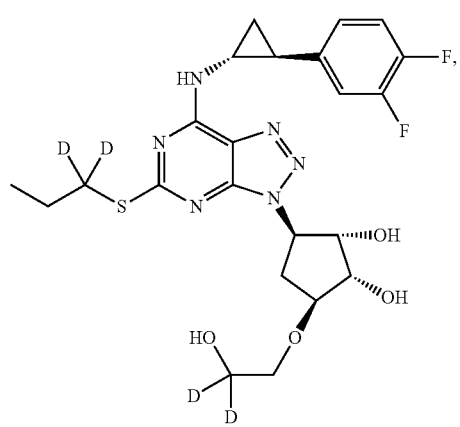

-continued

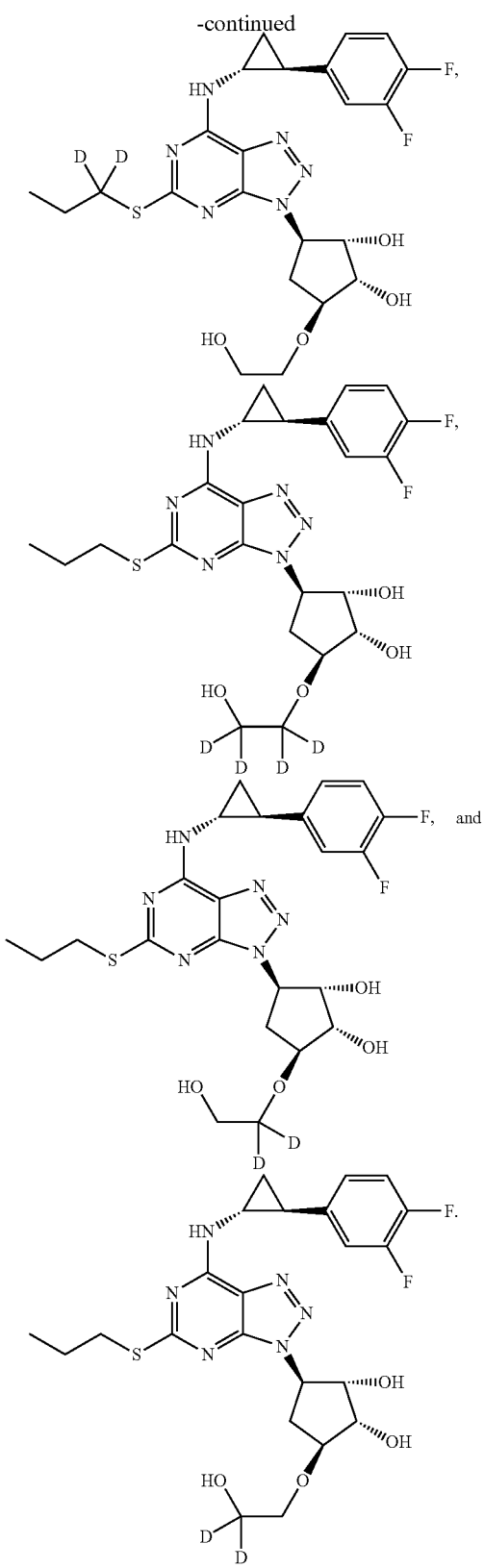

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In Vitro Liver Microsomal Stability Assay

Liver microsomal stability assays were conducted at 1 mg per mL liver microsome protein with an NADPH-generating system in 2% sodium bicarbonate (2.2 mM NADPH, 25.6 mM glucose 6-phosphate, 6 units per mL glucose 6-phosphate dehydrogenase and 3.3 mM magnesium chloride). Test compounds were prepared as solutions in 20% acetonitrile-water (20 µM stock solutions) and added to the assay mixture (final assay concentration 1 µM). Final concentration of acetonitrile in the assay should be <1%. The reactions were incubated at 37° C. Aliquots (50 µL) were taken out at times 0, 15, 30, 45, and 60 minutes, and diluted with ice cold acetonitrile (200 µL) to stop the reactions. Samples are centrifuged at 12,000 RPM for 10 minutes to precipitate proteins. Supernatants are transferred to microcentrifuge tubes and stored for LC/MS/MS analysis of the degradation half-life of the test compounds. It has thus been found that certain isotopically-enriched compounds disclosed herein that have been tested in this assay showed an increased degradation half-life as compared to the non-isotopically enriched drug. In certain embodiments, the increase in degradation half-life is at least 5%; at least 10%; at least 15%; at least 20%; at least 25%; or at least 30%.

In Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar NADP$^+$, 3.3 millimolar glucose-6-phosphate, 0.4 U/mL glucose-6-phosphate dehydrogenase, 3.3 millimolar magnesium chloride and 0.2 millimolar of a compound as disclosed herein, the corresponding non-isotopically enriched compound or standard or control in 100 millimolar potassium phosphate (pH 7.4) is incubated at 37° C. for 20 minutes. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 minutes. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Monoamine Oxidase A Inhibition and Oxidative Turnover

The procedure is carried out using the methods described by Weyler et al., *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM sodium phosphate buffer, pH 7.2, containing 0.2% Triton X-100 (monoamine oxidase assay buffer), plus 1 mM kynuramine, and the desired amount of enzyme in 1 mL total volume.

Monooamine Oxidase B Inhibition and Oxidative Turnover

The procedure is carried out as described in Uebelhack et al., *Pharmacopsychiatry* 1998, 31(5), 187-192, which is hereby incorporated by reference in its entirety.

Inhibition of Platelet Aggregation

The procedure is carried out as described in Husted et al., *Eur. Heart J.* 2006, 27(9), 1038-1047, which is hereby incorporated by reference in its entirety.

Measuring Pharmacokinetics, and Safety of Ticagrelor

The procedure is carried out as described in Husted et al., *European Heart Journal* 2006, 27(9), 1038-1047, which is hereby incorporated by reference in its entirety.

Detecting Ticagrelor and Ticagrelor Metabolites in Humans

The procedure is carried out as described in Butler, et al., *Drug Metab Rev* 2008, 40(*Suppl.* 3): *Abst* 280, which is hereby incorporated by reference in its entirety.

Bleeding Time

The procedure is carried out as described in Husted et al., *Eur. Heart J.* 2006, 27(9), 1038-1047, which is hereby incorporated by reference in its entirety.

Inhibition of Platelet Aggregation

The procedure is carried out as described in WO 2000034283, which is hereby incorporated by reference in its entirety.

Inhibition of Platelet Aggregation

The procedure is carried out as described in WO 199905142, which is hereby incorporated by reference in its entirety.

From the foregoing description, one skilled in the art can ascertain the essential characteristics of this invention, and without departing from the spirit and scope thereof, can make various changes and modifications of the invention to adapt it to various usages and conditions.

What is claimed is:

1. A compound having the structural formula:

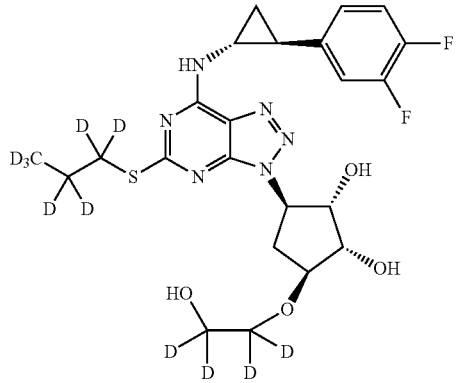 [SMILES: [2H]C([2H])([2H])C([2H])([2H])C([2H])([2H])Sc1nc(N[C@@H]2C[C@H]2c2ccc(F)c(F)c2)c2nnn([C@@H]3C[C@H](OC([2H])([2H])C([2H])([2H])O)[C@@H](O)[C@H]3O)c2n1]

wherein each position represented as D has deuterium enrichment of no less than about 10%.

2. The compound as recited in claim 1 wherein each position represented as D has deuterium enrichment of no less than about 50%.

3. The compound as recited in claim 1 wherein each position represented as D has deuterium enrichment of no less than about 90%.

4. The compound as recited in claim 1 wherein each position represented as D has deuterium enrichment of no less than about 98%.

5. A tablet or capsule comprising a compound as recited in claim 1 together with a pharmaceutically acceptable carrier.

* * * * *